US009101890B2

(12) United States Patent
Tonkovich et al.

(10) Patent No.: US 9,101,890 B2
(45) Date of Patent: Aug. 11, 2015

(54) SUPPORT FOR USE IN MICROCHANNEL PROCESSING

(75) Inventors: Anna Lee Tonkovich, Dublin, OH (US); Kai Tod Paul Jarosch, Bexley, OH (US); Jeffrey D. Marco, South Charleston, OH (US); Bin Yang, Columbus, OH (US); Sean Patrick Fitzgerald, Columbus, OH (US); Steven T. Perry, Galloway, OH (US); Thomas Yuschak, Lewis Center, OH (US); Francis P. Daly, Delaware, OH (US); Haibiao Chen, Powell, OH (US)

(73) Assignee: Velocys, Inc., Plain City, OH (US)

(*) Notice: Subject to any disclaimer, the term of this patent is extended or adjusted under 35 U.S.C. 154(b) by 1200 days.

(21) Appl. No.: 11/443,851

(22) Filed: May 25, 2006

(65) Prior Publication Data
US 2009/0326279 A1   Dec. 31, 2009

Related U.S. Application Data

(60) Provisional application No. 60/684,327, filed on May 25, 2005, provisional application No. 60/697,900, filed on Jul. 8, 2005, provisional application No. 60/727,126, filed on Oct. 13, 2005, provisional application No. 60/731,596, filed on Oct. 27, 2005, provisional application No. 60/785,180, filed on Mar. 23, 2006, provisional application No. 60/785,732, filed on Mar. 23, 2006, provisional application No. 60/745,614, filed on Apr. 25, 2006.

(51) Int. Cl.
| C07C 2/58 | (2006.01) |
| B01F 5/06 | (2006.01) |
| B01F 5/04 | (2006.01) |
| B01F 13/00 | (2006.01) |
| B01J 19/00 | (2006.01) |
| F28F 3/04 | (2006.01) |
| F28F 13/00 | (2006.01) |

(52) U.S. Cl.
CPC ............. B01F 5/0646 (2013.01); B01F 5/0475 (2013.01); B01F 5/061 (2013.01); B01F 5/0655 (2013.01); B01F 13/0059 (2013.01); B01J 19/0093 (2013.01); *B01J 2219/0086* (2013.01); *B01J 2219/00783* (2013.01); *B01J 2219/00835* (2013.01); *B01J 2219/00844* (2013.01); *B01J 2219/00867* (2013.01); *B01J 2219/00873* (2013.01); *B01J 2219/00889* (2013.01); *B01J 2219/00905* (2013.01); *B01J 2219/00918* (2013.01); *F28F 3/048* (2013.01); *F28F 13/003* (2013.01); *F28F 2260/02* (2013.01)

(58) Field of Classification Search
None
See application file for complete search history.

(56) References Cited

U.S. PATENT DOCUMENTS

| 3,882,049 | A | 5/1975 | Bertolacini et al. |
| 3,972,837 | A | 8/1976 | Acres et al. |
| 4,089,810 | A | 5/1978 | Diwell et al. |
| 4,096,095 | A | 6/1978 | Cairns |
| 4,289,652 | A | 9/1981 | Hunter et al. |
| 4,392,362 | A | 7/1983 | Little .............. 62/514 |
| 4,516,632 | A | 5/1985 | Swift et al. .......... 165/167 |
| 4,914,070 | A | 4/1990 | Ledoux et al. ........ 502/178 |
| 5,248,251 | A | 9/1993 | Dalla Betta et al. |
| 5,309,637 | A | 5/1994 | Moriarty ............ 29/890.054 |
| 5,317,805 | A | 6/1994 | Hoopman et al. ....... 29/890.03 |
| 5,334,414 | A | 8/1994 | Edie et al. ............ 427/189 |
| 5,536,694 | A | 7/1996 | Schuetz et al. ........ 502/301 |
| 5,597,773 | A | 1/1997 | Evans et al. .......... 502/348 |
| 5,611,214 | A | 3/1997 | Wegeng et al. ......... 62/498 |
| 5,668,188 | A | 9/1997 | Whinnery et al. ....... 423/345 |
| 5,689,966 | A | 11/1997 | Zess et al. ............ 62/238.6 |
| 5,727,618 | A | 3/1998 | Mundinger et al. ...... 165/80.4 |
| 5,744,075 | A | 4/1998 | Klett et al. ............ 264/29.6 |
| 5,811,062 | A | 9/1998 | Wegeng et al. ........ 422/129 |
| 5,858,314 | A | 1/1999 | Hsu et al. ............. 422/211 |
| 5,997,826 | A | 12/1999 | Lodeng et al. ......... 422/190 |
| 6,040,266 | A | 3/2000 | Fay, III et al. |
| 6,056,932 | A | 5/2000 | von Hippel et al. ...... 423/376 |
| 6,126,723 | A | 10/2000 | Drost et al. ............. 96/4 |
| 6,129,973 | A | 10/2000 | Martin et al. .......... 428/166 |
| 6,159,358 | A | 12/2000 | Mulvaney, III et al. ... 423/376 |
| 6,192,596 | B1 | 2/2001 | Bennett et al. .......... 34/76 |
| 6,200,536 | B1 | 3/2001 | Tonkovich et al. ...... 422/177 |
| 6,216,343 | B1 | 4/2001 | Leland et al. ......... 29/890.032 |

(Continued)

FOREIGN PATENT DOCUMENTS

| CA | 2247662 | 3/1999 |
| DE | 246257 | 6/1987 |

(Continued)

OTHER PUBLICATIONS

Kestenbaum; "Synthesis of ethylene oxide in a microreaction system"; *Microreaction Technology: Industrial Prospects;* IMRET 3: Proceedings of the Third International Converence on Microreaction Technology.

(Continued)

Primary Examiner — Randy Boyer

(74) *Attorney, Agent, or Firm* — Renner, Otto, Boisselle & Sklar, LLP

(57) ABSTRACT

The disclosed technology relates to an apparatus, comprising: at least one microchannel, the microchannel comprising at least one heat transfer wall; a porous thermally conductive support in the microchannel in contact with the heat transfer wall; a catalyst or a sorption medium supported by the porous support; and a heat source and/or heat sink in thermal contact with the heat transfer wall.

45 Claims, 73 Drawing Sheets

(56) References Cited

U.S. PATENT DOCUMENTS

| | | | |
|---|---|---|---|
| 6,220,497 B1 | 4/2001 | Benz et al. | 228/118 |
| 6,230,408 B1 | 5/2001 | Ehrfeld et al. | 29/890.039 |
| 6,284,217 B1 | 9/2001 | Wang et al. | 423/651 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,409,072 B1 | 6/2002 | Breuer et al. | 228/111.5 |
| 6,415,860 B1 | 7/2002 | Kelly et al. | 165/748 |
| 6,440,895 B1 | 8/2002 | Tonkovich et al. | |
| 6,451,864 B1 | 9/2002 | Wang et al. | 518/715 |
| 6,479,428 B1 | 11/2002 | Tonkovich et al. | 502/302 |
| 6,488,838 B1 | 12/2002 | Tonkovich et al. | 208/108 |
| 6,490,812 B1 | 12/2002 | Bennett et al. | 34/433 |
| 6,491,880 B1 | 12/2002 | Wang et al. | 422/211 |
| 6,503,298 B1 | 1/2003 | Monzyk et al. | 95/96 |
| 6,508,862 B1 | 1/2003 | Tonkovich et al. | 95/106 |
| 6,533,840 B2 | 3/2003 | Martin et al. | 95/45 |
| 6,540,975 B2 | 4/2003 | Tonkovich et al. | 423/659 |
| 6,558,634 B1 | 5/2003 | Wang et al. | 422/173 |
| 6,607,678 B2 | 8/2003 | Wang et al. | 252/373 |
| 6,616,909 B1 | 9/2003 | Tonkovich et al. | 423/648.1 |
| 6,622,519 B1 | 9/2003 | Mathias et al. | 62/611 |
| 6,652,627 B1 | 11/2003 | Tonkovich et al. | 95/104 |
| 6,660,237 B2 | 12/2003 | Wang et al. | 422/222 |
| 6,666,909 B1 | 12/2003 | TeGrotenhuis et al. | 95/273 |
| 6,675,875 B1 | 1/2004 | Vafai et al. | 165/80.4 |
| 6,680,044 B1 | 1/2004 | Tonkovich et al. | 423/652 |
| 6,713,036 B1 | 3/2004 | Vanden Bussche et al. | 423/584 |
| 6,734,137 B2 | 5/2004 | Wang et al. | 502/328 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,750,258 B2 | 6/2004 | Wang et al. | 518/715 |
| 6,755,211 B1 | 6/2004 | O'Connor et al. | 137/554 |
| 6,762,149 B2 | 7/2004 | Tonkovich et al. | 502/439 |
| 6,769,444 B2 | 8/2004 | Guzman et al. | 137/15.01 |
| 6,773,684 B2 | 8/2004 | Lesieur et al. | 422/198 |
| 6,814,781 B2 | 11/2004 | Tonkovich et al. | 95/90 |
| 6,851,171 B2 | 2/2005 | Schmitt | 29/469 |
| 6,875,247 B2 | 4/2005 | TeGrotenhuis et al. | 55/310 |
| 6,969,505 B2 | 11/2005 | Tonkovich et al. | 423/648.1 |
| 6,969,506 B2 | 11/2005 | Tonkovich et al. | 423/652 |
| 6,984,363 B2 | 1/2006 | Tonkovich et al. | 422/173 |
| 6,989,134 B2 | 1/2006 | Tonkovich et al. | 422/189 |
| 7,000,427 B2 | 2/2006 | Mathias et al. | 62/612 |
| 7,008,969 B2 | 3/2006 | Wang et al. | 518/715 |
| 7,011,760 B2 | 3/2006 | Wang et al. | 210/660 |
| 7,014,835 B2 | 3/2006 | Mathias et al. | 423/652 |
| 7,029,647 B2 | 4/2006 | Tonkovich et al. | 423/584 |
| 7,045,114 B2 | 5/2006 | Tonkovich et al. | 423/659 |
| 7,077,643 B2 | 7/2006 | Holladay et al. | 431/215 |
| 7,084,180 B2 | 8/2006 | Wang et al. | 518/712 |
| 7,234,514 B2 | 6/2007 | Vogel | 165/170 |
| 2001/0018140 A1 | 8/2001 | Hermann et al. | 429/20 |
| 2002/0028164 A1 | 3/2002 | Schutte et al. | 422/198 |
| 2002/0192118 A1 | 12/2002 | Zech et al. | 422/99 |
| 2003/0007904 A1 | 1/2003 | Tonkovich et al. | 422/180 |
| 2003/0045747 A1 | 3/2003 | Wurziger et al. | 562/418 |
| 2003/0103879 A1 | 6/2003 | Jahn et al. | 422/211 |
| 2003/0116503 A1 | 6/2003 | Wang et al. | 210/660 |
| 2003/0152488 A1 | 8/2003 | Tonkovich et al. | 422/99 |
| 2003/0219903 A1 | 11/2003 | Wang et al. | 436/37 |
| 2004/0033455 A1 | 2/2004 | Tonkovich et al. | 431/7 |
| 2004/0034111 A1 | 2/2004 | Tonkovich et al. | 518/726 |
| 2004/0055329 A1 | 3/2004 | Mathias et al. | 62/611 |
| 2004/0104010 A1 | 6/2004 | Kenny et al. | 165/80.4 |
| 2004/0123626 A1 | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131345 A1 | 7/2004 | Kylberg et al. | 392/465 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2004/0188326 A1 | 9/2004 | Tonkovich et al. | 208/139 |
| 2004/0220434 A1 | 11/2004 | Brophy et al. | 568/959 |
| 2004/0228781 A1 | 11/2004 | Tonkovich et al. | 422/222 |
| 2004/0228882 A1 | 11/2004 | Qiu et al. | 424/400 |
| 2004/0229752 A1 | 11/2004 | Long et al. | 502/303 |
| 2004/0234566 A1 | 11/2004 | Qiu et al. | 424/401 |
| 2005/0045030 A1 | 3/2005 | Tonkovich et al. | 95/90 |
| 2005/0163701 A1 | 7/2005 | Tonkovich et al. | 423/584 |
| 2005/0165121 A1 | 7/2005 | Wang et al. | 518/726 |
| 2005/0176832 A1 | 8/2005 | Tonkovich et al. | 518/726 |

FOREIGN PATENT DOCUMENTS

| | | |
|---|---|---|
| DE | 3926466 | 2/1991 |
| DE | 203 04 101 U1 | 5/2003 |
| DE | 20304101 U1 | 5/2003 |
| EP | 0 904 608 | 8/1999 |
| EP | 0 885 086 B1 | 8/2001 |
| EP | 1 311 341 B1 | 8/2001 |
| EP | 0 904 608 B1 | 12/2001 |
| EP | 1 232 790 A1 | 8/2002 |
| EP | 1 362 634 A1 | 11/2003 |
| EP | 1 382 382 A1 | 1/2004 |
| EP | 1102628 | 11/2006 |
| GB | 1531134 | 11/1978 |
| GB | 2077136 | 12/1981 |
| WO | 9421372 | 9/1994 |
| WO | 9700442 | 1/1997 |
| WO | 97/32687 | 9/1997 |
| WO | 9828073 | 7/1998 |
| WO | 9838147 | 9/1998 |
| WO | 98/55812 | 12/1998 |
| WO | 9916542 | 4/1999 |
| WO | 99/00186 | 7/1999 |
| WO | 99/48805 | 9/1999 |
| WO | 0006301 | 2/2000 |
| WO | 00/06295 | 10/2000 |
| WO | 01/10773 A1 | 2/2001 |
| WO | 01/12312 A2 | 2/2001 |
| WO | 01/54807 A1 | 8/2001 |
| WO | 01/95237 A2 | 12/2001 |
| WO | 02/14854 A1 | 2/2002 |
| WO | 02/087729 A1 | 7/2002 |
| WO | 02/064248 A2 | 8/2002 |
| WO | 03006149 | 1/2003 |
| WO | 03/080233 A1 | 2/2003 |
| WO | 03059813 | 7/2003 |
| WO | 03/078052 A1 | 9/2003 |
| WO | 03/106386 A2 | 12/2003 |
| WO | 2004/016347 A2 | 2/2004 |
| WO | 2004/030805 A1 | 4/2004 |
| WO | 2004/101138 A1 | 5/2004 |
| WO | 2004/037399 A2 | 6/2004 |
| WO | 2004/037418 A1 | 6/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2004/091771 A1 | 10/2004 |
| WO | 2004/099113 A1 | 11/2004 |
| WO | 2005/003025 A2 | 1/2005 |
| WO | 2006/020709 A1 | 2/2006 |

(56) References Cited

FOREIGN PATENT DOCUMENTS

WO  2006/053345 A1  5/2006
ZA  855317  7/1985

OTHER PUBLICATIONS

Besser, Ronald S. "New Directions in Reactor Design Through Miniaturization". Sep. 13, 2002, Tulane Engineering Forum.
Gohring et al.; "Gas Phase Reactions in Ceramic Microreactors"; IMERT 6, 10-14, New Orleans, USA, AIChE Conference Proceedings 55-60. Mar. 2002.
Hsing et al.; "Simulation of Microchannel Chemical Reactors for Heterogeneous Partial Oxidation Reactions"; Chemical Engineering Science 55 (2000) 3-13.
Matlosz et al.; "Microreactors as Tools in Chemical Research"; Microreaction Technology; IMRET 5: Proceedings of the Fifth International Conference on Microreaction Technology. (May 27-30, 2001).
Srinivasn et al.; "Micromachined Reactors for Catalytic Partial Oxidation Reactions"; AIChE Journal; Nov. 1997; vol. 43, No. 11; pp. 3059-3069.
TeGrotenhuis et al.; Optimizing Microchannel Reactors by Trading-Off Equilibrium and Reaction Kinetics through Temperature Management; Prepared for presentation at IMRET 6—6$^{th}$ International Conference on Microreaction Technology; Mar. 10-14, 2002.
Wegeng et al.; "Compact Fuel Processors for Fuel Cell Powered Automobiles Based on Microchannel Technology"; Fuel Cells Bulletin No. 28; pp. 8-13.
Rostami et al.; "Flow and Heat Transfer for Gas Flowing in Microchannels: a Review"; Heat and Mass Transfer 38 (2002) 359-367.
Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).
Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.
Beretta et al.; "Production of Olefins via Oxidative Dehydrogenation of Light Paraffins at Short Contact Times"; Catalysis Today; 2001 Elsevier Science B.V.; pp. 103-111.
Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.
Aartun et al.; "Catalytic conversion of propane to hydrogen in microstructured reactors" Chemical Engineering Journal 101 (2004) 93-99.
Ajmera et al.; "Microfabricated Differential Reactor for Heterogeneous Gas Phase Catalyst Testing"; Journal of Catalysis 209, 401-412 (2002).
Allen et al.; "Microreactor Systems for Hydrogen Generation and Oxidative Coupling of Methane"; Prepared for Presentation at AICHE 2000 Spring National Meeting, Mar. 5-9, 2000.
Beretta et al.; "Partial oxidation of light parafins to synthesis gas in short contact0time reactors"; Chemical Engineering Journal 99 (2004) 219-226.
Bharadwaj et al.; "Catalytic partial oxidation of natural gas to syngas"; Fuel Processing Technology 42 (1995) 109-127.
Chin et al.; "Preparation of a novel structured catalyst based on aligned carbon nanotube arrays for a microchannel Fischer-Tropsch synthesis reactor"; Catalysis Today 110 (2005) 47-52.
Daymo et al.; "Microchannel Fuel Processing for Man Portable Power"; Prepared for presentation at IMRET 4, Session 108, Microreactors for Energy Generation and Storage, Mar. 9, 2000.
DeLuga et al.; "Renewable Hydrogen from Ethanol by Autothermal Reforming"; Science, vol. 303, Feb. 13, 2004.

Flick et al.; "Oxidative Dehydrogenation of Ethane over a Pt-Coated Monolith versus Pt-Loaded Pellets: Surface Area and Thermal Effects"; Journal of Catalysis 178, 315-327 (1998).
Ganley et al.; "Porous anodic alumina optimized as a catalyst support for microreactors"; Journal of Catalysis 227 (2004) 26-32.
Groppi et al.; "Honeycomb supports with high thermal conductivity for gas/solid chemical processes"; Catalysis Today 105 (2005) 297-304.
Goralski, Jr., et al.; "Modeling homogeneous and heterogeneous chemistry in the production of syngas from methane"; Chemical Engineering Sciences 55 (2000) 1357-1370.
Hersch; "Hydrogen-Oxygen Chemical Reaction Kinetics in Rocket Engine Combustion"; NASA Technical Note, 1967.
Hickman et al.; "Synthesis gas formation by direct oxidation of methane over Rh monoliths"; Catalysis Letters 17 (1993) 223-237.
Huff et al.; "Ethylene Formation by Oxidative Dehydrogenation of Ethane over Monoliths at Very Short Contact Times"; J. Phys. Chem., 1993, 97, 11815-11822.
Jacquemin et al.; "Solubility of carbon dioxide, ethane, methane, oxygen, nitrogen, hydrogen, argon, and carbon monoxide in 1-butyl-3-methylimidazolium tetrafluoroborate between temperatures 283 K and 243 K and at pressures close to atmospheric"; J. Chem. Thermodynamics 38 (2006) 490-502.
Janicke et al.; "The Controlled Oxidation of Hydrogen from an Explosive Mixture of Gases using a Microstructured Reactor/Heat Exchanger and $Pt/Al_2O_3$ Catalyst"; Journal of Catalysis 191, 282-293 (2000).
Khassin et al.; "Performance of a catalytic membrane reactor for the Fischer-Tropsch synthesis"; Catalysis Today 105 (2005) 362-366.
Kolb et al.; "Propane steam reforming in micro-channels—results from catalyst screening and optimisation"; Applied Catalysis A: General 277 (2004) 155-166.
Kolodziej et al.; "Optimization of structured catalyst carriers for VOC combustion"; Catalysis Today 105 (2005) 378-384.
Kreutzer et al.; "Shouldn't catalysts shape up? Structured reactors in general and gas-liquid monolith reactors in particular"; Catalysis Today 111 (2006) 111-118.
Ma et al.; "Synthesis of gold nano-catalysts supported on carbon nanotubes by using electroless plating technique"; Materials Chemistry and Physics 97 (2006) 351-356.
Macak et al.; "Self-organized nanotubular $TiO_2$ matrix as support for dispersed Pt/Ru nanoparticles: Enhancement of the electrocatalytic oxidation of methanol"; Electrochemistry Communications 7 (2005) 1417-1422.
Schmidt et al.; "Syngas in millisecond reactors: higher alkanes and fast lightoff"; Chemical Engineering Science 58 (2003) 1037-1041.
Tonkovich et al.; "Microchannel reactors for fuel processing applications. I. Water gas shift reactor"; Chemical Engineering Science 54 (1999) 2947-2951.
Tonkovich et al.; "Microchannel process technology for compact methane steam reforming"; Chemical Engineering Science 59 (2004) 4819-4824.
Venkataraman et al.; "Millisecond catalytic wall reactors: dehydrogenation of ethane"; Chemical Engineering Science 57 (2002) 2335-2343.
Veser; "Experimental and theoretical investigation of $H_2$ oxidation in a high-temperature catalytic microreactor"; Chemical Engineering Science 56 (2001) 1265-1273.
Chen; "Development of tailored cellular structure as a novel catalyst integration platform for microreactors"; Stevens Institute of Technology; vol. 67-07B; pp. 4039; 2006.
Chen; "Infiltration of Patterned $Al_2O_3$ and $SiO_2$ Layers into Microtubes Using Sol-Gel Technique Combined with Self-Assembled Microsphere Templates"; A Thesis; Stevens Institute of Technology; 2003.
Chen; "Development of Tailored Cellular Structure as a Novel Catalyst Integration Platform for Microreactors"; A Dissertation; Stevens Institute of Technology; 2006.
Ajmera et al.; "Microfabricated cross-flow chemical reactor for catalyst testing"; Sensors and Actuators B; 82 (2002); pp. 297-306.
Allen et al.; "Microreactor Systems for Hydrogen Generation and Oxidative Coupling of Methane"; Prepared for presentation at AICHE, 2000, pp. 351-357.

(56) References Cited

OTHER PUBLICATIONS

Cybulski et al.; "Parallel-Passage and Lateral-Flow Reactors"; *Structured Catalysts and Reactors*, 2006, pp. 509-538.
Deluga et al.; "Renewable Hydrogen from Ethanol by Autothermal Reforming"; *Science;* vol. 303; Feb. 13, 2004.
Dietzsch et al.; "The formation of cycloalkenes in partial gas phase hydrogentaiton of c,t,t 1,5,9-cyclododecatrine, 1,5-cyclooctadiene and benzene in microchannel reactors"; Prepared for presentation at AiChE National Meeting; 2000.
Fitzgerald et al.; "A Compact Steam Reforming Reactor for Use in an Automotive Fuel Processor"; Prepared for presentation at International Microreaction Engineering Technology Conference, 2000.
Jarosch et al.; "Microchannel Reactors for Intensifying Gas-to-Liquid Technology"; *American Chemical Society,* 2005, pp. 258-272.
Kursawe et al.; "Selective Reactions in Microchannel Reactors"; International Conference on Microreaction Technology (IMRET 3), 1999, pp. 213-223.
Mayer et al.; "A Microstructured Reactor for the Catalytic Partial Oxidation of Methane to Syngas"; International Conference on Microreaction Technology (IMRET 3), 1999, pp. 187-196.
Mazanec; "Microchannel Technology for gas-to-liquids conversion"; *Petrochemicals and Gas Processing;* 2003, pp. 149-153.
O'Connor et al.; "High yields of synthesis gas by millisecond partial oxidation of higher hydrocarbons"; *Catalysis Letters* 70, 2000, pp. 99-107.
Pattekar et al.; "Fuel processing microreactors for hydrogen production in micro fuel cell applications"; International Conference on Microreaction Technology (IMERT-7), 2003.
Rebrov et al.; "Synthesis and Characterization of SZM-5 Zeolites on Prefabricated Stainless Steel Microchannels"; Prepared for presentation at AlChE conference, 2000.
Sato et al.; "The $Co-H_2$ and $CO—H_2O$ reactions over $TiO_2$ nanotubes filled with Pt metal nanoparticles"; *Catalysis Today* 111, 2006, pp. 164-170.
Reyes et al.; "Evolution of Processes for Synthesis Gas Production: Recent Developments in an Old Technology"; *Ind. Eng. Chem. Res.,* 2003, 42, pp. 1588-1597.
TeGrotenhuis et al.; Optimizing Microchannel Reactors by Trading-Off Equilibrium and Reaction Kinetics through Temperature Management; Prepared for presentation at IMERT-6 International Conference on Microreaction Technology, 2002.
Tonkovich et al.; "Overview of Early-Stage Microchannel Reactor Development at Pacific Northwest National Laboratory"; *American Chemical Society,* 2005, pp. 47-65.
Tonkovich et al.; "The Catalytic Partial Oxidation of Methane in a Microchannel Chemical Reactor"; Pacific Northwest National Laboratory (1998), pp. 45-53.
Tonkovich et al.; "Microchannel process technology for compact methane steam reforming"; *Chemical Engineering Science* 59, 2004, pp. 4819-4824.
Tonkovich et al.; "Microchannel Technology Scale-up to Commercial Capacity"; *Chemical Engineering Research and Design* (2005), 83 (A6), pp. 634-639.
VanderWiel et al.; "Carbon Dioxide Conversions in Microreactors"; Prepared for presentation at AlChE meeting, 2000, pp. 187-193.
Venkataramann et al.; Steam Reforming of Methane and Water-Gas Shift in Catalytic Wall Reactors; *AlChE Journal,* Vo. 49, No. 5, May 2003.
Veser et al.; "A Modular Microreactor Design for High-Temperature Catalytic Oxidation Reactions" International Conference on Microreaction Technology (IMRET 3) 1999, pp. 674-686.
Wang et al.; "Highly active and stable $Rh/MgO-Al_2O_3$ catalyst for methane steam reforming"; *Catalysis Today* 98, 2004, pp. 575-581.
International Application PCT/US2006/020220, International Preliminary Report on Patentability, mailed Sep. 11, 2007.
International Search Report and Written Opinion, Application No. PCT/US2006/020220, mailed Oct. 18, 2006.
Kestenbaum et al.; "Silver-Catalyzed Oxidation of Ethylene to Ethylene Oxide in a Microreaction System"; *Ind. Eng. Chem. Res.,* 2002, 41, 710-719.
Cao et al.; "Oxidative dehydrogenation of 3-Methyl-2-buten-1-ol in microreactors"; *Chemical Engineering Science* 59 (2004), 4803-4808.
Wiebmeier et al.; "Heterogeneously Catalyzed Gas-Phase Hyrogenation of cis, trans, trans-1,5,9-Cyclododecatriene on Palladium Catalysts Having Regular Pore Systems"; *Ind. Eng. Chem. Res.,* 1996, 35, 4412-4416.
Ouyang et al. "Flexible Microreactor System for Chemical Research at Moderate and High Temperatures". Stevens Institute of Technology. (No date shown on document but admitted as prior art).
Chen; "Sol-Gel Infiltration and Evaluation of Patterned Catalyst Support Layers in Microchannels"; Materials Research Society Fall Meeting, Dec. 4, 2002.
Chen et al.; "Performance analysis of a folding flow micromixer"; Microfluid Nanofluid (2009) 6:763-774.
MacInnes et al.; "Investigation of alternating-flow mixing in microchannels"; Chemical Engineering Science 60; 2005; pp. 3453-3467.
MacInnes et al.; "Numerial characterization of floding flow microchannel mixers"; Chemical Engineering Science 62; 2007; pp. 2718-2727.
MacInnes et al.; "Mixing Strategies for Flow in Microchannel Devices"; Chemical and Process Engineering, University of Sheffield, Nov. 24, 2004.
Iglesia; "Design, synthesis, and use of cobalt-based Fischer-Tropsch synthesis catalysts"; Applied Catalysis A: General 161 (1997); pp. 59-78.
Cybulski et al.; "Monoliths in Heterogeneous Catalysis"; Catal. Rev.—Sci. Eng., 36(2), 179-270 (1994).
Bennett et al.; "Microchannel cooled heatsinks for high average power laser diode arrays"; SPIE, vol. 1865; 1993; pp. 144-153.
European Office Action, Application No. 06 760 374.6, dated Nov. 21, 2011.
Canadian Office Action, Application No. 2,608,400, dated Jun. 28, 2012.

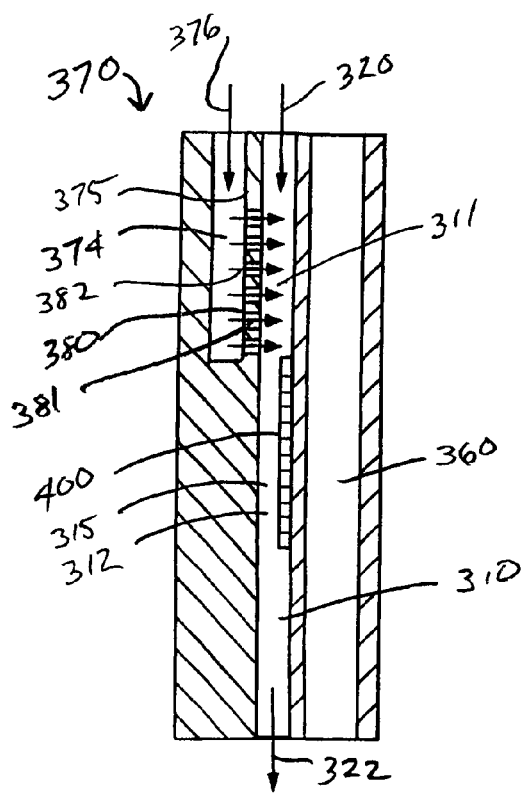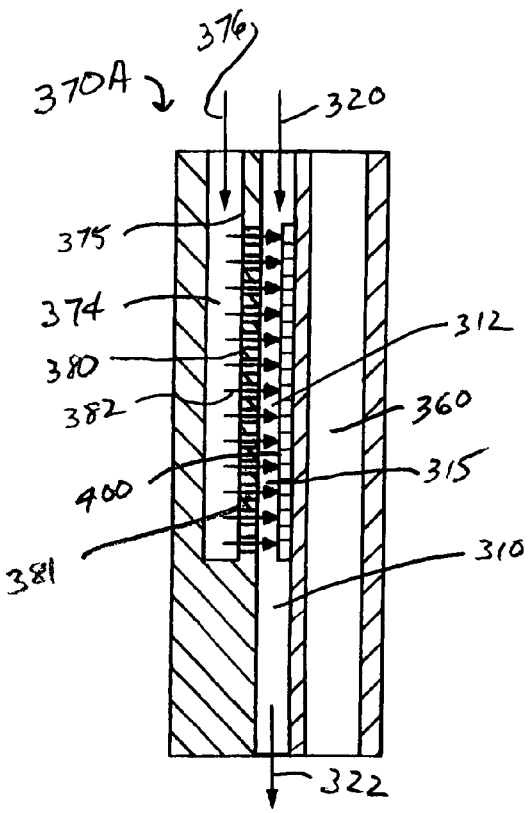
FIG. 9
FIG. 10
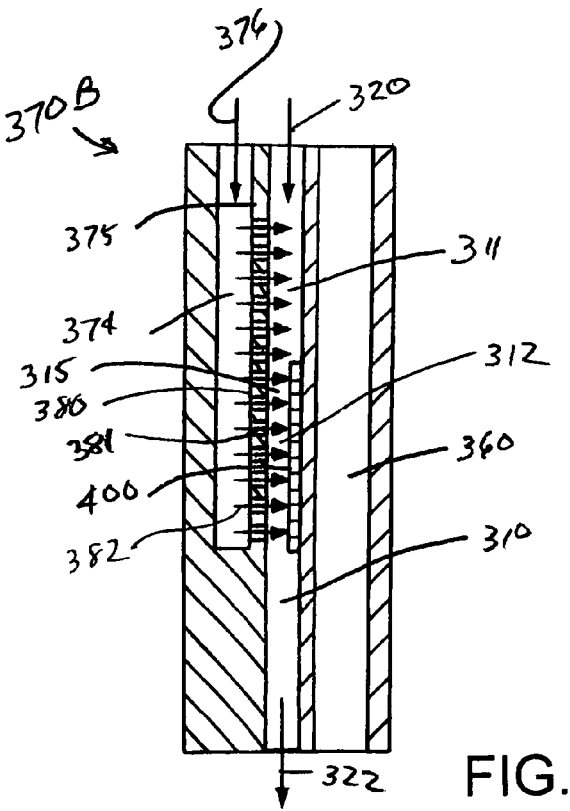
FIG. 11

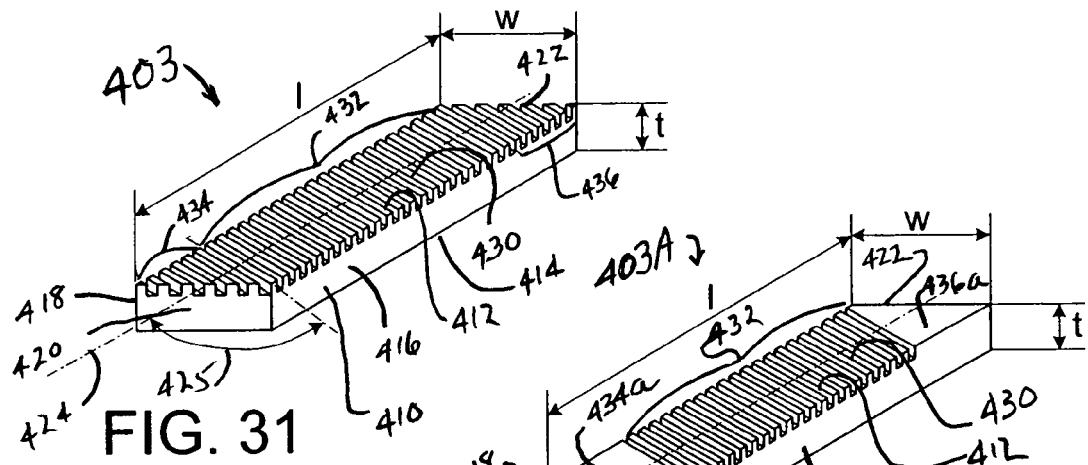
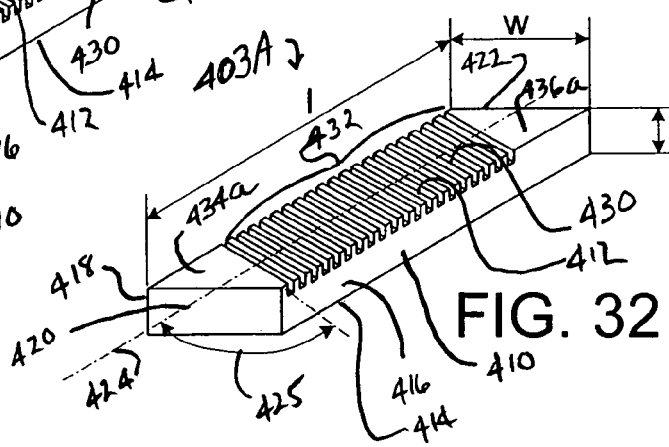
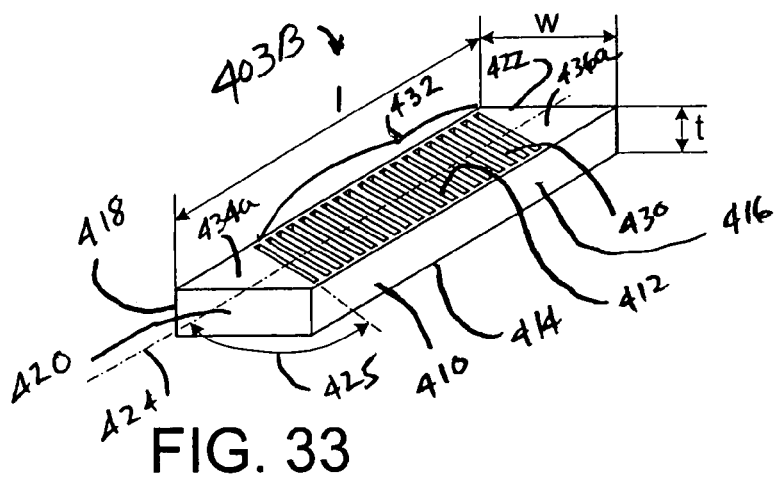

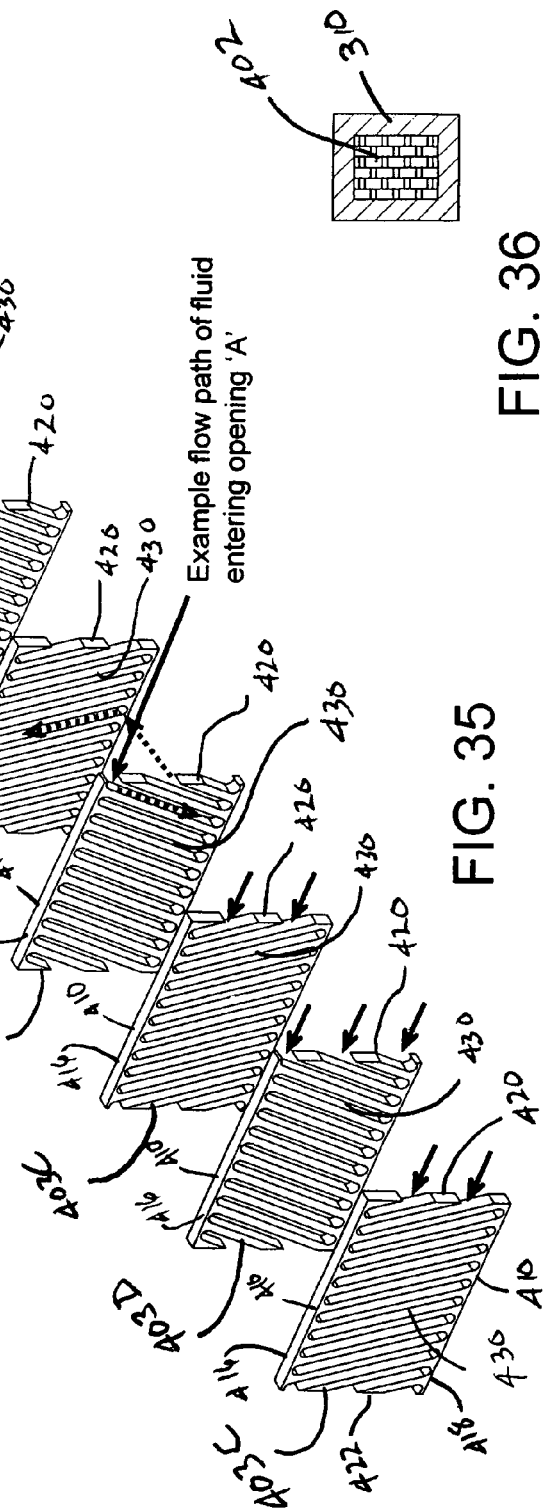
FIG. 34
FIG. 35
FIG. 36

SUPPORT FOR USE IN MICROCHANNEL PROCESSING

This application claims priority under 35 U.S.C. §119(e) to U.S. Provisional Application Ser. No. 60/684,327 filed May 25, 2005, U.S. Provisional Application Ser. No. 60/697,900, filed Jul. 8, 2005, U.S. Provisional Application Ser. No. 60/727,126, filed Oct. 13, 2005, U.S. Provisional Application Ser. No. 60/731,596, filed Oct. 27, 2005, U.S. Provisional Application Ser. No. 60/785,180, filed Mar. 23, 2006, U.S. Provisional Application Ser. No. 60/785,732, filed Mar. 23, 2006, and U.S. Provisional Application Ser. No. 60/745,614, filed Apr. 25, 2006. These applications are incorporated herein by reference.

TECHNICAL FIELD

The disclosed technology relates to supports for use in microchannel processing. These supports may be used for supporting catalysts used in microchannel reactors. The supports may be used for supporting sorption medium used in microchannel separators. The supports may be in the form of porous supports on interior walls of process microchannels in the microchannel reactors or separators. The porous supports may comprise microgrooved support strips or shims. The supports may comprise porous, thermally conductive treatment or coating layers. Microchannel reactors containing catalysts supported by these supports may be referred to as structured wall (SW) reactors.

BACKGROUND

Microchannel reactors may be used in a variety of catalytic processes wherein reactants contact a catalyst within the microchannel reactor and undergo reaction. These reactors have been shown to provide excellent performance and attractive economics for steam methane reforming (SMR) reactions at very short contact times using a catalyst coated on the interior walls of the microchannel reactor. However, reactions with longer contact times have in the past required either an engineered catalyst (e.g., a catalyst supported on a foam, felt, wad or fin) or a packed bed to increase the surface area for supporting the catalyst.

These approaches may result in one or more of a number of problems. These problems may include the fact that some engineered catalysts and packed beds tend to have relatively low effective thermal conductivities in the structure as well as in the interface between the structure and any adjacent heat transfer wall. Integration of a catalyst structure within a microchannel reactor after bonding may result in poor thermal contact with heat transfer walls. Pressure drop within the microchannel reactor may be relatively high when flow is predominately directed through the pores of the structure rather than by or past the structure. The use of reduced amounts of catalyst may equate to longer contact times.

This invention, in at least one embodiment, provides a solution to one or more of these problems.

SUMMARY

The disclosed technology relates to an apparatus, comprising: at least one microchannel, the microchannel comprising at least one heat transfer wall; a porous thermally conductive support in the microchannel in contact with the heat transfer wall; a catalyst or a sorption medium supported by the porous support; and a heat source and/or heat sink in thermal contact with the heat transfer wall.

In one embodiment, the disclosed technology relates to the foregoing apparatus wherein the apparatus is in the form of a microchannel reactor, the microchannel reactor comprising a plurality of the microchannels adapted to be operated in parallel, the microchannels being process microchannels, a header for providing for the flow of fluid into the microchannels, a footer for providing for the flow of fluid out of the microchannels, and a catalyst supported by the porous support.

In one embodiment, the disclosed technology relates to the foregoing apparatus wherein a second reactant stream channel is adjacent each process microchannel and an apertured section for permitting the staged addition of one or more reactants into the process microchannel is positioned between the second reactant stream channel and the process microchannel.

In one embodiment, the disclosed technology relates to the foregoing apparatus wherein the apparatus is in the form of an integrated combustion reactor comprising at least one reaction chamber and at least one combustion chamber, the reaction chamber and/or the combustion chamber comprising a plurality of the microchannels adapted to be operated in parallel.

In one embodiment, the disclosed technology relates to the foregoing apparatus wherein the apparatus is in the form of a microchannel separator, the microchannel separator comprising a plurality of the microchannels adapted to be operated in parallel, a header for providing for the flow of fluid into the microchannels, a footer for providing for the flow of fluid out of the microchannels, at least one heat exchange channel for exchanging heat with the microchannels, and a sorption medium supported by the porous support.

In one embodiment, the disclosed technology relates to an apparatus, comprising: at least one microchannel, the microchannel comprising at least one heat transfer wall; a porous thermally conductive support in the microchannel in contact with the heat transfer wall; a catalyst or a sorption medium supported by the porous support; the microchannel and/or porous support containing surface features for modifying flow, the surface features being on or in one or more walls of the microchannel and/or on or in the porous support; a heat source and/or heat sink in thermal contact with the heat transfer wall.

In one embodiment, the disclosed technology relates to an apparatus, comprising: at least one microchannel, the microchannel comprising at least one heat transfer wall; a porous thermally conductive support in the microchannel in contact with the heat transfer wall; a catalyst or a sorption medium supported by the porous support; a heat source and/or heat sink in thermal contact with the heat transfer wall; the effective thermal conductivity of the combined porous support and heat transfer wall being in the range from about 0.5 to about 500 W/m-K.

In one embodiment, the disclosed technology relates to an apparatus, comprising: at least one microchannel, the microchannel comprising at least one heat transfer wall; a porous thermally conductive support in the microchannel in contact with the heat transfer wall; a gap positioned in the microchannel adjacent to the porous support, the gap being of sufficient dimension to permit fluid to flow in the gap; a catalyst or a sorption medium supported by the porous support; and a heat source and/or heat sink in thermal contact with the heat transfer wall.

In one embodiment, the disclosed technology relates to an apparatus, comprising: at least one microchannel, the microchannel comprising at least one heat transfer wall; a porous thermally conductive support in the microchannel in contact with the heat transfer wall, at least about 20% of the pore volume of the porous support having an average pore size in the range from about 0.1 to about 700 microns; a gap positioned in the microchannel adjacent to the porous support, the gap being of sufficient dimension to permit fluid to flow in the gap, the ratio of the thickness of the porous support to the height of the gap being in the range from about 0.1 to about 20; a catalyst supported by the porous support; and a heat source and/or heat sink in thermal contact with the heat transfer wall.

In one embodiment, the disclosed technology relates to an apparatus, comprising: at least one microchannel, the microchannel comprising at least one heat transfer wall; a porous thermally conductive support in the microchannel in contact with the heat transfer wall, the porous support having a tortuosity in the range from about 1 to about 10; at least about 20% of the pore volume of the porous support having an average pore size in the range from about 0.1 to about 700 microns; a gap positioned in the microchannel adjacent to the porous support, the gap being of sufficient dimension to permit fluid to flow in the gap, the ratio of the thickness of the porous support to the height of the gap being in the range from about 0.1 to about 20; a catalyst supported by the porous support; and a heat source and/or heat sink in thermal contact with the heat transfer wall.

In one embodiment, the disclosed technology relates to a process for conducting a chemical reaction in a microchannel reactor, the microchannel reactor comprising: at least one microchannel, the microchannel comprising at least one heat transfer wall; a porous thermally conductive support in the microchannel in contact with the heat transfer wall; a catalyst supported by the porous support; a heat source and/or heat sink in thermal contact with the heat transfer wall; the process comprising flowing a first reactant and a second reactant in the microchannel in contact with the catalyst to form a product, the heat flux intensity being in the range from about 100 to about 800,000 $W/m^2$-K.

In one embodiment, the disclosed technology relates to a process for conducting a chemical reaction in a microchannel reactor, the microchannel reactor comprising: at least one microchannel, the microchannel comprising at least one heat transfer wall; a porous thermally conductive support in the microchannel in contact with the heat transfer wall; a catalyst supported by the porous support; a heat source and/or heat sink in thermal contact with the heat transfer wall; the process comprising flowing a first reactant and a second reactant in the microchannel in contact with the catalyst to form a product, the mass flux intensity being in the range from about 1 to about 20 moles/$m^2$/sec.

In one embodiment, the disclosed technology relates to a process for conducting a chemical reaction in a microchannel reactor, the microchannel reactor comprising: at least one microchannel, the microchannel comprising at least one heat transfer wall; a porous thermally conductive support in the microchannel in contact with the heat transfer wall; a catalyst supported by the porous support; a heat source and/or heat sink in thermal contact with the heat transfer wall; the process comprising flowing a first reactant and a second reactant in the microchannel in contact with the catalyst to form a product, the contact time being in the range from about 0.4 to about 4 ms, the heat flux being in the range from about 10 to about 100 $W/cm^2$, and the pressure drop in the microchannel being less than about 15 atmospheres per meter.

In one embodiment, the disclosed technology relates to a process for conducting an equilibrium limited chemical reaction in a microchannel reactor, the microchannel reactor comprising: at least one microchannel, the microchannel comprising at least one heat transfer wall; a porous thermally conductive support in the microchannel in contact with the heat transfer wall; a catalyst supported by the porous support; a heat source and/or heat sink in thermal contact with the heat transfer wall; the process comprising flowing a first reactant and a second reactant in the microchannel in contact with the catalyst to form a product, the contact time being in the range from about 0.4 to about 4 ms, the heat flux being in the range from about 10 to about 100 $W/cm^2$, the pressure drop in the microchannel being less than about 15 atmospheres per meter, and the approach to equilibrium conversion being at least about 75%.

BRIEF DESCRIPTION OF THE DRAWINGS

In the annexed drawings, like parts and features have like designations. A number of the annexed drawings are schematic illustrations which are not necessarily proportioned accurately or drawn to scale.

FIG. 5(a) shows the catalyst on two interior walls of the process microchannel, which is the same as shown in FIG. 5. FIG. 5(b) shows an alternate embodiment wherein the catalyst is on one interior wall. FIG. 5(c) shows another alternate embodiment wherein the catalyst is on three interior walls. FIG. 5(d) shows another alternate embodiment wherein the catalyst is on four interior walls of the process microchannel.

FIG. 8 shows a plurality of the repeating units illustrated in FIG. 7 positioned side-by-side.

FIG. 9 is a schematic illustration of a staged addition repeating unit that may be used in the microchannel reactor shown in FIG. 2. This repeating unit comprises a process microchannel, an apertured section, a second reactant stream channel, and a heat exchange channel. The process microchannel contains a porous catalyst. The catalyst is positioned in a reaction zone within the process microchannel. The process microchannel has a mixing zone upstream of the reaction zone.

FIG. 10 is a schematic illustration of an alternate embodiment of a staged addition repeating unit that may be used in the microchannel reactor shown in FIG. 2. This repeating unit comprises a process microchannel, an apertured section, a second reactant stream channel, and a heat exchange channel. The process microchannel contains a porous catalyst. The catalyst is positioned in a reaction zone within the process microchannel.

FIG. 11 is a schematic illustration of another alternate embodiment of a staged addition repeating unit that may be used in the microchannel reactor shown in FIG. 2. This repeating unit comprises a process microchannel, an apertured section, a second reactant stream channel, and heat exchange channel. The process microchannel contains a porous catalyst. The catalyst is positioned in a reaction zone within the process microchannel. The process microchannel has a mixing zone upstream of the reaction zone.

3. The surface features are in the form of spherical depressions in opposite interior walls of the microchannel.

Figure 2:
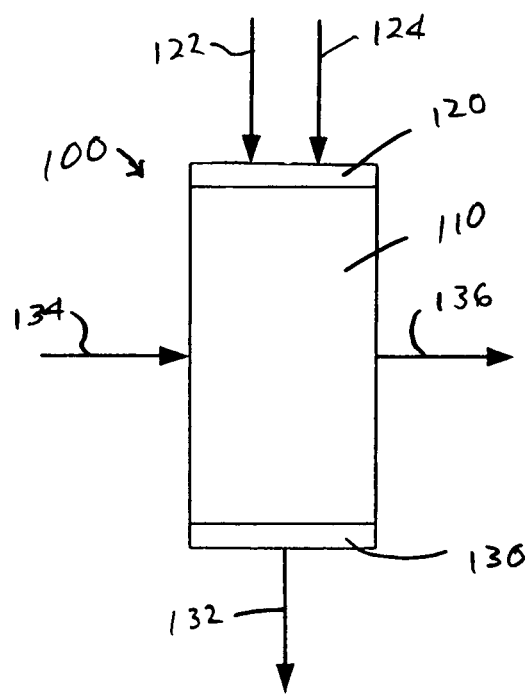
FIG. 2 is a schematic illustration of a microchannel reactor that may be used with a porous catalyst to conduct a chemical reaction. The microchannel reactor may comprise a microchannel reactor core, a reactant header and a product footer. The microchannel reactor may also provide for heat exchange within the microchannel reactor core.
Figure 3:
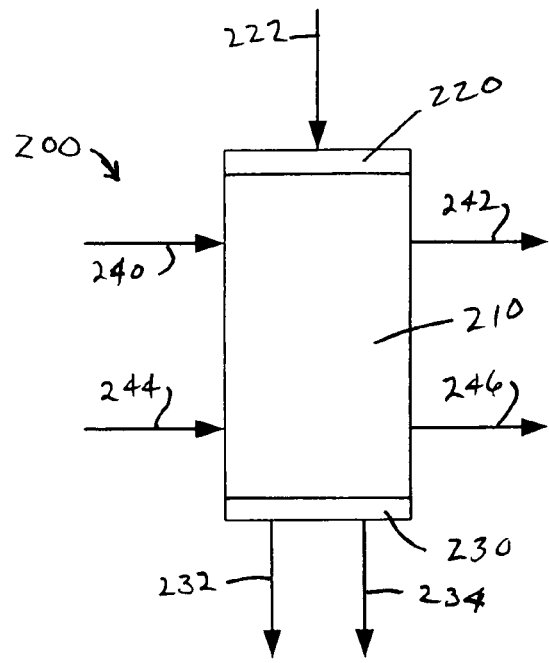
FIG. 3 is a schematic illustration of a microchannel separator that may be used with a porous sorption medium to conduct a separation process. The microchannel separator may comprise a microchannel separator core, a fluid inlet header and a fluid outlet footer. The microchannel separator may also provide for heat exchange within the microchannel separator core.
Figure 24:
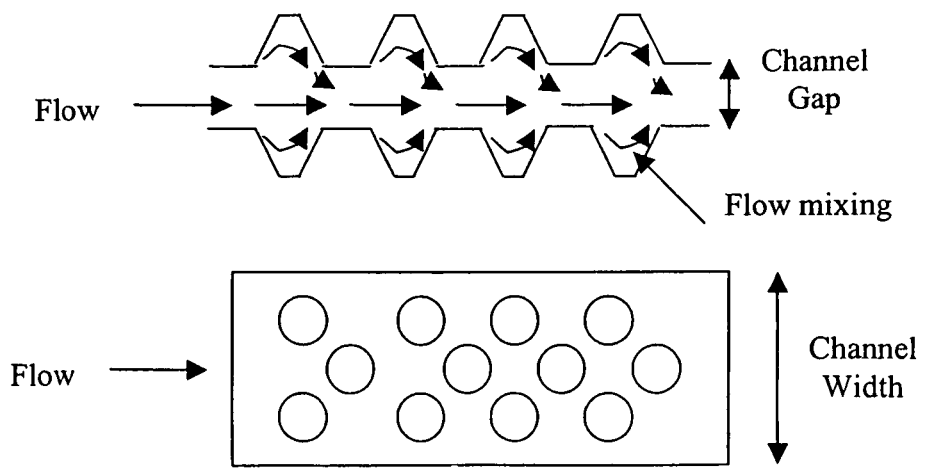

FIG. 24 is a schematic illustration of surface features which may be used in microchannels that may be used in the microchannel reactor illustrated in FIG. 2 or microchannel separator illustrated in FIG. 3. The surface features are in the form of frustum depressions in opposite interior walls of the microchannel.

Figure 25:
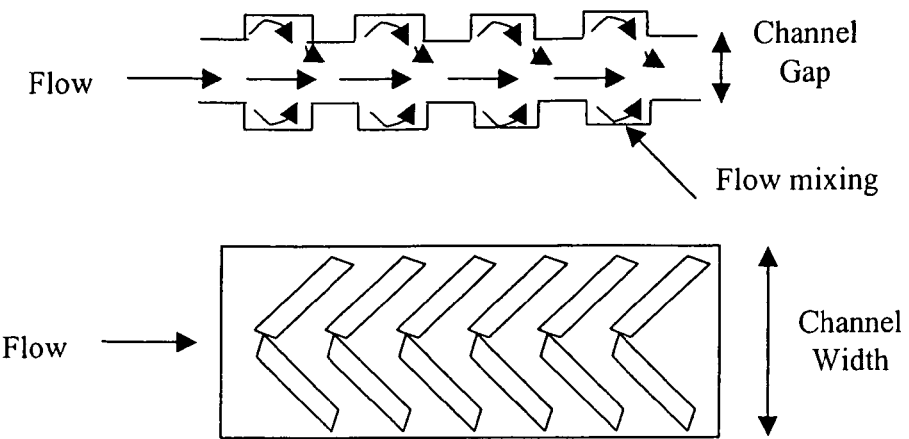

FIG. 25 is a schematic illustration of surface features which may be used in microchannels (e.g., process microchannels, second reactant stream microchannels, heat exchange microchannels) that may be used in the microchannel reactor illustrated in FIG. 2 or microchannel separator illustrated in FIG. 3. The surface features are in the form of angled rectangular depressions in opposite interior walls of the microchannel.

Figure 26:
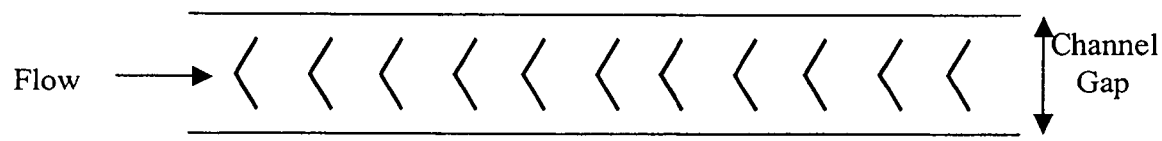

FIG. 26 is a schematic illustration of vanes that may be used as surface features in microchannels (e.g., process microchannels, second reactant stream microchannels, heat exchange microchannels) which may be used in the microchannel reactor illustrated in FIG. 2 or microchannel separator illustrated in FIG. 3.

Figure 27:
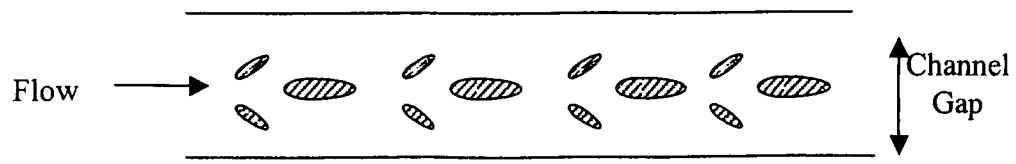

FIG. 27 is a schematic illustration of surface features in the form of air-foils that may be used in the microchannels (e.g., process microchannels, second reactant stream microchannels, heat exchange microchannels) which may be used in the microchannel reactor illustrated in FIG. 2 or microchannel separator illustrated in FIG. 3.

Figure 28:
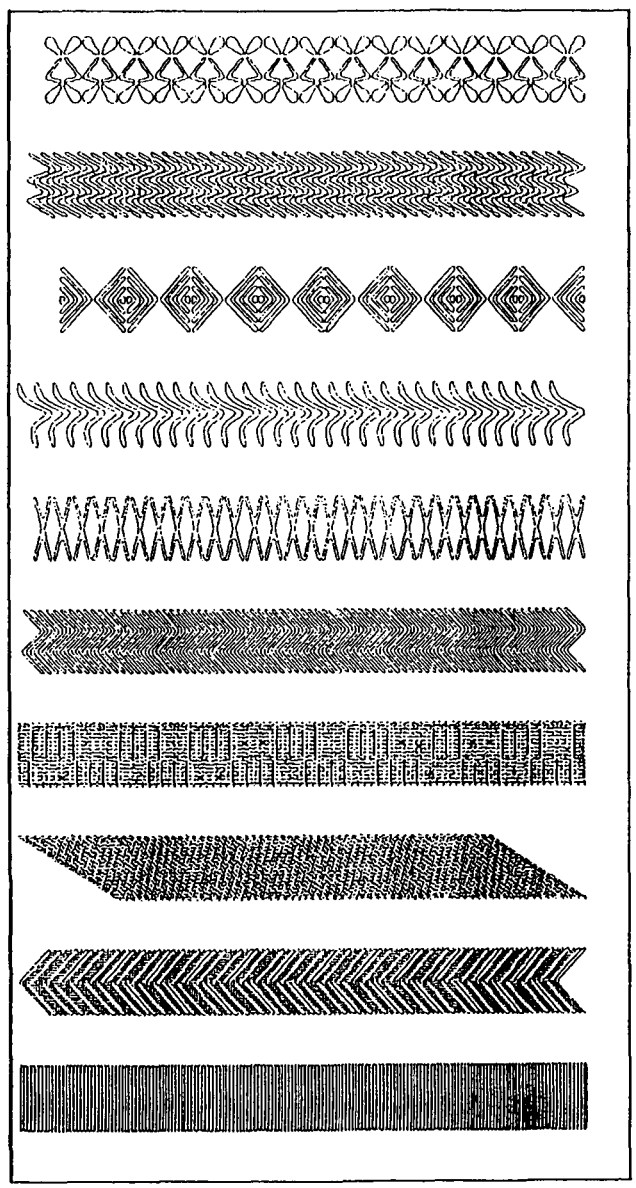

FIG. 28 is a schematic illustration of various surface feature designs that may be used in the microchannels (e.g., process microchannels, second reactant stream microchannels, heat exchange microchannels) used in the microchannel reactor illustrated in FIG. 2 or microchannel separator illustrated in FIG. 3.

Figure 29:
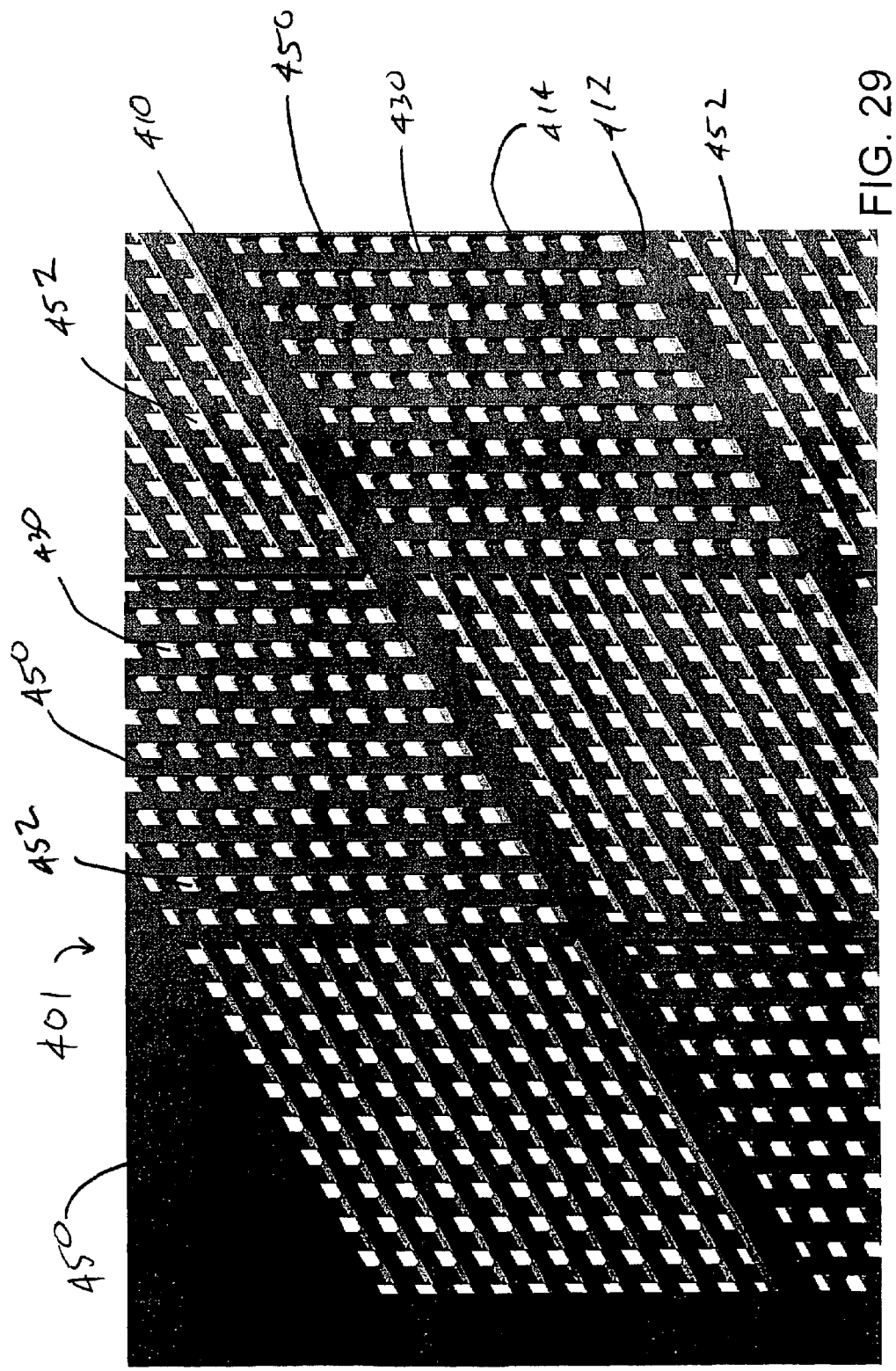

FIG. 29 is a schematic illustration of a porous support in the form of a support strip with a front or first surface and a back or second surface, and a plurality of microgrooves formed in each surface. The microgrooves formed in the front surface are parallel to each other and are positioned in an array of block patterns wherein in a first block pattern the microgrooves are aligned in a first or horizontal direction and then in a next adjacent second block pattern the microgrooves are aligned in a second or vertical direction. The array of block patterns comprises a plurality of block patterns arranged in successive rows positioned one above another, the successive rows forming a plurality of columns positioned side by side one another. The microgrooves formed in the back surface are also parallel to each other and are positioned in an array of block patterns similar to the block patterns in the front surface with the exception that where the front surface has microgrooves that are aligned in a first or horizontal direction the back surface has microgrooves that are aligned in a second or vertical direction. Similarly, where the first surface has microgrooves that are aligned in a second or vertical direction the back surface has microgrooves that are aligned in a first or horizontal direction. The microgrooves in the front surface and the microgrooves in the back surface partially penetrate the support strip. The penetration of the microgrooves in the front and back surface is sufficient for the microgrooves in the front surface to intersect the microgrooves in the back surface with the result being the formation of an array of openings in the support strip in the regions where the front and back microgrooves intersect. The resulting openings are of sufficient size to permit a fluid to flow or diffuse through the openings.

Figure 30:
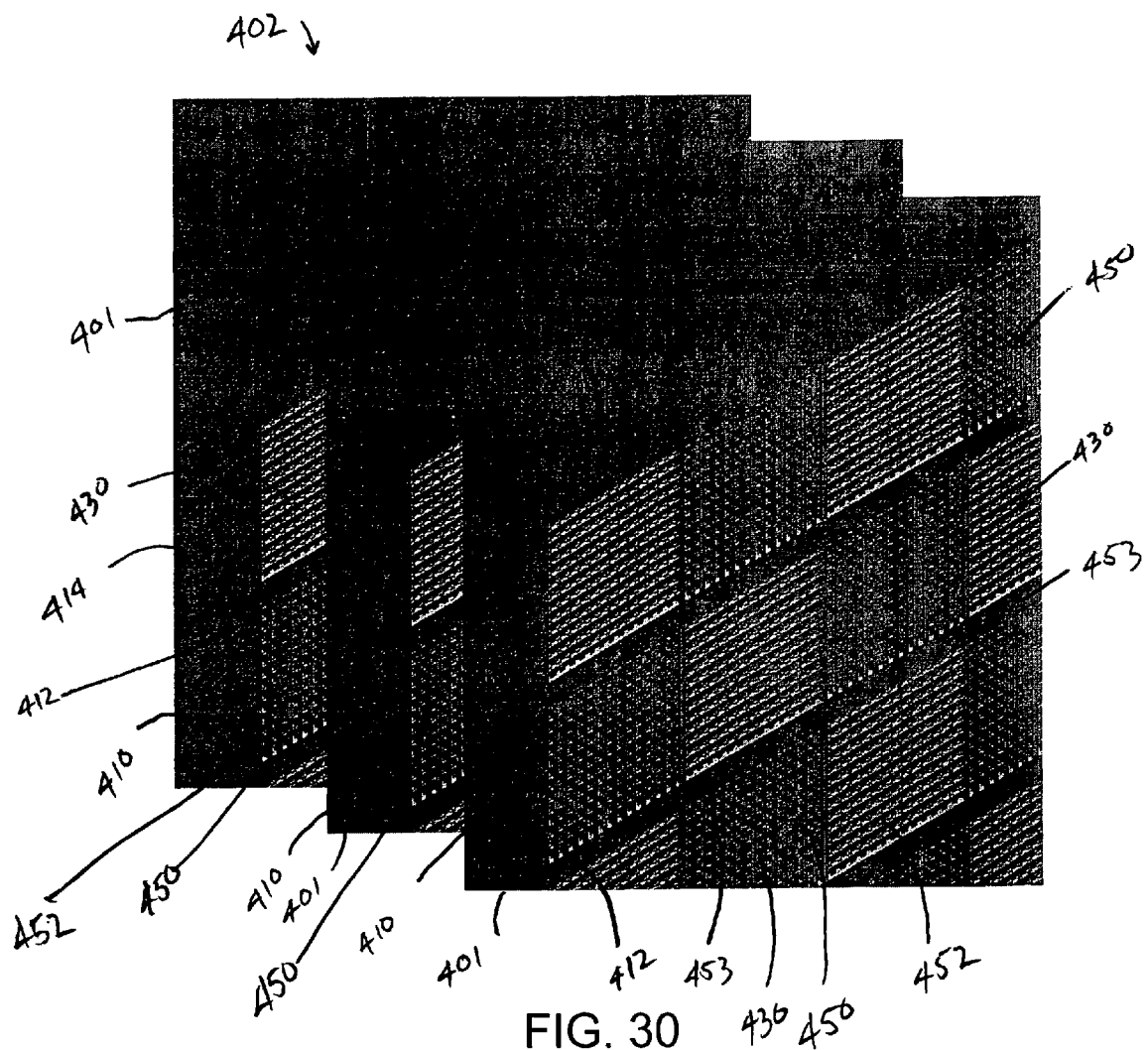

FIG. 30 is a schematic illustration of a composite porous support structure comprising a plurality of the porous supports illustrated in FIG. 29 positioned side by side.

FIG. 31 is a schematic illustration of a porous support comprising a support strip with a plurality of microgrooves formed in one of its surfaces. The front edge, back edge and side edges of the support strip are sufficiently open to permit fluid to flow through the front, back and side edges.

FIG. 32 is a schematic illustration of a porous support comprising a support strip with a plurality of microgrooves formed in one of its surfaces. This support is similar to the support illustrated in FIG. 31 with the exception that the front edge and the back edge of the microgrooved support strip illustrated in FIG. 32 are closed and thus do not permit fluid to flow through the front and back edges.

FIG. 33 is a schematic illustration of a porous support comprising a support strip with a plurality of microgrooves formed in one of its surfaces. This support is similar to the support illustrated in FIG. 32 with the exception that the side edges of the microgrooved support strip illustrated in FIG. 33 are closed and thus do not permit fluid to flow through the side edges. The microgrooves may penetrate part way or all the way through the support strip. Penetration of the microgrooves all the way through the support strip may permit fluid to flow through the microgrooves in the direction from the top surface to the bottom surface, or vice versa.

FIG. 34 is a schematic illustration of a porous support comprising a plurality of support strips with a plurality of microgrooves formed in one of the surfaces of each support strip. The support strips are positioned side by side one another forming a composite support structure, the front and back edges of each of the microgrooved support strips being open sufficiently to permit fluid to flow through such edges. The microgrooves in each of the support strips project through the support strips sufficiently to permit fluid to flow through the support strips from one support strip to another.

FIG. 35 is a schematic illustration of an exploded view of the porous support illustrated in FIG. 34. The porous support illustrated in FIG. 35 comprises four (4) first microgrooved support strips and four (4) second microgrooved support strips positioned side by side in alternating sequence. The microgrooves in each of the support strips project through the support strips sufficiently to permit fluid to flow through the support strips from one support strip to another. The first microgrooved support strips employ microgrooves that form angles with the center axis of the support strips that are oriented toward the front edges and first side edges of the support strips and are more than about 0° and less than 90°, for example, in the range from about 60° to about 80°. The second microgrooved support strips employ microgrooves that form angles with the center axis of the support strips that are oriented toward the front edges and first side edges of the support strips and are more than 90° and less than about 180°, for example, in the range from about 100° to about 120°.

FIG. 36 is a cross-sectional view of a process microchannel containing the porous support illustrated in FIG. 34. The porous support illustrated in FIG. 36 is a flow-through support.

Figure 37:

FIG. 37 is a photograph of a porous support comprising a microgrooved support strip made of an alloy of iron, chromium, aluminum and yttrium, the thickness of the support structure being 0.002 inch (50.8 microns), the ribs dividing the microgrooves having a thickness of 0.007 inch (178 microns), and the microgrooves having a width of 0.007 inch (178 microns).

Figure 38:
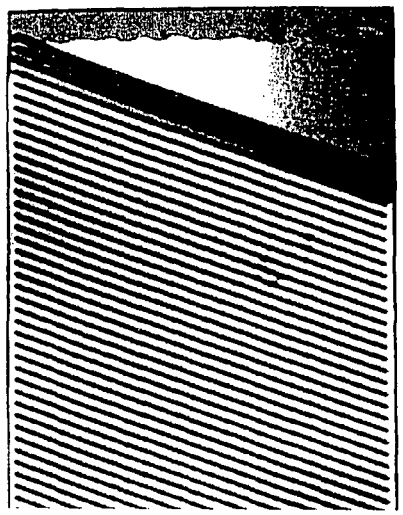

FIG. 38 is a photograph of a porous support comprising a microgrooved support strip similar to the support strip illustrated in FIG. 37 with the exception that the microgrooved support strip illustrated in FIG. 38 is made of stainless steel.

Figure 39:
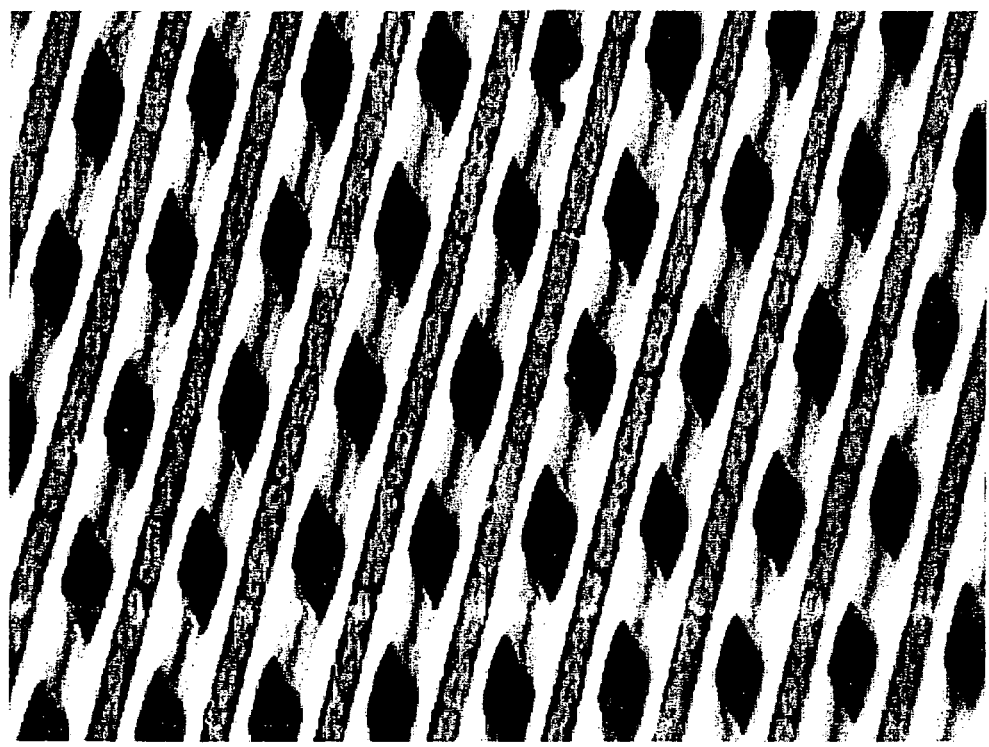

FIG. 39 is a microphotograph enlarged 50× showing a porous support comprising a microgrooved support strip with catalyst particles deposited in the microgrooves of the microgrooved support strip, the microgrooved support strip being made of stainless steel 304, the catalyst comprising 0.7% $K_2O$-15% $MoO_3/SiO_2$—$TiO_2$.

Figure 40:
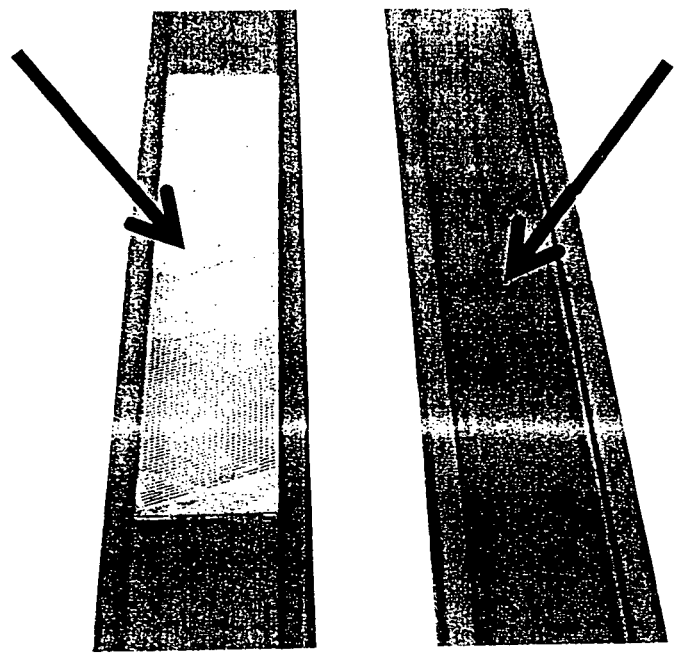

FIG. 40 is a photograph of a process microchannel containing two porous supports of the type shown in FIG. 33. The process microchannel has a length of 2.5 inches (6.35 cm), a width of 0.5 inch (12.7 mm), and a height of 0.002 inch (50.8 microns). A top plate for the process microchannel is shown on the right side of FIG. 40.

Figure 43:
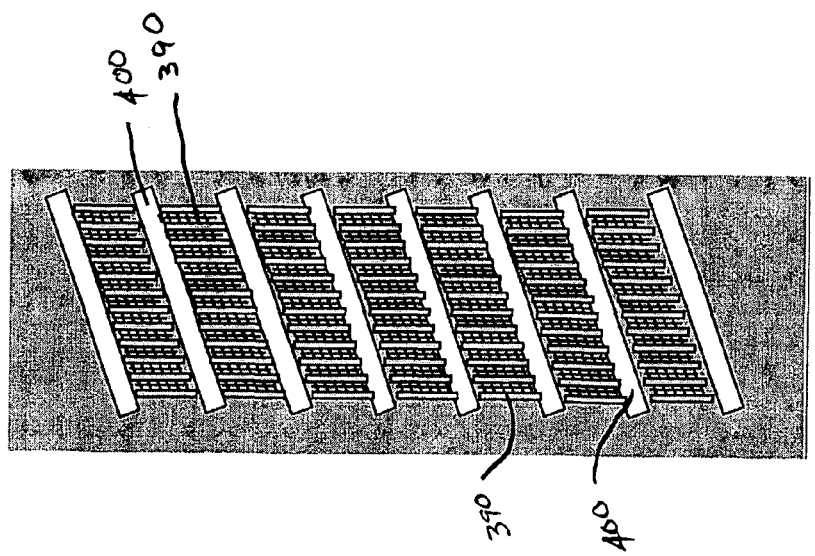
Figure 42:
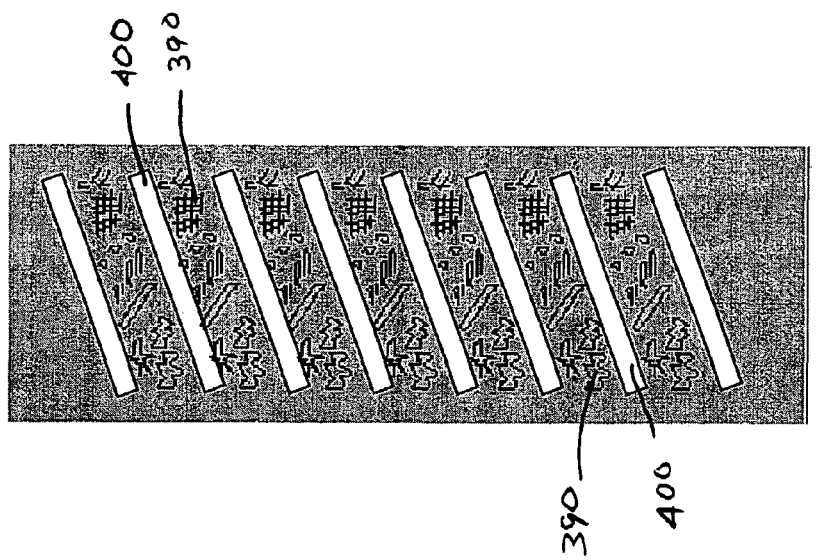
Figure 41:
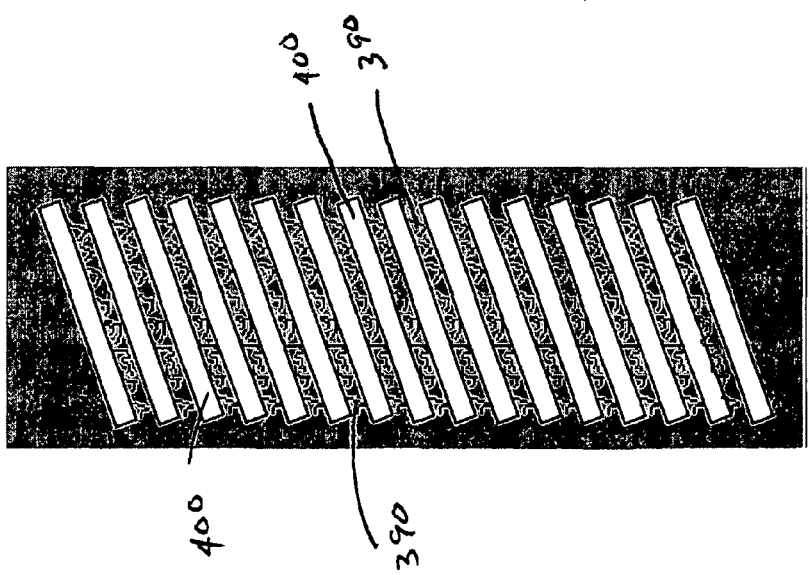

FIGS. 41-43 are schematic illustrations of microchannel walls with microgrooved support strips positioned on the walls in combination with surface features positioned in or projecting from the walls.

Figure 44:
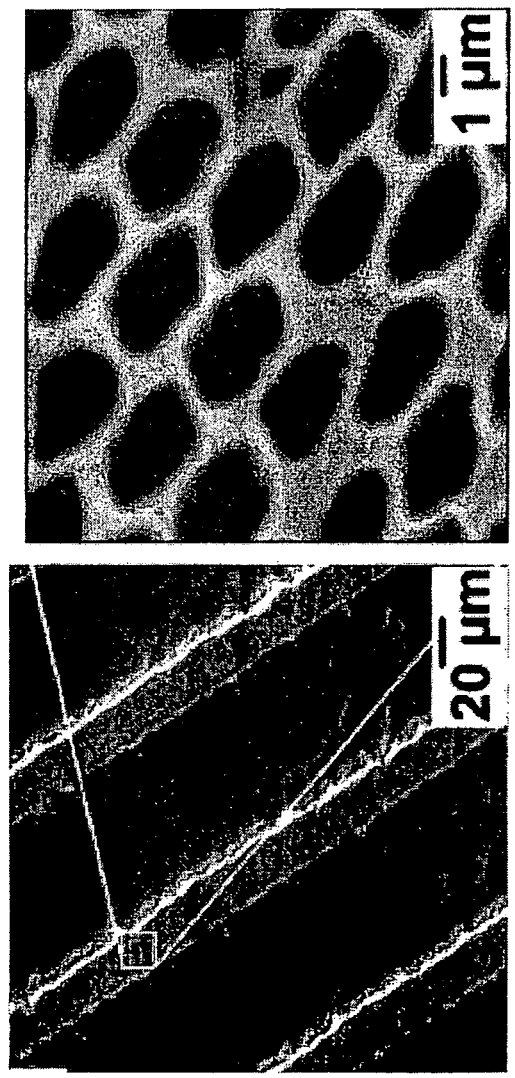

FIG. 44 is an SEM micrograph of a porous support comprising a macroporous SiCN catalyst support in the form of a three-dimensional interconnected pore structure containing pores with diameters of about 1 micron formed by pyrolysis.

Figure 45:
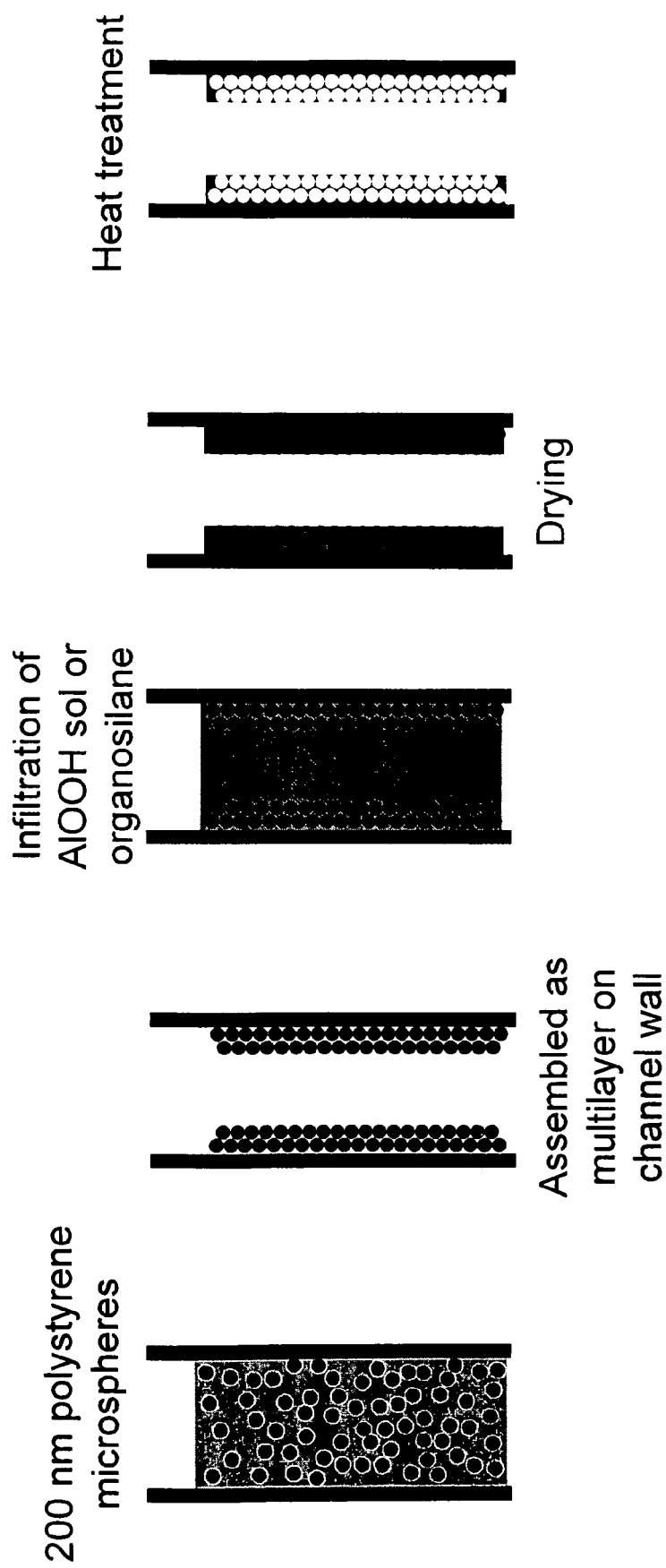

FIG. 45 is a schematic illustration showing a two-step process for making a macroporous alumina or silicon carbide layer which may be used as a porous support.

Figure 46:
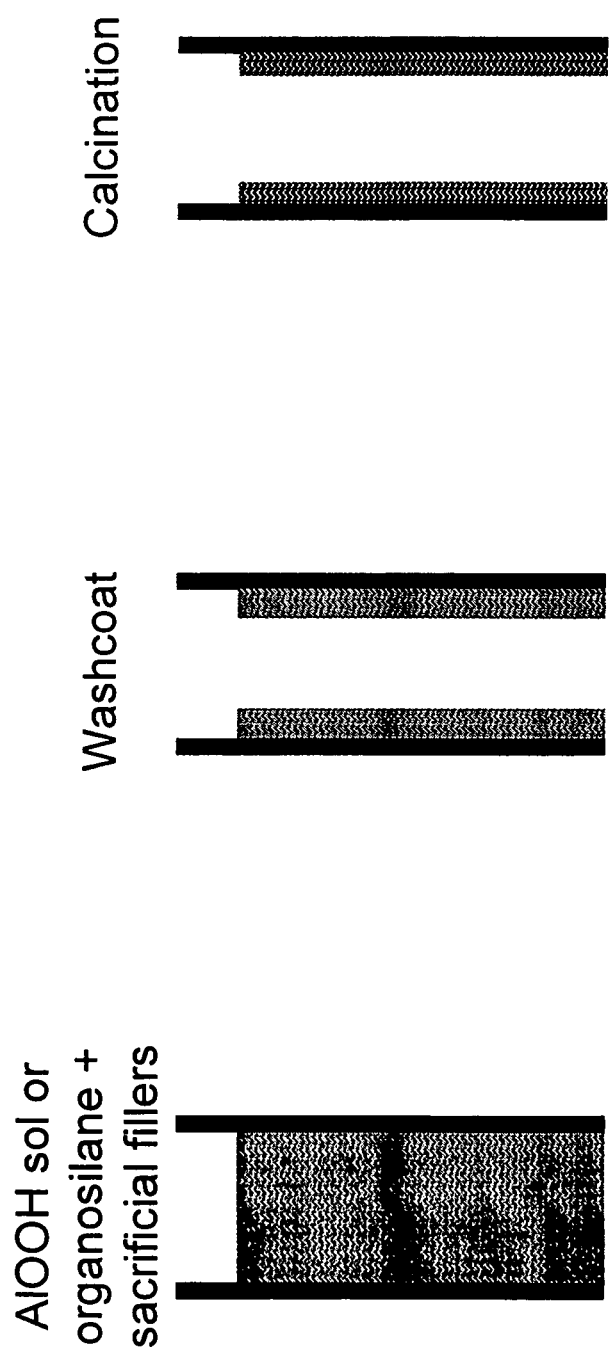

FIG. 46 is a schematic illustration showing a one-step process for making a macroporous alumina or silicon carbide layer which may be used as a porous support.

Figure 47:
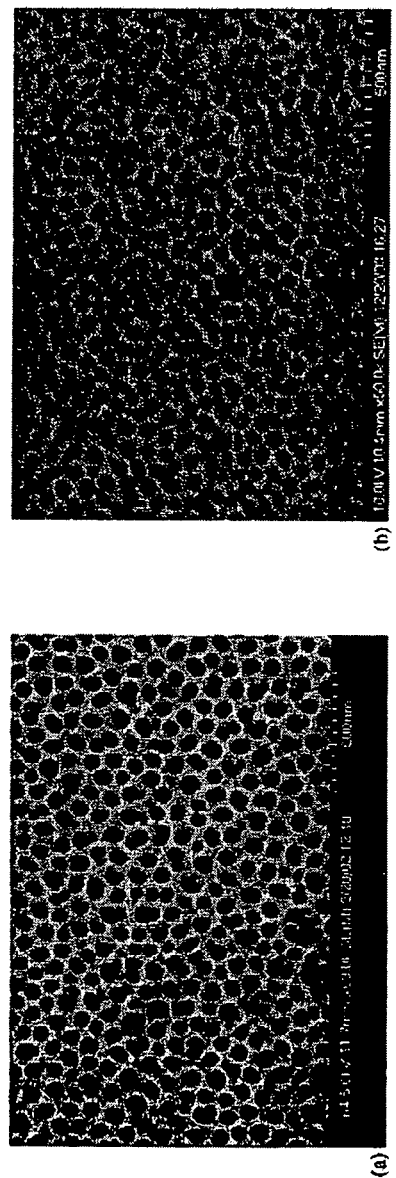

FIG. 47 shows SEM micrographs of alumina nanotubes formed using anodization. The nanotubes may be used to form a porous support. The micrograph on the left labeled (a) shows the surface morphology of the anodized surface as synthesized. The micrograph on the right labeled (b) shows the surface morphology of the anodized surface after being hydrothermally treated. The surface area before hydrothermal treatment is about 150 $m^2/g$ while the surface area after hydrothermal treatment is about 1500 $m^2/g$.

Figure 48:
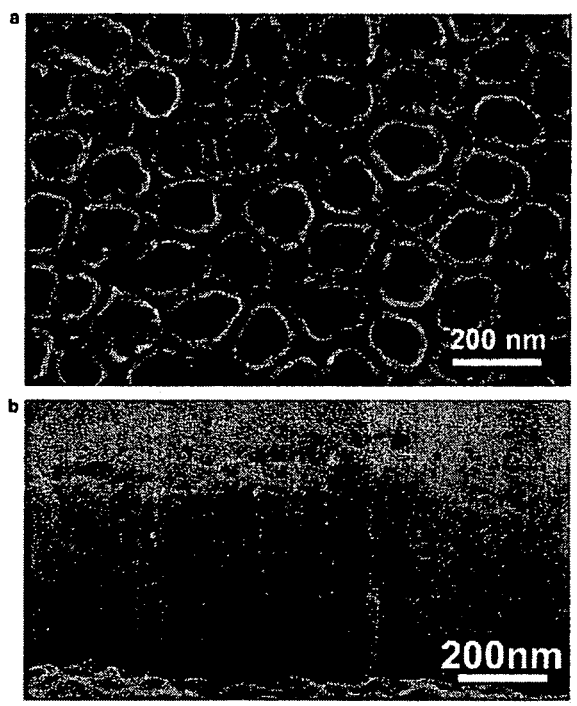

FIG. 48 shows SEM micrographs of an annealed $TiO_2$ layer which may be used as a porous support. The $TiO_2$ layer comprises $TiO_2$ nanotubes. The image on top labeled "a" is a top view of the nanotube layer. The image on the bottom labeled "b" is a cross-sectional view of the nanotube layer. The abbreviation "nm" is for nanometer.

Figure 49:
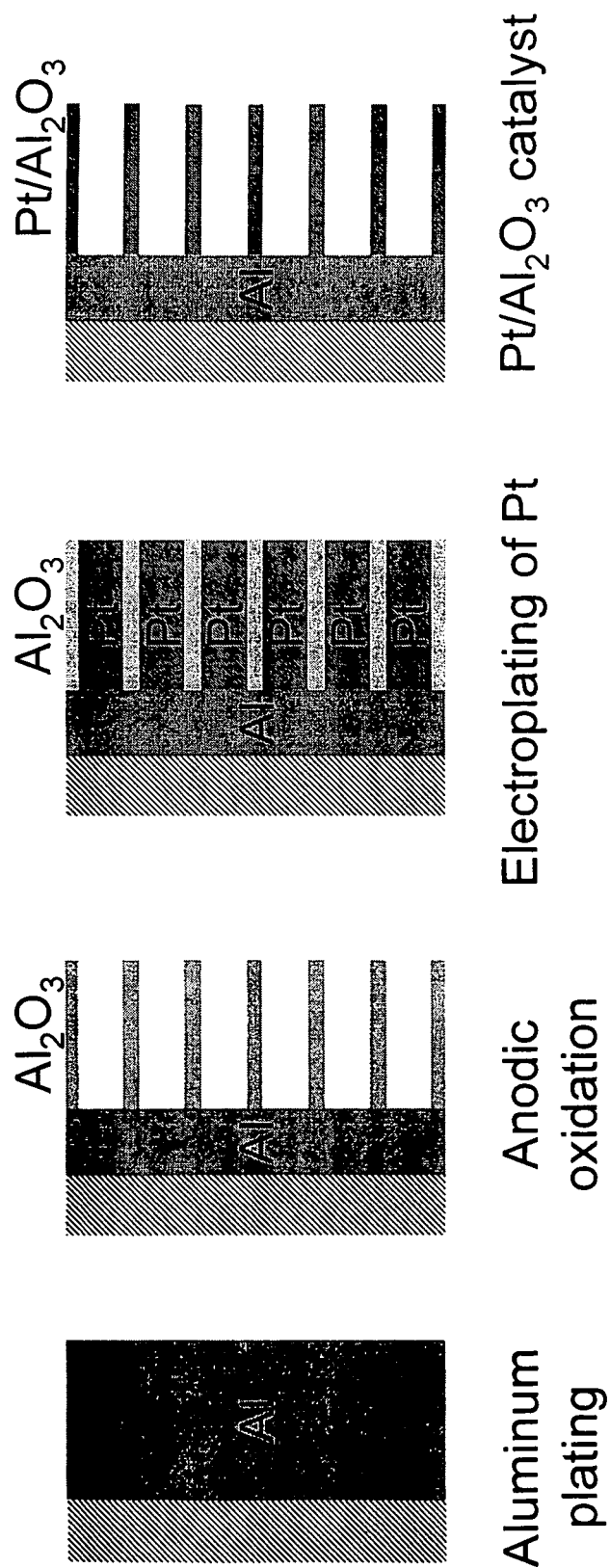

FIG. 49 is a schematic illustration showing a process for making platinum/alumina nanofibers which may be used as a porous catalyst.

Figure 50:
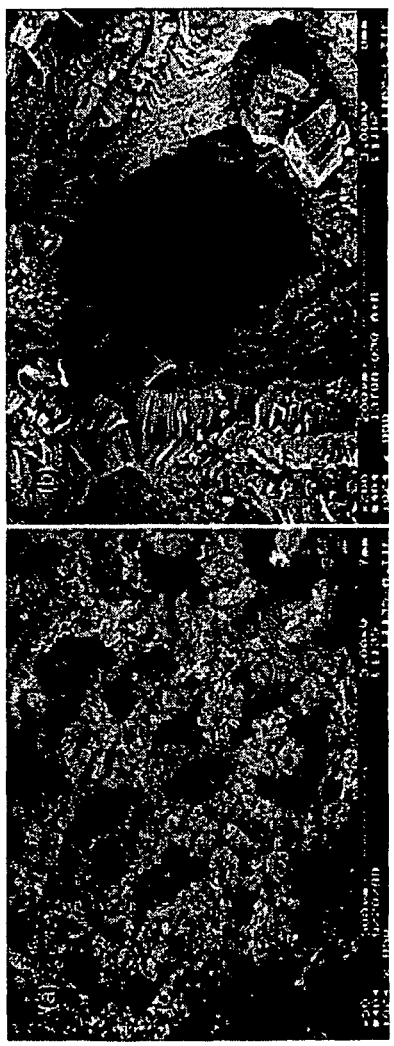

FIG. 50 shows SEM micrographs of carbon nanotubes grown on FeCrAlY foam structures. The nanotubes may be used to form a porous support. The micrograph on the left is at a magnification of 50×. The micrograph on the right is at a magnification of 200×.

Figure 51:

FIG. 51 shows SEM micrographs of carbon nanotubes grown on FeCrAlY foam structures with alumina coatings. The micrograph labeled (a) is at a magnification of 50×. The micrograph labeled (b) is at a magnification of 1000×. The micrograph labeled (c) is at a magnification of 10000×.

Figure 52:
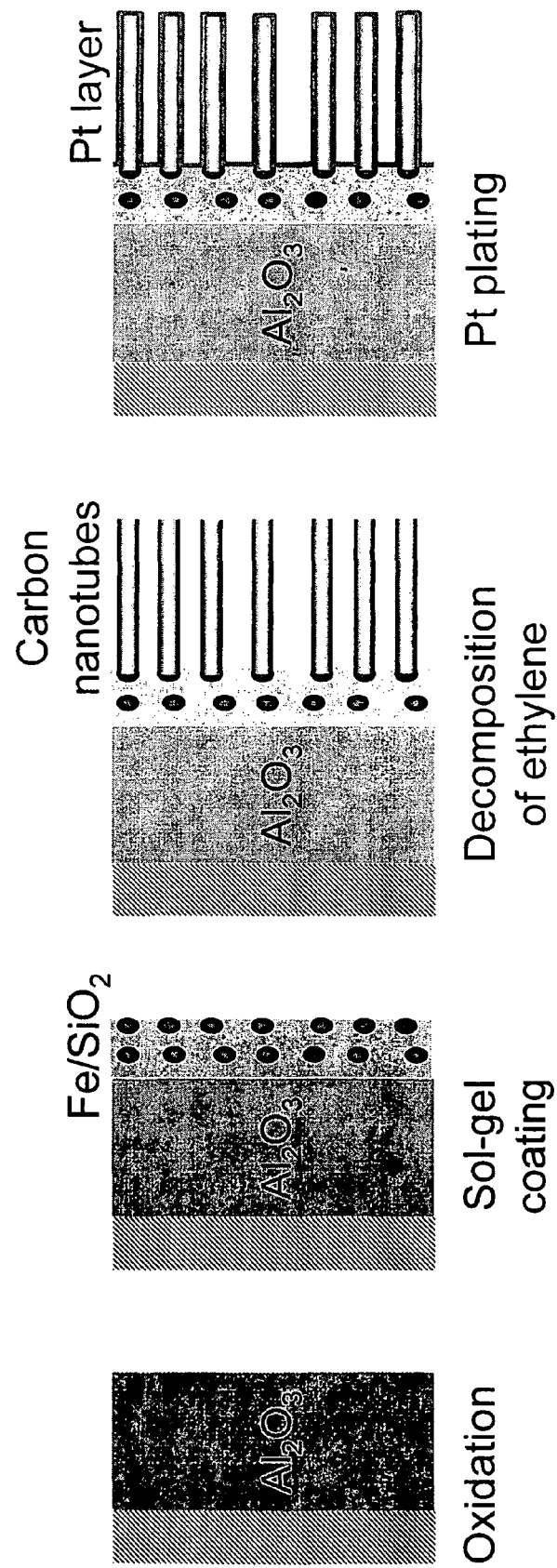

FIG. 52 is a schematic illustration showing a process for making carbon nanotubes coated with platinum. These coated nanotubes may be used as a porous catalyst.

Figure 53:
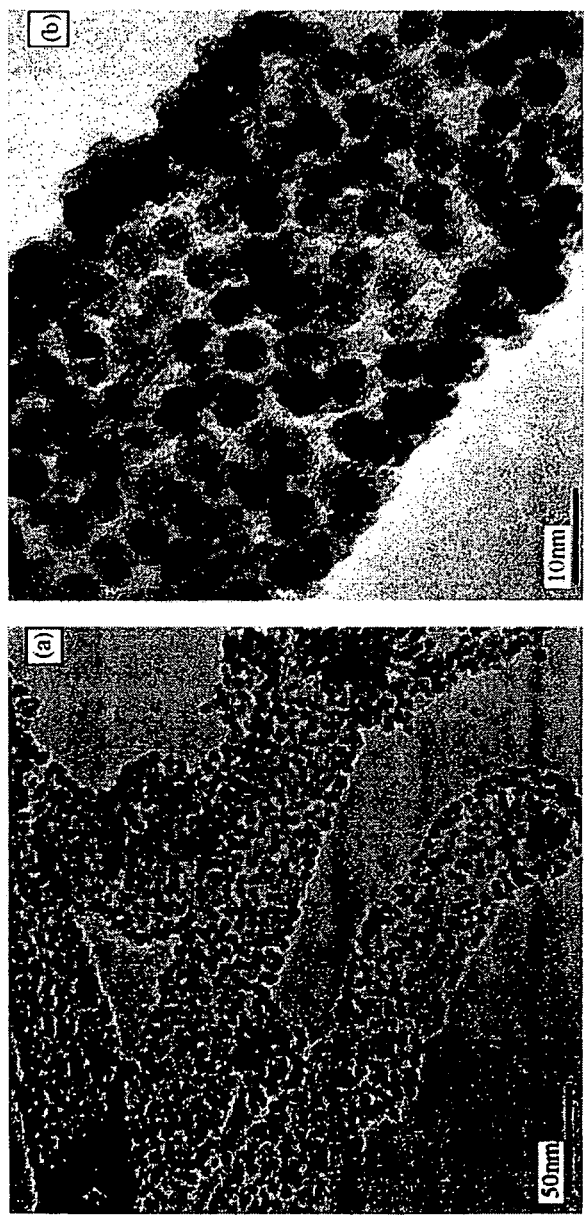

FIG. 53 shows high-resolution transmission electron microscopic (HRTEM) images of gold particles dispersed on the surface of carbon nanotubes prepared using electroless plating. The image on the left labeled (a) is at a low magnification. The image on the right labeled (b) is at a high magnification. The structures disclosed in FIG. 53 may be used as porous catalysts.

Figure 54:
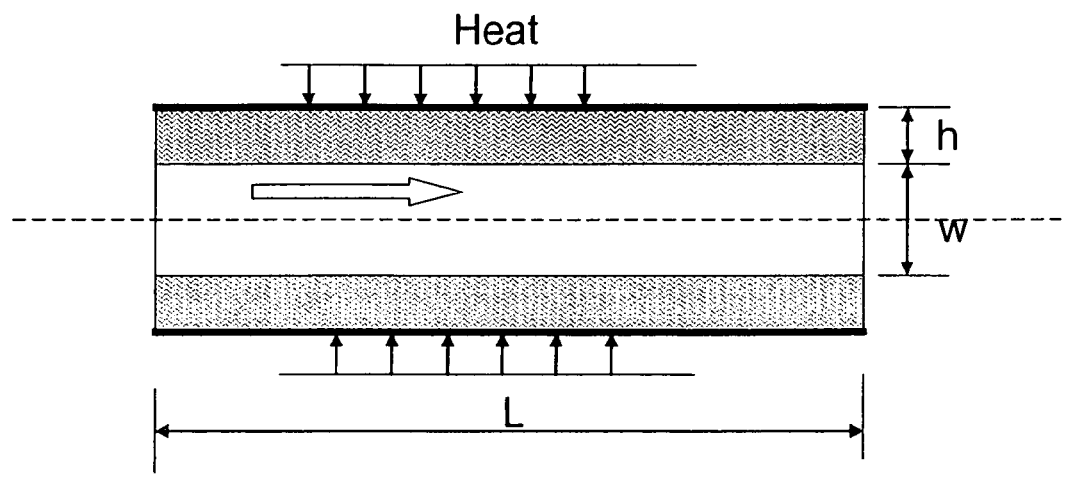

FIG. 54 is a schematic illustration of the microchannel reactor used in the Computational Fluid Dynamics (CFD) modeling simulation disclosed in Example 1.

Figure 55:
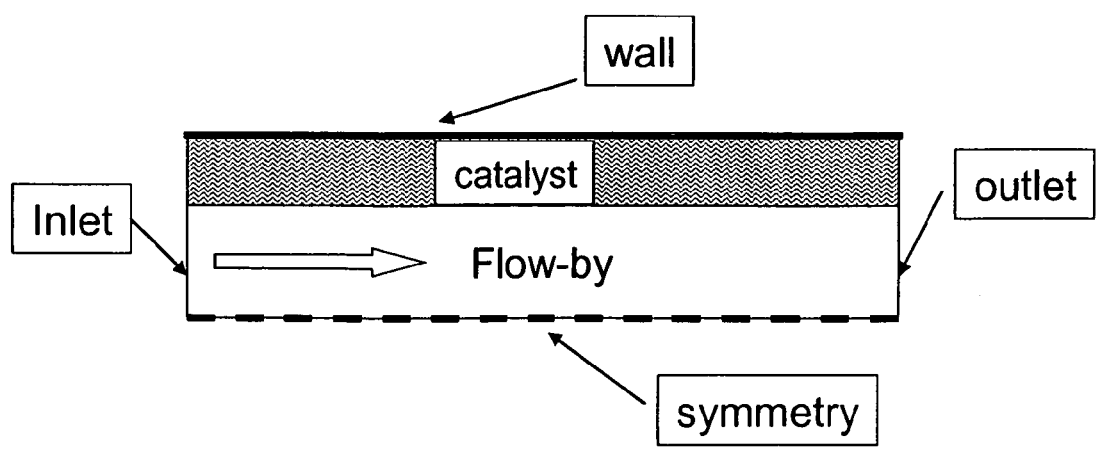

FIG. 55 is a schematic illustration of the model domain used in the CFD simulation disclosed in Example 1.

Figure 56:
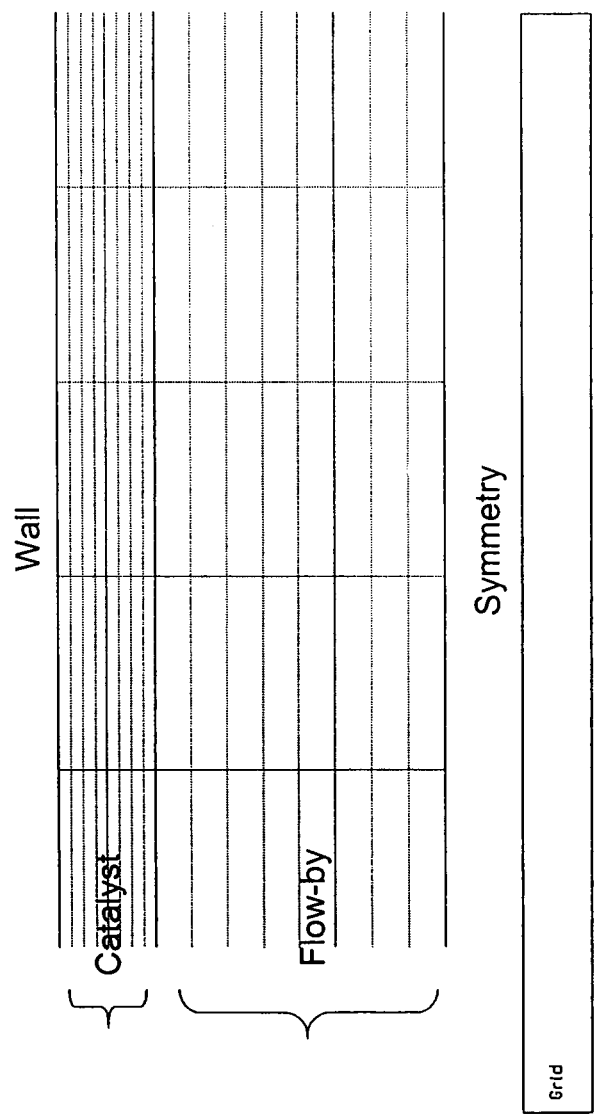

FIG. 56 is a schematic illustration of the mesh used in the CFD simulation disclosed in Example 1.

Figure 57:
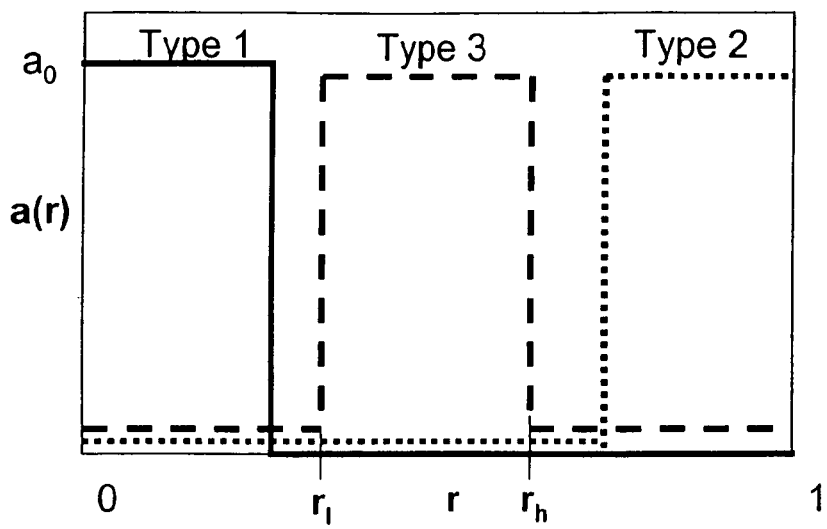

FIG. 57 is a schematic illustration showing hypothetical catalyst activity distribution in the transverse direction for the CFD simulation disclosed in Example 1. r is the normalized distance into the structure from the interface with the flow-by channel. r=0: interface with the flow-by channel. r=1: channel wall.

Figure 58:
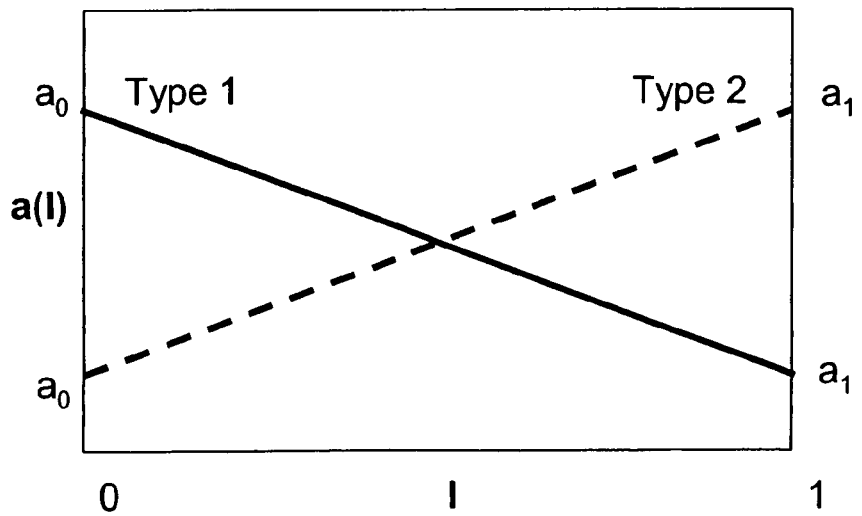

FIG. 58 shows catalyst activity distribution in the axial direction (along the reaction chamber length) for the CFD simulation disclosed in Example 1. l is the axial location normalized by the reactor total length. l=0: the beginning of the reactor. l=1: the end of the reactor.

Figure 59:
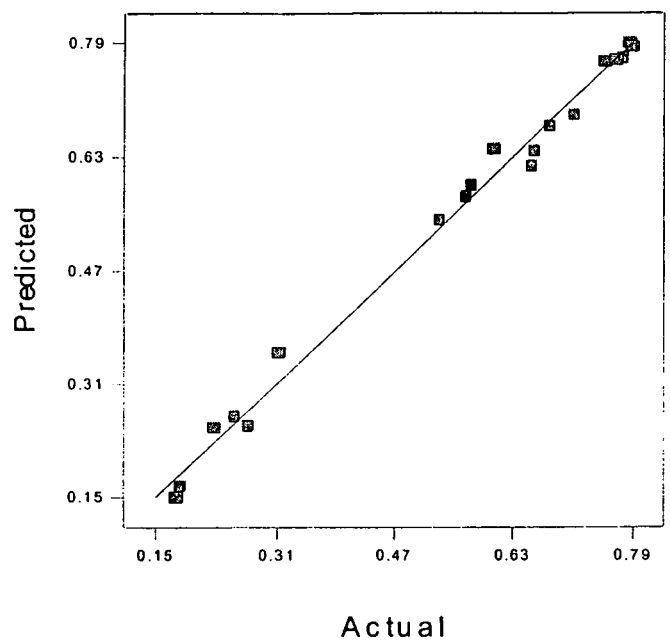

FIG. 59 is a parity plot of SMR reaction methane conversion predicted via quadratic curve-fit of CFD predictions versus actual CFD predictions for the conditions of Set 1 in Table 1. SMR refers to methane steam reforming.

Figure 60:
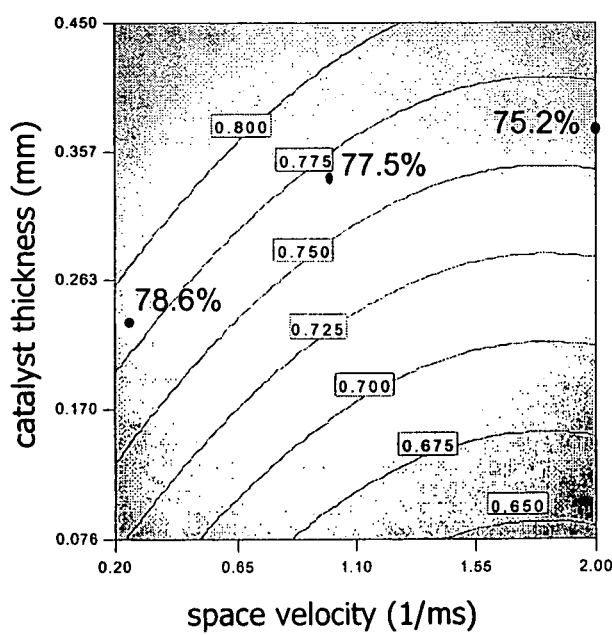

FIG. 60 is a plot showing predicted SMR reaction methane fractional conversion for the conditions of Set 1 in Table 1, with a constant thermal conductivity of 1.85 W/m-K, and a flow-by gap of 0.05 mm.

Figure 61:
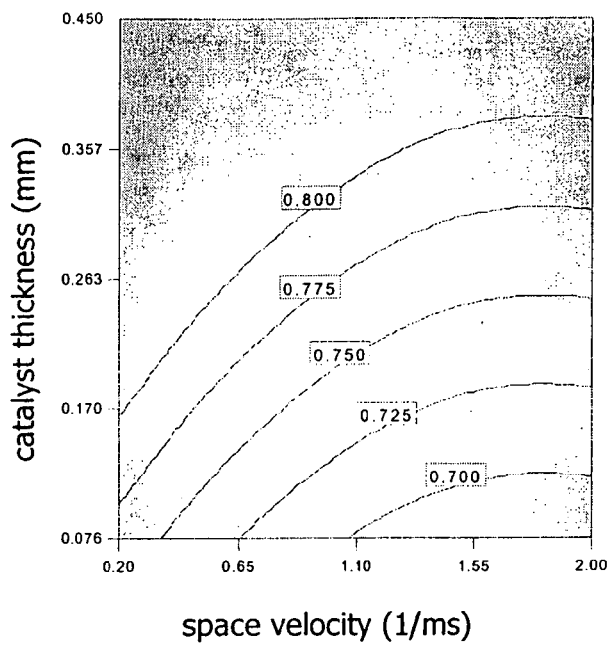

FIG. 61 is a plot showing predicted SMR reaction methane fractional conversion for the conditions of Set 1 in Table 1, with a constant thermal conductivity of 3 W/m-K, and a flow-by gap of 0.05 mm.

Figure 62:
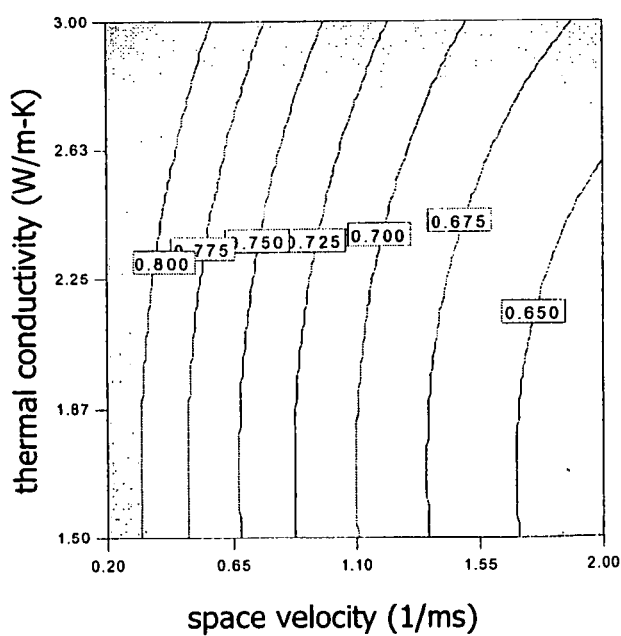

FIG. 62 is a plot showing predicted SMR reaction methane fractional conversion for the conditions of Set 1 in Table 1, with a constant catalyst thickness of 0.374 mm, and a flow-by gap of 0.2 mm.

Figure 63:
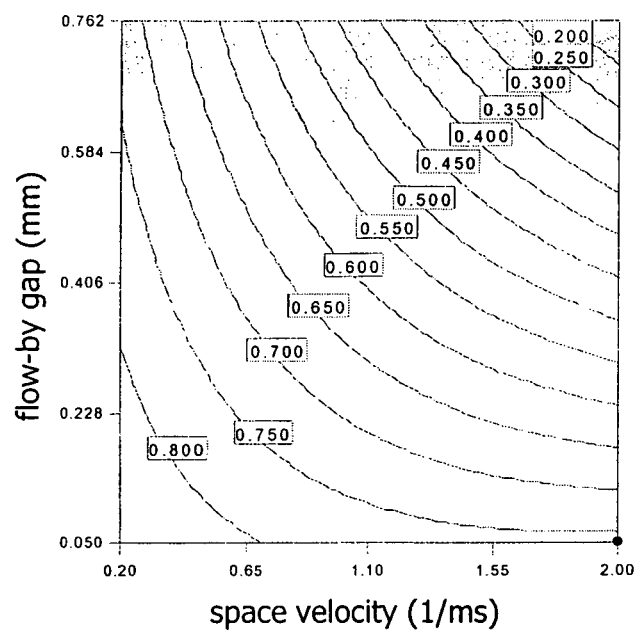

FIG. 63 is a plot showing predicted SMR reaction methane fractional conversion for the conditions of Set 1 in Table 1, with a constant thermal conductivity of 1.85 W/m-K, and a catalyst thickness of 0.374 mm.

Figure 64:
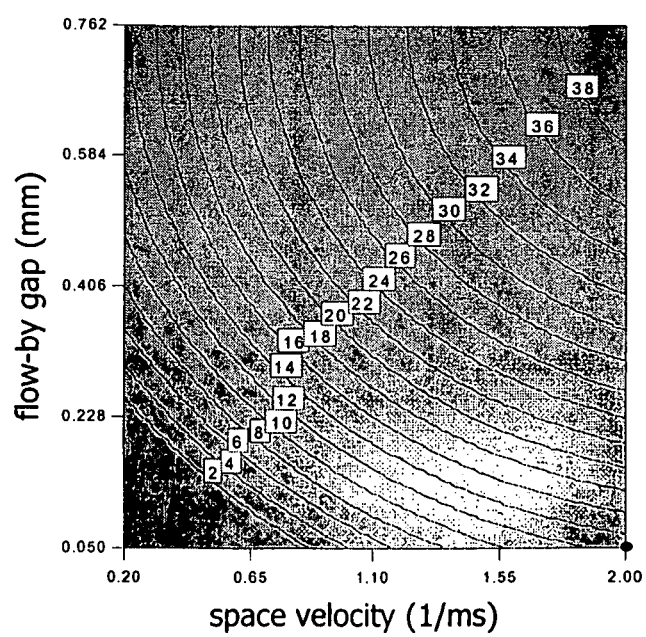

FIG. 64 is a plot showing predicted heat flux in $W/cm^2$ consumed by the endothermic methane reforming reaction for the conditions of Set 1 in Table 1, with a constant thermal conductivity of 1.85 W/m-K, and a catalyst thickness of 0.374 mm.

Figure 65:
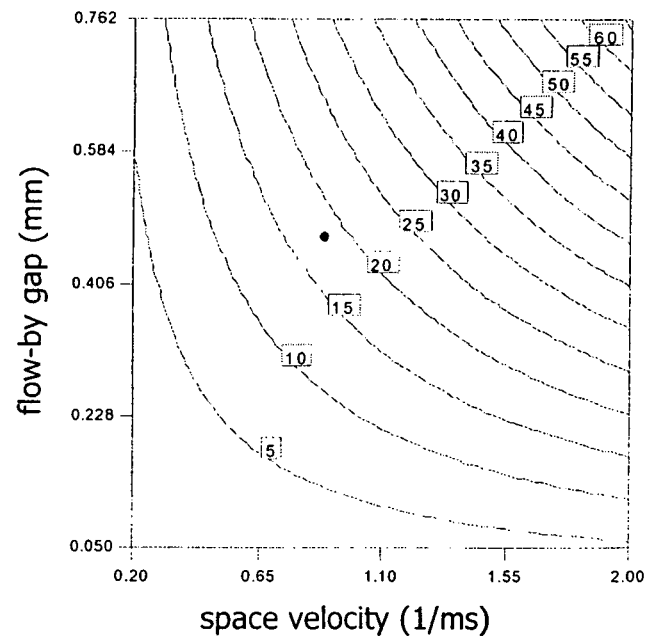

FIG. 65 is a plot showing SMR reaction inlet flow per channel in standard liters per minute (based on a 3:1 methane to steam molar ratio) for the conditions of Set 1 in Table 1, with a constant thermal conductivity of 1.85 W/m-K, and a catalyst thickness of 0.374 mm.

Figure 66:
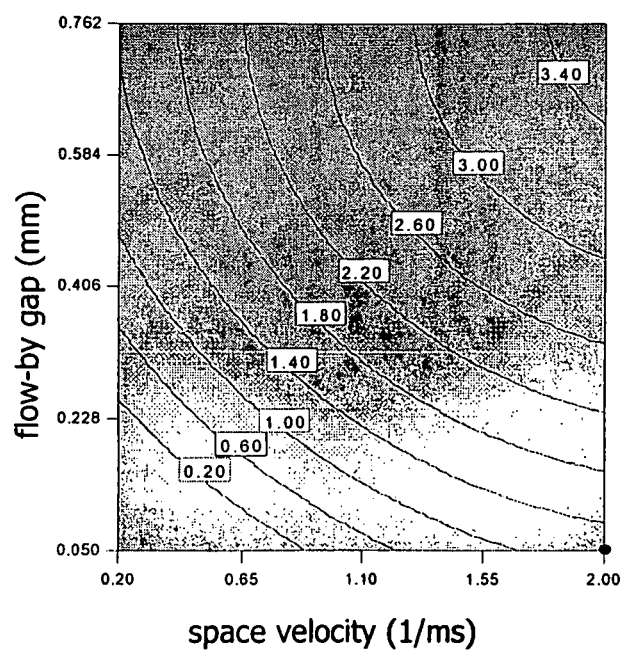

FIG. 66 is a plot showing predicted SMR reaction productivity in standard liters per minute of methane converted for the conditions of Set 1 in Table 1, with a constant thermal conductivity of 1.85 W/m-K, and a catalyst thickness of 0.374 mm.

Figure 67:
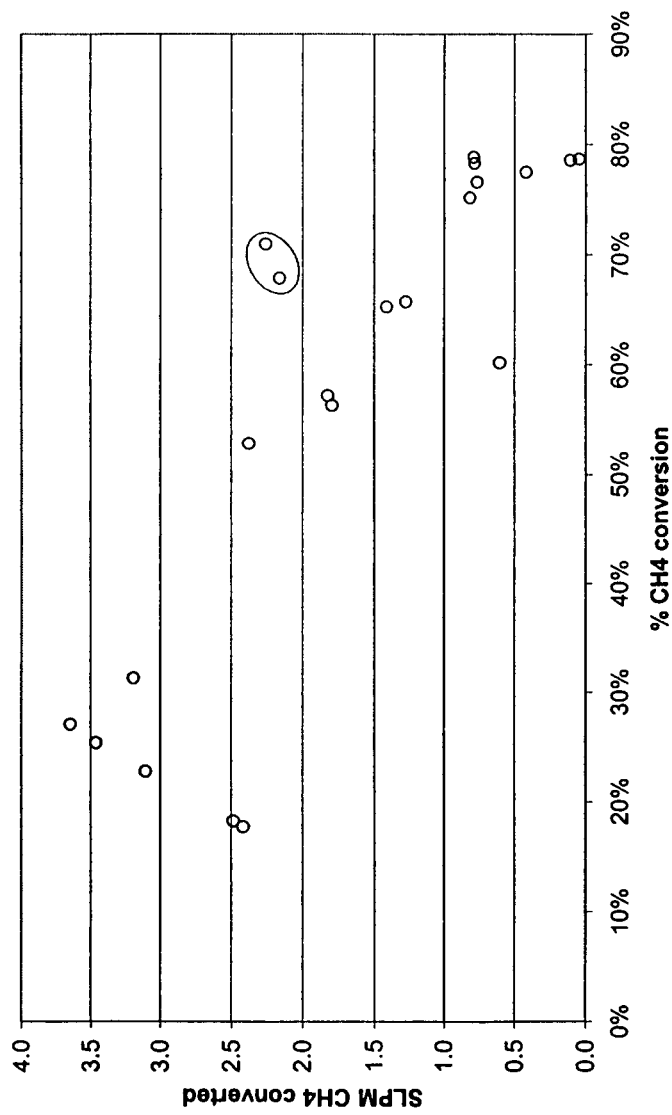

FIG. 67 is a plot showing CFD predictions of SMR reaction productivity in standard liters per minute of methane converted and percent methane conversion for the full set of conditions of Table 2.

Figure 68:
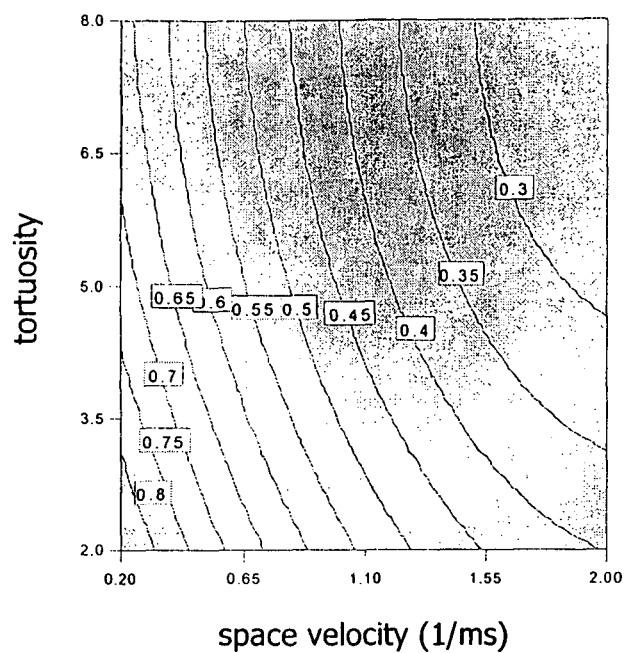

FIG. 68 is a plot showing predicted SMR reaction methane fractional conversion for the conditions of Set 2 in Table 1, with a 0.36 mm flow-by gap, catalyst on both major walls, and a constant catalyst thickness of 0.127 mm.

Figure 69:
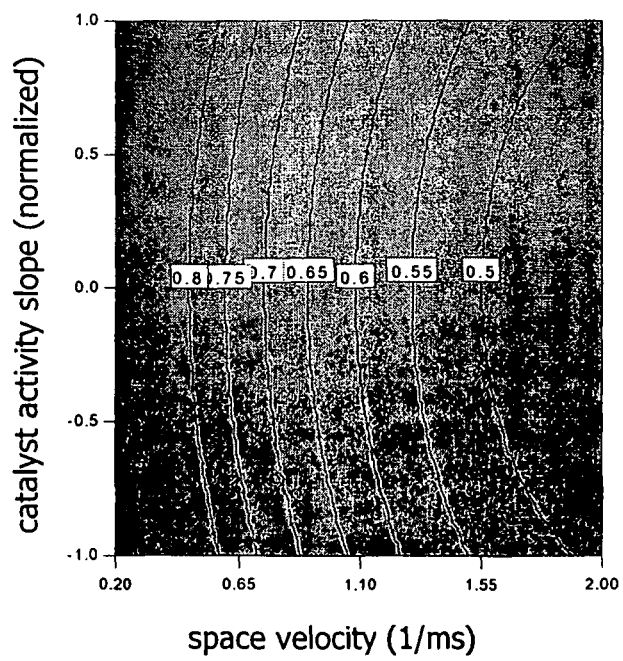

FIG. 69 is a plot showing predicted SMR reaction methane fractional conversion for the conditions of Set 2 in Table 1, with a 0.36 mm flow-by gap, and a constant catalyst pore tortuosity of 1.

Figure 70:
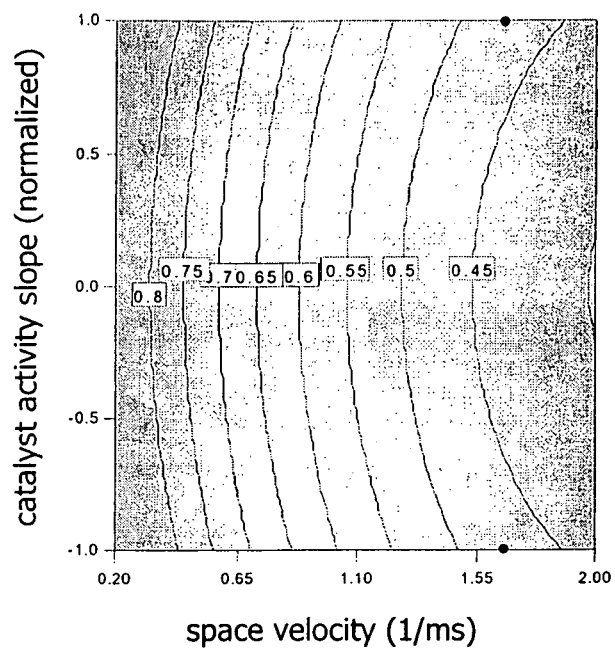

FIG. 70 is a plot showing predicted SMR reaction methane fractional conversion for the conditions of Set 2 in Table 1, with a 0.36 mm flow-by gap, and a constant catalyst pore tortuosity of 2.

Figure 71:
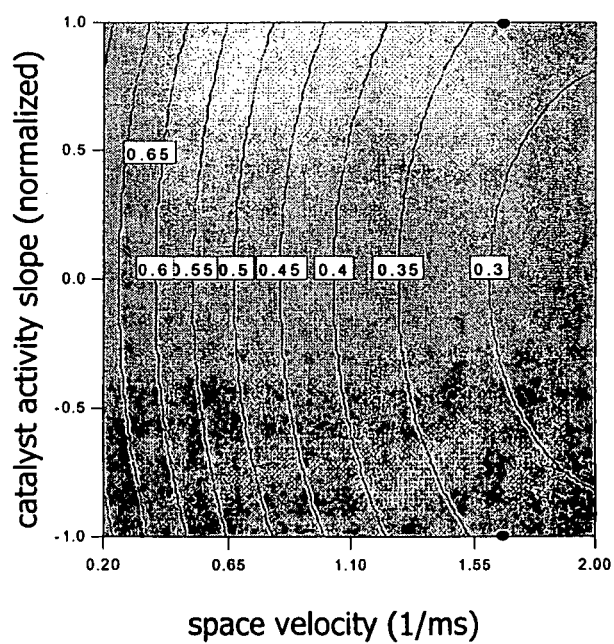

FIG. 71 is a plot showing predicted SMR reaction methane fractional conversion for the conditions of Set 2 in Table 1, with a 0.36 mm flow-by gap, and a constant catalyst pore tortuosity of 10.

Figure 72:
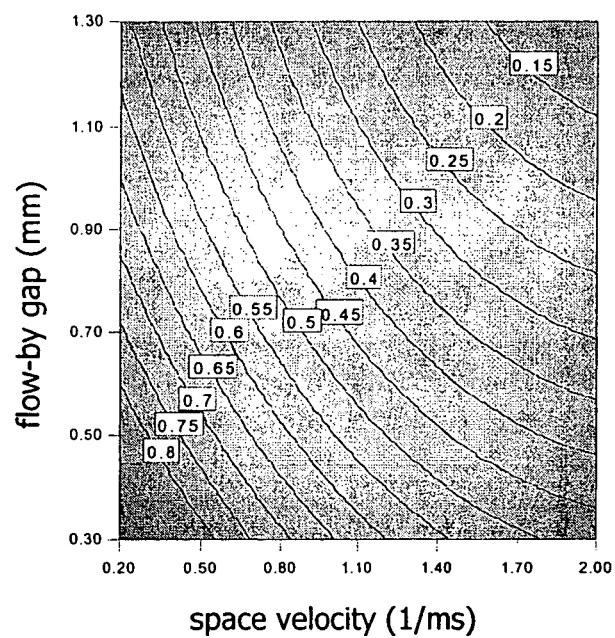

FIG. 72 is a plot showing predicted SMR reaction methane fractional conversion for the conditions of Set 2 in Table 1, with a constant catalyst thickness of 0.127 mm, and a constant catalyst pore tortuosity of 1.

Figure 73:
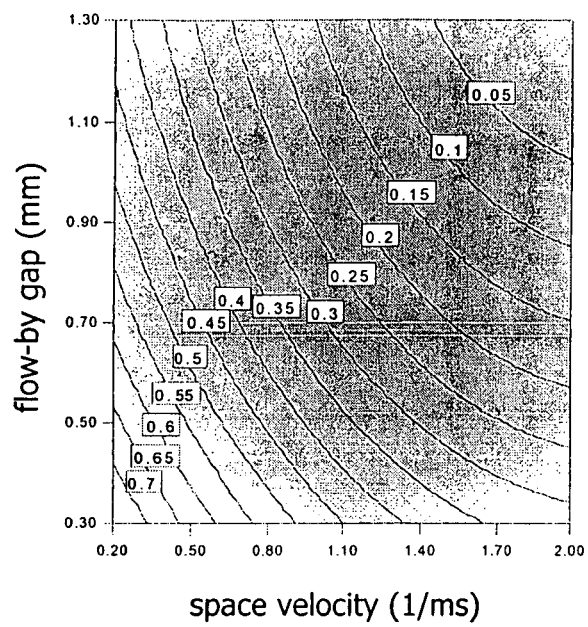

FIG. 73 is a plot showing predicted SMR reaction methane fractional conversion for the conditions of Set 2 in Table 1, with a constant catalyst thickness of 0.127 mm, and a constant catalyst pore tortuosity of 5.

Figure 74:
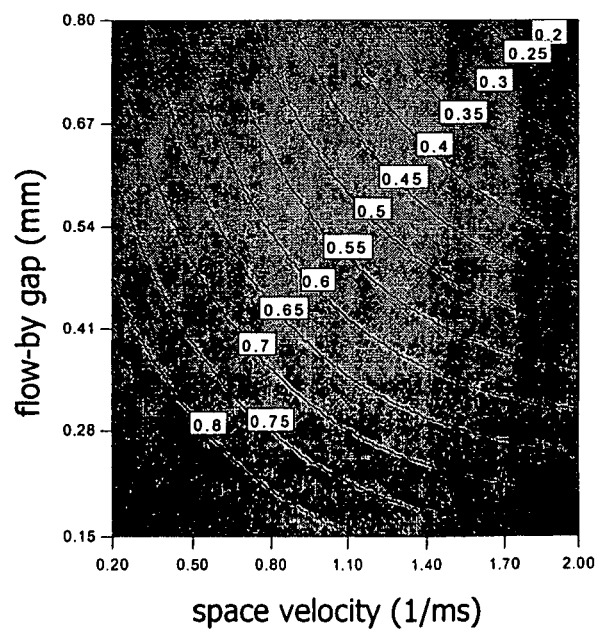

FIG. 74 is a plot showing predicted SMR reaction methane fractional conversion for the conditions of Set 3 in Table 1, with a constant catalyst thickness of 0.127 mm, and a constant wall temperature of 850° C. (extrapolated).

Figure 75:
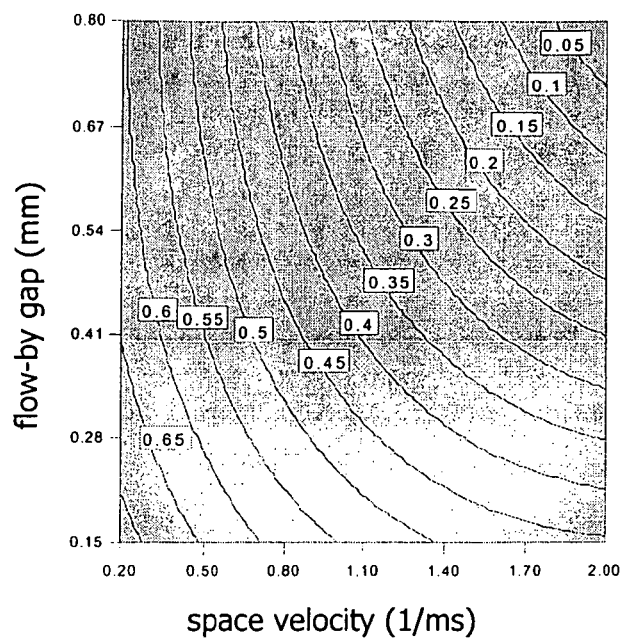

FIG. 75 is a plot showing predicted SMR reaction methane fractional conversion for the conditions of Set 3 in Table 1, with a constant catalyst thickness of 0.127 mm, and a wall temperature gradient from 650° C. at the inlet to 850° C. at the outlet.

Figure 76:
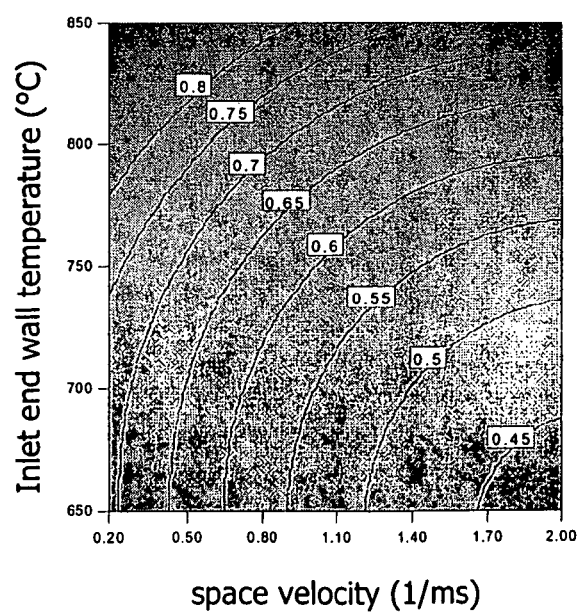

FIG. 76 is a plot showing predicted SMR reaction methane fractional conversion for the conditions of Set 3 in Table 1, with a constant catalyst thickness of 0.127 mm, and a flow-by gap of 0.18 mm.

Figure 77:
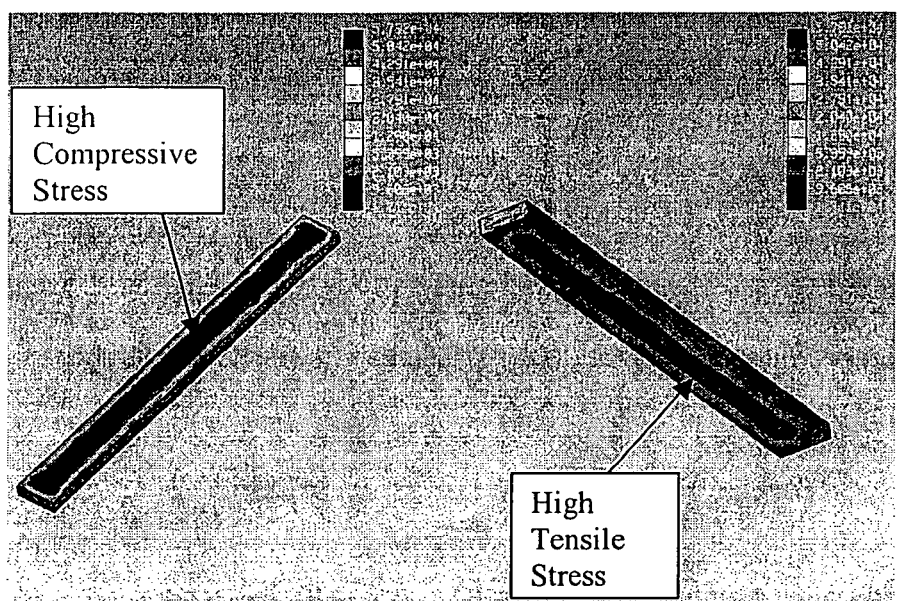

FIG. 77 is a picture which shows high compressive stress in the higher coefficient of thermal expansion material and high tensile stress in the lower coefficient of thermal expansion material disclosed in Example 1.

Figure 78:
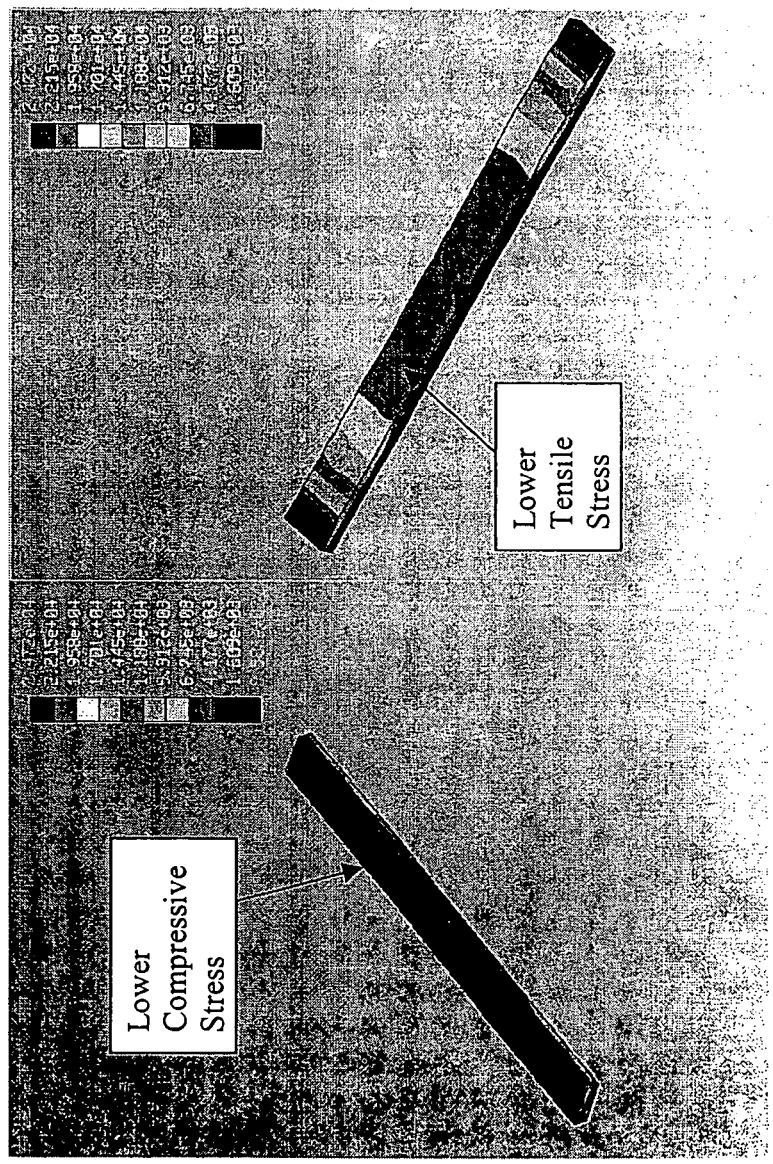

FIG. 78 shows a picture of an intermediate material modeled as having a modulus of elasticity of 0.01 times that of stainless steel, the stress being reduced by 57% as disclosed in Example 1.

Figure 79:
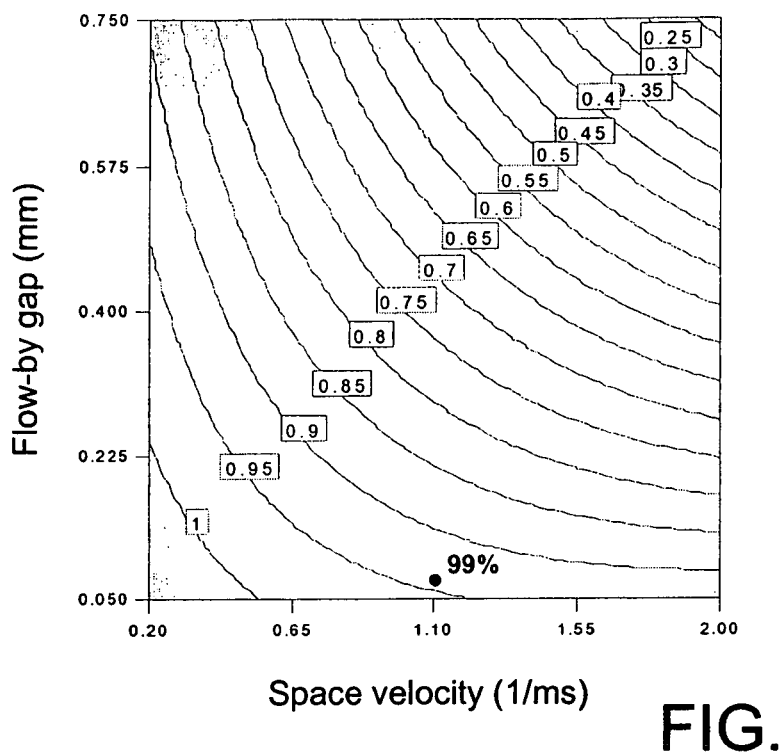

FIG. 79 is a plot showing predicted SMR reaction approach to equilibrium methane conversion for the conditions of Set 1 in Table 1, with a constant thermal conductivity of 0.9 W/m-K, and a catalyst thickness of 0.28 mm.

Figure 80:
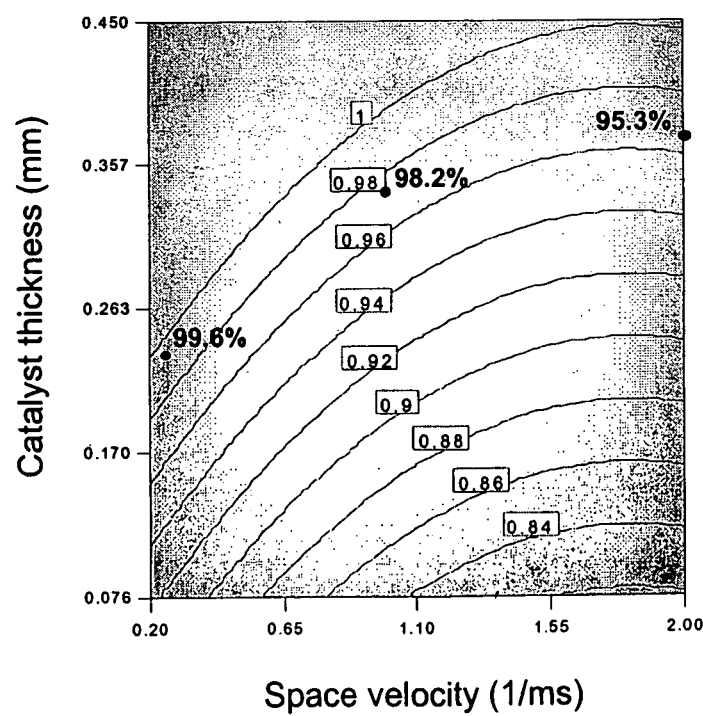

FIG. 80 is a plot showing predicted SMR reaction approach to equilibrium methane conversion for the conditions of Set 1 in Table 1, with a constant thermal conductivity of 1.85 W/m-K, and a flow-by gap of 0.05 mm. The labels on dots indicate actual CFD simulation predicted percent approach to equilibrium. The contours show curve fits for predicted fractional approach to equilibrium.

Figure 81:
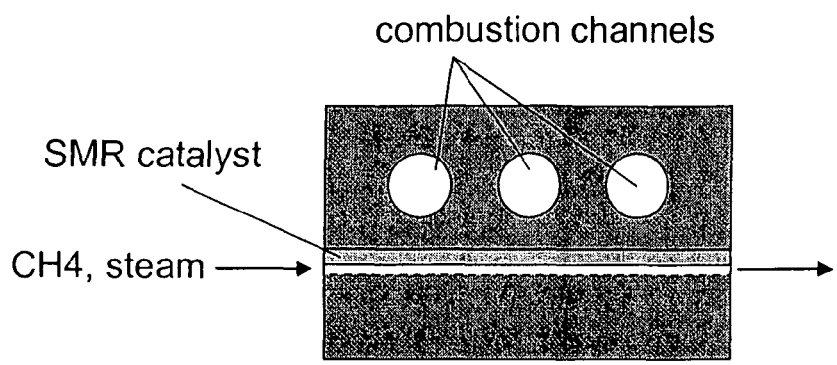

FIG. 81 is a schematic illustration of a single channel microchannel reactor for Example 2. Thermocouples are placed in the metal between the reforming channel and the combustion channels.

Figure 82:
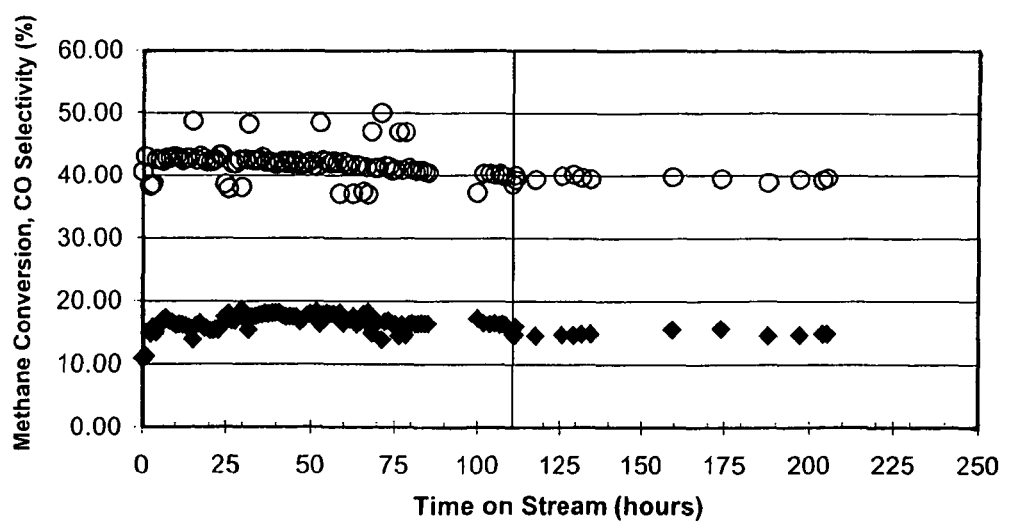

FIG. 82 is a plot showing time on stream (TOS) performance for the 90 microsecond case in Example 2 where conversion is shown with the filled diamonds and selectivity to CO is shown with open circles. At 110 hours TOS an upset (shown with a vertical line) occurs where the hydrogen fuel is temporarily lost to the combustion side of the reactor.

Figure 83:
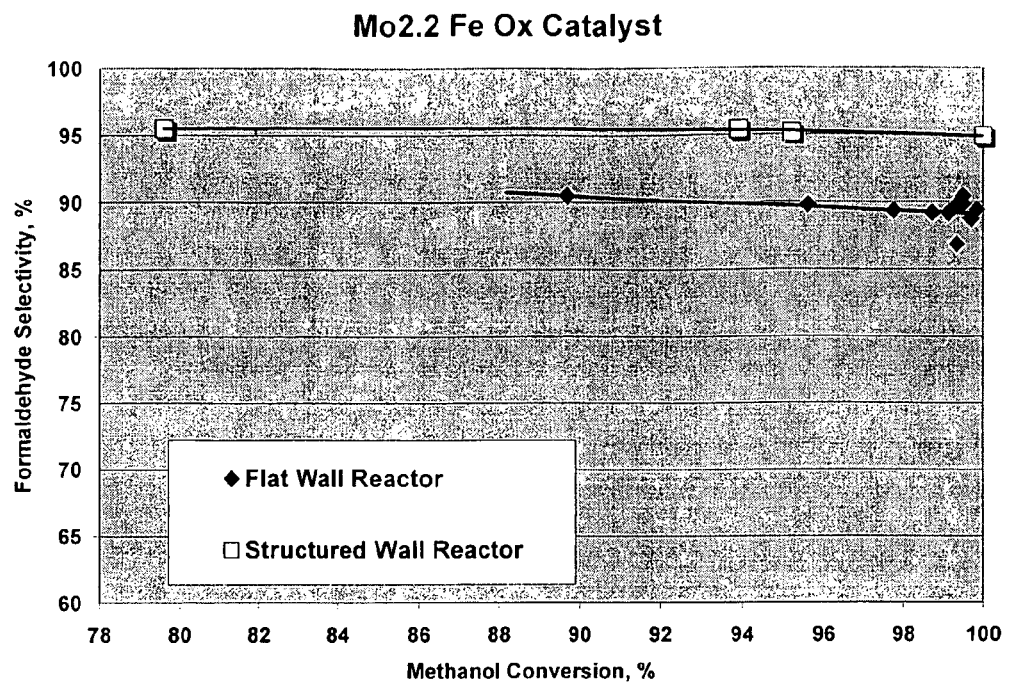

FIG. 83 is a plot of formaldehyde selectivity versus methanol conversion using a Mo—Fe catalyst for the process disclosed in Example 4.

Figure 84:
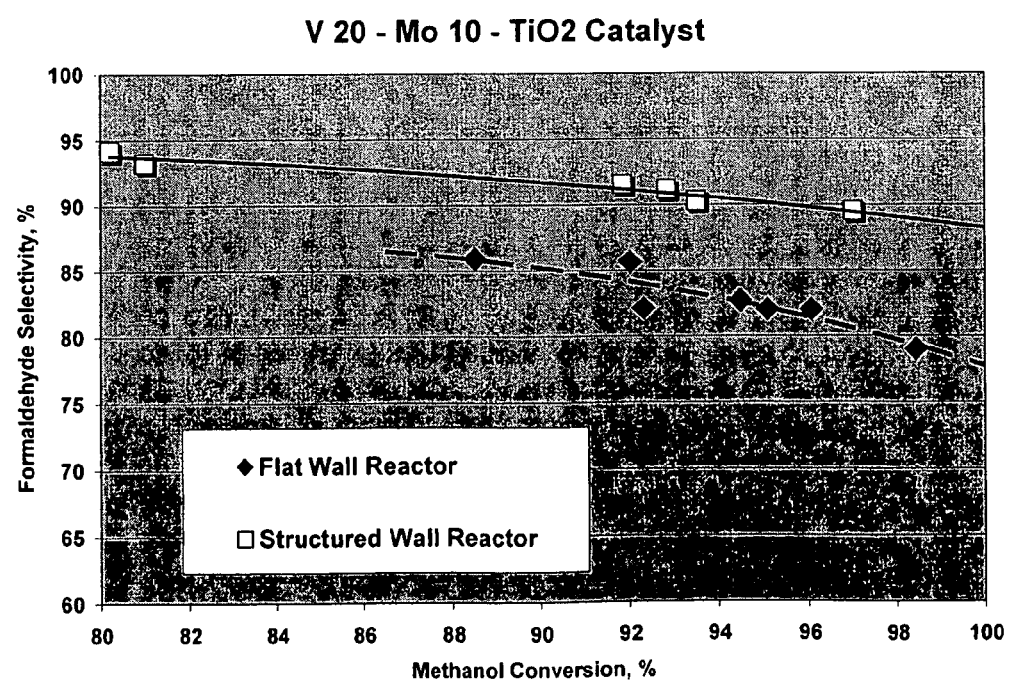

FIG. 84 is a plot of formaldehyde selectivity versus methanol conversion for a V-mo catalyst for the process disclosed in Example 5.

Figure 85:
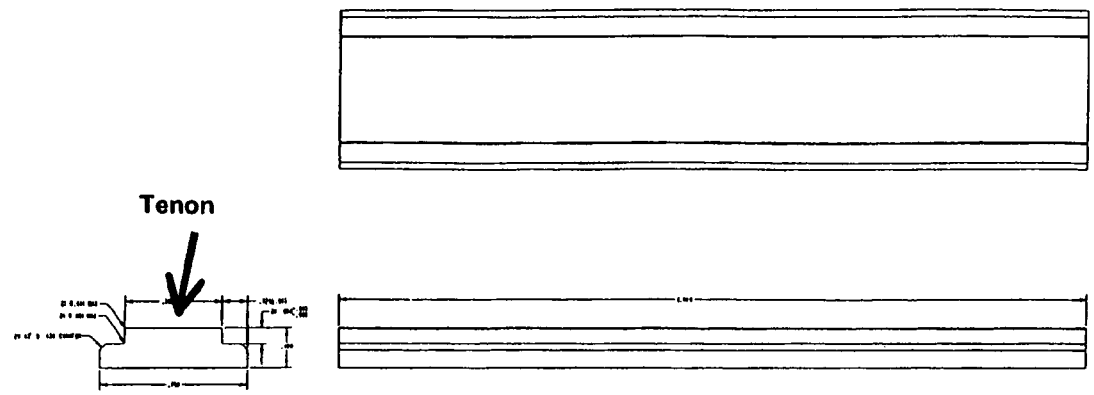

FIG. 85 consists of drawings of a body backing plate used in the microchannel reactor disclosed in Example 7.

Figure 86:
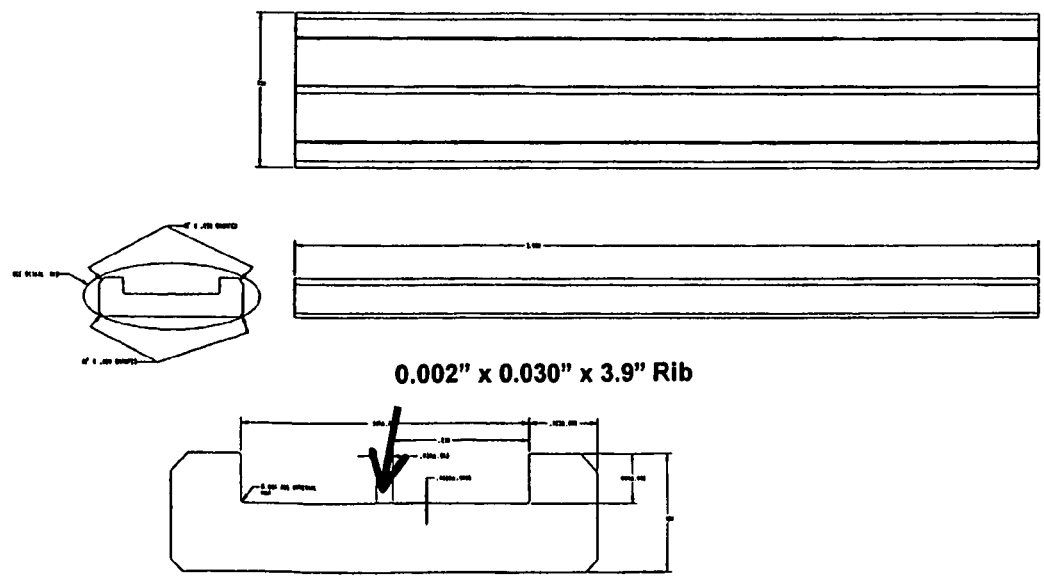

FIG. 86 consists of drawings of the body cover plate used in the microchannel reactor disclosed in Example 7.

Figure 87:
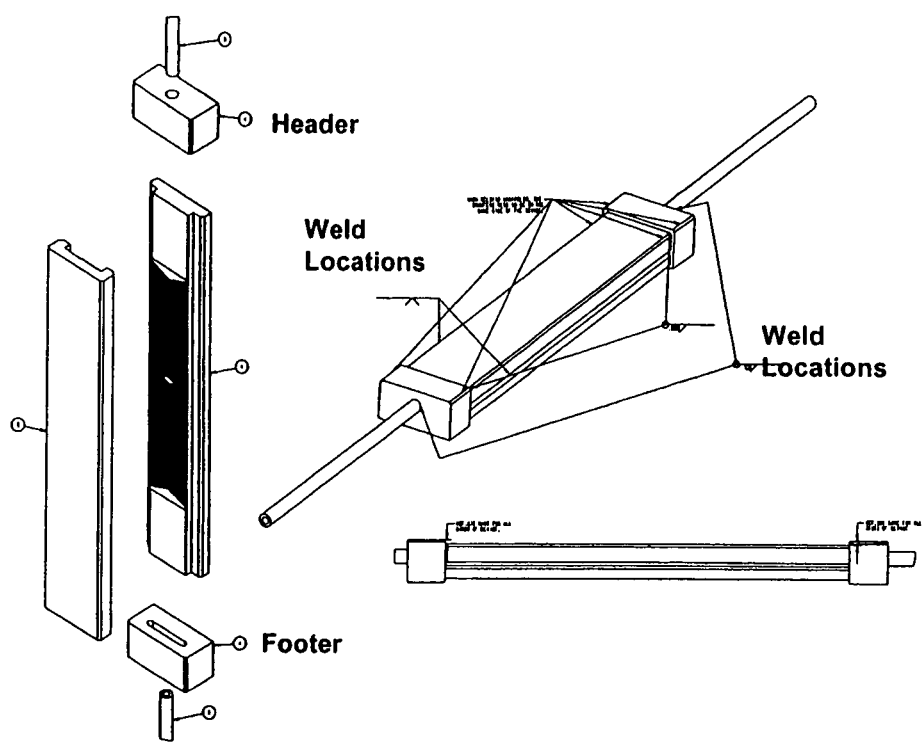
Figure 88:
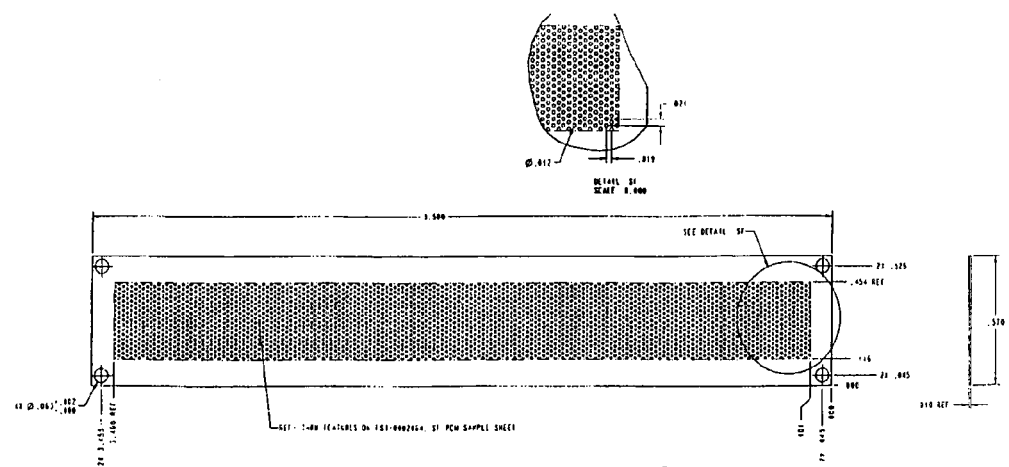
Figure 89:
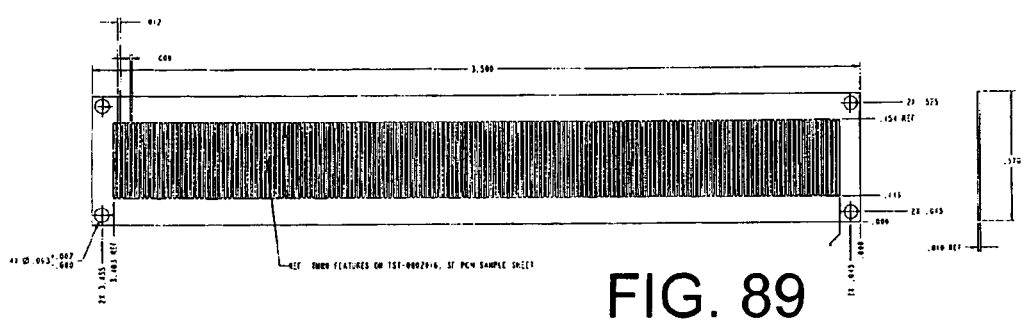
Figure 90:
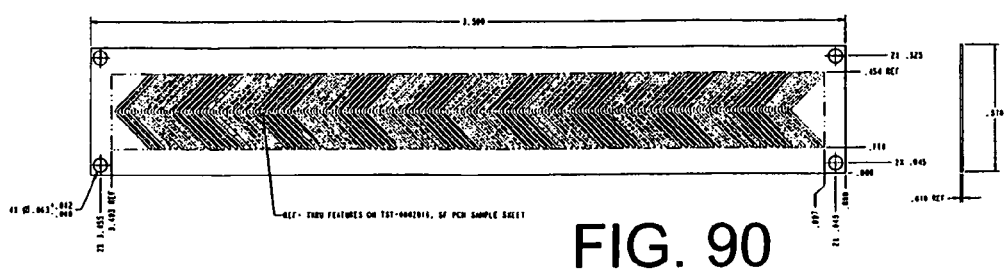

FIG. 87 is a schematic illustration of the microchannel reactor disclosed in Example 7.

Figure 91:
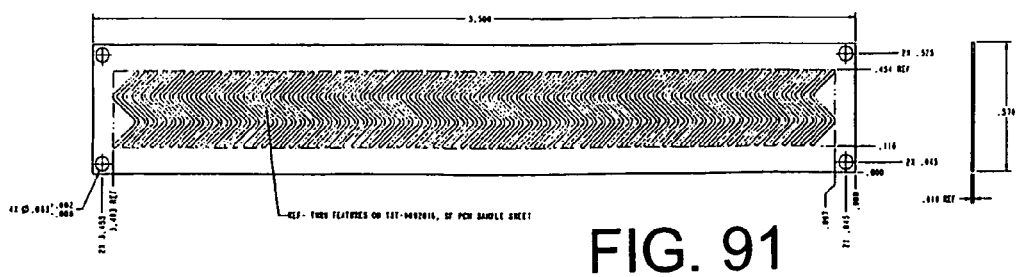

FIGS. 88-91 disclose four types of surface feature patterns used with the microgrooved support strips described in Example 5. The patterns are circles (FIG. 88), horizontal bars (FIG. 89), chevrons (FIG. 90) and zig-zags (FIG. 91).

Figure 92:
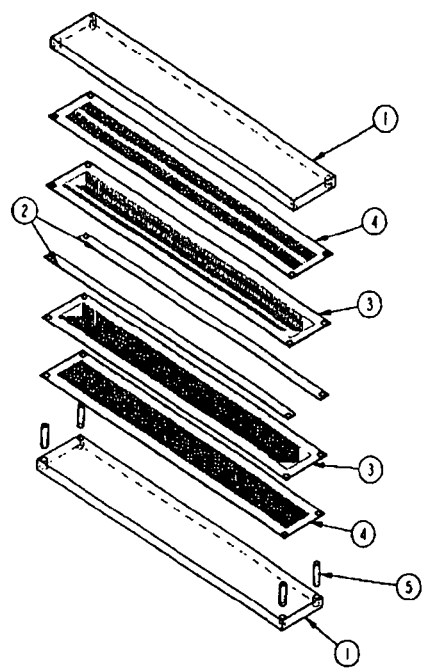

FIG. 92 is an exploded view of a microgrooved test device without header, footer or cooling jacket in place. The test device is used in Example 5.

Figure 93:
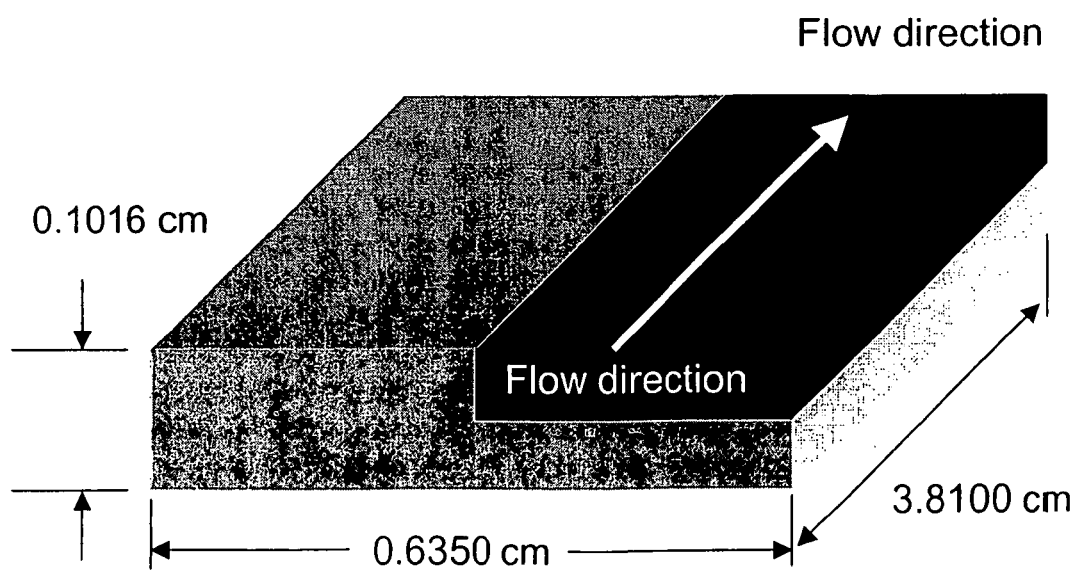

FIG. 93 is a schematic illustration showing the dimensions of the packed bed microchannel reactor, with quarter model section, disclosed in Example 9.

Figure 94:
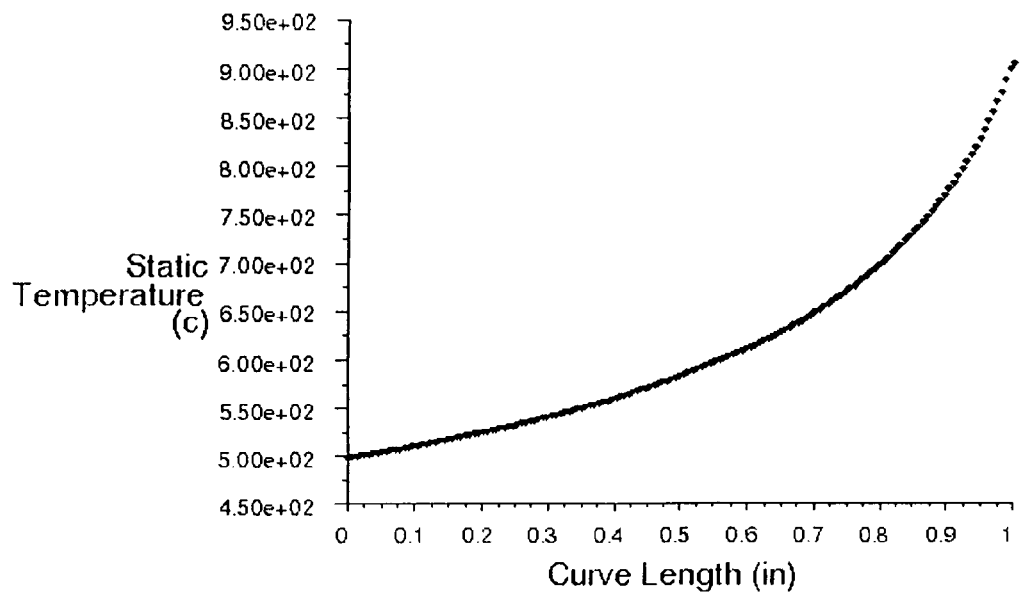

FIG. 94 is a center line temperature plotted versus position in the bed for quartz tube case 3 described in Example 9.

Figure 95:
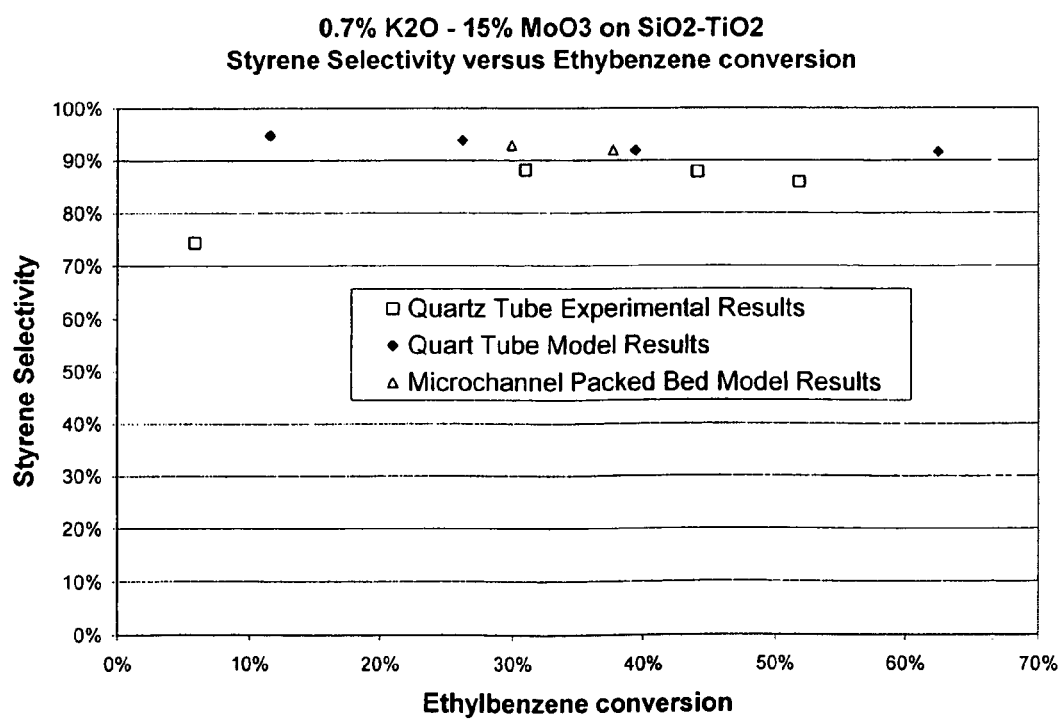

FIG. 95 is a plot of styrene selectivity versus ethylbenzene conversion for the two 0.06 inch gap microchannel cases described in Example 9.

Figure 96:
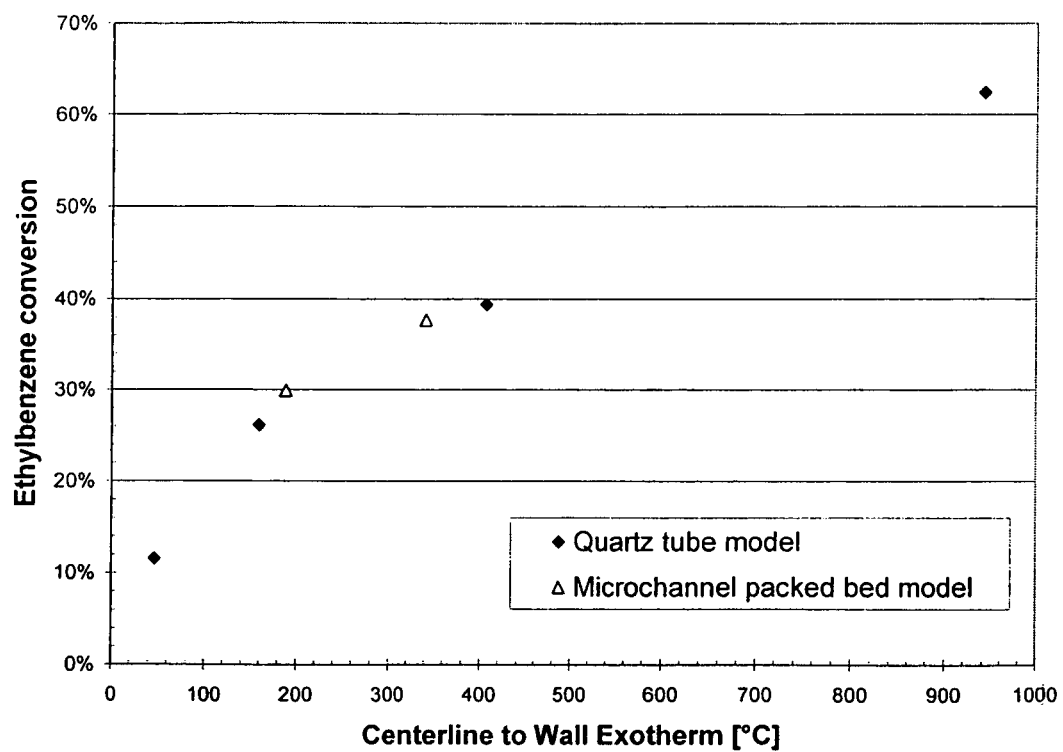

FIG. 96 is a plot of ethylbenzene conversion versus center to wall exotherm in ° C. for the CFD model showing the quartz tube and 0.06 inch (1.52 mm) gap microchannel reactor models disclosed in Example 9.

Figure 97:
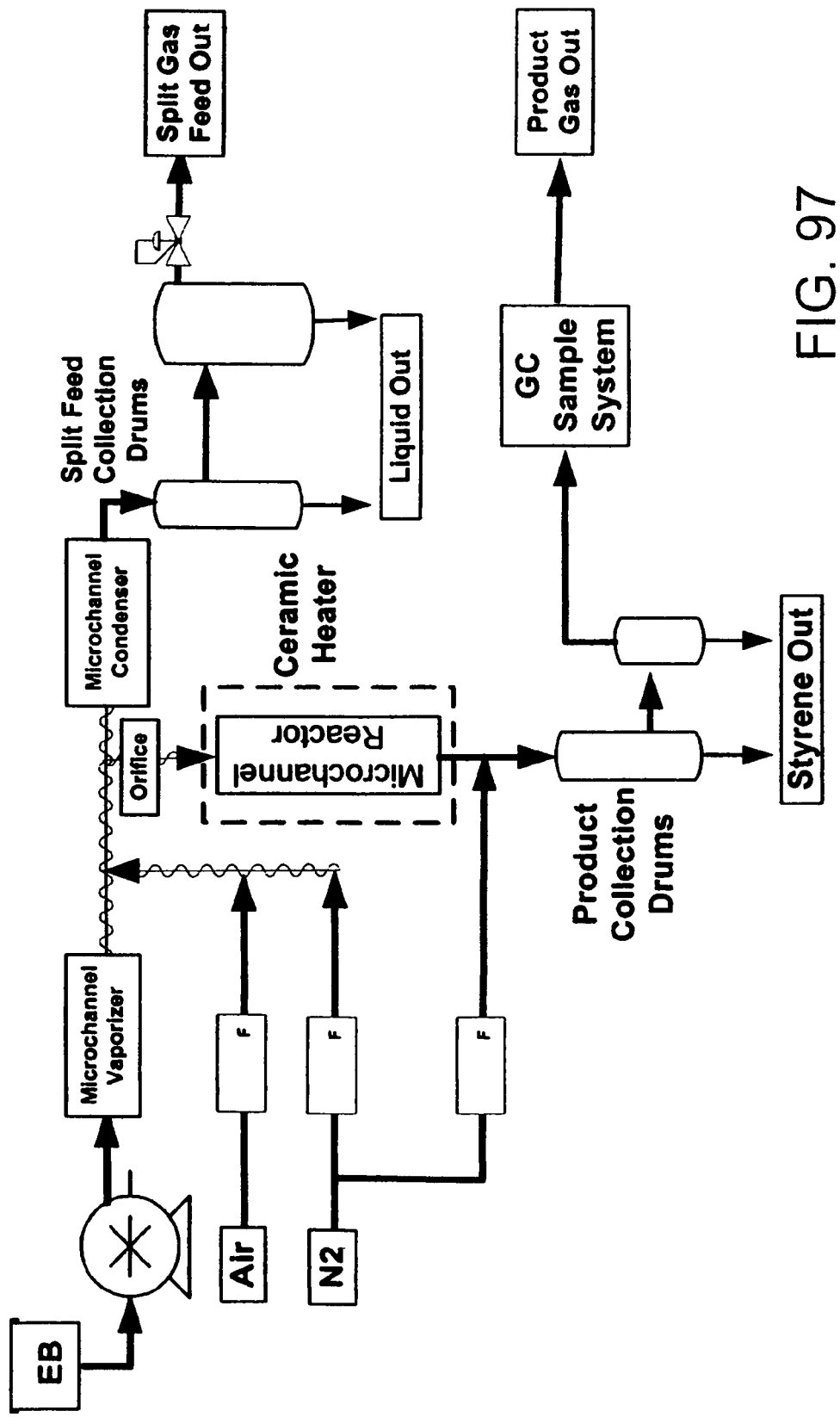

FIG. 97 is a schematic illustration of the test set up for the microchannel reactor disclosed in Example 7.

Figure 98:
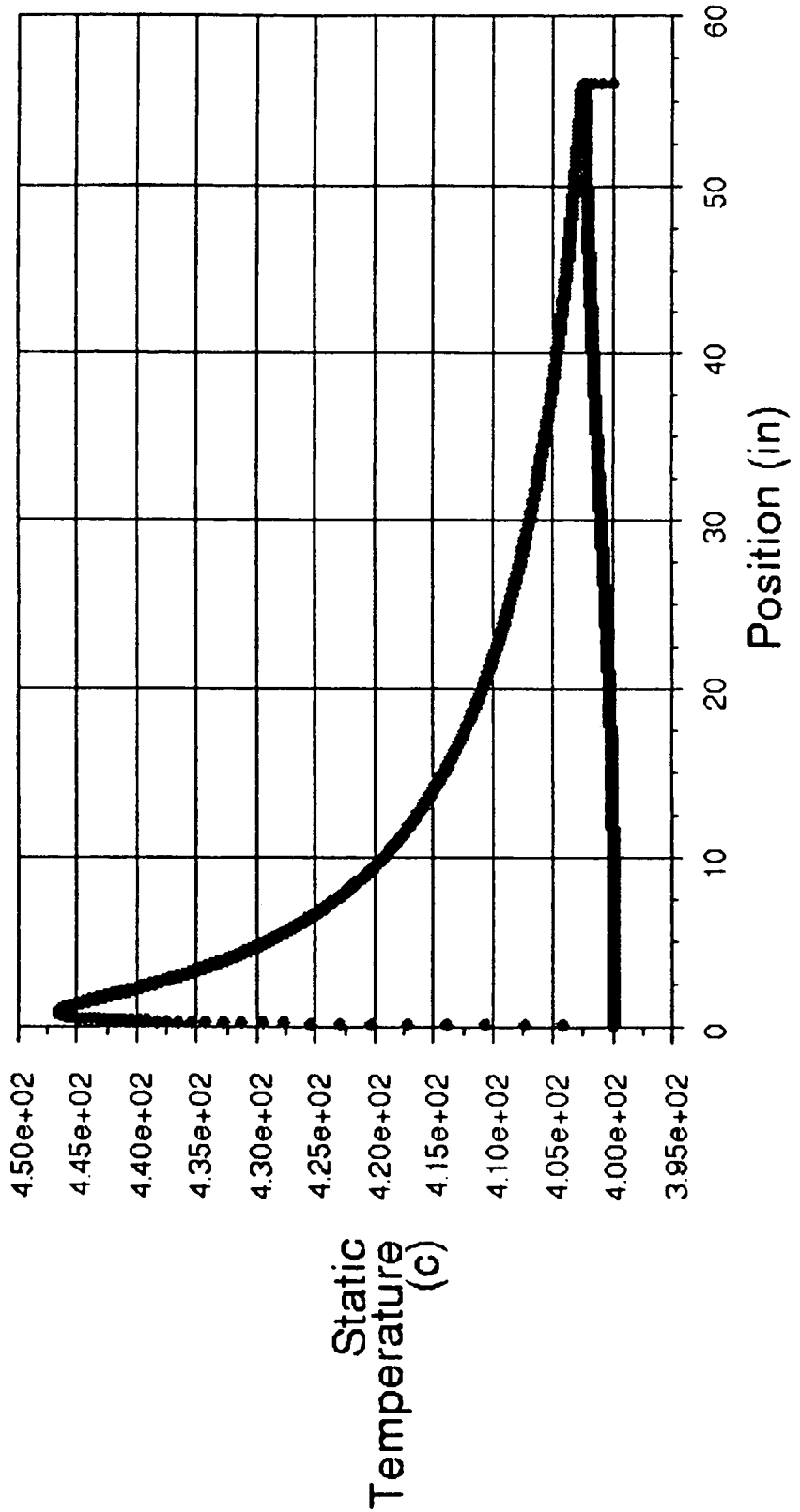

FIG. 98 is a plot showing temperature profiles at two locations along the length of the reactor disclosed in Example 10. The catalyst loading is 6.78 E8 mg-cat/m$^3$. The ethylbenzene to oxygen molar ratio is 2. The temperature is 400° C.

Figure 99:
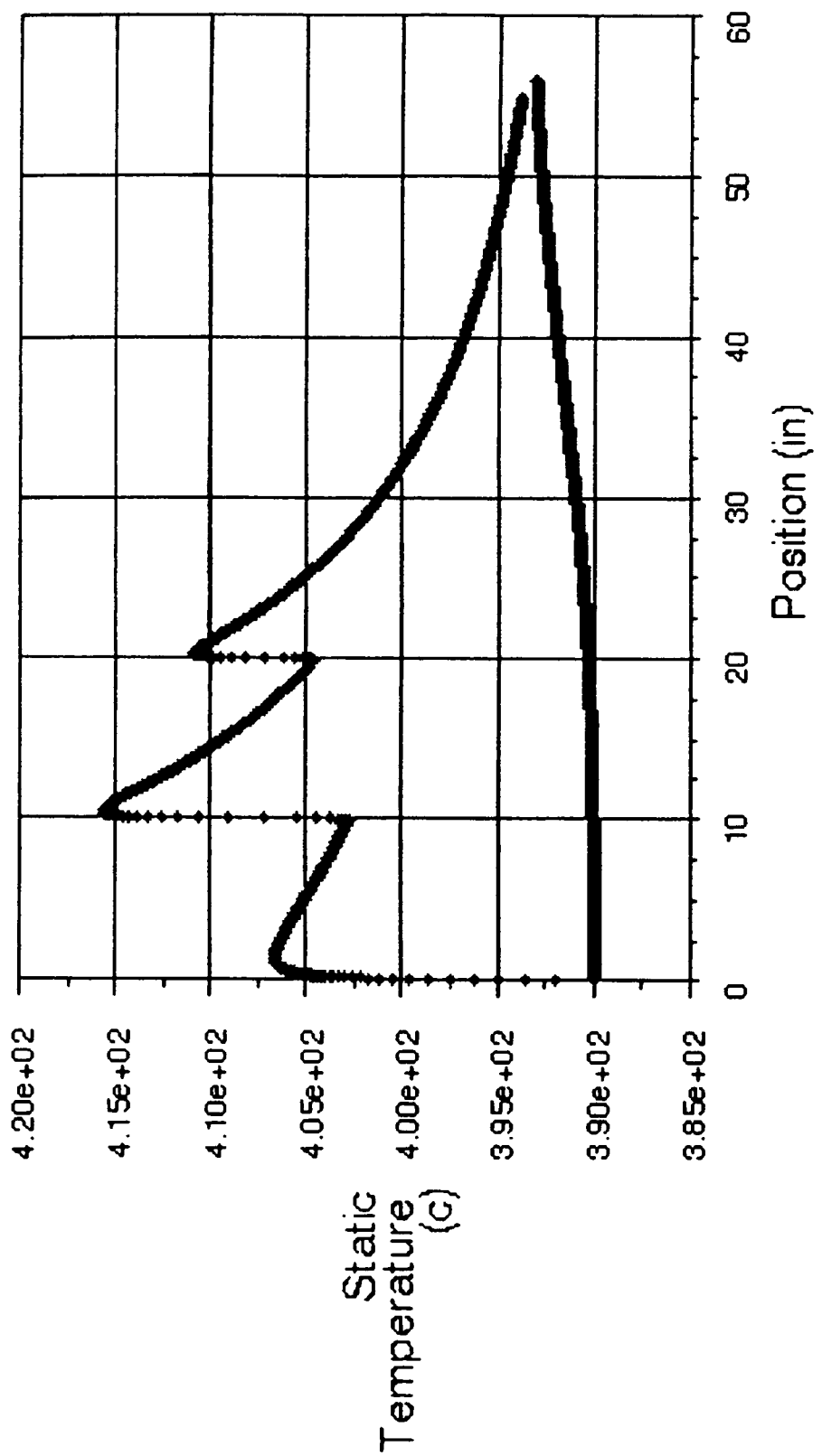

FIG. 99 is a plot of temperature profiles along the length of the reactor disclosed in Example 10 wherein the temperatures are measured at two locations. This plot shows temperature profiles for a non-uniform catalyst activity distribution.

Figure 100:
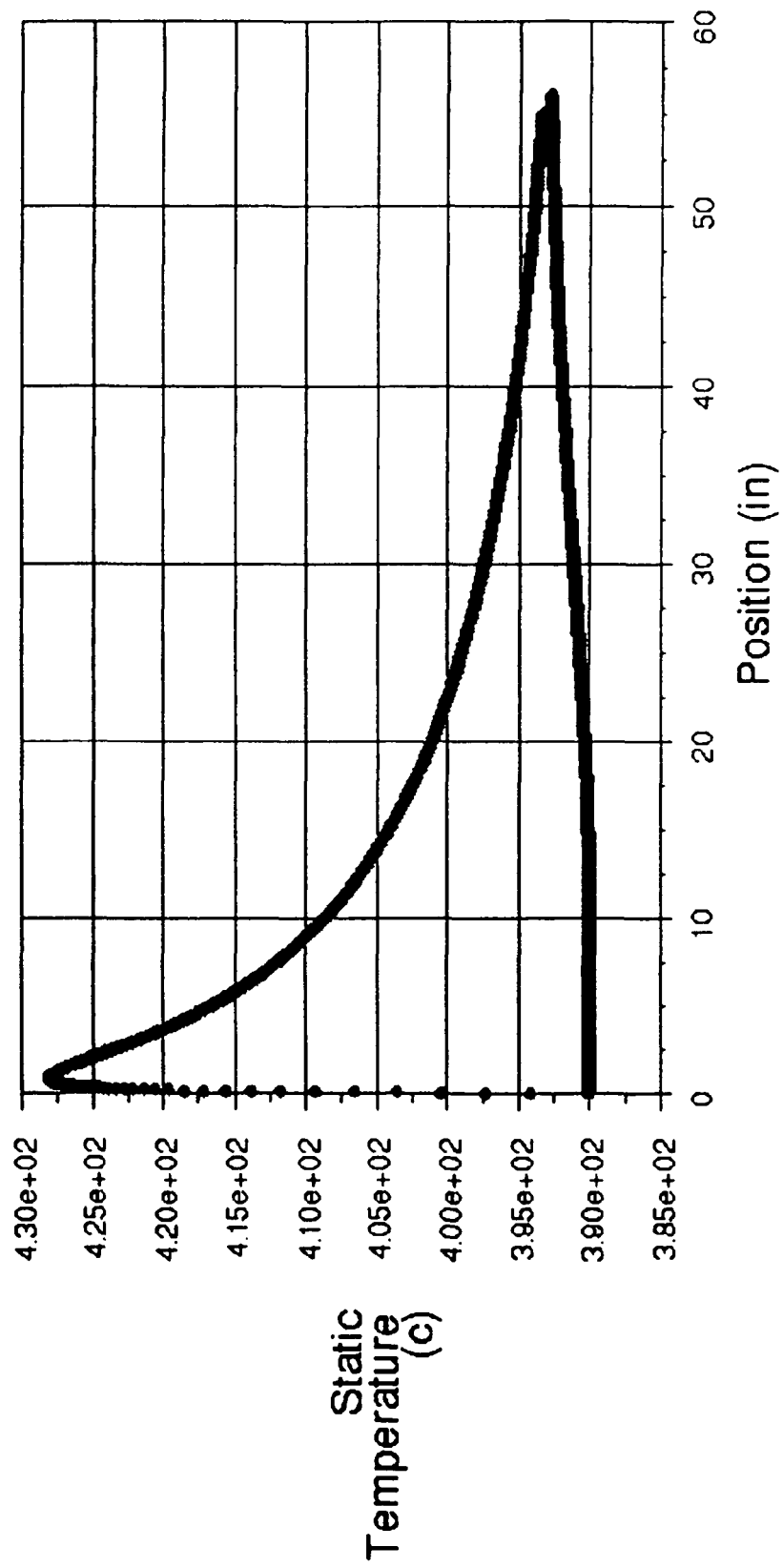

FIG. 100 is a plot of temperature profiles along the length of the reactor disclosed in Example 10 wherein a uniform catalyst activity distribution is used.

Figure 101:
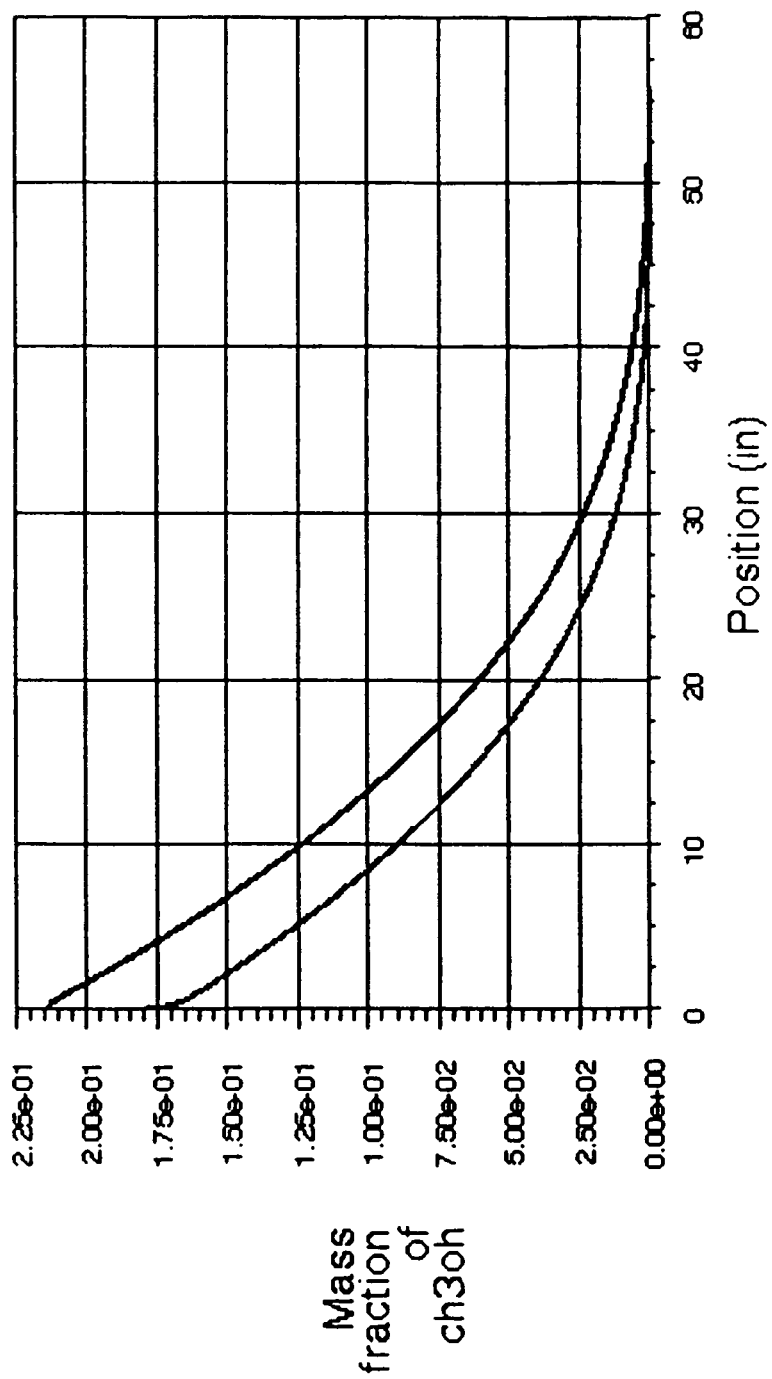

FIG. 101 is a plot showing mass fraction of methanol along the length of the reactor disclosed in Example 11. The catalyst is catalyst A, which is disclosed in the example. The temperature is 360° C.

Figure 102:
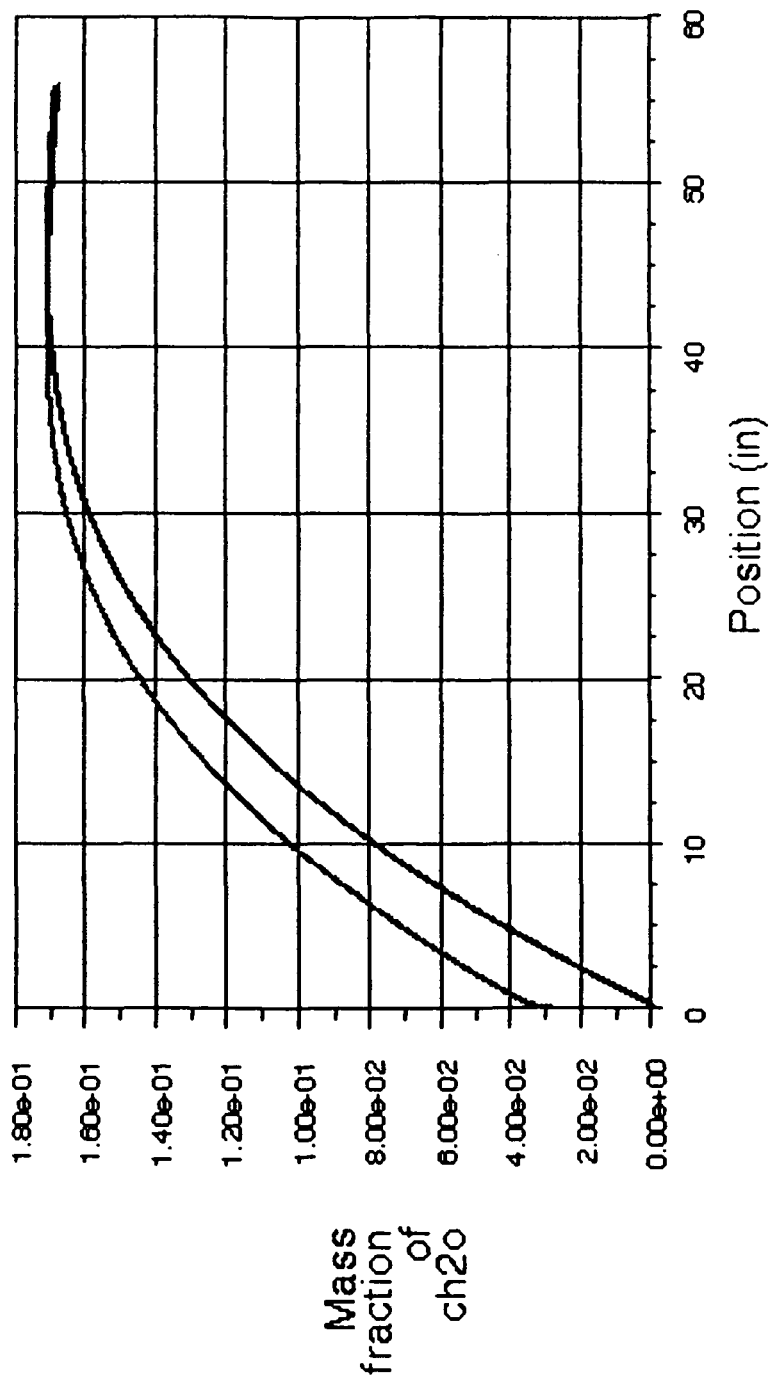

FIG. 102 is a plot showing $CH_2O$ mass fraction along the length of the reactor disclosed in Example 11. The catalyst is catalyst A, which is disclosed in the example. The temperature is 360° C.

Figure 103:
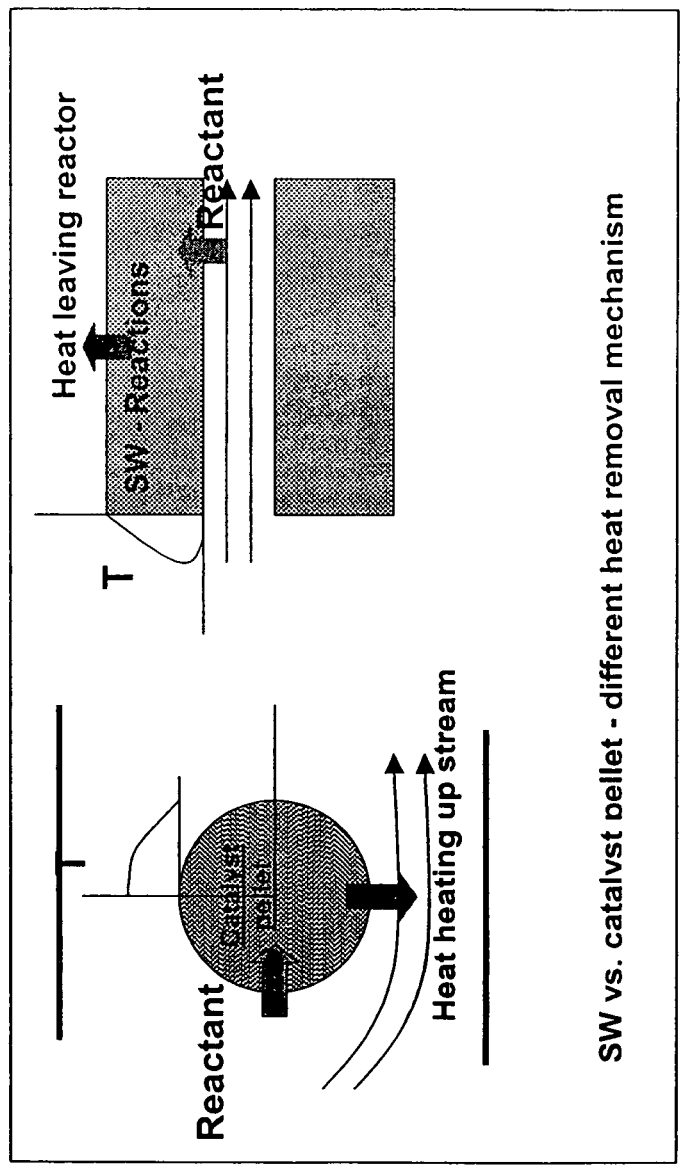

FIG. 103 is a schematic illustration showing heat removal mechanisms for a catalyst pellet and for a structured wall microchannel. This illustration is referred to in Example 11.

Figure 104:
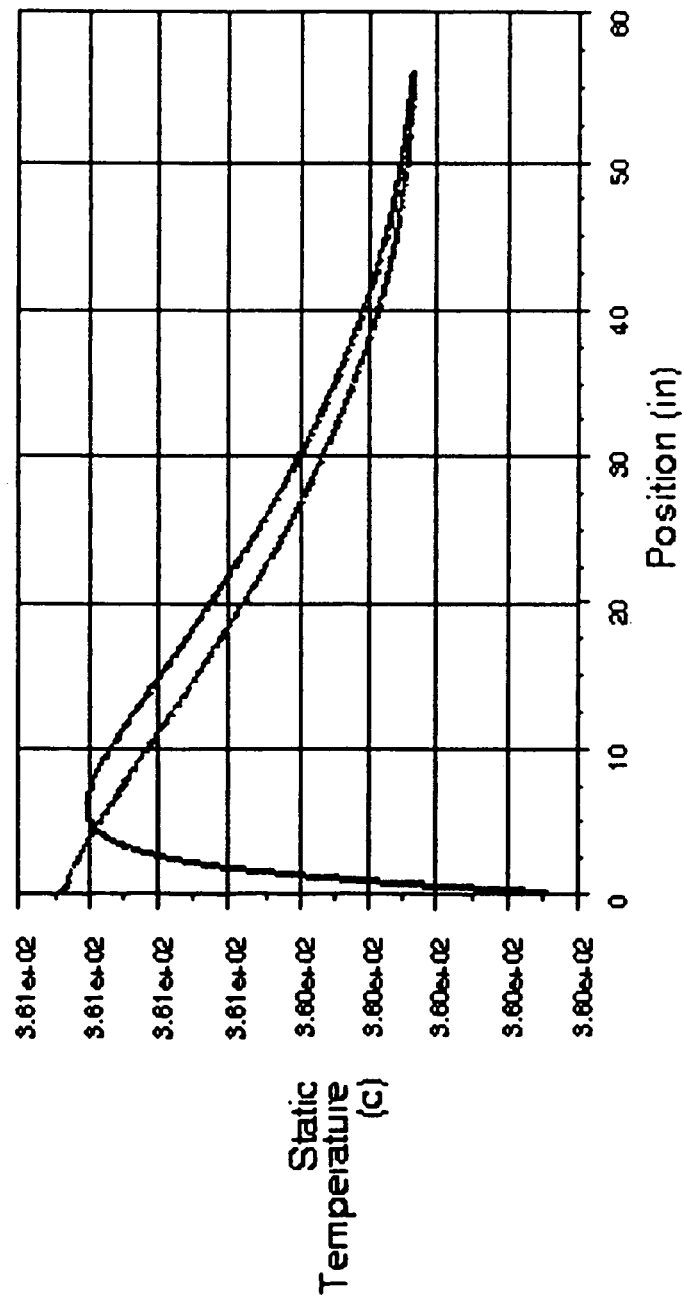

FIG. 104 is a plot of temperature profiles at two locations along the length of the reactor disclosed in Example 11. The catalyst is catalyst A, which is disclosed in the example. The temperature is 360° C.

Figure 105:
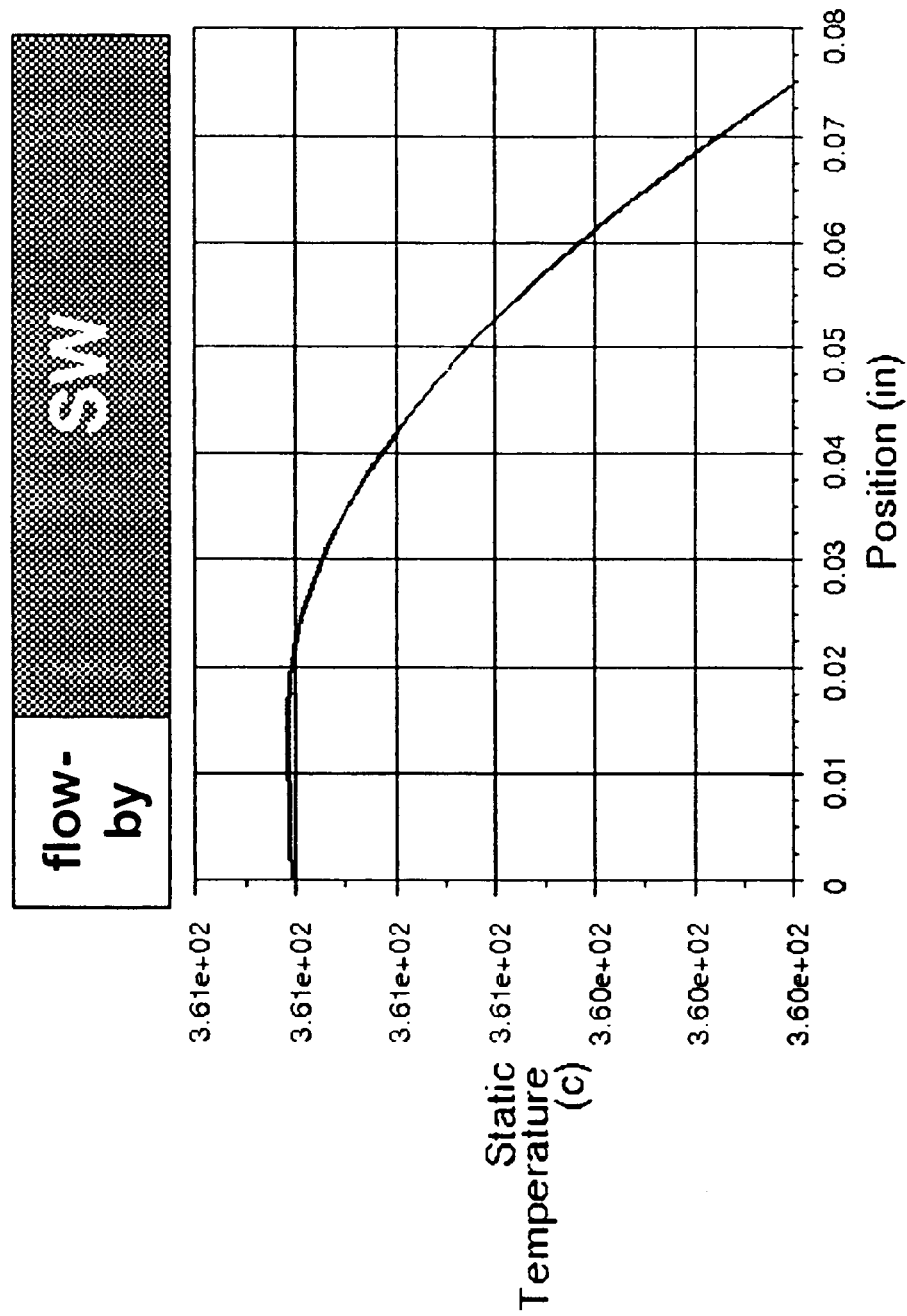

FIG. 105 is a plot of a temperature profile in the transverse direction for the reactor disclosed in Example 11. The catalyst is catalyst A, which is disclosed in the example. The abbreviation "SW" refers to structured wall. The profile is taken at a point 6 inches (15.24 cm) from the beginning of the structured wall.

Figure 106:
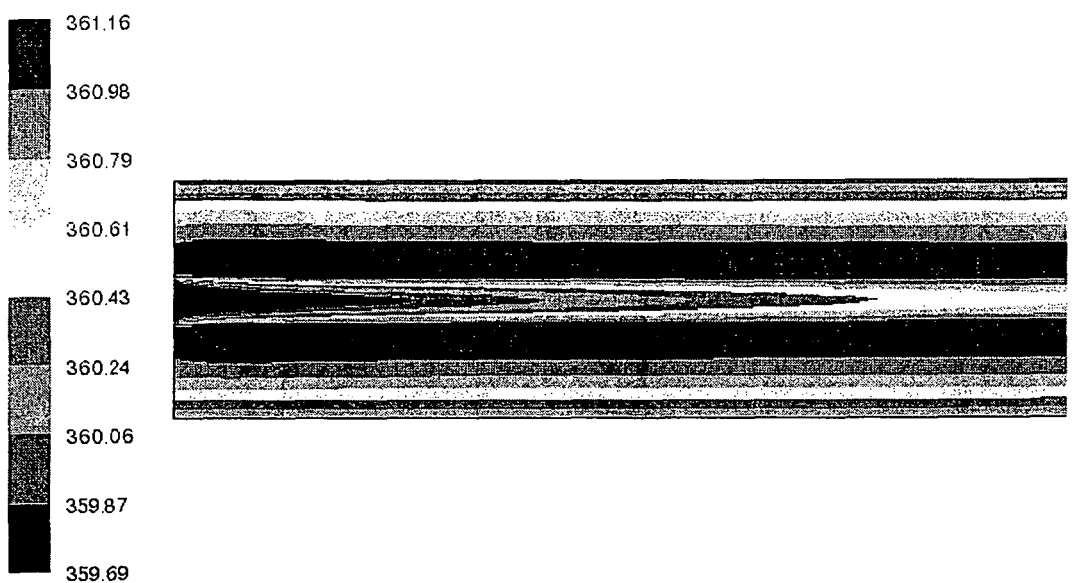

FIG. 106 is a plot of temperature distribution for the reactor disclosed in Example 11. The baseline temperature is 360° C.

Figure 107:
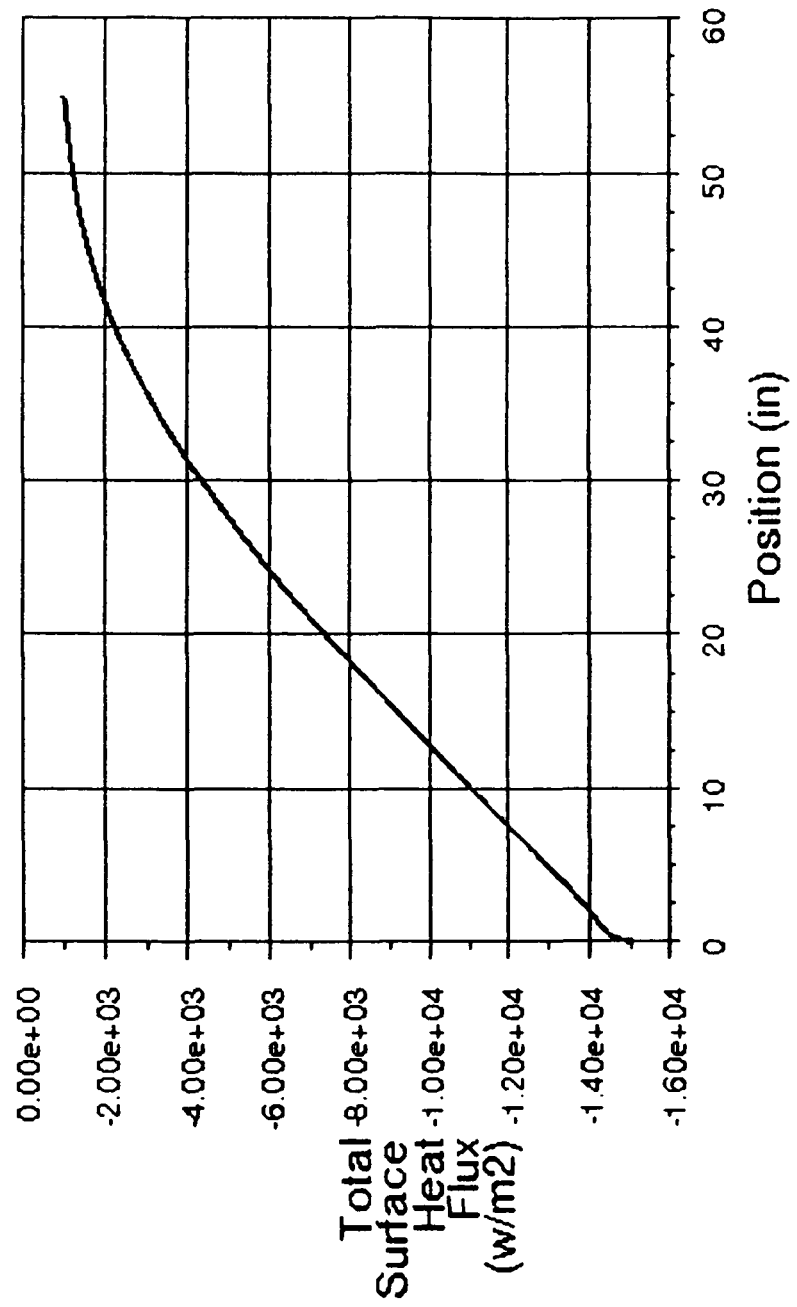

FIG. 107 is a plot of the heat flux profile along the reactor wall of the reactor disclosed in Example 11.

Figure 108:
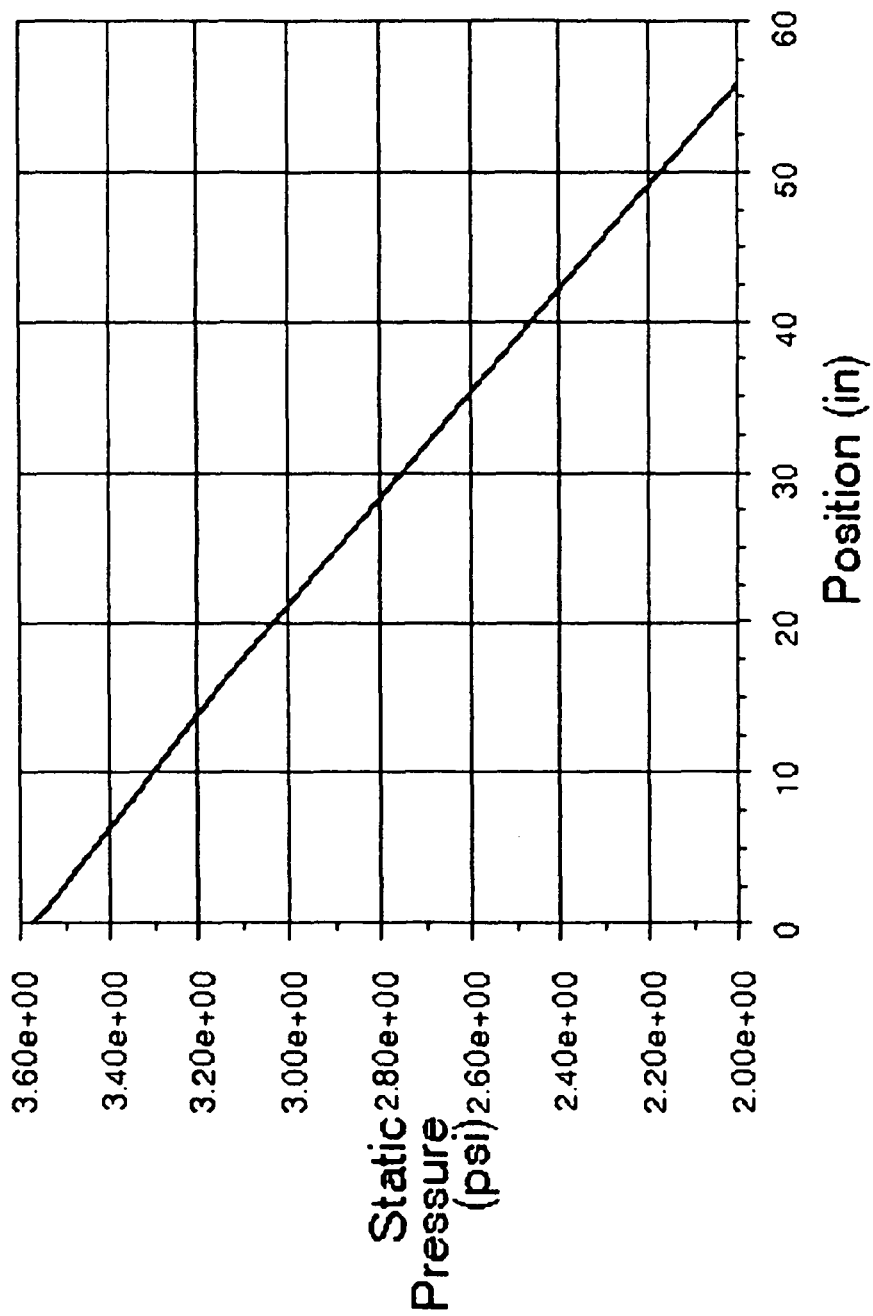

FIG. 108 is a plot of static pressure along the length of the reactor disclosed in Example 11. The catalyst is catalyst A, which is disclosed in the example. The temperature is 360° C.

Figure 109:
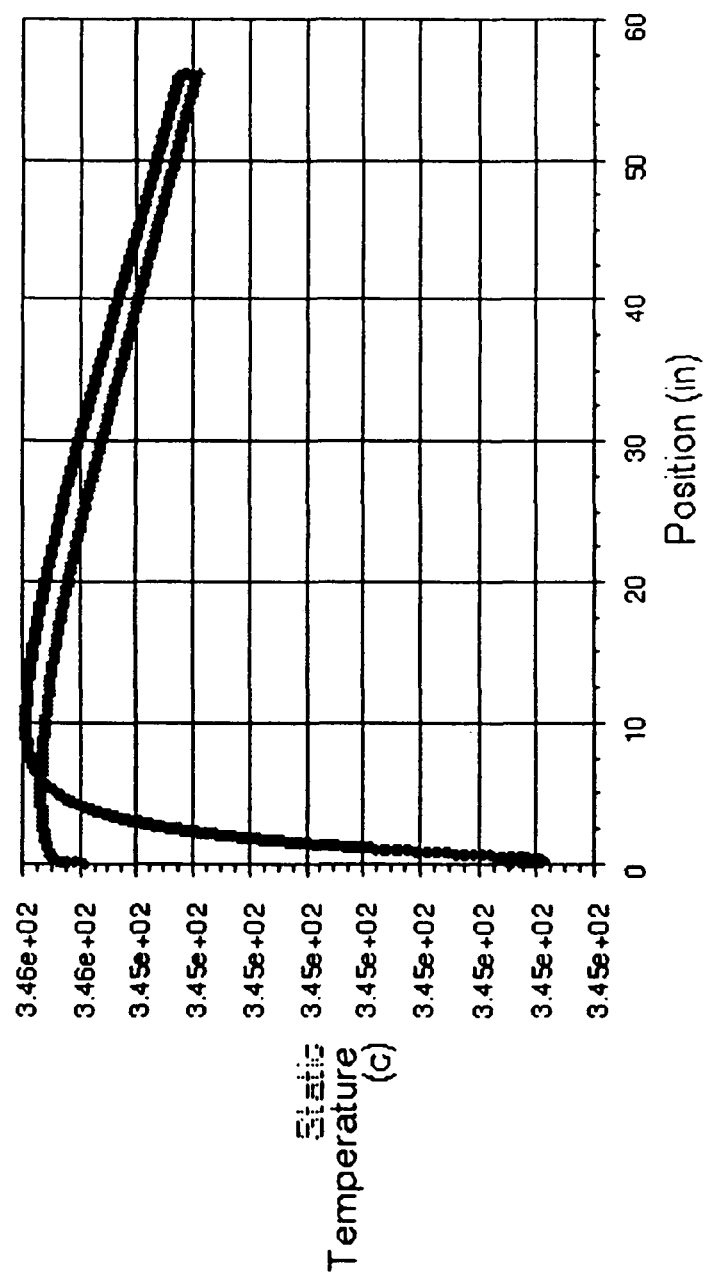

FIG. 109 is a plot of temperature profiles at two locations along the length of the reactor disclosed in Example 11.

Figure 110:
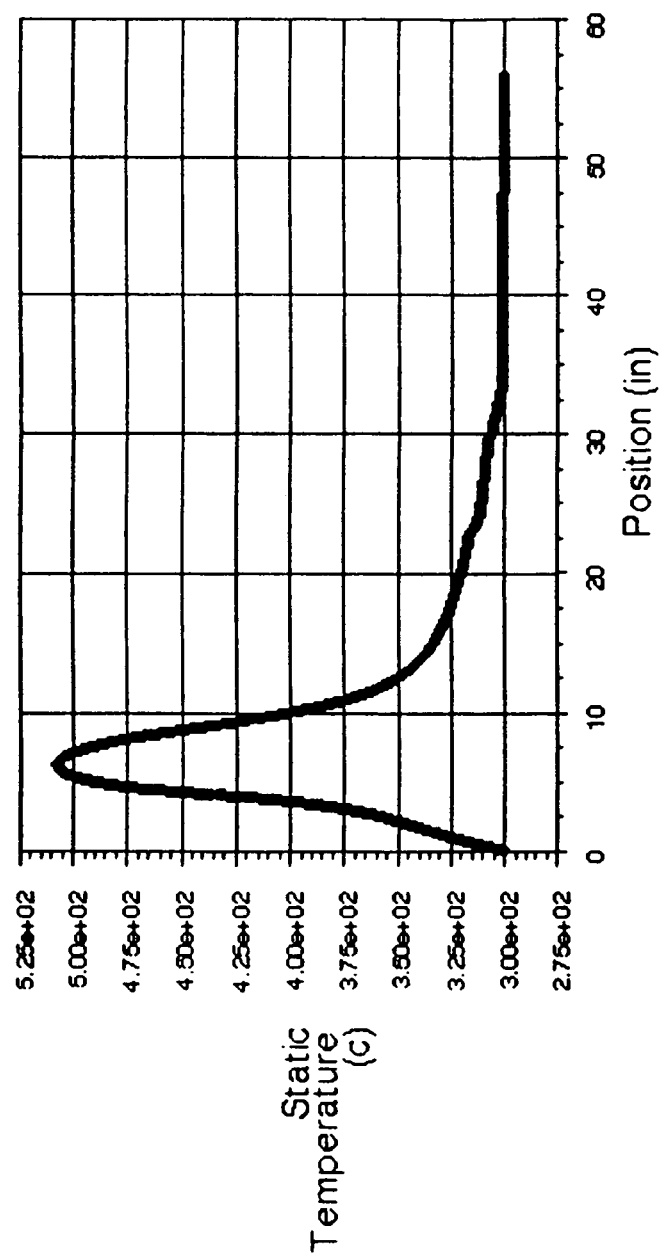

FIG. 110 is a plot of the center line temperature profile along the reactor length for the packed bed reactor disclosed in Example 11. The catalyst is catalyst B, which is disclosed in the example.

Figure 111:
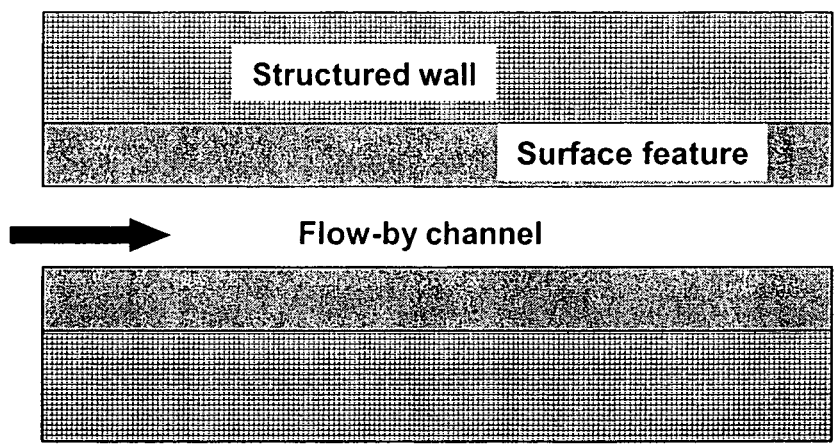

FIG. 111 is a schematic illustration of the reactor disclosed in Example 13.

Figure 112:
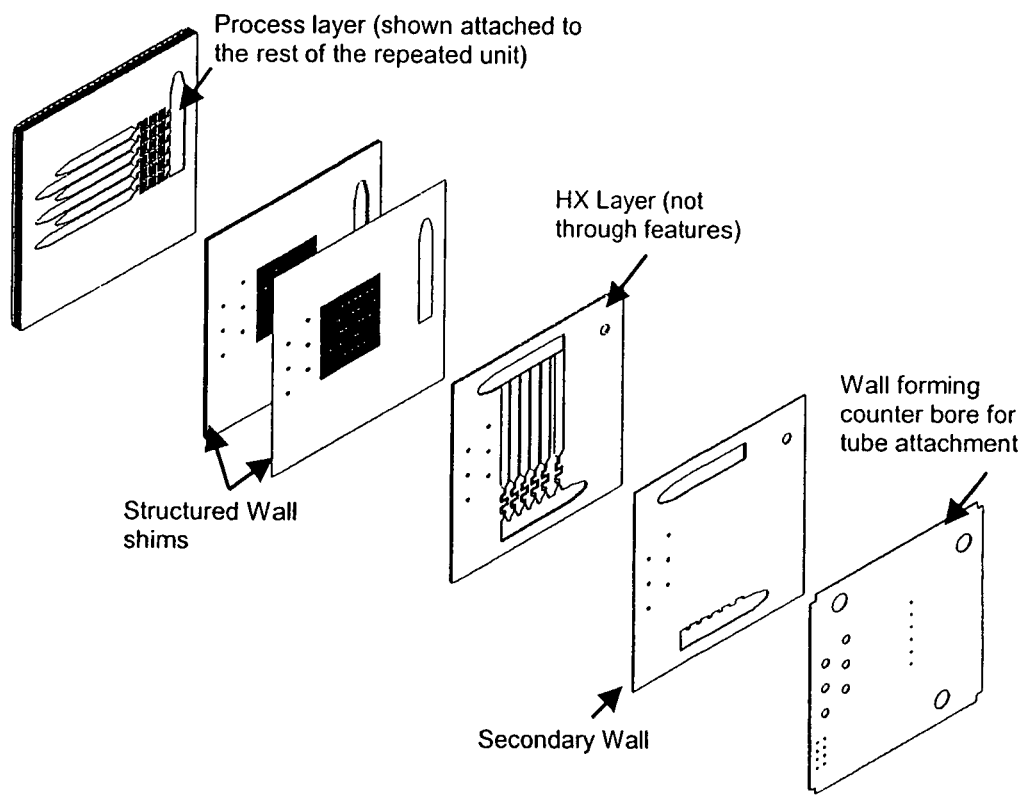
Figure 113:
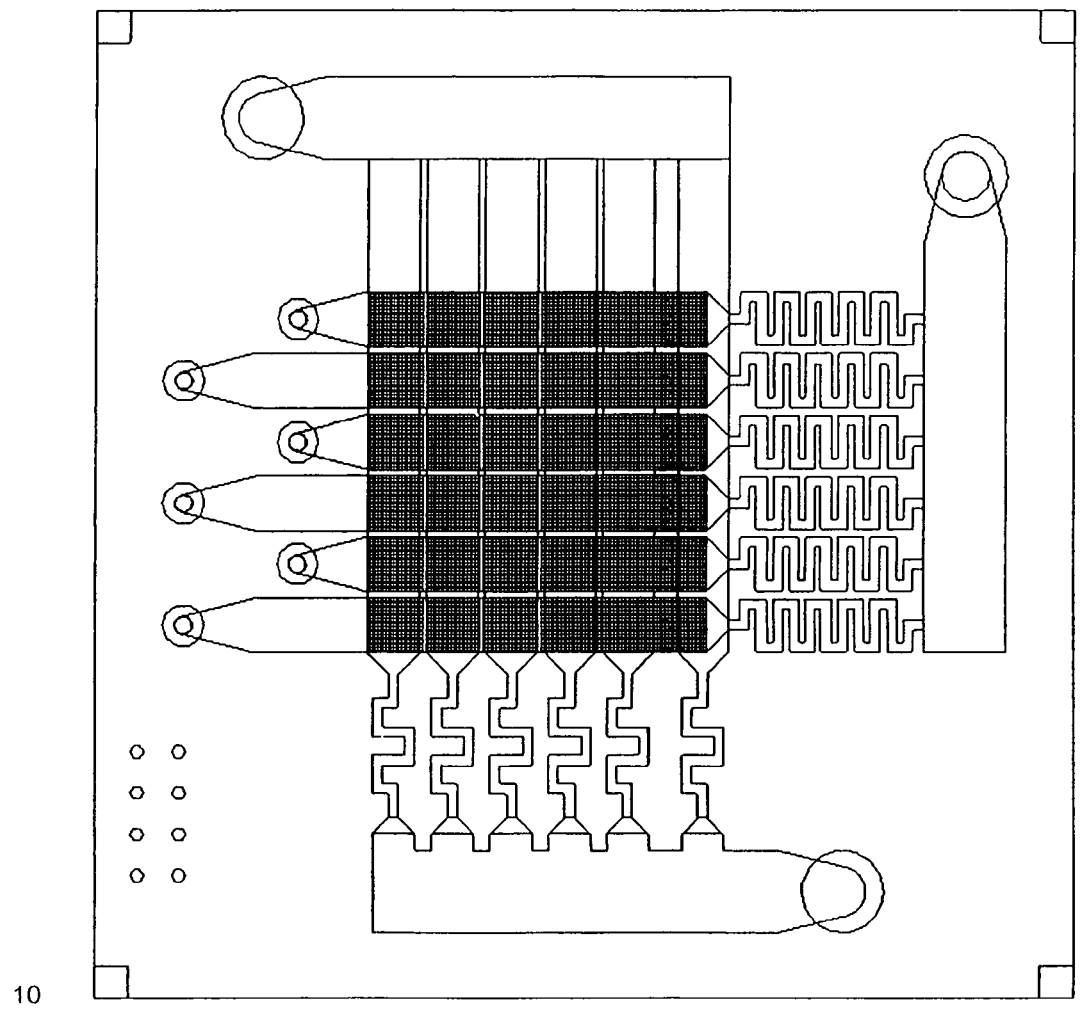
Figure 114:
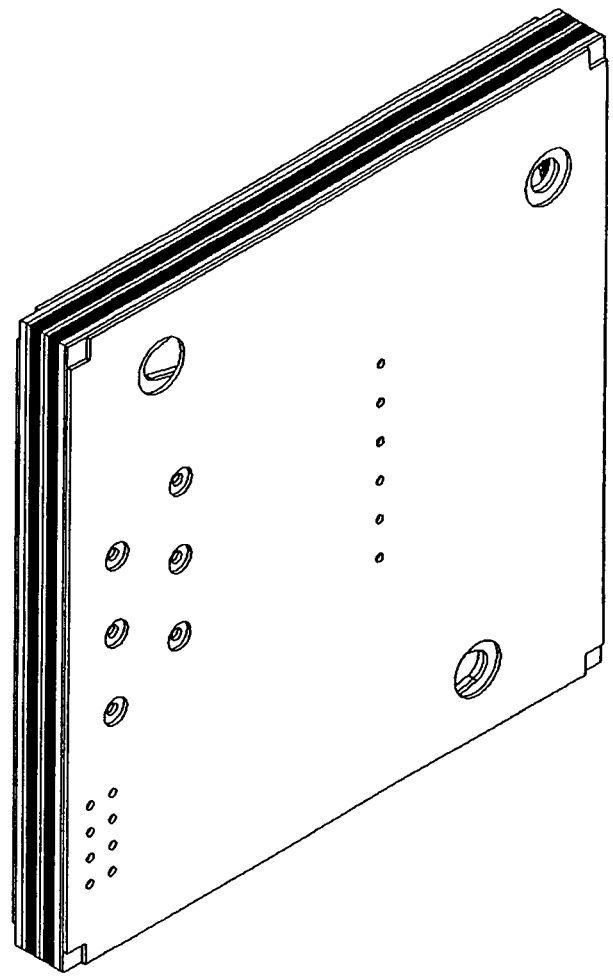

FIGS. 112-114 are schematic illustrations of a device for evaluating multiple catalysts on a porous wall within a microchannel reactor. The device is discussed in Example 14.

Figure 115:
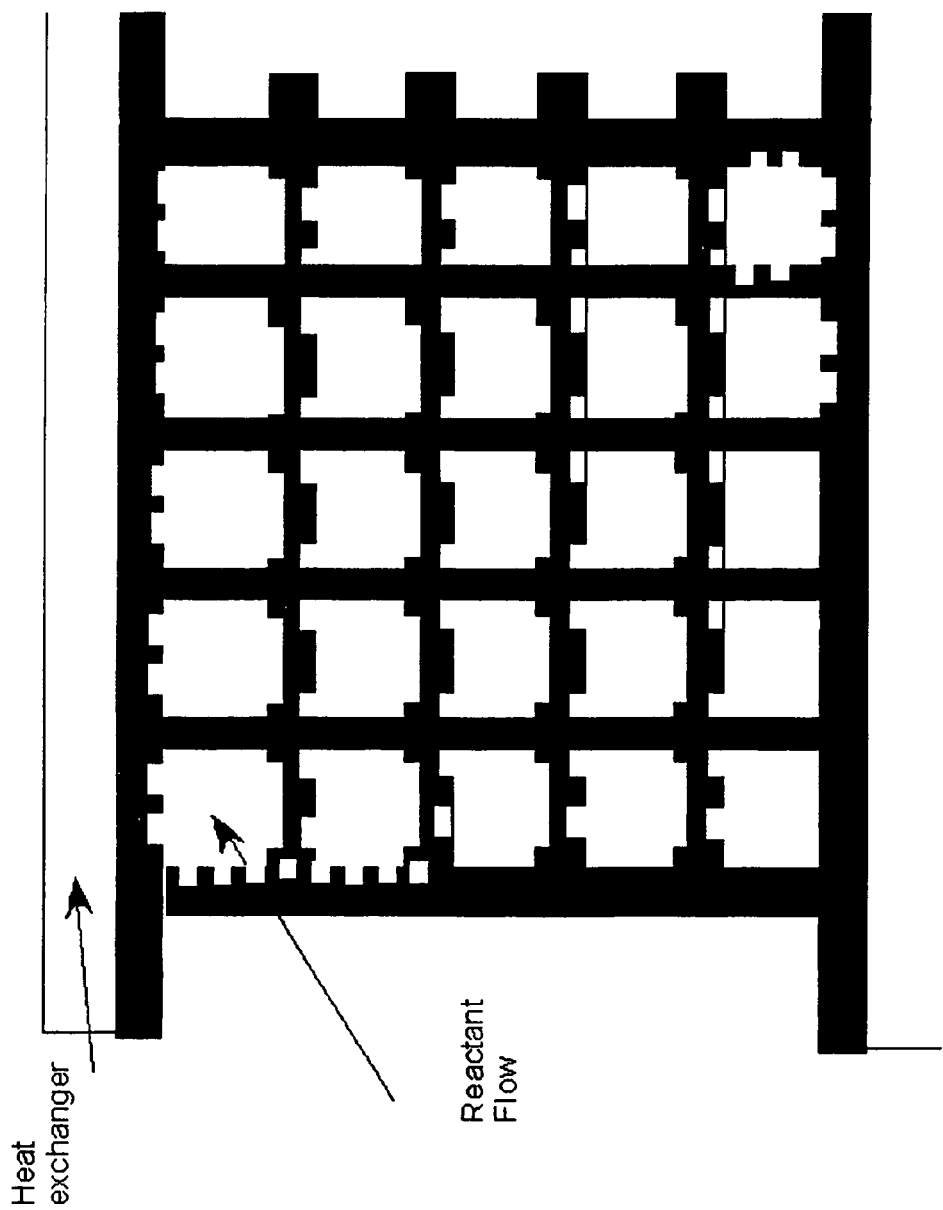

FIG. 115 is a schematic illustration of flow-through catalyst support.

DETAILED DESCRIPTION

The term "porous" or "porosity" may refer to a material that is sufficiently porous to permit fluid to flow or diffuse into and out of the support and/or flow in or through the support.

The term "porous support" may refer to a support structure for a catalyst or a sorption medium having a pore volume in the range from about 1% to about 99%, and in one embodiment in the range from about 5% to about 98%, and in one embodiment in the range from about 30% to about 95%. In one embodiment, at least about 20%, and in one embodiment at least about 50% of the pore volume may comprise pores in the average size (diameter) range from about 0.1 to about 700 microns, and in one embodiment from about 0.3 to about 500 microns, and in one embodiment from about 1 to about 200 microns. Pore volume and pore size distribution may be measured by Mercury porisimetry and nitrogen adsorption or SEM analysis of the resulting structure. Mercury porisimetry and nitrogen adsorption are complementary techniques with mercury porisimetry being more accurate for measuring large pore sizes (larger than about 30 nm) and nitrogen adsorption more accurate for small pores (less than about 50 nm). Pore sizes in the range from about 0.1 to about 700 microns may be of sufficient dimension to enable molecules to diffuse through the porous material using molecular versus Knudsen diffusion. The porosity may be geometrically regular or geometrically tortuous or random. The porous support may be thermally conductive. The porous support may comprise a support strip having a front or first surface and a back or second surface. The support strip may comprise a shim. The support strip may be made of a thermally conductive material. The support strip may have a plurality of microgrooves formed in either one or more surfaces of the support strip. The microgrooves may penetrate part way through or all the way through the support strip. When the microgrooves are formed on both sides of the support strip, the microgrooves from one side may intersect microgrooves from the other side with the result being the formation of a plurality of openings or through holes in the support strip. The porous support may comprise a single layered microgrooved support strip, or a plurality of the microgrooved support strips stacked one above another or positioned side by side to form a microgrooved composite structure. The plurality of microgrooved support strips may be connected with a fluid passageway such that a fluid may flow or diffuse to multiple layers. The fluid passageway may be connected through all or part of the stack of microgrooved support strips at different points along the length of the microgrooved support strips. It may be advantageous to have a fluidic connection through different portions of the stack of microgrooved support strips for different parts of the reactor to tailor the reaction temperature profile and resulting conversion, selectivity, and productivity of the assembled microchannel reactor. The porous support may comprise a porous thermally conductive coating layer applied to one or more interior surfaces of a microchannel. Multiple zones of differing surface area to volume ratio may exist within the porous support along the length of the microchannel and along the depth (or thickness) of the porous support.

The term "porous catalyst" may refer to a catalyst supported by a porous support. The porous catalyst may be in the form of a flow-by catalyst or a flow-through catalyst. The porous support of a porous catalyst may be referred to as a first catalyst structure. The active catalyst or active catalytic material supported by the porous support may be referred to as a second catalyst structure. The second catalyst structure may comprise a mesoporous layer, a microporous layer, or both. The pore size of the mesoporous and microporous layers may be smaller than the size of the first porous support. Molecules may diffuse via Knudsen diffusion in the mesoporous and microporous layers. For some mesoporous layers, the pore size may be intermediate and large enough for molecular diffusion rather than Knudsen diffusion. In one embodiment, one or more reactants may flow into or diffuse into the porous catalyst, contact the active catalyst supported by the porous support, and react to form one or more products. The one or more products may flow out of or diffuse out of the porous catalyst.

The term "porous sorption medium" may refer to a sorption medium supported by a porous support. In one embodiment, the porous sorption medium may comprise a sorption medium supported by a porous support wherein the porous support comprises a single layer comprising a microgrooved or surface treated support strip.

The term "shim" may refer to a planar or substantially planar sheet or plate. The thickness of the shim may be the smallest dimension of the shim and may be up to about 5 mm, and in one embodiment in the range from about 0.01 to about 2 mm, and in one embodiment in the range of about 0.05 to about 1 mm, and in one embodiment in the range from about 0.05 to about 0.5 mm. The shim may have any length and width.

Figure 1:
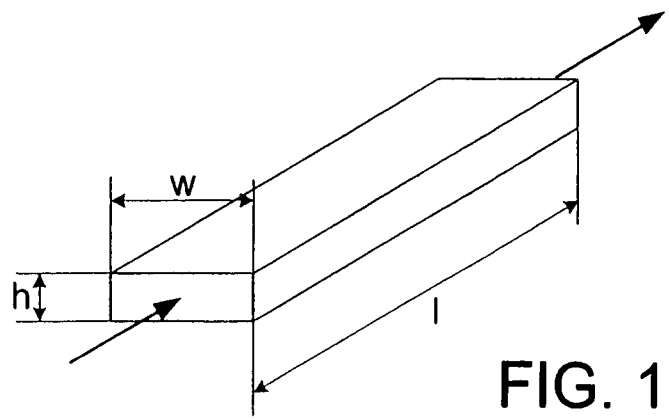
FIG. 1 is a schematic illustration of a microchannel that may be used in the disclosed microchannel reactor or microchannel separator.

The term "microchannel" may refer to a channel having at least one internal dimension of height or width of up to about 10 millimeters (mm), and in one embodiment up to about 5 mm, and in one embodiment up to about 2 mm, and in one embodiment up to about 1 mm. An example of a microchannel that may be used is illustrated in FIG. 1. Referring to FIG. 1, the illustrated microchannel has a height (h), width (w) and length (l). Fluid may flow through the microchannel in the direction indicated by the arrows. Both the height (h) and width (w) are perpendicular to the bulk flow of fluid through the microchannel. One of the dimensions of height (h) or width (w) may be in the range from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other dimension of height (h) or width (w) may be of any dimension, for example, up to about 3 meters, and in one embodiment from about 0.01 to about 3 meters, and in one embodiment from about 0.1 to about 3 meters. The length (l) of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. Although the microchannel illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "process microchannel" may refer to a microchannel containing a catalyst or a sorption medium. One or more reactants may flow in the process microchannel, contact the catalyst and react to form one or more products. A fluid mixture may flow into the process microchannel, contact the sorption medium, and separate into separate fluid components.

The term "microgroove" may refer to a groove in a substrate having a depth of up to about 2000 microns, and in one embodiment in the range from about 1 to about 1000 microns, and in one embodiment in the range from about 1 to about 2000 microns, and in one embodiment in the range from about 1 to about 500 microns, and in one embodiment in the range from about 1 to about 200 microns, and in one embodiment in the range from about 1 to about 100 microns. The width may be in the range up to about 50 cm, and in one embodiment in the range from about 0.1 micron to about 50 cm, and in one embodiment in the range from about 0.1 micron to about 10 cm, and in one embodiment in the range from about 1 micron to about 1 cm, and in one embodiment in the range from about 1 to about 1000 microns, and in one embodiment in the range from about 1 to about 100 microns. The depth may be measured at the deepest point of penetration into the substrate. The width may be the width measured at the widest point of the microgroove that is orthogonal to the direction of flow. The microgroove may have any length, for example, up to about 10 cm, and in one embodiment from about 0.1 micron to about 1 cm. The length may be defined as being parallel to flow. The microgroove may have a cross section of any shape. These may include square, rectangle, vee, semi-circle, dovetail and trapezoid. The shape and/or size of the cross section of the microgroove may vary over the length of the microgroove. The microgroove may have a depth, width and length. The width of a vee shaped microgroove may be measured at the top of the groove and this dimension would be the width of the microgroove at its widest dimension. The depth of a vee shaped microgroove may be measured at the bottom of the vee and this would be the deepest point of penetration for the vee shaped microgroove. The microgrooves having tapered sides (e.g., dovetail, trapezoid) may have widths at the bottom of the groove and widths at the top of the groove that are different. The widest of these widths would be the width at its widest dimension.

The term "structured wall" or "SW" may refer to an interior channel wall, for example, a microchannel wall, with one or more porous supports positioned or mounted on its surface. A single layer or two or more layers of microgrooved support strips stacked one above another or positioned side by side may be positioned or mounted on the channel wall. A catalyst or sorption medium may be supported by the porous support.

The term "structured wall reactor" may refer to a microchannel reactor comprising at least one process microchannel wherein the process microchannel contains one or more structured walls. A catalyst may be supported by the porous support of the structured wall. A gap may be positioned in the process microchannel adjacent the structured wall.

The term "pillar structure" may refer to any porous support which has substantially the same pattern of solid material and open area extending through the entire thickness (smallest dimension) of the porous support.

The term "heat source" may refer to a substance or device that gives off heat and may be used to heat another substance or device. The heat source may be in the form of a heat exchange channel having a heat exchange fluid in it that transfers heat to another substance or device; the another substance or device being, for example, a channel that is adjacent to and/or in thermal contact with the heat exchange channel. The heat exchange fluid may be in the heat exchange channel and/or it may flow through the heat exchange channel. The heat source may be in the form of a non-fluid heating element, for example, an electric heating element or a resistance heater. The heat source may comprise an exothermic chemical reaction or a phase changing (i.e., condensing) heat exchange fluid.

The term "heat sink" may refer to a substance or device that absorbs heat and may be used to cool another substance or device. The heat sink may be in the form of a heat exchange channel having a heat exchange fluid in it that receives heat transferred from another substance or device; the another substance or device being, for example, a channel that is adjacent to and/or in thermal contact with the heat exchange channel. The heat exchange fluid may be in the heat exchange channel and/or it may flow through the heat exchange channel. The heat sink may be in the form of a cooling element, for example, a non-fluid cooling element. The heat sink may be in the form of a Peltier electronic element. The heat sink may comprise an endothermic chemical reaction or a phase changing (i.e., boiling) heat exchange fluid.

The term "heat source and/or heat sink" may refer to a substance or a device that may give off heat and/or absorb heat. The heat source and/or heat sink may be in the form of a heat exchange channel having a heat exchange fluid in it that transfers heat to another substance or device adjacent to and/or in thermal contact with the heat exchange channel when the another substance or device is to be heated, or receives heat transferred from the another substance or device adjacent to or in thermal contact with the heat exchange channel when the another substance or device is to be cooled. The heat exchange channel functioning as a heat source and/or heat sink may function as a heating channel at times and a cooling channel at other times. Part or parts of the heat exchange channel may function as a heating channel while another part or parts of the heat exchange channel may function as a cooling channel.

The term "heat exchange channel" may refer to a channel having a heat exchange fluid in it that may give off heat and/or absorb heat. The heat exchange channel may be a microchannel.

The term "heat exchange fluid" may refer to a fluid that may give off heat and/or absorb heat.

The term "adjacent" when referring to the position of one channel relative to the position of another channel may mean directly adjacent such that a wall separates the two channels. This wall may vary in thickness. However, "adjacent" channels may not be separated by an intervening channel that would inhibit heat transfer between the channels. An intervening channel may be included between adjacent channels if it serves as a heat transfer medium between the two other channels. The term "adjacent" when referring to the position of a gap or an open space relative to the position of a catalyst or sorption medium may mean directly adjacent such that a fluid flowing in the gap or open space may contact the catalyst or sorption medium. The term "adjacent" also may include the cases when a non-equal number of mass transfer or reaction channels and heat exchange channels may be used. For example, two reaction channels may be next to each other and heat exchange channels may be on the outside of the two adjacent reaction channels. In one embodiment, three reactions channels may be adjacent to each other and one or two heat exchange channels may flank the reaction channels on the outside. In an alternate embodiment, four, five or more reaction channels may be flanked by one or two heat exchange channels. These arrangements may be repeated to achieve any number of channels in a large capacity device.

The term "heat transfer wall" may refer to a common wall between a process microchannel and an adjacent heat exchange channel where heat transfers from one channel to the other through the common wall. The heat transfer wall may have an assembly of one or more microgrooved support strips or shims in thermal contact to enhance heat transfer in the heat exchange channel.

The term "thermal contact" may refer to two bodies, for example two channels, that may not necessarily be in contact with each other or adjacent to each other but still may exchange heat with each other. One body in thermal contact with another body may heat or cool the other body.

The term "fluid" may refer to a gas, a liquid, or a gas or a liquid containing dispersed solids, or a mixture thereof. The fluid may be in the form of a gas containing dispersed liquid droplets. The fluid may be in the form of a liquid containing dispersed gas bubbles.

The term "microchannel reactor" may refer to an apparatus comprising at least one process microchannel containing at least one porous catalyst. The catalyst may be a flow-by catalyst or a flow-through catalyst. The catalyst may have an adjacent gap or open area forming a bulk flow path for reactants to flow in and contact the catalyst. Part or all of the reactants may diffuse into the porous catalyst and react to form one or more products. The products may diffuse out of the catalyst back into the bulk flow path and flow out of the process microchannel. The microchannel reactor may comprise a plurality of the process microchannels that may be operated in parallel, a header or manifold assembly for providing for the flow of fluid into the process microchannels, and a footer or manifold assembly providing for the flow of fluid out of the process microchannels. The microchannel reactor may further comprise at least one heat source and/or heat sink. The heat source and/or heat sink may comprise one or more heat exchange channels, for example one or more heat exchange microchannels, adjacent to and/or in thermal contact with the process microchannels for cooling and/or heating the fluids in the process microchannels. The microchannel reactor may be in the form of a staged addition reactor wherein second reactant stream channels may be positioned adjacent to the process microchannels.

The term "ICR" or "integrated combustion reactor" may refer to a reactor that comprises at least one combustion chamber adjacent to at least one reaction chamber. Either or both chambers may comprise one or more microchannels. A catalyst may be positioned in one or more of the microchannels of the combustion chamber and/or the reaction chamber. The catalyst in either or both chambers may be a porous catalyst. The catalyst may have an adjacent gap or open area forming a bulk flow path for fluid to flow by and contact the catalyst. A reactant may enter the microchannel and flow in the bulk flow path in contact with the catalyst. When the catalyst is a porous catalyst, part or all of the reactant may diffuse into the porous catalyst and react to form one or more products. The one or more products may diffuse back into the bulk flow path and flow out of the channel.

The term "microchannel separator" may refer to an apparatus comprising at least one process microchannel containing a porous sorption medium. The microchannel separator may be used to separate one or more fluids from a fluid mixture containing the one or more fluids. The microchannel separator may comprise a plurality of process microchannels that may be operated in parallel, a header or manifold assembly for providing for the flow of fluid into the process microchannels, and a footer or manifold assembly providing for the flow of fluid out of the process microchannels. The microchannel separator may comprise a heat source and/or heat sink, for example, one or more heat exchange channels, in thermal contact with the process microchannels for cooling and/or heating the contents of the process microchannels. The heat exchange channels may be microchannels.

The term "surface feature" may refer to a depression in a microchannel wall and/or a projection from a microchannel wall that modifies flow and/or mixing within the microchannel. The surface features may be in the form of circles, spheres, frustrums, oblongs, squares, rectangles, angled rectangles, checks, chevrons, vanes, air foils, wavy shapes, and the like. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. Examples are illustrated in FIGS. 20-28 and 41-43. The surface features may be formed on or in one or more of the interior walls of a microchannel. The surface features may be formed on or adjacent to porous supports, porous catalysts or a porous sorption medium. The surface features may be referred to as passive surface features or passive mixing features. The surface features may be used to disrupt laminar flow streamlines and create advective flow at an angle to the bulk flow direction. This may enhance heat exchange, mass exchange and/or enhance contact between reactants and catalysts or fluid mixtures and sorption medium.

The term "residence time," which may also be referred to as the "average residence time," may be the internal volume of a channel occupied by a fluid flowing through the channel divided by the average volumetric flowrate for the fluid flowing through the channel at the temperature and pressure being used.

The terms "upstream" and "downstream" may refer to positions within a channel (e.g., a process microchannel) that is relative to the direction of flow of a fluid stream in the channel. For example, a position within the channel not yet reached by a portion of a fluid stream flowing toward that position would be downstream of that portion of the fluid stream. A position within the channel already passed by a portion of a fluid stream flowing away from that position would be upstream of that portion of the fluid stream. The terms "upstream" and "downstream" do not necessarily refer to a vertical position since the channel used herein may be oriented horizontally, vertically or at an inclined angle.

The term "sorb" may refer to adsorption and/or absorption.

The terms "standard cubic feet" or "standard cubic meters" may refer to volumes measured at a temperature of 0° C. and atmospheric pressure.

The term "standard liters" or "normal liters" may refer to volumes measured at a temperature of 0° C. and atmospheric pressure.

The term "gauge pressure" may refer to absolute pressure, less atmospheric pressure. For example, a gauge pressure of zero atmospheres corresponds to atmospheric pressure. However, throughout the text and in the appended claims, unless otherwise indicated, all pressures are absolute pressures.

The term "psi" may refer to pounds per square inch. The term "psig" may refer to pounds per square inch gauge pressure.

The term "conversion" of a reactant may refer to the change between the moles or molar flow of the reactant at the inlet (or before reaction) and the moles or molar flow of the reactant at the outlet (or in the product after reaction) divided by the moles or molar flow of the reactant at the inlet.

The term "cycle" may refer to a single pass of the reactants through the microchannel reactor.

The term "ml (milliliter) per gram of catalyst per hour" may refer to a volume (ml) of product produced per gram of catalyst per hour wherein the gram of catalyst refers to catalytic material in the catalyst but not any support that may be present.

The term "yield" may refer to moles of reactant converted to a specific product divided by the number of moles of reactant converted. The yield may be calculated by multiplying the conversion of the reactant by the selectivity to the product in question.

The term "unit operation" may refer to a unit or apparatus wherein a chemical reaction, mixing, vaporization, condensation, compression, separation, distillation, condensation, heating and/or cooling may be conducted.

The term "bulk flow path" or "bulk flow region" may refer to an open area or gap within a channel, e.g., a process microchannel. The bulk flow path or region may be adjacent to a catalyst or a sorption medium. A contiguous bulk flow path or bulk flow region may allow for rapid fluid flow through the channel with a relatively low pressure drop.

The term "equilibrium conversion" may refer to the maximum attainable conversion of a reactant in an equilibrium limited reaction. The equilibrium conversion may be a function of reactor temperature, pressure and/or feed composition. For example, for the case of a hydrocarbon steam reforming reaction, the equilibrium conversion may increase with increasing temperature and decrease with increasing pressure.

The term "reaction chamber" may refer to a chamber wherein a chemical reaction occurs. The reaction chamber may comprise one or more channels, for example, one or more process microchannels. The reaction may be an endothermic reaction or an exothermic reaction.

The term "reaction chamber heat flux" may refer to reaction chamber heat duty divided by reaction chamber volume. The reaction may be exothermic or endothermic.

The term "heat exchange chamber" may refer to a chamber that may give off heat and/or absorb heat. A chemical reaction may occur in the heat exchange chamber. The "heat exchange chamber" may comprise one or more microchannels. The reaction may be an endothermic reaction or an exothermic reaction.

The term "average area heat flux" may refer to a reaction chamber heat duty divided by the area of the reaction chamber heat transfer surface. The reaction chamber heat transfer surface may refer to a planar area, which may be intermittent in the case of ribs or other structures in the reaction chamber, above which there is area for flow of process fluid and below which there is a wall that separates the reaction chamber and an adjacent heat exchange chamber. This area may form a path for heat transfer between the reaction chamber and the heat exchange chamber. A chemical reaction of opposite thermicity to the reaction conducted in the reaction chamber may be conducted in the heat exchange chamber.

The term "heat flux intensity" may refer to the average area heat flux divided by the absolute value of the average temperature difference across the thickness of the heat transfer wall (in the direction of heat flow), that is, flux/dT.

The term "mass flux intensity" may refer to the number of moles of reactant converted per heat transfer surface area.

The term "heat transfer surface area" may refer to the area of a plane that separates a process microchannel and an adjacent heat exchange channel. The term "heat transfer surface area" may refer to the area of a plane that separates an endothermic chamber or channel from an adjacent to exothermic chamber or channel.

The term "endothermic chamber" or "endothermic channel" may refer to a chamber or channel with a fluid in the chamber or channel that absorbs heat from another chamber or channel in thermal contact with the endothermic chamber or channel. If an endothermic reaction occurs in the endothermic chamber or channel, it may be referred to as an "endothermic reaction chamber" or "endothermic reaction channel."

The term "exothermic chamber" or "exothermic channel" may refer to a chamber or channel with a fluid in the chamber or channel that transfers heat to another chamber or channel in thermal contact with the exothermic chamber or channel. If an exothermic reaction occurs in the exothermic chamber or channel, it may be referred to as an "exothermic reaction chamber" or an "exothermic reaction channel."

The term "reaction channel" may refer to a channel wherein a chemical reaction occurs. The reaction channel may be an endothermic reaction channel or an exothermic reaction channel.

The term "web" may refer to a wall that separates a reaction channel or chamber and an adjacent heat exchange channel or chamber.

The terms "tortuous" or "tortuosity" may refer to the ratio of the length of a diffusion path for a fluid flowing through a porous support, porous catalyst or porous sorption medium to the thickness of the porous support, porous catalyst or porous sorption medium. A tortuosity value of 1.0 refers to a straight line path. Tortuosity values higher than 1.0 refer to paths that are not straight line paths. A tortuosity of 5, for example, implies that the molecules need to diffuse a length equal to 5 times the linear or straight line distance between two points.

The term "volume" may refer to the internal volume of a channel (e.g., a process microchannel). The internal volume may include an open area or gap for fluid flow that may be adjacent to a catalyst or sorption medium, but may not include the catalyst or sorption medium volume. The volume may include volume within surface features that may be positioned in the channel.

The term "open channel" or "flow-by channel" or "open path" may refer to a channel (e.g., a microchannel) with a gap of at least about 0.01 mm that extends all the way through the channel such that fluid may flow through the channel with relatively low pressure drop. The gap may extend up to about 10 mm.

The term "contact time" may refer to the volume in an open channel divided by the volumetric feed rate into the channel at standard conditions.

The term "standard conditions" may refer to a temperature of 0° C. and atmospheric pressure.

The term "space velocity" may refer to the inverse of contact time. That is, space velocity=1/CT where CT is contact time.

The term "approach to equilibrium conversion" or "approach to theoretical conversion" may refer to the measured or predicted conversion in an equilibrium limited reaction of a limiting reactant to a desired product divided by the equilibrium conversion of the limiting reactant to the desired product times 100%.

The term "ultrafast reaction" may refer to a reaction wherein the contact time is less than about 4 ms, and in one embodiment in the range from about 0.4 to about 4 ms; the heat flux may be greater than about 10 W/cm$^2$, and in one e embodiment in the range from about 10 to about 100 W/cm$^2$; the pressure drop may be less than about 15 atmospheres per meter, and in one embodiment less than about 13.8 atmospheres per meter. In one embodiment, the reaction may be an equilibrium limited reaction and the approach to equilibrium conversion may be greater than about 75%.

The term "cross-sectional area" or "an area of a cross-section" of a channel (e.g., process microchannel) may refer to an area measured perpendicular to the direction of the bulk flow of fluid in the channel and may include all areas within the channel including any catalyst or sorption medium that may be present (e.g., catalyst particles, catalyst monolith and/or catalyst wall coating), but does not include the channel walls. For channels that curve along their length, the cross-sectional area may be measured perpendicular to the direction of bulk flow at a selected point along a line that parallels the length and is at the center (by area) of the channel. The term "a cross sectional area varies" may mean that there is a significant variation in cross sectional area within the channel, not merely a variation in surface roughness of an interior wall within the channel. Dimensions of height and width may be measured from one channel wall to the opposite channel wall. These dimensions may not be changed by application of a coating to the surface of the wall. These dimensions may be average values that account for variations caused by surface roughness, corrugations, and the like.

The term "graded catalyst" may refer to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel; or a lower concentration of catalytically active metal nearer the center (i.e., midpoint) of a process microchannel and a higher concentration nearer a process microchannel wall, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. The graded catalyst may also be achieved by changing the size of the microgrooves in the microgrooved strips such that the surface area to volume ratio is higher or lower in different parts of the reactor followed by the application of the same catalyst coating everywhere or a hybrid combination of the preceding embodiments. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "mm" may refer to millimeter. The term "nm" may refer to nanometer. The term "ms" may refer to millisecond. The term "µs" may refer to microsecond. The term "µm" may refer to micron.

The porous support may be used to support a catalyst in a microchannel reactor or a sorption medium in a microchannel separator. A microchannel wall with a porous support on the wall may be referred to as a structured wall (SW). An example of a suitable microchannel reactor is illustrated in FIG. 2. Referring to FIG. 2, microchannel reactor 100 may include microchannel reactor core 110, header or manifold assembly 120, and footer or manifold assembly 130. The microchannel reactor core 110 may comprise a plurality of repeating units that may be operated in parallel, each repeating unit comprising at least one process microchannel. In one embodiment, the microchannel reactor 100 may be a staged addition reactor and each repeating unit may further comprise at least one second reactant stream channel positioned adjacent to the process microchannel. The header or manifold assembly 120 provides for the flow of reactants into the process microchannels, and in one embodiment the second reactant stream channels. The footer or manifold assembly 130 provides for the flow of product out of the process microchannels. The microchannel reactor core 110 may further comprise a heat source and/or heat sink in thermal contact with the process microchannels. The heat source and/or heat sink may comprise one or more heat exchange channels in thermal contact with the process microchannels, and in one embodiment the second reactant stream channels. The heat exchange channels may be microchannels. When the reaction that is conducted in the process microchannels is an exothermic reaction, the heat exchange channels may be used to provide cooling to the process microchannels. When the reaction that is conducted in the process microchannels is an endothermic reaction, the heat exchange channels may be used to provide heat to the process microchannels. Various combinations of heating and cooling may be employed to provide for desired temperature profiles within and along the length of the process microchannels, and in one embodiment along the length of the second reactant stream channels. Each of the process microchannels may contain one or more porous catalysts. In operation, two or more reactants may flow into the microchannel reactor core 110 as indicated arrows 122 and 124. The reactants may be mixed upstream of the microchannel reactor 100, in the header or manifold assembly 120, or in the process microchannels within the microchannel reactor core 110. Within the process microchannels, the reactants may be mixed with each other upstream of a reaction zone containing the catalyst or in the reaction zone containing the catalyst. The reactants may be mixed partly upstream of the reaction zone containing the catalyst and partly in the reaction zone. The reactants may undergo reaction in the process microchannels to form the product. The product may flow through the footer or manifold assembly 130 and out of the microchannel reactor 100 as indicated by arrow 132. Heat exchange fluid may enter the microchannel reactor core 110, as indicated by arrow 134, circulate through heat exchange channels in the microchannel reactor core 110, heat and/or cool the process microchannels, and flow out of the microchannel reactor core 110, as indicated by arrow 136.

The microchannel reactor 100 may be used to conduct any chemical reaction that may involve one or more fluid reactants and one or more catalysts. The reactions that may be conducted may include one or more of the following reactions: acetylation addition, acylation, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, water-gas shift, dehalogenation, dimerization, epoxidation, esterification, Fischer-Tropsch reaction, halogenation, hydrohalogenation, homologation, hydration, dehydration, hydrogenation, dehydrogenation, oxidative dehydrogenation, hydrocarboxylation, hydroformylation, hydrogenolysis, hydrometallation, hydrosilation, hydrolysis, hydrotreating, isomerization, methylation, demethylation, metathesis, methanol synthesis, nitration, oxidation, partial oxidation, polymerization, reduction, reformation, steam methane reforming reaction, reverse water gas shift, sulfonation, telomerization, transesterification, dimerization, trimerization, oligomerization, Sabatier reaction, carbon dioxide reforming, preferential oxidation, preferential methanation, or a combination of two or more of the foregoing reactions.

An endothermic reaction that may be conducted in the microchannel reactor 100 is steam reforming in which water (steam) and a hydrocarbon (or hydrocarbons) are reacted to form hydrogen and carbon oxides. A variety of hydrocarbons may be reformed to produce hydrogen, including methane, ethane, propane, butane, isobutane, higher alkanes, cycloalkanes, alkenes, aromatics, alcohols, ethers, ketones, and the like including blends and mixtures such as gasoline, diesel, kerosene, and the like.

In one embodiment, oxidative dehydrogenation may be used to convert ethylbenzene to styrene.

An example of a microchannel separator that may be used is illustrated in FIG. 3. Referring to FIG. 3, microchannel separator 200 may include microchannel separator core 210, header or manifold assembly 220, and footer or manifold assembly 230. The microchannel separator core 210 may comprise a plurality of process microchannels that may be operated in parallel. The header or manifold assembly 220 provides for the flow of fluid into the process microchannels. The footer or manifold assembly 230 provides for the flow of fluid out of the process microchannels. Heat exchange channels may be used to provide for the flow of cold heat exchange fluid and hot exchange fluid in the microchannel separator core 210. Each of the process microchannels may contain one or more of the porous supports with a sorption medium supported by the porous support. The microchannel separator may be operated as a temperature swing adsorption (TSA) device. In operation, a fluid mixture flows through the header or manifold assembly 220 into the microchannel separator core 210 as indicated by arrow 222. The fluid mixture flows through the header or manifold assembly into the process microchannels where it contacts the porous sorption medium. A cold heat exchange fluid flows through the microchannel separator core 210 as indicated by arrows 240 and 242 causing the sorption medium and the fluid in the process microchannel to cool to a desired cold temperature. At the desired cold temperature, a first fluid from the fluid mixture may be preferentially sorbed by the porous sorption medium. The remaining components of the fluid mixture may be removed from the microchannel separator core 210 as indicated by arrow 232. The microchannel separator core 210 may then be heated by flowing a heated heat exchange fluid through the microchannel separator core 210 as indicated by arrows 244 and 246. The heating of the microchannel separator core 210 results in the heating of the process microchannels and the porous sorption medium. This may cause the sorbed first fluid to desorb from the sorption medium. The desorbed first fluid flows out of the microchannel separator core 210 as indicated by arrow 238.

The sorption step may be continued until a desired loading of the sorption medium by the first fluid is achieved. The desired loading level may be in the range from about 0.001 to about 1 gram of the first fluid per gram of porous sorption medium, and in one embodiment from about 0.01 to about 0.1 gram of the first fluid per gram of sorption medium. At the end of this sorption step the non-sorbed parts of the fluid mixture may be removed from the process microchannels. During the sorption step, the average sorbent temperature within the process microchannels may be in the range from about −40° C. to about 200° C., and in one embodiment from about −40° C. to about 150° C., and in one embodiment from about 0° C. to about 100° C., and in one embodiment about 20° C. to about 60° C., and in one embodiment from about 20° C. to about 45° C., and in one embodiment about 40° C. The pressure within the process microchannels during the sorption step may be in the range from about 0.0001 to about 100 atmospheres of absolute pressure, and in one embodiment from about 0.01 to about 50 atmospheres, and in one embodiment from about 0.1 to about 30 atmospheres, and in one embodiment from about 1 to about 20 atmospheres, and in one embodiment from about 1 to about 10 atmospheres absolute pressure. The period of time for the sorption to occur may be in the range from about 0.1 to about 10 seconds, and in one embodiment about 1 to about 5 seconds. During the desorption step, the temperature within the process microchannels may be increased by about 1° C. to about 200° C., and in one embodiment from about 5° C. to about 50° C., and in one embodiment from about 10° C. to about 30° C. The time required for performing the desorbing step may be in the range from about 0.1 to about 10 seconds, and in one embodiment from about 1 to about 5 seconds.

The microchannel separator 200 may be used to separate any fluid component from any fluid mixture containing the fluid component. Examples of such separations may include oxygen from air, olefins (e.g., ethylene) from mixtures of olefins and paraffins (e.g., ethane), and the like. The fluid components that may be separated or purified may include oxygen, hydrogen, nitrogen, $NO_x$ (e.g., NO, $NO_2$), CO, $CO_2$, $H_2S$, HCN, $SO_2$, $CH_3SCH_3$, olefins (e.g., ethylene), paraffins (e.g., ethane), aromatic compounds (e.g., benzene), isomers, halogenated compounds (e.g., chlorides), nitrates, sulfates, sugars, esters, alcohols, ethers, nitro compounds, hydroxylamines, or mixtures of two or more thereof. The microchannel separator 200 may be used to separate nitrogen from methane. The microchannel separator 200 may be used in a process for upgrading sub-quality methane gas wherein the microchannel separator is used to separate out nitrogen. The microchannel separator may be used to provide simultaneous or sequential reaction and separation of one or more reaction products. The means of separation may include sorption as well as separations comprising distillation, absorption and/or phase separation.

Figure 4:
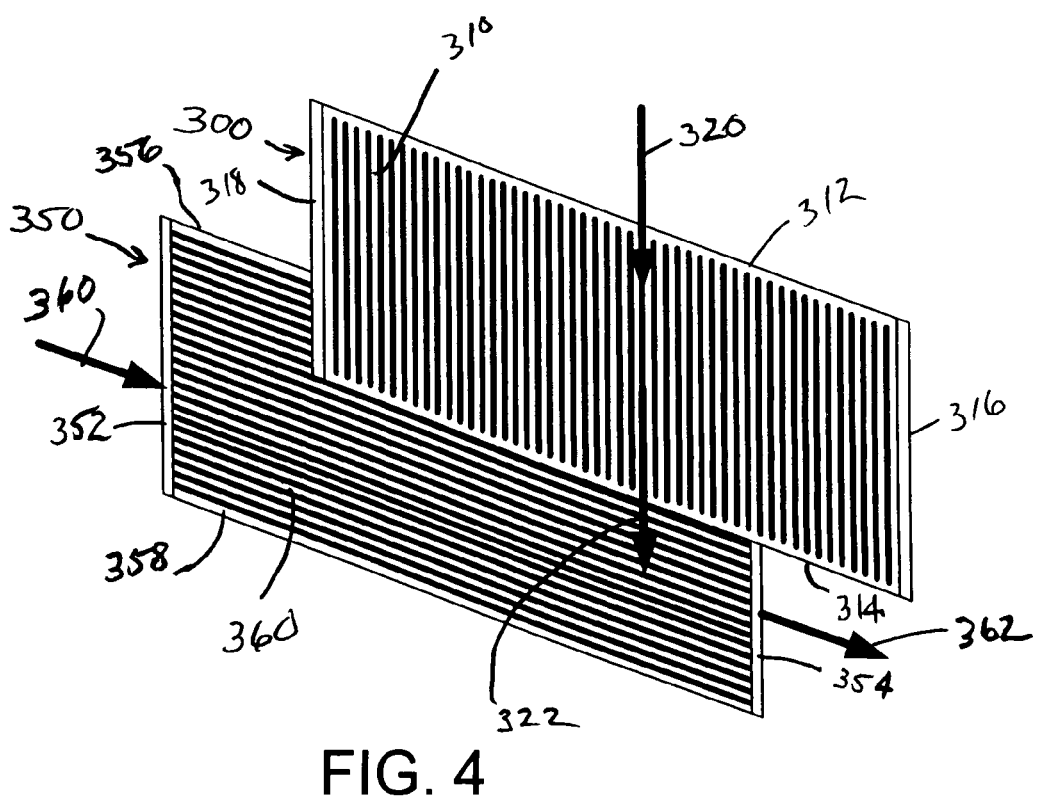
FIG. 4 is a schematic illustration of a layer of process microchannels and a layer of heat exchange channels that may be used in the microchannel reactor illustrated in FIG. 2 or the microchannel separator illustrated in FIG. 3. Each of the process microchannels may contain one or more porous supports. The supports may support a catalyst for the microchannel reactor or a sorption medium for the microchannel separator.

The microchannel reactor core 110 and microchannel separator core 210 may contain repeating units comprising layers 300 of process microchannels and layers 350 of heat exchange channels aligned side by side as illustrated in FIG. 4. Alternately, the layers 300 and 350 may be stacked one above the other. The heat exchange channels may be microchannels. For each heat exchange layer 350, one or more process microchannel layers 300 may be used. Thus, for example, two, three, four, five, six or more process microchannel layers 300 may be employed with a single heat exchange layer 350. Alternatively, two or more heat exchange layers 350 may be employed with each process microchannel layer 300. Process microchannel layer 300 may provide for the flow of process fluid. Heat exchange channel layer 350 may provide for the flow of heat exchange fluid. The heat exchange layers 350 may be used for heating and/or cooling. Each process microchannel layer 300 may be positioned between adjacent heat exchange microchannel layers 350. Two or more process microchannel layers 300 may be positioned adjacent to each other to form a vertically or horizontally oriented stack of process microchannel layers, and a heat exchange layer 350 may be positioned on one or both sides of the stack.

Process microchannel layer 300 may contain a plurality of process microchannels 310 aligned in parallel, each process microchannel 310 extending along the length of microchannel layer 300 from end 312 to end 314. The plurality of process microchannels 310 in the layer 300 extend along the width of the process microchannel layer 300 from end 316 to end 318. The catalyst or porous sorption medium may be contained within one or more of the process microchannels 310. The flow of process fluid through the process microchannels 310 may be in the direction indicated by arrows 320 and 322. Each of the process microchannels 310 may have a cross section having any shape, for example, a square, rectangle, circle, semi-circle, etc.

Heat exchange channel layer 350 may contain a plurality of heat exchange channels 360 aligned in parallel, each heat exchange channel 360 extending along the width of channel layer 350 from end 352 to end 354, the plurality of heat exchange channels 360 in the channel layer 350 extending along the length of channel layer 350 from end 356 to end 358 of channel layer 350. The heat exchange channels 360 may be microchannels. The heat exchange fluid may flow through the heat exchange channels 360 in the direction indicated by arrows 360 and 362. The flow of heat exchange fluid in the direction indicated by arrows 360 and 362 is cross-current to the flow of process fluid flowing through process microchannels 310, as indicated by arrows 320 and 322. Alternatively, the heat exchange channels 360 may be oriented to provide for flow of the heat exchange fluid along the length of the channel layer 350 from end 356 to end 358, or from end 358 to end 356. This would result in the flow of heat exchange fluid in a direction that would be co-current or counter-current to the flow of process fluid through the process microchannels 310. Each of the heat exchange channels 360 may have a cross section having any shape, for example, a square, rectangle, circle, semi-circle, etc.

The number of channels 310 and 360 in each of the channel layers 300 and 350 may be any desired number, for example, one, two, three, four, five, six, eight, ten, hundreds, thousands, tens of thousands, hundreds of thousands, millions, etc. Similarly, the number of channel layers 300 and 350 in the microchannel reactor core 110 or microchannel separator core 210 may be any desired number, for example, one, two, three, four, six, eight, ten, hundreds, thousands, etc.

The channels 310 and 360 may have rectangular cross sections and be aligned in side-by-side vertically oriented interleaved planes or horizontally oriented interleaved stacked planes. These planes may be tilted at an inclined angle from the horizontal. These configurations may be referred to as parallel plate configurations. An array of these rectangular channels may be arranged in a modularized compact unit for scale-up.

Figure 5A:
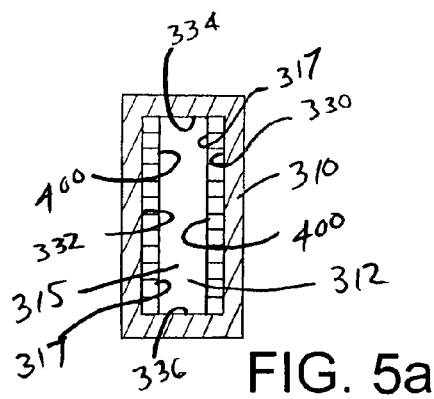
FIGS. 5(a)-5(d) show cross sections of the process microchannel illustrated in FIG. 5 taken along line 5(a-d)-5(a-d) in FIG. 5.
Figure 5B:
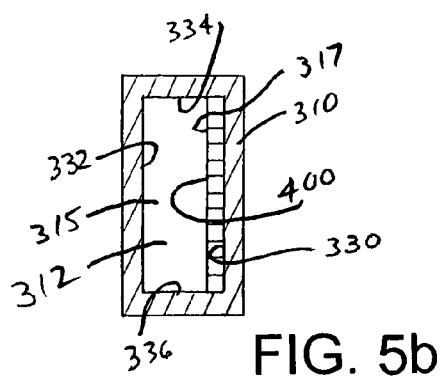
Figure 5C:
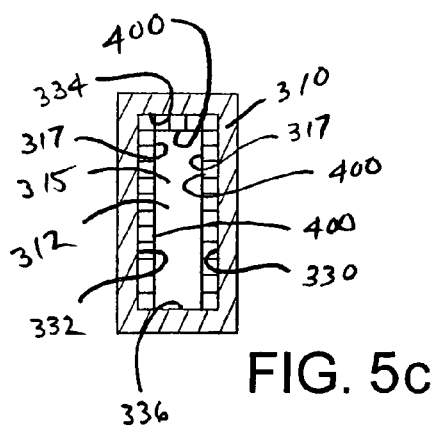
Figure 5D:
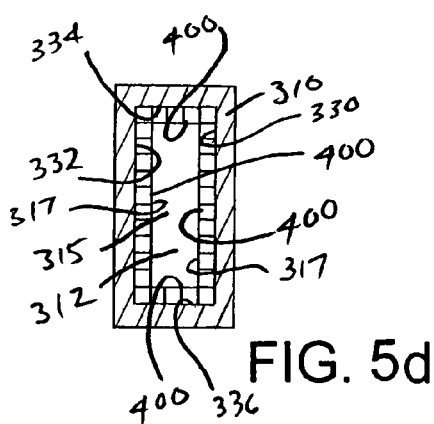
Figure 5:
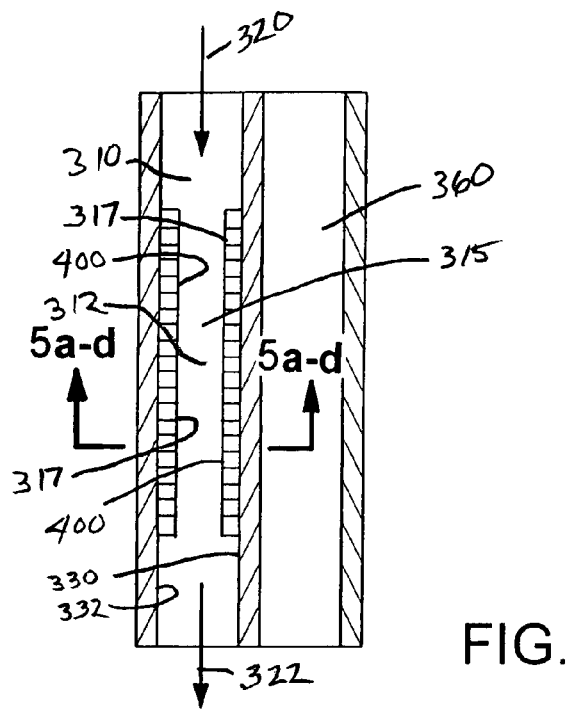
FIG. 5 is a schematic illustration of a repeating unit comprising a process microchannel and an adjacent heat exchange channel that may be used in the microchannel reactor core of the microchannel reactor shown in FIG. 2. The flow of heat exchange fluid in the heat exchange channel may be co-current or counter-current relative to the flow of process fluid in the heat exchange channels. The process microchannel contains a porous catalyst.
Figure 6:
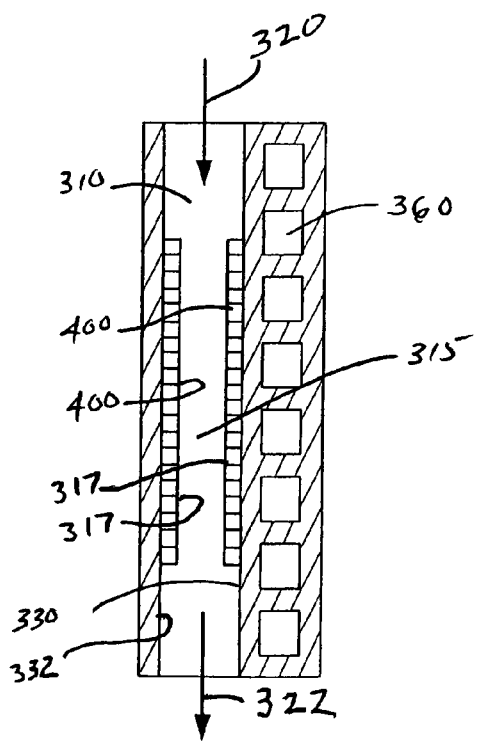
FIG. 6 is a schematic illustration of a repeating unit similar to the repeating unit illustrated in FIG. 5 except that the repeating unit in FIG. 6 contains a plurality of heat exchange channels extending lengthwise at right angles relative to the lengthwise direction of the process microchannel. The flow of heat exchange fluid in the heat exchange channels may be cross-current relative to the flow of process fluids in the process microchannel.

Repeating units that may be used in the microchannel reactor core 110 or microchannel separator core 210 are illustrated in FIGS. 5 and 6. These repeating units may comprise process microchannel 310 and porous supports 400 positioned in the microchannel. Heat exchange channel 360 is adjacent to the process microchannel 310. Referring to FIGS. 5, 5a and 6, the porous support 400 is positioned on interior walls 330 and 332 of process microchannel 310. Alternatively, the porous support 400 may be positioned on wall 330 (FIG. 5b), walls 330, 332 and 334 (FIG. 5c), or walls 330, 332, 334 and 336 (FIG. 5d). The walls with porous supports may be referred to as structured walls. Bulk flow region or gap 315 is an open space within the process microchannel 310 above the porous support 400. FIG. 5d illustrates an embodiment wherein the porous support 400 has an open path through the porous support. In one embodiment, the process microchannel 310 may contain two or more zones along the length of the channel and/or along the depth (from a side wall to the center axis) of the channel containing the porous support 400. The porous support 400 in each of these zones may have the same or a different surface to volume ratio. Process fluid flows through the process microchannel 310 as indicated by arrows 320 and 322. In flowing through the process microchannel 310, the process fluid flows through the gap 315 in contact with the porous support 400. The porous support 400 may support a catalyst if the process microchannel 310 is to be used in microchannel reactor 100. The porous support 400 may support a sorption medium if the process microchannel 310 is to be used in microchannel separator 200. The porous support 400 is illustrated in FIGS. 5 and 6 is a flow-by support. However, some of the process fluid may diffuse into and out of the porous support in contact with the catalyst or sorption medium. A heat exchange fluid may flow in the heat exchange channel 360 in a direction that is co-current or counter-current relative to the flow of process fluid in the process microchannel 310 (FIG. 5). Alternatively, the heat exchange fluid may flow in the heat exchange channels 360 in a direction that is cross-current relative to the flow of process fluid in the process microchannel 310 (FIG. 6). The process microchannel wall 330 may be referred to as a heat transfer wall since it is adjacent to the heat exchange channel 360 (FIG. 5) or channels 360 (FIG. 6).

Figure 7:
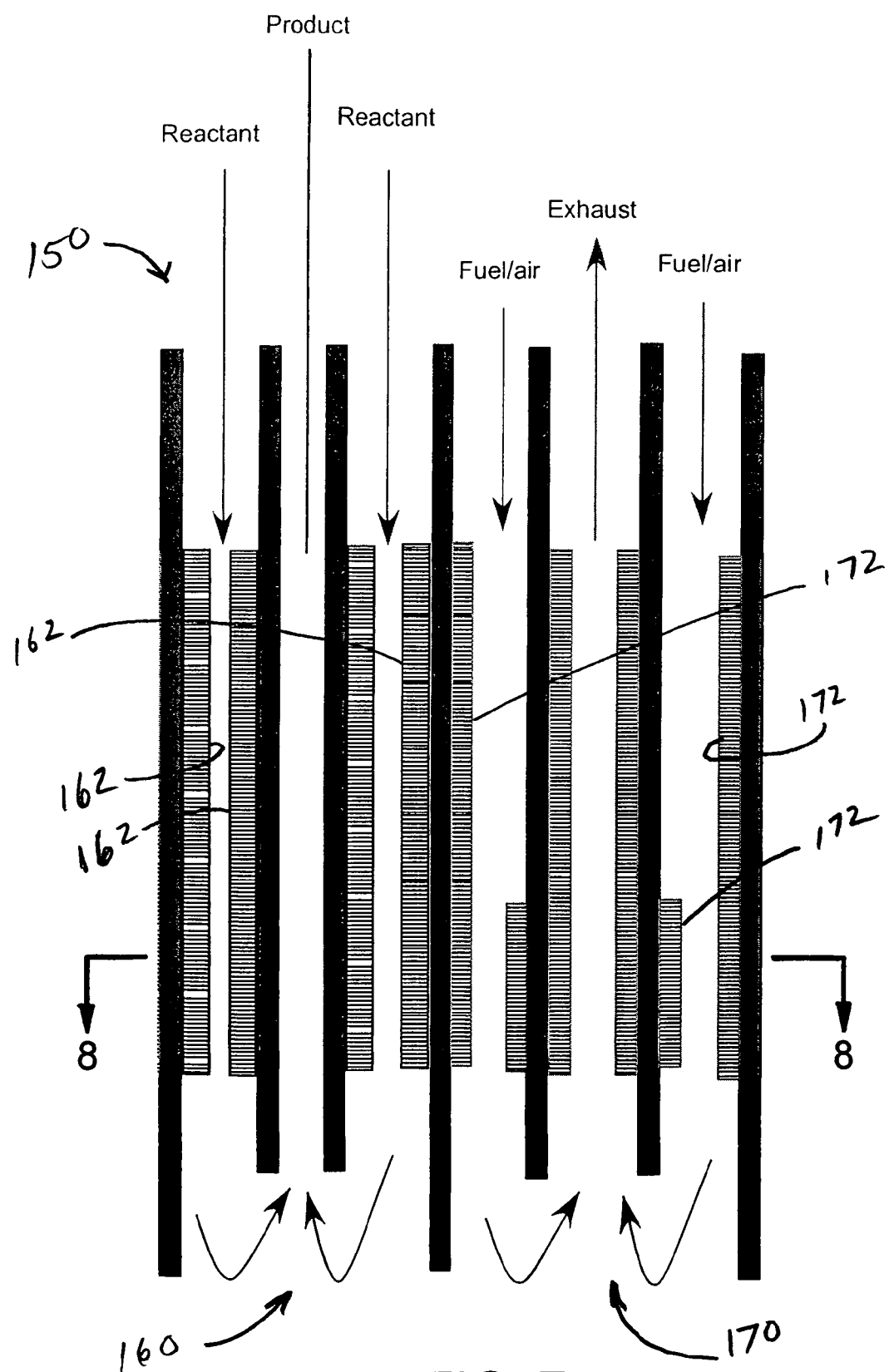
FIG. 7 is a schematic illustration of a repeating unit that may be used in the microchannel reactor core of the microchannel reactor shown in FIG. 2. The repeating unit illustrated in FIG. 7 may be referred to as an integrated combustion reactor and comprises at least one reaction chamber and at least one combustion chamber adjacent to the reaction chamber. The reaction chamber comprises parallel reaction microchannels containing a porous catalyst, and a product channel positioned between the reaction microchannels for removing product from the repeating unit. The reaction microchannels may be referred to as process microchannels. The reactants flow into the reaction microchannels, contact the catalyst and react to form one or more products. The products flow from the reaction microchannels to and through the product channel and then out of the repeating unit. The reaction chamber may be referred to as an endothermic chamber. The combustion chamber comprises parallel combustion microchannels and an exhaust microchannel positioned between the parallel combustion microchannels. A fuel/air mixture flows through the combustion microchannels, contacts a catalyst within the combustion microchannels and undergoes a combustion reaction. The exhaust gas resulting from the combustion reaction flows out of the repeating unit through the exhaust microchannel. The exhaust microchannel also contains a catalyst for treating the exhaust gas. The combustion microchannels and the exhaust gas microchannel may be referred to as process microchannels. The combustion chamber may be referred to as an exothermic chamber.
Figure 8:
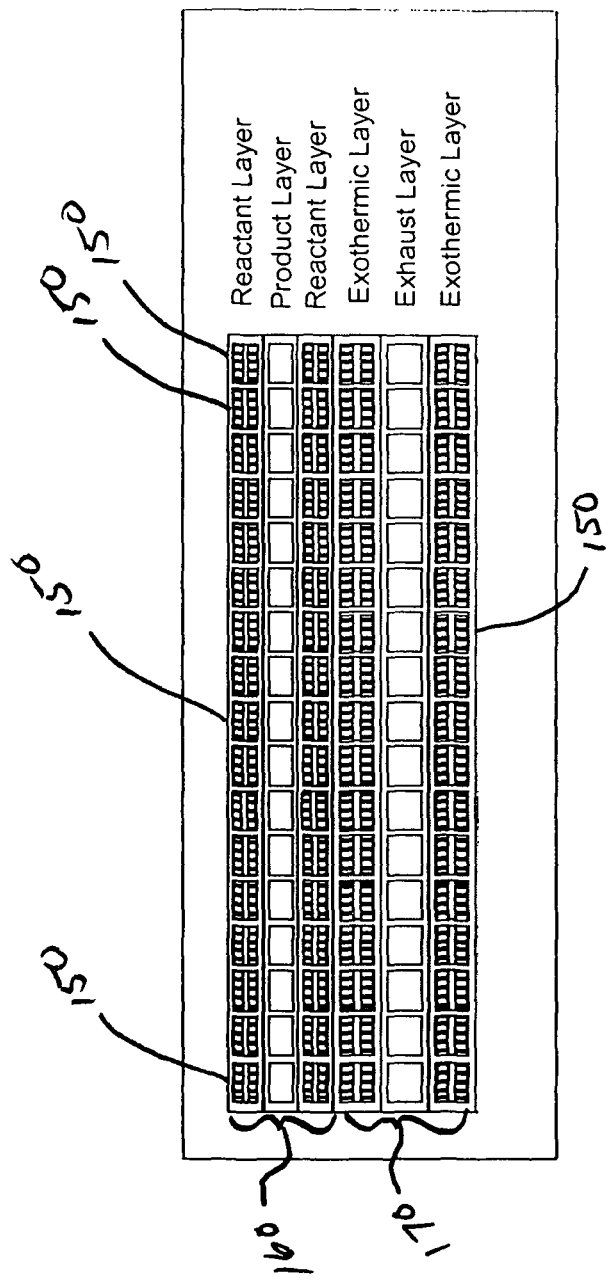
FIG. 8 is a cross-sectional view of the repeating unit illustrated in FIG. 7 taken along line 8-8 in FIG. 7.

The microchannel reactor 100 may be in the form of an integrated combustion reactor (ICR). An example of a repeating unit that may be used in an ICR is illustrated in FIGS. 7 and 8. Referring to FIGS. 7 and 8, the ICR repeating unit 150 comprises reaction chamber 160 and combustion chamber 170. These chambers are adjacent to each other. Either or both chambers may comprise one or more microchannels. A catalyst 162 may be positioned in process microchannels in the reaction chamber 160. A catalyst 172 may be positioned in process microchannels in the combustion chamber 170. The catalyst in at least one of the chambers is a porous catalyst. The catalyst may have an adjacent gap or open area forming a bulk flow path for fluid to flow by and contact the catalyst. A reactant may enter the microchannel and flow in the bulk flow path in contact with the catalyst. When the catalyst is a porous catalyst, part or all of the reactant may diffuse into the porous catalyst and react to form one or more products. The one or more products may diffuse back into the bulk flow path and flow out of the channel. In one embodiment, the reaction conducted in the reaction chamber may be an SMR reaction and the catalyst may be a porous SMR catalyst. For providing sufficient heat to an endothermic reaction in the reaction chamber 160, it may be advantageous to employ a reaction in the combustion chamber 170 that is highly exothermic. Combustion of hydrogen, CO, or any hydrocarbon or hydrocarbon mixture may be useful.

The microchannel reactor 100 may be a staged addition reactor. The staged addition reactor may contain a plurality of staged addition repeating units in the microchannel reactor core 110. Examples of the staged addition repeating units that may be used are illustrated in FIGS. 9-11. Referring to FIG. 9, repeating unit 370 comprises process microchannel 310, heat exchange channel 360, second reactant stream channel 374, and apertured section 380. A common wall 375 separates process microchannel 310 and second reactant stream channel 374. The apertured section 380 is positioned in common wall 375. The process microchannel 310 has a mixing zone 311, and a reaction zone 312. The reaction zone 312 includes bulk flow region 315. Porous support 400, which supports a catalyst, is positioned in the reaction zone 312. The mixing zone 311 is upstream from the reaction zone 312. A first reactant flows into process microchannel 310, as indicated by the arrow 320, and into the mixing zone 311. A second reactant flows into second reactant stream channel 374, as indicated by arrow 376, and from the second reactant stream channel 374 through the apertured section 380 into mixing zone 311, as indicated by arrows 282. The direction of flow of the second reactant in the second reactant stream channel 374, as indicated by arrow 376, is cocurrent with the direction of flow of the first reactant in the process microchannel 310, as indicated by arrow 320. Alternatively, the flow of the second reactant in the second reactant stream channel 374 may be counter-current or cross-current relative to the flow of the first reactant in the process microchannel 310. The first reactant and the second reactant contact each other in the mixing zone 311 and form a reactant mixture. The reactant mixture flows from the mixing zone 311 into the reaction zone 312, contacts the catalyst, and reacts to form the desired product. The product exits the process microchannel 310, as indicated by arrow 322. Heat exchange fluid may flow in the heat exchange channel in a direction that is co-current, counter-current or cross-current relative to the flow of process fluid in the process microchannel 310.

In an alternate embodiment of the repeating unit 370 illustrated in FIG. 9, a supplemental mixing zone may be provided in the process microchannel 310 between the mixing zone 311 and the reaction zone 312.

The repeating unit 370A illustrated in FIG. 10 is identical to the repeating unit 370 illustrated in FIG. 9 with the exception that the repeating unit 370A does not contain the separate mixing zone 311. With repeating unit 370A, the second reactant flows through the apertured section 380 into the reaction zone 312 where it is mixed with the first reactant and reacts to form the desired product. The product then flows out of the process microchannel 310, as indicated by arrow 322.

The repeating unit 370B illustrated in FIG. 11 is identical to the repeating unit 370 illustrated in FIG. 9 with the exception that part of the second reactant mixes with the first reactant in the mixing zone 311, and the remainder of the second reactant mixes with the first reactant in the reaction zone 312. The amount of the second reactant that mixes with the first reactant in the mixing zone 311 may be from about 1% to about 99% by volume of the second reactant, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second reactant. The remainder of the second reactant mixes with the first reactant in the reaction zone 312.

The porous support 400 may comprise one or more thermally conductive metals or other thermally conductive materials such as silicon carbide, graphite, and the like. Combinations of these may be used. In one embodiment, the porous support may be characterized by the absence of aluminum metal. In one embodiment, the porous support may comprise a high surface area alumina support layer. The porous support may comprise a hybrid or composite structure that contains multiple layers to provide a structure that is thermally conductive. For good thermal transfer the porous support 400 may be positioned on one or more microchannel walls (see, FIGS. 5a to 5d). This may be accomplished by forming or growing the porous support on the one or more walls of the microchannel. In one embodiment, a first template may be created to confine the porous support to a heat transfer wall of the microchannel. The first template may comprise fine grooves or slots that are stamped, etched, cut, or otherwise machined into the heat transfer wall or in an adjacent support strip or shim that is subsequently bonded in place to provide good thermal contact. The thickness of the first template may be in the range from about 0.005 mm to about 2 mm. A fluid solution of a first templating agent may be allowed to fill the first template. The orientation of the first template may be such that draining is minimal. More than about 20% of the first template may be filled with the first templating agent solution. The first templating agent solution may contain a polymeric material that is dried in place. A second metallic templating solution may be introduced and fill in the interstices or voids provided by the first templating fluid. The resulting structure may be heated to high temperatures in an oxidizing environment such that the polymeric material is removed and a porous metallic structure is retained that is in intimate contact with the heat transfer wall of the microchannel. As the first and second templating fluids are drained from the microchannel the bulk flow path or open gap may be drained. Capillary forces may act to retain the templating fluids in any recessed or protruded surface features that may be present in the microchannel.

The porous support 400 and the heat transfer wall 330 of the microchannel 310 may comprise a laminate structure. An example of such a structure may comprise a sheet of sintered metal powder intimately bonded to a sheet of solid metal. Sheets of sintered metal powder may be commercially available. Examples may include stainless steel, Inconel® and Hastealloy®. The laminate structure may be designed to have the solid sheet to provide mechanical strength and the porous layer optimized for thermal conductivity. A porous support that has a high thermal conductivity may be highly advantageous for high heat-flux applications. The laminate may comprise multiple layers of porous materials, each layer having a separately specified thickness, porosity, pore size and/or thermal conductivity. Metal alloys may be characterized as having greater mechanical strength than non-alloy metals. However, the thermal conductivities of metal alloys may be lower than their constituent metals. A laminate of a porous layer of pure metal on a solid sheet of alloy may be useful. Inconel 617, a nickel based alloy, has a thermal conductivity of about 27 W/m-K at 900° C. On the other hand, pure nickel has a thermal conductivity of about 75 W/m-K at the same temperature. For a porosity of 50%, the apparent thermal conductivity of the porous nickel may be about 37 W/m-K. Even at a porosity of about 70%, the apparent thermal conductivity of the porous nickel may be about 23 W/m-K, which is close to that of solid Inconels 617.

Porous nickel may be formed on Inconel 617 after bonding. One method may be to conduct a CVD aluminization to cover the Inconel with a layer of nickel aluminide. Thickness of the aluminide layer may be in the range up to about 100 microns, and in one embodiment in the range from about 0.1 to about 50 microns. Leaching with an alkaline solution may be used to remove aluminum from the aluminide, resulting in a layer of porous nickel. The porosity may be controlled by controlling the aluminum content in the aluminide. For example, beta nickel aluminide (NiAl) may lead to a porosity of about 50% with the aluminum leached out. Gamma prime nickel aluminide ($Ni_3Al$) may lead to a porosity of about 25%. Partial leaching may be used to control porosity. For example, a thermally conductive layer having a porosity of about 50% or less may be obtained. The catalyst layer may have a porosity decreasing as a function of distance from the interface with the open gap.

For alloys that are characterized by a small amount of or the absence of nickel, a porous nickel layer may still be possible. This may be accomplished by plating the alloy with a layer of nickel before bonding. Alternatively, the alloy surface may be plated after bonding, for example, by using electroless plating. CVD aluminization and alkaline leaching may be performed to form the porous nickel layer.

Metals of high thermal conductivities in addition to nickel that may be used may include silver, copper, gold, chromium and aluminum. The foregoing methods of forming porous articles may be used with these metals.

The thickness of the porous catalyst may range up to about 10 mm, and in one embodiment from about 10 microns to about 10 mm, and in one embodiment from about 50 microns to about 5 mm, and in one embodiment from about 50 microns to about 2 mm, and in one embodiment from about 50 microns to about 1 mm, and in one embodiment from about 50 microns to about 0.5 mm. The thermal conductivity of the porous catalyst may be in the range from about 0.5 W/m-K to about 500 W/m-K.

An open gap for flow may be positioned adjacent to the porous wall of the porous catalyst. In one embodiment, the gap may be positioned between two porous walls such that the mean diffusion length of reactants to the catalyst structure may be one-half the height of the open flow gap. The open flow gap may have a height in the range from about 25 microns to about 5000 microns. Flow may be convectively enhanced to transport from the open flow passage to the porous catalyst layer if surface features are used as an intervening layer between the open flow passage way and the porous catalyst on at least one side or portion of the microchannel reactor. In one embodiment, a surface feature layer may be disposed on two sides of the open flow passageway and porous catalysts may be disposed beneath the surface feature wall and be in thermal contact with the heat transfer wall.

The non-porous wall may be made of a metal or other thermally conductive material. The thickness may be determined in part by mechanical and structural requirements of the design which may be dictated by the operating temperatures and/or pressures. Thinner walls may be used in combination with support ribs and/or other structures that may be used to reinforce the thin wall against high differential pressures.

The porous support may be in the form of a support strip or shim with microgrooves formed in both the front or first surface and the back or second surface of the strip or shim. These microgrooves may intersect to form a plurality of through holes or openings in the support strip. Examples are illustrated in FIGS. 29 and 30. FIG. 29 illustrates porous support 401 which comprises a support strip or shim 410 which has a front or first surface 412 and a back or second surface 414, and a plurality of microgrooves 430 formed in each surface. The microgrooves 430 formed in the front surface 412 are parallel to each other and are positioned in an array of block patterns 450 wherein in a first block pattern 450 the microgrooves are aligned in a first or horizontal direction and then in an adjacent second block pattern 450 the microgrooves are aligned in a second or vertical direction. The array of block patterns 450 comprises a plurality of block patterns 450 arranged in successive rows positioned one above another, the successive rows forming a plurality of columns positioned side by side one another. The microgrooves 430 formed in the back surface 414 are also parallel to each other and are positioned in an array of block patterns 450 similar to the block patterns 450 in the front surface 412 with the exception that where the front surface 412 has microgrooves that are aligned in a first or horizontal direction the back surface 414 has microgrooves 430 that are aligned in a second or vertical direction. Similarly, where the front surface 412 has microgrooves 430 that are aligned in a second or vertical direction the back surface 414 has microgrooves that are aligned in a first or horizontal direction. The microgrooves 430 in the front surface 412 and the microgrooves 430 in the back surface 414 partially penetrate the support strip 410. The penetration of the microgrooves 430 in the front and back surface is sufficient for the microgrooves 430 in the front surface 412 to intersect the microgrooves 430 in the back surface 414 with the result being the formation of an array of through holes or openings 452 in the support strip 410 at the points where the microgrooves intersect. The openings 452 may be of sufficient size to permit a fluid to flow or diffuse through the openings 452. The number of openings may range from about 1 to about 200,000 openings per $cm^2$, and in one embodiment from about 10 to about 100,000 openings per $cm^2$. The openings 452 may have average dimensions (e.g., diameter) in the range from about 1 to about 2000 microns, and in one embodiment from about 10 to about 1000 microns. The block patterns 450 may have the dimensions of about 0.01 by about 500 mm, and in one embodiment about 0.5 by about 20 mm. The separation between each block pattern 450 and the next adjacent block pattern may be in the range from about 0.01 to about 10 mm, and in one embodiment about 0.1 to about 1 mm. In this embodiment, the pattern is alternated in an A, B, A, B fashion. In an alternate embodiment the geometry may be varied such that the surface area to volume of the structure may be different along the length of the reactor or in different zones of the reactor to accommodate the reaction kinetics. By this manner a reaction with a very high rate of heat release near the top of the reactor may be advantaged by the use of a structure with a higher surface area to volume near the middle or end of the reactor where the kinetics are slower and the rate of heat transfer lower. The resulting heat generation rate along the reactor length or heat flux profile along the reactor length may be made more even or uniform. The pattern may be further optimized to maximize selectivity to the desired reaction products. The pattern may also be optimized to create a tailored gradient within the catalyst structure, along the length of the catalyst structure or both.

FIG. 30 illustrates a composite porous support structure 402 comprising a plurality of the porous supports 401 illustrated in FIG. 29 positioned side by side. Alternatively, the porous supports 401 may be stacked one above another. Any number of the porous supports 401 may be stacked one above the other or positioned side by side in the composite support structure 402. For example, 2, 3, 4, 6, 8, 10, 20, 30, 50, 100, etc., porous supports 401 may be stacked one above another or positioned side by side.

The porous support may be in the form of a microgrooved support strip or shim wherein microgrooves are formed on one side of the support strip or shim. The microgrooves may be parallel to each other. Examples are shown in FIGS. 31-40. Referring to FIG. 31, microgrooved support strip 403 comprises support strip 410 which is rectangular in shape and has a length (l), width (w) and thickness (t). The support strip 410 may be a shim. The support strip 410 has a first or top surface 412, a second or bottom surface 414, a first side edge 416, a second side edge 418, a front edge 420 and a back edge 422. The support strip 410 has a center axis 424 extending along the length (l) of the support strip. A plurality of parallel microgrooves 430 are formed in the first surface 412. A first group 432 of parallel microgrooves 430 extends from the first side edge 416 of the support strip 410 to the second side edge 418. A second group 434 of the microgrooves 430 extends from the front edge 420 to the second side edge 418. A third group 436 of the microgrooves 430 extends from the first side edge 416 of the support strip 410 to the back edge 422. The microgrooves 430 are oriented at an angle 425 relative to the center axis 424 that is sufficient to permit fluid to flow in the microgrooves 430 in a general direction from the front edge 420 toward the back edge 422 or from the back edge 422 toward the front edge 420. The front edge 420, back edge 422 and side edges 416 and 418 of the microgrooved support strip 401 are open. That is, the microgrooves 430 have open ends that project through the front edge 420, back edge 422 and side edges 416 and 418. These open ends may permit the flow of fluid through the front edge, back edge and side edges. Each of the microgrooves 430 may be oriented toward the front edge 420 and the first side edge 416 and forms an angle 425 with the center axis 424 that is sufficient to permit fluid to flow in the microgrooves in a direction toward the second side edge 418 and back edge 422. The angle 425 may be more than about 0° and less than 90°. The angle 425 may be in the range from about 50° to about 80°, and in one embodiment from about 60° to about 75°.

The microgrooved support strip 403A illustrated in FIG. 32 is the same as the microgrooved support strip 403 illustrated in FIG. 31 with the exception that the second group 434 of microgrooves 430 and third group 436 of microgrooves 430 that are present in the microgroove support strip 403 are not present in the microgrooved support strip 403A. The microgrooved support strip 403A includes non-grooved sections 434a and 436a which provide the microgrooved support strip 403A with a front edge 420 and a back edge 422 that are closed. That is, the front edge 420 and the back edge 422 of the microgrooved support strip 403A are sufficiently blocked to prevent fluid from flowing through the front edge 420 and back edge 422.

The microgrooved support strip 403A is also shown in FIGS. 37 and 38. FIG. 37 is a photograph of a microgrooved support structure made of an alloy of iron, chromium, aluminum and yttrium, the thickness of the support structure being 0.002 inch (50.8 microns), the ribs dividing the microgrooves having a thickness of 0.007 inch (178 microns), and the microgrooves having a width of 0.007 inch (178 microns). FIG. 38 is a photograph of a microgrooved support structure similar to the support structure illustrated in FIG. 37 with the exception that the microgrooved support structure illustrated in FIG. 38 is made of stainless steel.

The microgrooved support strip 403B illustrated in FIG. 33 is the same as the microgrooved support strip 403A illustrated in FIG. 32 with the exception that the side edges 416 and 418 in the microgrooved support strip 403B are closed The microgrooves 430 extend between the sides 416 and 418 but not through the side edges. Thus, the flow of fluid through the side edges 416 and 418 may be blocked. Also, the microgrooves 430 may penetrate part way or all the way through the support strip 410. Penetration of the microgrooves 430 all the way through the support strip 410 may be sufficient to permit fluid to flow through the support strip 410 from the top surface 412 to the bottom surface 414, or vice versa.

The microgrooved support strip 403B may be used as flow-through and/or flow-by support structure in a microchannel. Microgrooved support strips 403 and 403A may be used as a flow by support structures in a microchannel.

In one embodiment, a plurality of the microgrooved support strips may be stacked one above another or positioned side by side to form the composite support structure 404 illustrated in FIGS. 34-36. Referring to FIGS. 34 and 35, each of the support strips 403C and 403D have an open front edge 420 and an open back edge 422, closed side edges 416 and 418, and microgrooves 430 that penetrate all the way through the support strip 410 from the top surface 412 to the bottom surface 414. The open front edges 420, back edges 422 and microgrooves 430 permit fluid to flow through the microgrooved support strips from one support strip to another support strip within the composite support structure as the fluid flows through the composite support structure. The number of microgrooved support strips employed in such a composite support structure may be of any number, for example up to about 50, and in one embodiment up to about 30, and in one embodiment up to about 15, and in one embodiment up to about 10. The composite support structure may also include end plates to prevent fluid from flowing out of the sides of the composite support structure.

The composite support structure 404 illustrated in FIGS. 34 and 35 comprises eight (8) microgrooved support strips, four each of microgrooved support strips 403C and 403D positioned side by side in alternating sequence and two end plates 409 (only one end plate is shown in FIGS. 34 and 35). The microgrooved support strips 403C and 403D each comprise support strip 410 which is rectangular in shape and has a length, width and thickness. The support strip 410 has a center axis extending along the length of the support strip. A plurality of parallel microgrooves 430 are formed in the support strip 410 and project through the support strip from the top surface 412 to the bottom surface 414. The open front 420 and back edges 422 and the open microgrooves 430 permit fluid to flow from one microgrooved support strip to another within the composite support structure 404. A first group of parallel microgrooves extends from the first side edge 416 of the support strip 410 to the second side edge 418. A second group of the microgrooves 430 extends from the front edge 420 to the second side edge 418. A third group of the microgrooves 430 extends from the first side edge 416 of the support strip 410 to the back edge 422. The front edge 420 and the back edge 422 are open sufficiently to permit fluid to flow through these edges. The side edges 416 and 418 are closed and do not permit fluid to flow through these edges. The microgrooves 430 extend to the side edges 416 and 418 but do not project through these side edges. The end plates 409 prevent fluid from flowing out of the sides of the composite support structure 404. The microgrooves 430 in the support strips 403C are oriented at an angle relative to the center axis of the support strip and the side edge 416 that is more than 90° and less than 180°, and in one embodiment in the range from about 100° to about 150°. The microgrooves 430 in the support strip 403D are oriented at an angle relative to the center axis of the support strip and the side edge 416 that is more than 0° and less than 90°, and in one embodiment in the range from about 50° to about 80°. Fluid flows through the composite structure 404 by entering the front edge 420 of the support strips 403C and 403D, flowing through the microgrooves 430, and transferring from the microgrooves 430 in one support strip (403C or 403D) to the microgrooves 430 in another support (403C or 403D) until the fluid reaches the back edge 422 of the support strips and then flows out of composite support structure 403. FIG. 35 shows an example of a flow path through the composite support structure 404 for a fluid entering opening 'A' of the composite support structure illustrated in FIG. 34. The flow of fluid through the composite support structure 404 may be described as permeating, diffusing and advecting from one layer to another until the fluid passes from the front end of the composite support structure to the back end.

The composite support structure 404 may be a flow-through structure and fill the cross-section of the process microchannel 310 as illustrated in FIG. 36. Alternatively, the composite support structure may fill only part of the cross-section of the process microchannel and a gap may be positioned adjacent the composite support structure 404 to permit bulk flow in the process microchannel.

The microgrooves 430 may have cross-sections in the form of squares. Alternatively, each of the microgrooves 430 may have a rectangular cross-section, a vee shaped cross-section, a semi-circular cross-section, a dovetail shaped cross-section, or a trapezoid shaped cross-section. Those skilled in the art will recognize that microgrooves with other cross-sectional shapes may be used in place of the foregoing. Each of the microgrooves 430 has a depth, width and length. The depth of each of the microgrooves 430 may be in the range up to about 1000 microns, and in one embodiment from about 0.1 to about 1000 microns, and in one embodiment in the range from about 1 to about 500 microns, and in one embodiment in the range from about 1 to about 200 microns, and in one embodiment in the range from about 1 to about 100 microns. The width, which would be the width at its widest dimension, for each of the microgrooves 430 may be in the range up to about 1000 microns, and in one embodiment from about 0.1 to about 1000 microns, and in one embodiment in the range from about 1 to about 500 microns, and in one embodiment in the range from about 1 to about 200 microns, and in one embodiment in the range from about 1 to about 100 microns. The length of each of the microgrooves 430 may be of any dimension which depends upon the width of the support strip 410. The length of each microgroove 430 may be in the range up to about 10 cm, and in one embodiment from about 0.1 to about 10 cm. The spacing between the microgrooves may be in the range up to about 1000 microns, and in one embodiment in the range from about 0.1 to about 1000 microns, and in one embodiment in the range from about 1 to about 500 microns, and in one embodiment in the range from about 1 to about 200 microns, and in one embodiment in the range from about 1 to about 100 microns. The microgrooves may be formed in the support strip 410 using any suitable technique, including photochemical machining, laser etching, water jet machining, and the like.

The support strip or shim 410 may have a thickness in the range from about 0.1 to about 5000 microns, and in one embodiment from about 1 to about 1000 microns, and in one embodiment in the range from about 1 to about 500 microns, and in one embodiment in the range from about 1 to about 200 microns, and in one embodiment in the range from about 50 to about 150 microns. The support strip 410 may have any width and any length, the width and length depending upon the dimensions of the microchannel for which the support strip 410 is to be used. The support strip 410 may have a width in the range from about 0.01 to about 100 cm, and in one embodiment from about 0.1 to about 10 cm. The length of the support strip 410 may be in the range of about 0.01 to about 100 cm, and in one embodiment from about 0.1 to about 10 cm. The support strip 410 as illustrated is in the form of a rectangle. However, it is to be understood that the support strip 410 may have any configuration, for example, square, circle, oval, etc., to conform to the design of the microchannel for which it is to be used.

The support strip or shim 410 may contain surface features as discussed in greater detail below. These surface features may have subfeatures within the main features that are smaller in size. There may be multiple sizes of surface features on the same microgrooved support strip. There may be different sized features on different microgrooved sheets that when assembled make a stack of varying sized surface features into the depth of the stack of microgrooved support strips.

The support strip or shim 410 may be made of any material that provides sufficient strength, dimensional stability and heat transfer characteristics to permit the use of the porous support 400 in a microchannel for supporting a catalyst or a sorption medium. The support strip may be thermally conductive. The support strip 410 may be made of a thermally conductive material such as a metal, silicon carbide, graphite or a combination of two or more thereof. The metal may comprise steel, aluminum, titanium, nickel, platinum, rhodium, copper, chromium, brass, or an alloy of any of the foregoing metals. The support strip 410 may be made of stainless steel or an alloy comprising iron, chromium, aluminum and yttrium.

The porous support 400 may comprise one or more porous thermally conductive treatment or coating layers formed on one or more interior walls of the process microchannel 310. This coating layer may comprise a macroporous layer having an average pore size in the range from about 50 nm to about 10 microns, and in one embodiment in the range from about 50 nm to about 1 micron; a mesoporous layer having an average pore size in the range from about 2 to about 50 nm; or a microporous layer having an average pore size in the range up to about 2 nm, and in one embodiment in the range from about 0.1 to about 2 nm. The macroporous layer may comprise one or more metal oxides or mixtures of one or more metal oxides with one or more catalytic materials. The macroporous layer may comprise polymer templated cellular $Al_2O_3$, $TiO_2$, $SiO_2$, SiC, $ZrO_2$, or SiCN. The mesoporous layer may comprise sol gel deposited $Al_2O_3$ or $TiO_2$, surfactant templated $SiO_2$, anodized $Al_2O_3$ or $TiO_2$ nanotubes, or multiwall nanotubes (e.g., multiwall carbon nanotubes). The microporous layer may comprise single wall nanotubes, sol-gel $SiO_2$ or zeolites. This treatment or coating layer may have a thickness in the range from about 1 micron to about 1 mm, and in one embodiment from about 1 micron to about 0.5 mm. This treatment or coating layer may have a surface area in the range from about 1 to about 4000 $m^2/m^3$, and in one embodiment from about 50 to about 1000 $m^2/m^3$.

The macroporous layer may be formed using a sacrificial organic template and a colloidal precursor. The macroporous support layer may comprise interconnected spherical pores in the range from about of 50 nm to about 10 μm, and in one embodiment in the range from about 50 nm to about 1 μm. The layer may be deposited on one or more of the interior walls of the microchannel. The synthesis procedure may be carried out either before or after the strips or shims are stacked or bonded together to form the microchannel. The thickness of the microporous layer may be in the range of about 1 to about 20 μm, depending on the size of the pores. The surface enhancement factor to a smooth channel surface may be in the range of about 10 to about 1000 times, depending on the size of the pores and the thickness of the layer. The porosity of the macroporous layer may be in the range of about 50% to about 90%. The macroporous layer may be made from various materials including metals, e.g. nickel or copper as well as oxides, such as silica, alumina, zirconia, and titania. Active catalysts may be integrated on to the skeletal surface of the structure by electroless plating or wet-impregnation.

Alumina or titania nanotubes may be grown from an aluminum or titanium surface respectively by anodic oxidation in oxalic, phosphoric, or sulfuric acid. Synthesis may be carried out before the strips or the shims are bonded. The internal diameter of the nanotubes may be in the range from about 50 nm to about 500 nm, depending on the acid concentration and applied voltage. The height of the nanotubes, which may also be the thickness of the layer, may be in the range up to about 100 μm. This may be controlled by anodization time. The porosity of the nanotube layer may be in the range from about 20% to about 50%. The surface area enhancement factor to a smooth surface may be in the range from 1 to about 1000, depending on the internal diameter of the nanotubes and the thickness of the layer. Active catalysts may be deposited into the nanotubes by electroless plating or wet-impregnation. Metal (platinum, silver, etc.) nanowires may be grown in the nanotubes from the underneath aluminum or titanium surface by electroplating.

Multiwalled carbon nanotubes may be grown on a surface which is coated with iron catalyst supported on silica. The synthesis procedure may be carried out either before or after the strips or shims are stacked or bonded to form the microchannel. The diameter of the carbon nanotubes may be in the range from about 50 to about 80 nm and the length may be up to about 100 μm. The surface area enhancement factor to a smooth surface may be in the range from about 1 to about 1000, depending on the length of the nanotubes. This may also be the thickness of the layer. Active metal catalysts may be electroless plated on the carbon nanotubes as nanoparticles or wet-impregnated onto the carbon nanotube layer.

The porous support 400 may comprise a macroporous silicon carbonitride (SiCN) or silicon carbide (SiC) treatment layer formed on one or more interior walls of the porous microchannel 310. These macroporous layers may have average pore sizes in the range from about 50 nm to about 1 micron, and average surface areas in the range from about $10^5$ to about $10^8$ $m^2/m^3$. These macroporous layers may be formed by capillary filling packed beds of polystyrene or silica spheres with a low-viscosity preceramic polymer based liquid (e.g., polyvinylsilazane or alkylhydridopolycarbosilane), curing the preceramic polymer, pyrolyzing the cured preceramic polymer, and removing the polystyrene or silica spheres to provide the macroporous SiCN or SiC structure. An SiCN structure that may be prepared by this method is shown in FIG. 44.

A two step process for forming a high-surface area, macroporous layer of $Al_2O_3$, which may be used as the porous support 400, is illustrated in FIG. 45. The macroporous layer may have an average pore size in the range from about 50 nm to about 1 micron. The macroporous layer may be formed on one or more interior walls of the process microchannel 310. The process may comprise assembling polystyrene microspheres (average diameter of about 200 nm) on one or more of the process microchannel walls, infiltrating the channel with an AlOOH sol or an organosilane, drying the channel contents, and then heat treating the channel in an oxidizing environment such as air at a temperature sufficiently high to oxidize the polystyrene microspheres, leaving behind a porous high surface area $Al_2O_3$ structure. Alternatively, a one-step process, as illustrated in FIG. 46, wherein the channel walls are washcoated with AlOOH sol or an organosilane in combination with one or more sacrificial fillers (e.g., cellulose, starch gel, protein powder, emulsion). The washcoated microchannel may be calcined to drive off the sacrificial filler and thereby provide the macroporous $Al_2O_3$ layer.

The porous support 400 may comprise a mesoporous $Al_2O_3$ treatment layer that is applied to one or more of the walls of the process microchannel 310 using annodization. The average pore size of this mesoporous layer may be in the range from about 2 to about 50 nm. The mesoporous layer may be in the form of $Al_2O_3$ nanotubes as shown in FIG. 47. The $Al_2O_3$ layer may be formed by annodizing an aluminum alloy shim (e.g., aluminum alloy 1100) in oxalic acid. The annodization potential may be in the range from about 30 to about 60 volts. The oxalic acid concentration may be in the range from about 0.2 to about 0.6 M. The anodized layer may be hydrothermally treated to increase the surface area. FIG. 47 shows SEM micrographs of alumina nanotubes formed using this process. The micrograph on the left labeled (a) shows the surface morphology of the anodized surface as synthesized. The micrograph on the right labeled (b) shows the surface morphology of the anodized surface after being hydrothermally treated. The surface area before hydrothermal treatment may be about 15 $m^2/g$ while the surface area after hydrothermal treatment may be about 150 $m^2/g$.

The mesoporous $Al_2O_3$ treatment layer may be electroplated with Pt to form a porous catalyst comprising $Pt/Al_2O_3$ nanofibers. This is schematically illustrated in FIG. 49.

The porous support 400 may comprise a mesoporous $TiO_2$ treatment or coating layer that is applied to one or more of the walls of the process microchannel 310 using annodization. The average pore size of this mesoporous layer may be in the range from about 2 to about 50 nm. The mesoporous layer may be in the form of $TiO_2$ nanotubes as shown in FIG. 48. The $TiO_2$ nanotube layer may comprise individual tubes with diameters of about 100 nm, lengths of about 500 nm and wall thicknesses of about 15 nm. The $TiO_2$ layer may be formed by annodizing a titanium sheet in an acidic solution containing sulfuric acid and hydrofluoric acid. The annodization potential may be about 20 volts. The annodized layer may be annealed to provide the mesoporous $TiO_2$ layer.

The porous support 400 may comprise a mesoporous layer comprising carbon nanotubes formed on one or more interior walls of the process microchannel 310 by the catalytic decomposition of ethylene. The nanotubes may be in the form of aligned multiwalled carbon nanotube arrays as shown in FIGS. 50 and 51. This support layer may have an average pore size in the range from about 2 to about 50 nm. This support layer may be formed on a suitable substrate, for example an FeCrAlY alloy substrate using the process shown in FIG. 52. The process may involve first forming a native aluminum oxide layer on the substrate, then forming a dense aluminum oxide layer over the native aluminum oxide layer using metal-organic chemical vapor deposition at a temperature of about 900° C. Aluminum isopropoxide may be used as a precursor. The alumina coated substrate may then be dipped in a precursor sol of $Fe/SiO_2$, followed by drying and then calcining at about 450° C. for about 2 hours to form a 1 to 2 micron thick film of supported iron oxide nanoparticles over mesoporous $SiO_2$. The coated substrate may then be heated to about 700° C. under nitrogen in a quartz reactor at atmospheric pressure. Ethylene gas may be added to the reactor. The reactor may be cooled to about 450° C. Air may be added to the reactor, and then the reactor may be cooled to room temperature with the result being the formation of the carbon nanotube layer. Platinum may be applied to the carbon nanotubes using plating to provide a porous catalyst.

The porous support 400 may comprise a layer of multi-walled carbon nanotubes. This layer may have an average pore size in the range from about 2 to about 50 nm and may be used to support catalytic gold nanoparticles. The layer of carbon nanotubes may be formed by the catalytic decomposition of acetylene using a silica-supported cobalt catalyst to form a carbon nanotube-Co/SiO$_2$ composite. The carbon nanotubes may be extracted from this composite using an aqueous solution of HF and nitric acid at room temperature resulting in the dissolution of the SiO$_2$ and cobalt particles. The residues may be washed in distilled water and dried at about 100° C. The resulting carbon nanotube powder may be oxidized by refluxing the nanotube powder in a H$_2$SO$_4$—HNO$_3$ blend acid at about 140° C. for about six hours, and then washing the nanotube powder with distilled water and drying in air at about 100° C. The oxidized carbon nanotube powder may be sonicated in an activating solution containing HCl, distilled water, PdCl$_2$ and SnCl$_2$.H$_2$O, and then plated with gold nanoparticles on the microchannel walls using electroless plating. FIG. 53 shows gold nanoparticles supported on carbon nanotubes.

The structured wall or porous support described herein may be differentiated by the fact that it is preferably not a pillar structure and may be characterized by repeat patterns, however complex, of open and thermally connected regions. These regions may be solid regions. These patterns may exist in planes parallel to the plane in which the fluid flows or in a plane orthogonal to which the fluid flows or may be in both plains. The patterns in each plane may or may not be the same. The structured walls may tend to be of low tortuosity.

The repeat patterns in a structured wall or porous support may be likened to the structure of a crystalline solid and the method of characterizing the structured walls may be analogous to the use of x-ray diffraction in the characterization of crystalline solids and their differentiation from amorphous solids. One test to determine whether a porous support structure may be a structured wall as described here would be to assess the distribution of line densities as measured through the thickness of the porous support at locations spanning the face of the porous support or at locations along any given cross-section of the structured wall which includes the thickness. In this case line density may be defined as the length fraction of a line passing through the thickness (smallest dimension) of the porous support structure that passes through something other than open space. This may be tested by taking a sample of the structure (with or without adherent catalyst/sorption media) and impregnating it with epoxy in a manner similar to that for the preparation of cross sectional SEM. The sample may then be polished to reveal a representative cross section and then examined under scanning electron microscopy (SEM) or scanning electron microscopy with energy dispersive x-ray spectroscopy (SEM-EDS). Lines running from one face of the structure (adjacent the open channel or a wall to the other face (adjacent a solid wall) and at right angles to at least one of the surfaces may then be traced and the fraction of the length passing across structure or structure plus catalyst/sorption medium may be assessed. The area of examination may encompass an area of at least the thickness of the structure multiplied by 5 times the thickness of the structure. For example if the structure is 1.5 mm thick, the length of the area to be examined may be 7.5 mm. The number lines used to estimate line density distribution may be at least about 50 and may be distributed uniformly across the area of examination. The densities may be divided in classes. The relative frequencies may also be calculated according to Mendenhall and Sincich as disclosed in *Statistics for Engineering and the Sciences*, Dellen Publishing Company, San Francisco, ©1992. The distribution of line densities (as a histogram) in a structured wall may not approximate a normal or Gaussian distribution. They may follow or approximate other distributions such as uniform, piece-wise uniform, Weibul, or multimodal. In one embodiment, a distribution of line densities with three or more modes may be used. On the other hand the distribution of line densities (as a histogram) in a support structure that is not a structured wall may approximate a normal or Gaussian distribution.

Another method for determining the nature of the structure may be to employ a transmission absorbance methodology for example x-ray examination. A representative sample of a structure that is at least as wide as it is thick and about five times its thickness may be irradiated with radiation or other emanation such as ultrasound that may be transmitted or adsorbed based on the density of the structure. The emanations may be directed towards one of the large faces of the sample. The emanations may strike the large surface at a right angle. If the image or response map so produced is analyzed by assessing the absorbance or transmittance in at least 50 locations distributed uniformly across the area of analysis and processed in the manner described above then the distribution of absorbance or transmittance measurements (as a histogram) in a structured wall may not approximate a normal or Gaussian distribution but may follow or approximate other distributions such as uniform, piece-wise uniform, Weibul, or multimodal. In some embodiments, a distribution of line densities with three or more modes may be used. On the other hand the distribution of absorbance or transmittance measurements (as a histogram) in a support structure that is not a structured wall may approximate a normal or Gaussian distribution.

The catalyst that may be supported by the porous support 400 may comprise any catalyst that is suitable for use in chemical reactors involving the use of fluid reactants. The catalyst may comprise elements in the IUPAC Group IIA, IVA, VA, VIA, VIIA, VIIIA, IB, IIB, IVB, Lanthanide series and Actinide series. Catalyst layers, if present, may be porous. The average pore size (volume average) of the active catalyst layer(s) may be smaller than the average pore size of the porous support. The average pore size of the active catalyst layer(s) positioned on the porous support may be in the range from 1 to about 100 nanometers (nm) as measured by N$_2$ adsorption with BET method. In one embodiment, at least about 50 volume % of the total pore volume of the active catalyst layer(s) may comprise pores in the size range from about 1 to about 100 nm in diameter. Diffusion within the pores in the catalyst layer(s) may be Knudsen in nature wherein molecules collide with the walls of the pores more frequently than with other molecules.

For a catalyst which has a coefficient of thermal expansion greater or lesser than the surface to which is attached, a change in temperature may cause high strains in the catalyst causing cracking or other damage to the catalyst. To reduce this effect, a material (or materials) with an intermediate coefficient of thermal expansion value may be layered between the active catalyst layer and the surface of the porous support to reduce the strain on the catalyst. A layer which has low mechanical stiffness, such as a porous foam structure, may be applied between the active catalyst layer and the surface of the porous support. The intermediate layer may be resilient enough to deform due to the thermal expansion difference without exceeding its allowable stress.

The catalyst may be useful for conducting one or more of the following chemical reactions: acetylation addition, acylation, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, water-gas shift, dehalogenation, dimerization, epoxidation, esterification, Fischer-Tropsch reaction, halogenation, hydrohalogenation, homologation, hydration, dehydration, hydrogenation, dehydrogenation, oxidative dehydrogenation, hydrocarboxylation, hydroformylation, hydrogenolysis, hydrometallation, hydrosilation, hydrolysis, hydrotreating, isomerization, methylation, demethylation, metathesis, methanol synthesis, nitration, oxidation, partial oxidation, polymerization, reduction, reformation, steam methane reforming reaction, reverse water gas shift, sulfonation, telomerization, transesterification, trimerization, Sabatier reaction, carbon dioxide reforming, preferential oxidation, or preferential methanation.

The catalyst may comprise one or more: catalyst metals, including noble metals, transition metals and combinations thereof; metal oxides, including oxides of alkali metals, alkaline earth metals, boron, gallium, germanium, arsenic, selenium, tellurium, thallium, lead, bismuth, polonium, magnesium, titanium, vanadium, chromium, manganese, iron, nickel, cobalt, copper, zinc, zirconium, molybdenum, tin, calcium, aluminum, silicon, lanthanum series element (s), and combinations thereof; composites; zeolite(s); nitrides; carbides; sulfides; halides; phosphates; and combinations of any of the above.

The sorption medium that may be supported by the porous support 400 may comprise any sorption medium that sorbs one or a first fluid in a fluid mixture with a preferential affinity over the other fluid(s) in the fluid mixture at one temperature, and then desorbs the one or first fluid at a different temperature. Examples of the separations that may be conducted include oxygen from air, olefins (e.g., ethylene) from mixtures of olefins and paraffins (e.g., ethane), and the like. The fluid components that may be separated or purified include oxygen, hydrogen, nitrogen, $NO_x$ (e.g., NO, $NO_2$), CO, $CO_2$, $H_2S$, HCN, $SO_2$, $CH_3SCH_3$, olefins (e.g., ethylene), paraffins (e.g., ethane), aromatic compounds (e.g., benzene), isomers, halogenated compounds (e.g., chlorides), nitrates, sulfates, sugars, esters, alcohols, ethers, nitro compounds, hydroxyl amines, or mixtures of two or more thereof. In one embodiment, the sorption medium may sorb methane or nitrogen from a fluid mixture containing methane and nitrogen.

The sorption medium may comprise activated carbon, microporous carbon powder, porous carbon foam, carbon nanotubes, activated aluminia, zeolites, copper metal complexes, metal-organic complexes, or a combination of two or more thereof. In one embodiment, multiple sorbents such as combinations of activated carbon, activated alumina and/or carbon nanotubes may be used.

The sorption medium may comprise a mixture of activated carbon particulates and thermally conductive particulates. An example of such thermally conductive particulates is diamond powder, for example, industrial diamond powder MBG-660, which is available from Diamond Innovations (Worthington, Ohio, USA). Additional examples include copper, gold, silver, and the like. The thermally conductive particulates may be thermally conductive polymers such as those available under the trade designation Cool Poly®E-Series Thermally Conductive Plastics from EMI Solutions. Mixtures of two or more of these can be used.

The sorption medium may comprise metal ions that are complexed (e.g., chelated) by ligands. The metal ions may complex with methane or nitrogen. The metal ions that may be used include Fe(II), Co(II), Cu(I), V(II), Mn(II), Mn(III), Cr(II), Ag(I), Rh(I), Rh(II), Rh(III), U(IV), V(IV), Ru(II), Ru(IV), Ti(III), Cr(IV), Bi(III), Ni(II), W(V), W(IV), Mo(II), Mo(III), Mo(IV), Mo(V), Mo(VI), or a combination of two or more thereof. The Roman numerals in the foregoing indicate oxidation states or valence numbers for the ions.

The ligands that may be used to complex the metal ions include dipyridyl; 2,6-[1-(2-imidazol-4-ylethylimino)ethyl pyridine]; cyclen; cyclam; a Schiff base ligand; acetyl acetonate or an oligomer or polymer thereof; a carboxylate; bipyridyl or an oligomer or polymer thereof; a porphyrin or an oligomer or polymer thereof; a corin or an oligomer or polymer thereof; a polyamide; a protein; 8-hydroxy quinoline or an oligomer or polymer thereof; ethyl cysteinate or an oligomer or polymer thereof; an N-alkyl alkanohydroxamic acid; dimethylglyoxime; sym-diethylethylenediamine; or a combination of two or more thereof. The ligands may include fluoride-carbon bonds. The ligands may be fluorinated (e.g., perfluourinated).

The sorption medium may be inorganic. Examples of inorganic sorption mediums that may be used include $Sb_2O_5$, AgO, PtO, $CrO_2$, PbO, HgO, $Cu_2O$, MnO, $Mn_2O_3$, $Bi_2O_4$, NiO, $NiO_2$, $Cu_2O_3$, SnO, $SnO_2$, $WO_2$, $WO_3$, $W_2O_5$, perfluorinated film, Pt/-alumina, Fe/-alumina, Cu/-alumina, Zn/-alumina, Co/-alumina, zeolite, or a combination of two or more thereof. Included in this group are metal cyanide oligomers and polymers. These include the oligomers and polymers represented by the formulae $[Cu(I)(CN)_x]_n$, $[Fe(II)(CN)_y]_n$, or $[Co(II)(CN)_y]_n$, wherein x is 3; y is 5; and n is a number that is at least 2, and in one embodiment is in the range of about 2 to about 16,500, and in one embodiment about 1000 to about 10,000.

The catalyst or sorption medium may be deposited on the porous support using conventional techniques. These may include washcoating the catalyst or sorption medium on the porous support, growing the catalyst or sorption medium on the porous support, or depositing the catalyst or sorption medium on the porous support using vapor deposition. The vapor deposition may be chemical vapor deposition or physical vapor deposition. The catalyst or sorption medium may be deposited by slurry-coating, sol-coating, solution-coating, electroless plating as well as other methods suitable for depositing a heterogeneous catalyst. In one embodiment, the catalyst or sorption medium may be in the form of microsized particulates deposited in the microgrooves or pores of the porous support. The microsized particulates may have average particle sizes in the range from about 0.01 to about 10 microns, and in one embodiment in the range from about 0.1 to about 10 microns, and in one embodiment in the range from about 0.1 to about 7 microns, and in one embodiment in the range from about 0.1 to about 5 microns, and in one embodiment in the range from about 0.1 to about 3 microns, and in one embodiment in the range from about 0.1 to about 2 microns, and in one embodiment in the range from about 0.1 to about 1 micron, and in one embodiment in the range from about 0.1 to about 0.5 micron.

The reaction zone 312 in the process microchannel 310 may include an open gap or bulk flow path 315 adjacent the porous catalyst 400. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region may be laminar. In one embodiment, the flow of fluid may be transition, turbulent, or have non-linear pathlines as evidenced by swirling, chaotic or other non-straight stream lines if surface features are used to stir the flow. Bulk flow regions within each process microchannel 310 may have a cross-sectional area of about 0.05 to about 10,000 $mm^2$, and in one embodiment about 0.05 to about 5000 $mm^2$, and in one embodiment about 0.1 to about 2500 $mm^2$. The bulk flow regions 315 may comprise from about 5% to about 95%, and in one embodiment about 30% to about 80% of the cross-section of the process microchannel 310.

The flow and/or mixing within the process microchannels 310, second reactant stream channels 374, and/or heat exchange channels 360 may be modified by the use of surface features formed on one, two or more interior walls of such channels. The surface features may be formed on or in the porous support 400. The surface features may be on or in the microchannel wall underlying the porous support 400. The surface features may be in the form of depressions in and/or projections from one or more of the channel walls. These surface features may be oriented at angles relative to the direction of flow through the channels. The surface features may be aligned at an angle from about 1° to about 89°, and in one embodiment from about 30° to about 75°, relative to the direction of flow. The angle of orientation may be an oblique angle. The angled surface features may be aligned such that they converge in the direction of flow or such that they diverge from the direction of flow, or both (for multiple angles). The flow of fluids in contact with the surface features may force one or more of the fluids into depressions in the surface features, while other fluids may flow above the surface features. Flow within the surface features may conform with the surface feature and be at an angle relative to the average direction of the bulk flow in the channel. As fluid exits the surface features it may exert momentum in the x and y direction for an x,y,z coordinate system wherein the bulk flow is in the z direction. This may result in a churning or rotation in the flow of the fluids. This pattern may be helpful for mixing a two-phase flow as the imparted velocity gradients may create fluid shear that breaks up one of the phases into small and well dispersed droplets.

Two or more surface feature regions within the process microchannels 310 may be placed in series such that mixing of the process fluids may be accomplished using a first surface feature region, followed by at least one second surface feature region where a different flow pattern may be used. The second flow pattern may be used to separate one or more liquids or gases from the fluid mixture. In the second surface feature region, a flow pattern may be used that creates a centrifugal force that drives one liquid toward the interior walls of the process microchannels while another liquid remains in the fluid core. One pattern of surface features that may create a strong central vortex may comprise a pair of angled slots on the top and bottom of the process microchannel. This pattern of surface features may be used to create a central swirling flow pattern.

The apertured section 380 may comprise an interior portion that forms part of one or more of the interior walls of process microchannel 310. A surface feature sheet may overlie this interior portion of the apertured section. Surface features may be formed in and/or on the surface feature sheet. The second reactant stream may flow through the apertured section and the surface feature sheet into the process microchannel. Part of the second reactant stream may be detached from the surface of the surface feature sheet while part may flow within the surface features of the surface feature sheet. The surface feature sheet may contain angled surface features that have relatively small widths or spans relative to the overall flow length. The surface feature sheet may provide mechanical support for the apertured section. The surface features may impart a vortical flow pattern to the fluids in the process microchannel and promote good mixing and/or promote the formation of small droplets. The vortical flow pattern may impart shear to the second reactant stream flowing through the apertured section and thus reduce the size of gas bubbles and/or liquid droplets in the bulk flow path.

Examples of the surface features include those illustrated in FIGS. 20-28. The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. The flow may rotate in the first level of surface features and diffuse molecularly into the second or more sublayers to promote reaction. In one embodiment, the surface features may be formed within the porous support. In one embodiment, surface features may be present in the wall opposite or adjacent the porous support. Three-dimensional surface features may be made via metal casting, photochemical machining, laser cutting, etching, ablation, or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations.

The use of surface features or fully etched plates with patterns may be advantageous to provide structural support for thin or weak apertured plates or sheets used to form the apertured section 380. In one embodiment, the apertured section 380 may be made from a polymeric material that has very small mean pore diameters (less than 1 micron) but can withstand a high pressure differential (greater than about 10 psi, or greater than about 50 psi, or greater than about 100 psi, or larger) that may be required to force the second reactant stream through the apertured section 380 into the process microchannel 310. The open span required for structural support may be reduced from the cross section of the process microchannel 310 to the open span and run the length of the surface feature. The span of the surface feature may be made smaller as required if the apertured sheet or plate has reduced mechanical integrity. One advantage of the surface features, may be that convective flow, which may occur within the surface features, may create a significant shear stress at the wall of the apertured section 380 to assist with the detachment of small gas bubbles and/or liquid droplets.

An example of a three-dimensional surface feature structure may comprise recessed chevrons at the interface adjacent the bulk flow path of the microchannel. Beneath the chevrons there may be a series of three-dimensional structures that connect to the surface features adjacent to the bulk flow path but are made from structures of assorted shapes, depths, and/or locations. It may be further advantageous to provide sub-layer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

The length and width of a surface feature may be defined in the same way as the length and width of a microchannel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are less than about 2 mm, and in one embodiment less than about 1 mm, and in one embodiment in the range from about 0.01 to about 2 mm, and in one embodiment in the range from about 0.01 to about 1 mm, and in one embodiment in the range from about 0.01 mm to about 0.5 mm. The width of the surface features may be sufficient to nearly span the microchannel width (for example, herringbone designs), but in one embodiment (such as fill features) may span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a microchannel, including surface features that recess at different depths into one or more microchannel walls. The spacing between recesses may be in the range from about 0.01 mm to about 10 mm, and in one embodiment in the range from about 0.1 mm to about 1 mm. The surface features may be present throughout the entire length of a microchannel or in portions or regions of the microchannel. The portion or region having surface features may be intermittent so as to promote a desired mixing or unit operation (for example, separation, cooling, etc.) in tailored zones. For example, a one-centimeter section of a microchannel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

The surface features may be positioned in one or more surface feature regions that extend substantially over the entire axial length of a channel. In one embodiment, a channel may have surface features extending over about 50% or less of its axial length, and in one embodiment over about 20% or less of its axial length. In one embodiment, the surface features may extend over about 10% to about 100% of the axial length of the channel, and in one embodiment from about 20% to about 90%, and in one embodiment from about 30% to about 80%, and in one embodiment from about 40% to about 60% of the axial length of a channel.

FIGS. 20-28 show a number of different patterns that may be used for surface features. Other patterns may be used. These patterns may be used in different axial or lateral sections of a microchannel.

Figure 20:
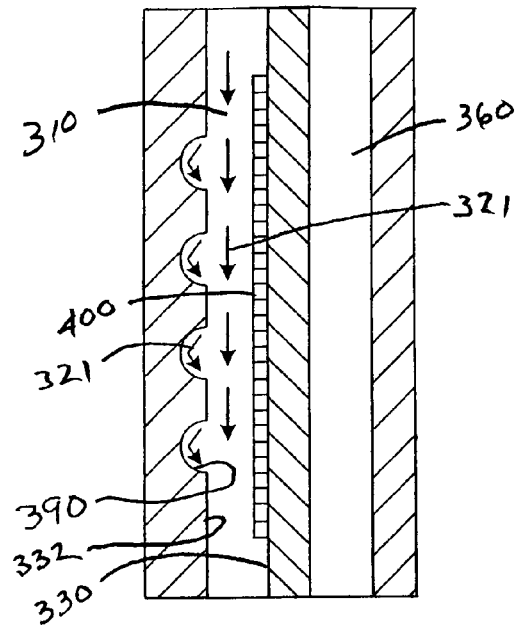
FIG. 20 is a schematic illustration of a repeating unit comprising a process microchannel and an adjacent heat exchange channel that may be used in the microchannel reactor illustrated in FIG. 2 or microchannel separator illustrated in FIG. 3. The process microchannel contains a porous catalyst or porous sorption medium on one interior wall and surface features for modifying the flow of process fluid in the process microchannel on an opposite interior wall. The surface features are in the form of spherical depressions in the interior wall of the process microchannel. The flow of process fluid in the process microchannel is indicated by the arrows in FIG. 20.
Figure 21:
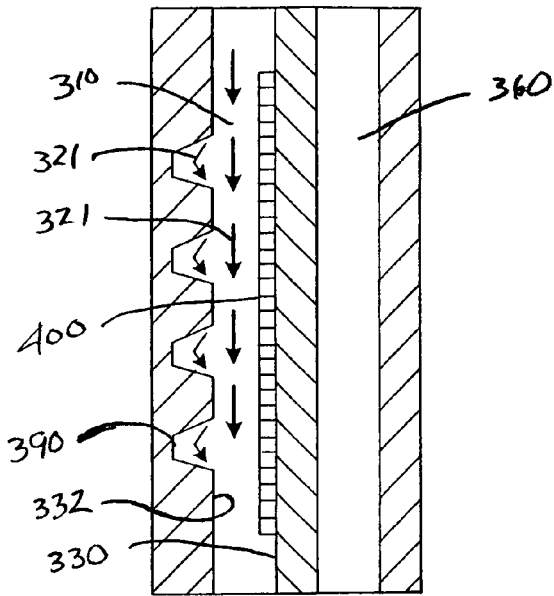
FIG. 21 is a schematic illustration of a repeating unit comprising a process microchannel and an adjacent heat exchange channel that may be used in the microchannel reactor illustrated in FIG. 2 or microchannel separator illustrated in FIG. 3. The process microchannel contains a porous catalyst or porous sorption medium on one interior wall and surface features for modifying the flow of process fluid in the process microchannel on an opposite interior wall. The surface features are in the form of frustrum depressions in the interior wall of the process microchannel. The flow of process fluid in the process microchannel is indicated by the arrows in FIG. 21.
Figure 22:
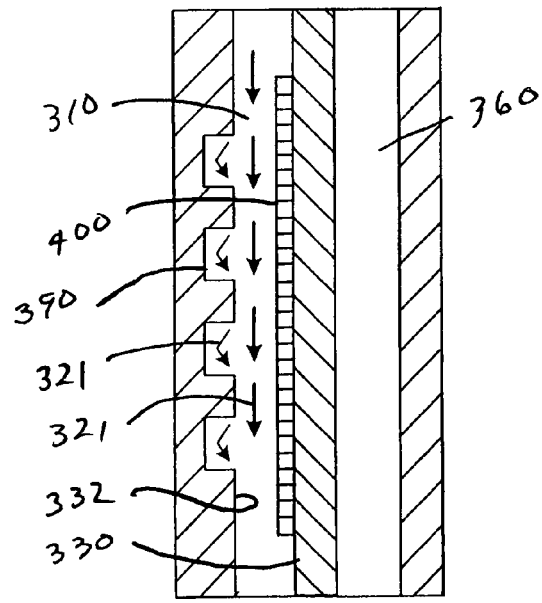
FIG. 22 is a schematic illustration of a repeating unit comprising a process microchannel and an adjacent heat exchange channel that may be used in the microchannel reactor illustrated in FIG. 2 or microchannel separator illustrated in FIG. 3. The process microchannel contains a porous catalyst or porous sorption medium on one interior wall and surface features for modifying the flow of process fluid in the process microchannel on an opposite interior wall. The surface features are in the form of angled rectangular depressions in the interior wall of the process microchannel. The flow of process fluid in the process microchannel is indicated by the arrows in FIG. 22.

The process microchannels 310 may contain surface features on one or more of the microchannel walls to enhance mixing and contact with the porous catalyst or porous sorption medium. Examples of repeating units containing these surface features are illustrated in FIGS. 20-22. Referring to FIG. 20, repeating unit 371 comprises microchannel 310 and heat exchange channel 360. Porous support 400 is mounted on interior wall 330 and surface features 390 are formed in the opposite interior wall 332. If the repeating unit 371 is used in microchannel reactor 100, the porous support 400 is used to support a catalyst. If the repeating unit 371 is used in microchannel separator 200, the porous support 400 is used to support a sorption medium. Process fluid flows through the process microchannel 310 as indicated by arrows 321. The flow of the process fluid is modified as the process fluid flows through surface features 390. The surface features 390 illustrated in FIG. 20 are in the form of spherical depressions in the microchannel wall 332. The modification of the flow of the process fluid by the surface features 390 enhances contact between the process fluid and the catalyst or sorption medium supported by the porous support 400. Heat exchange fluid may flow in the heat exchange channel 360 in a direction that is co-current, counter-current or cross-current relative to the flow of process fluid in the process microchannel 310.

The repeating unit 371A illustrated in FIG. 21 is similar to the repeating unit 371 illustrated in FIG. 20 with the exception that the surface features are in the form of frustrum depressions in the microchannel wall 332.

The repeating unit 371B illustrated in FIG. 22 is similar to the repeating unit 371 illustrated in FIG. 20 with the exception that the surface features in FIG. 22 are in the form of rectangular depressions in the microchannel wall 332.

Figure 23:
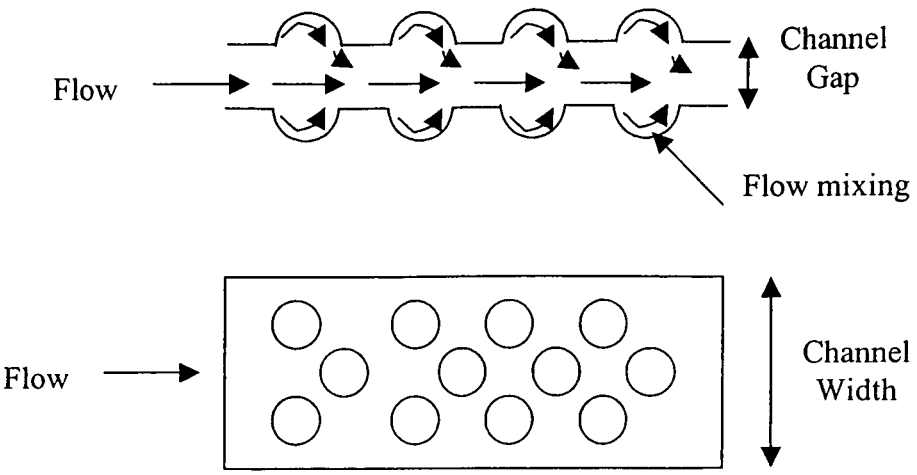
FIG. 23 is a schematic illustration of surface features which may be used in microchannels (e.g., process microchannels, second reactant stream microchannels, heat exchange microchannels) that may be used in the microchannel reactor illustrated in FIG. 2 or microchannel separator illustrated in FIG.

The surface features may have different forms than those illustrated in FIGS. 20-22. Also, the surface features may be positioned on opposite interior walls of the process microchannels 310 to enhance mixing and/or the heat exchange channels 360 to enhance heat exchange. Examples are illustrated in FIGS. 23-28. FIGS. 23-25 show surface features on opposite interior walls of a process microchannel or heat exchange channel. The surface features shown in FIG. 23 are spherical depressions. Frustrum depressions are shown in FIG. 24. Angled rectangular depressions are shown in FIG. 25. The surface features in FIG. 26, which are in the form of depressions in or projections from the microchannel wall, are in the form of vanes. The surface features illustrated in FIG. 27, which are in the form of depressions in or projections from the microchannel wall, are in the form of air foils. Surface features of various designs are illustrated in FIG. 28. Each of the surface features illustrated in FIG. 28 may be in the form of a depressions in or a projections from a microchannel wall.

Enhanced results may be achieved by the use of structured walls wherein surface features in or projecting from a channel wall are combined with one or more microgrooved support strips positioned on the same wall. These structured walls may be particularly useful in microchannel reactors wherein the surface features may be used to enhance contact between reactants and catalyst supported by the microgrooved supports. Examples are illustrated in FIGS. 41-43. In each of these drawings, microgrooved support strips 400 and surface features 390 are positioned on a channel wall. The channel wall may be referred to as a structured wall. The surface features 390 may be in the form of partial etches or grooves in the channel wall. Referring to FIG. 41, the surface features 390 are positioned between the microgrooved support strips 400. The surface features and microgrooved supports are substantially angled. The surface features 390 in FIG. 42 may have any shape that increases surface area for a chemical reaction. The surface features 390 depicted in FIG. 43 have regular shapes or connections between microgrooves in the microgrooved support strips 400 and between partial etch paths that connect the microgrooves.

In one embodiment, a surface feature sheet may be positioned next to one or more porous supports to provide directed flow toward and near a catalyst supported by the porous support. The surface feature sheet may underlie the porous supports. Surface features may be positioned within the porous supports. The porous supports may contain larger surface features in the supports cut or formed to direct or advect flow or to promote molecular diffusion over Knudsen diffusion. The surface features in the porous supports may be angled to promote flow advection from the bulk flow channel toward the catalyst.

Surface features may be etched or formed as partial etch features in ridges that separate through features for flow advection or diffusion through or around or past the structured wall. As shown in FIG. 41, surface features may be placed on walls or ribs that separate the microgrooved support strips. The microgrooved supports may include small surface features that use capillary forces to preferentially retain catalyst fluids during a washcoating step, and/or promote flow rotation from the bulk flow path to the interior of the porous support structures. Partially etched surface features may improve heat transfer between the catalyst positioned in the microgrooved supports and heat exchange channels in thermal contact with the microgrooved supports.

Partially etched surface features may be provided along ridges or walls separating the microgrooved support. These may be either large or small. Smaller surface features may increase the amount of surface area for a porous catalyst. Larger surface features may preferentially promote more flow rotation in the bulk flow path.

For a flow-by porous catalyst, where the gap adjacent the porous catalyst is substantially free of obstacles and flow is advected or diffused to the structured wall, a second tier of partially etched surface features within the walls that separate the porous catalyst may increase the surface area of the catalyst. As a second tier effect, the surface features may promote some flow movement into the porous catalyst based on the natural mass and thermal convection that may occur within the structured wall resulting from high conversion and/or a density change based on a change in moles upon reaction.

For a flow-through process microchannel, where the main flow channel is filled with the porous catalyst, the use of partially etched surface features on the microchannel walls may act to perturb the flow path. Flow may be preferentially pushed and pulled into and out of the surface feature regions and as such mass transfer resistance from the bulk flow passage to catalyst positioned within active surface features may be reduced.

Partially etched surface features in the microchannel wall between the wall and the porous catalyst may have any pattern or shape. They may be variable in depth, width, and/or length. They may be regular in shape or irregular in a manner that optimizes surface area and the location of the surface area that may later contain a catalyst relative to the rate of reaction and heat release requirement.

The porous catalyst may create at least three length scales for a chemical reactor to reduce transport resistance (both heat and mass) while also maintaining a relatively low pressure drop per unit length. The first length scale may be for bulk flow and may be either found above the porous catalyst where flow is substantially by the porous catalyst or it may be through the porous catalyst if flow is substantially through the openings formed in the porous catalyst. For the case of flow through the porous catalyst, the flow may move between at least two microgrooved or surface treated support strips. For the flow by case, flow may diffuse molecularly between two or more microgrooved or surface treated support strips. The relatively large openings in the microgrooved support strips, which may be in the range from about 10 microns to about 1000 microns, may provide for a relatively low pressure drop without incurring a large mass transfer resistance. A typical pore size for Knudsen diffusion may be less than about 1 micron, and in one embodiment less than about 0.1 micron.

A second length scale for the flow by porous catalyst may be the size of the pores or microgrooves themselves that may create a passage way for mass diffusion to interior active catalyst sites. The passageway may be substantially regular with low tortuosity (for example, less than about 5) and large enough to offer relatively little resistance to mass transfer (for example, from about 10 to about 1000 micron openings). For the flow-by porous catalyst in the form of a composite construction comprising a plurality of the microgrooved support strips stacked together, the second length scale may be formed by the partially etched microgrooved support strips, where the length is defined as the span or opening of the etched features. Smaller etched features may allow more surface area for the catalyst, thus multiple etched features on each wall that spans between two microgrooves on a microgrooved support strip may be useful. In general, about 2 to about 10, and in one embodiment about 5 to about 10, or more surface features per wall that spans two porous supports may be useful. The dimension for this span may be in the range from about 1 micron to about 500 microns. This length may be distinct and smaller than the dimension of the pores or microgrooves in the porous support such that when a catalyst is applied as a solution, the feature size in the etched features in the wall between two pores or microgrooves may be less than the main flow channel such that capillary forces hold the catalyst in place within the partially etched features in the wall between two pores or microgrooves while the main flow channel is drained with the liquid solution that contains or contained the catalyst.

A third length scale for the porous support when positioned in a flow-by reactor may be either partially etched features on the walls between the pores or microgrooves in the porous support which are smaller than the mouth or opening of the pores or microgrooves in or from an active catalyst positioned in the microgrooves. If partially etched features are notched or formed on the walls between the pores or microgrooves and then an active catalyst is deposited, four length scales may be appropriate for the flow-by configuration. A minimum three length scales may be used for the flow-by configuration using porous supports where the partial etched features on the wall between the porous supports.

In one embodiment, a flow-through catalyst support, where the bulk flow is substantially through the structure rather than by or past the structure, may be used. For the flow-through configuration, the third length scale may be from the active catalyst that is positioned within partially etched features within the wall that separates two pores or microgrooves in the porous support. For the flow-through configuration, the flow may impinge on the elements of the structure and traverses convectively through the length of the structure throughout the width and depth of the structure. In flow-through embodiments, for a plurality of parallel microchannels as required for scaling up reactors to larger capacity units, the pressure drop variation from channel to channel may be taken into consideration for providing sufficient flow distribution. In one embodiment, less than about 20% variation in pressure drop from channel to channel after the catalyst is applied to the porous structure may be achieved. The variation may be less than about 15%, or less than about 10%, or less than about 5% pressure drop from channel to channel. In one embodiment the variation in pressure drop from channel to channel may be less than about 2%, and in one embodiment less than about 1% after the catalyst is applied. Achieving a low variance in pressure drop from channel to channel after the catalyst is applied may be accomplished by the incorporation of the catalyst in regions of the first porous structure that do not substantially contribute to the open volume where flow convectively traverses during reaction. In flow-through embodiments, at least one second sub feature or porosity may be required within the first porous structure, wherein the size of the at least second set of pores may be less than the first set of pores. The size may be about 80% or less, and in one embodiment about 50% or less, and in one embodiment about 10% or less the size of the first set of pores. These structures may also be referred to as capillary features where capillary forces preferentially retain the catalyst fluid during the application of the catalyst. The features may be recessed or indented from the primary flow passage way that is defined by the first porous structure. The at least second set of pores may be substantially or partially filled with the catalyst solution during application. Upon drying a solid heterogeneous catalyst layer with at least a third porosity may be retained on the walls of the first and second porous structure. The mean thickness on the first porous structure may be less than the mean thickness on the second porous structure. The thickness on the first porous structure may reduce the hydraulic diameter of the main flow passage way through the first porous structure and thus restrict flow and increase pressure drop per unit length per unit flowrate. The increase in pressure drop per unit length per unit flowrate through the flow-through porous structure after the application of the catalyst may be less than about 20%, and in one embodiment less than about 10%, and in one embodiment less than about 5% over the pressure drop per unit length per unit flowrate of the channel before the application of catalyst. The resulting porous catalyst may have at least three porosities. The first and largest may be the main pore for convective flow of the reactants. The second and intermediate pore size may be the sub features recessed within the first porous structure for preferentially retaining the catalyst. The third and smallest size pores may be found within the active catalyst disposed on the surface of the first and second pores.

The second set of pores may be formed in shims or lamina using a partial etch or partial removal of material. The etched features that form the second set of pores may be discontinuous along the shim where flow does not substantially convectively flow within the second set of pores but rather diffuses molecularly. FIG. 115 shows a flow through structure with the first set of pores where flow convectively travels through the reactor. The second set of pores are shown as the smaller indents or recesses found within the first set of pores. Catalyst may be preferentially held or retained within the second set of pores. There may also be catalyst layers deposited within the first porous structure. The third set of pores may be found in the active catalyst layer not shown in this figure but disposed on the walls of the first and second set of pores.

For the flow-through configuration, the third length scale may be from the active catalyst that is positioned within partially etched features within the wall that separates two pores or microgrooves in the porous support.

The apertures 381 in the apertured section 380 may be of sufficient size to permit the flow of the second reactant stream through the apertured section. The apertures may be used to mix two like or dislike phases, including gases, miscible liquids or immiscible liquids. The apertures may be referred to as pores. The apertured sections 380 may have thicknesses in the range from about 0.01 to about 50 mm, and in one embodiment about 0.05 to about 10 mm, and in one embodiment about 0.1 to about 2 mm. The apertures 381 may have average diameters in the range up to about 1000 microns, and in one embodiment up to about 250 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures 381 in the apertured sections 380 may be in the range from about 1 to about $5 \times 10^8$ apertures per square centimeter, and in one embodiment about 1 to about $1 \times 10^6$ apertures per square centimeter. The apertures may or may not be isolated from each other. A portion or all of the apertures may be in fluid communication with other apertures within the apertured section; that is, a fluid may flow from one aperture to another aperture. The ratio of the thickness of the apertured sections 380 to the length of the apertured sections along the process flow path of the fluids flowing in the process microchannels 310 may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

Figure 12:
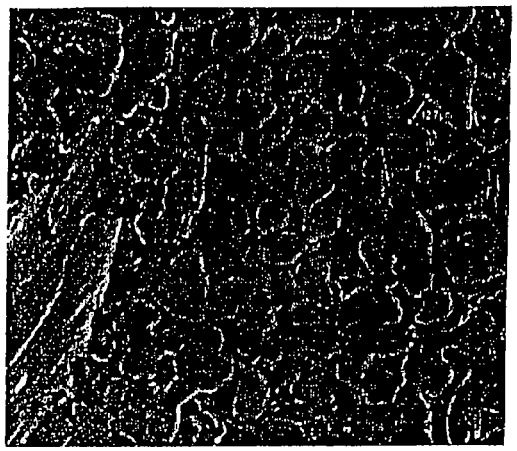
FIG. 12 is a scanning electron microscopic (SEM) image of a porous stainless steel substrate. This substrate may be used for making an apertured section for the staged addition repeating units illustrated in FIGS. 9-11.
Figure 13:
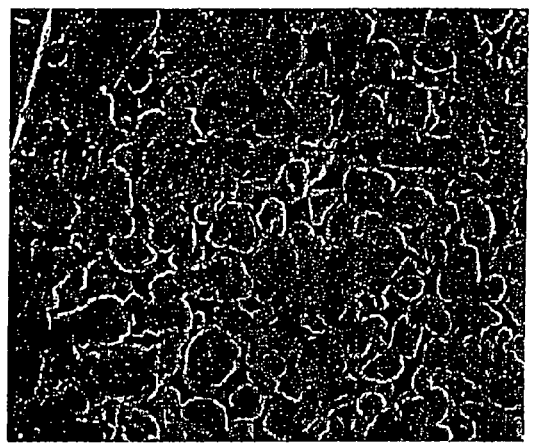
FIG. 13 is an SEM image of the substrate illustrated in FIG. 12 except that it is heat treated. This substrate may be used for making an apertured section for the staged addition repeating units illustrated in FIGS. 9-11.

The apertured sections 380 may be constructed of any material that provides sufficient strength and dimensional stability to permit the operation of the process. These materials may include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling, or electrochemical or photochemical etching. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The apertures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The apertures may be reduced in size by heat treating as well as by methods that form an oxide scale or coating on the internal side walls of the apertures. These techniques may be used to partially occlude the apertures to reduce the size of the openings for flow. FIGS. 12 and 13 show a comparison of SEM surface structures of a stainless steel porous substrate before and after heat treatment at the same magnification and the same location. FIG. 12 shows the surface before heat treating and FIG. 13 shows the surface after heat treating. The surface of the porous material after the heat treatment has a significantly smaller gap and opening size. The average distance between the openings is correspondingly increased.

Figure 14:
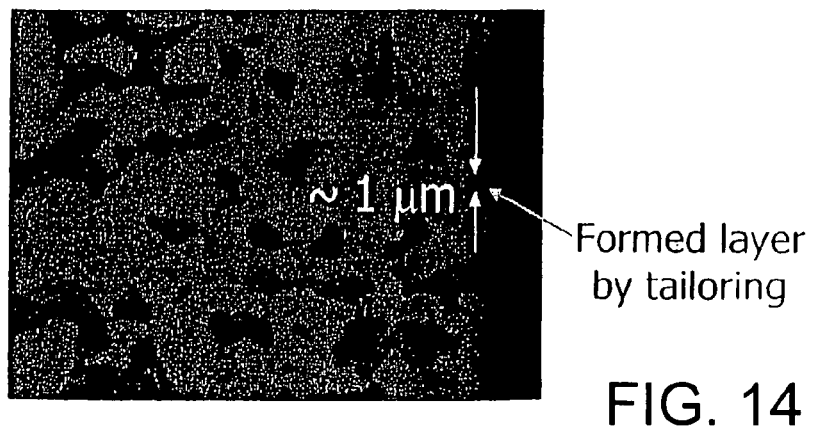
FIG. 14 is an SEM image of a tailored porous substrate which may be used for making an apertured section for the staged addition repeating units illustrated in FIGS. 9-11.

The apertured sections 380 may be made from a metallic or nonmetallic porous material having interconnected channels or pores of an average pore size in the range from about 0.01 to about 200 microns. These pores may function as the apertures 381. The porous material may be made from powder or particulates so that the average inter-pore distance is similar to the average pore size. When very small pore sizes are used, the inter-pore distance may also be very small. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance. An SEM image of a tailored substrate or apertured section is shown in FIG. 14.

The making of substrates for use as apertured sections 380 with sufficiently small apertures or pores 381 to provide reactants having gas bubble or liquid droplet sizes smaller than about one micron may be problematic. A reason for this lies in the fact that relatively high surface roughness occurs with untreated regular porous materials such as a metallic porous substrates made from powder/particles by compression and/or sintering. These metallic porous substrates may not have the required pore size in the surface region when a given nominal pore size is lower than a certain value. While the bulk of the porous material may have the specified nominal pore size, the surface region may be characterized by merged pores and cavities of much larger sizes. This problem may be overcome by tailoring these substrates to provide for the desired pore size and inter-pore distance in the surface region. This may be done by removing a surface layer from the porous substrate and adding a smooth new surface with smaller openings. The gas bubble or liquid droplet size in the reactant mixture that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler may then be removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

Figure 15:
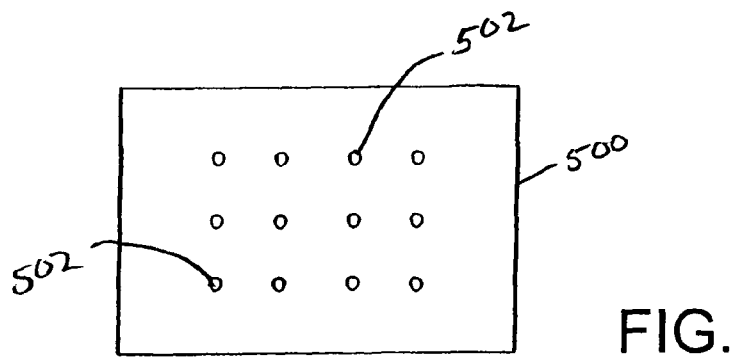
FIG. 15 is a schematic illustration of a plan view of an apertured sheet which may be used in making an apertured section for the staged addition repeating units illustrated in FIGS. 9-11.
Figure 16:
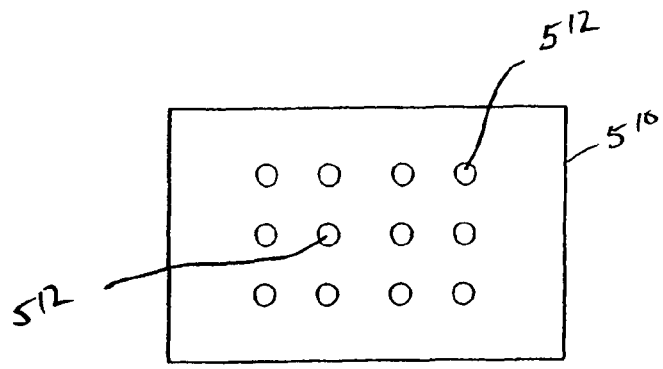
FIG. 16 is a schematic illustration of a plan view of an apertured sheet or plate which may be used in making an apertured section for the staged addition repeating units illustrated in FIGS. 9-11.
Figure 17:
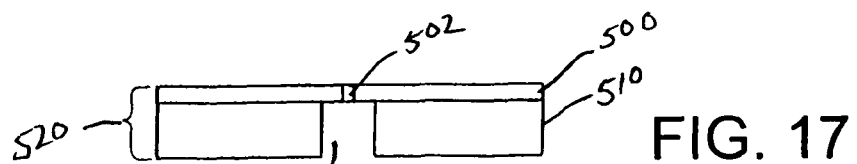
FIG. 17 is a schematic illustration of a relatively thin apertured sheet overlying a relatively thick apertured sheet or plate which may be used in making an apertured section for the staged addition repeating units illustrated in FIGS. 9-11.

Referring to FIGS. 15-17, the apertured section 380, in one embodiment, may be constructed of a relatively thin sheet 500 containing relatively small apertures 502, and a relatively thick sheet or plate 510 containing relatively large apertures 512. The apertures 502 may be aligned with or connected to the apertures 512. The relatively thin sheet 500 overlies and is bonded to the relatively thick sheet or plate 510, the relatively thin sheet 500 facing the interior of process microchannel 310 and the relatively thick sheet 510 facing the interior of the second reactant stream channel 374. The relatively thin sheet 500 may be bonded to the relatively thick sheet 510 using any suitable procedure (e.g., diffusion bonding) to provide a composite construction 520 with enhanced mechanical strength. The relatively thin sheet 500 may have a thickness in the range from about 0.001 to about 0.5 mm, and in one embodiment about 0.05 to about 0.2 mm. The relatively small apertures 502 may have any shape, for example, circular, triangular or rectangular. The relatively small apertures 502 may have an average diameter in the range from about 0.05 to about 50 microns, and in one embodiment about 0.05 to about 20 microns. The relatively thick sheet or plate 510 may have a thickness in the range from about 0.01 to about 5 mm, and in one embodiment about 0.1 to about 2 mm. The relatively large apertures 512 may have any shape, for example, circular, triangular or rectangular. The relatively large apertures 512 may have an average diameter in the range from about 0.01 to about 4000 microns, and in one embodiment about 1 to about 2000 microns, and in one embodiment about 10 to about 1000 micron. The total number of apertures 502 in sheet 500 and the total number of apertures 512 in sheet or plate 510 may be in the range from about 1 to about 10000 apertures per square centimeter, and in one embodiment from about 1 to about 1000 apertures per square centimeter. The sheet 500 and the sheet or plate 510 may be constructed of any of the materials described above as being useful for constructing the apertured section 380. The apertures 502 and 512 may be aligned or connected in such a manner that fluid flowing through the apertured section 380 flows initially through the apertures 512 then through the apertures 502. The relatively short passageway for the fluid to flow through the relatively small apertures 502 enables the fluid to flow through the apertures 502 with a relatively low pressure drop as compared to the pressure drop that would occur if the passageway in the apertures had a depth equal to the combined depth of apertures 502 and 512.

Figure 18:
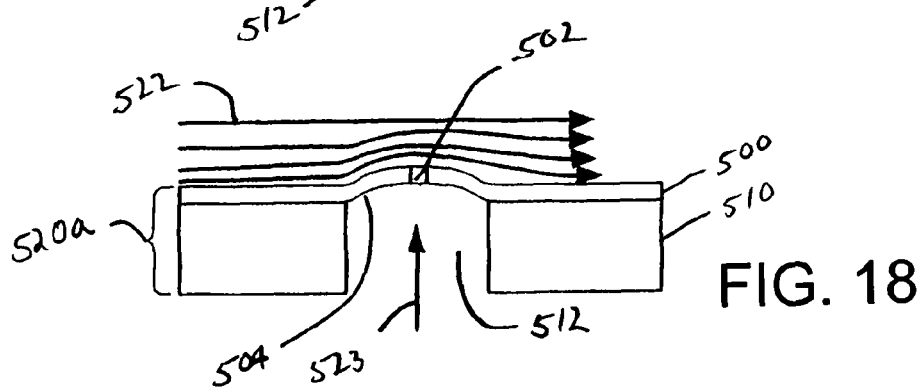
FIG. 18 is a schematic illustration of a relatively thin apertured sheet overlying a relatively thick apertured sheet or plate which may be used in making an apertured section for the staged addition repeating units illustrated in FIGS. 9-11.

In the embodiment illustrated in FIG. 18, the composite construction 520a has the same design as illustrated in FIG. 17 with the exception that convex portion 504 of the relatively thin sheet 500 covering the aperture 512 is provided. Convex portion 504 provides increased local shear force in the adjacent channel. The second reactant feed stream flows through the apertures 512 and 502 in the direction indicated by arrow 523. The directional arrows 522 in FIG. 18 show the flow of the first reactant feed stream in the process microchannel adjacent to the aperture 502. The increased local shear force may lead to a smaller gas bubble or liquid droplet size for the fluid flowing through the aperture 502.

Figure 19:
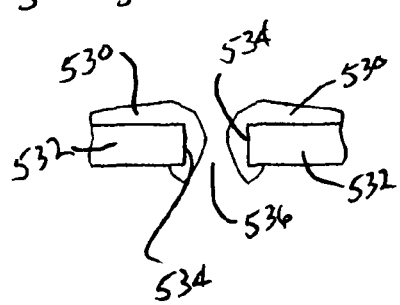
FIG. 19 is a schematic illustration of an alternate embodiment of an aperture that may be used in the apertured section of the staged addition repeating units illustrated in FIGS. 9-11. The aperture has a coating partially filling it and overlying its sidewalls.

In the embodiment illustrated in FIG. 19, a surface coating 530 is deposited on the surface of sheet or plate 532 and on the internal sidewalls 534 of aperture 536. This coating provides a facilitated way of reducing the diameter of the apertures. The coating material used to form coating 530 may be alumina, nickel, gold, or a polymeric material (e.g., Teflon). The coating 530 may be applied to the sheet or plate 532 using known techniques including chemical vapor deposition, metal sputtering, metal plating, sintering, sol coating, and the like. The diameter of the apertures may be controlled by controlling the thickness of the coating 530.

The apertured section 380 may be formed from an asymmetric porous material, for example, a porous material having multiple layers of sintered particles. The number of layers may be two, three, or more. An advantage of these multilayered substrates is that they may provide enhanced durability and adhesion. Examples may include sintered ceramics that have relatively large pores on one side and relatively small pores on the other side. The relatively small pores may have diameters in the range form about 2 to about 10 nanometers (nm). The relatively small pores may be positioned in a relatively thin layer of the multilayered substrate. The relatively thin layer may have a thickness in the range from about 1 to about 10 microns. The side with the relatively small pores may be placed facing the interior of the process microchannel 310 to take advantage of relatively high shear forces to remove the relatively small gas bubbles of reactant as they are formed.

The apertured section 380 may extend along at least about 5% of the axial length of the process microchannel 310, and in one embodiment at least about 20% of the axial length of the process microchannel, and in one embodiment at least about 35% of the axial length of the process microchannel, and in one embodiment at least about 50% of the axial length of the process microchannel, and in one embodiment at least about 65% of the axial length of the process microchannel, and in one embodiment at least about 80% of the axial length of the process microchannel, and in one embodiment at least about 95% of the axial length of the process microchannel, and in one embodiment from about 5% to about 100% of the axial length of the process microchannel, and in one embodiment from about 10% to about 95% of the axial length of the process microchannel, and in one embodiment from about 25% to about 75% of the axial length of the process microchannel, and in one embodiment from about 40% to about 60% of the axial length of the process microchannel 310.

The gas bubbles or liquid droplets of the second reactant formed in the process microchannel 310 may have volume-based mean diameters in the range up to about 200 microns, and in one embodiment about 0.01 to about 200 microns, and in one embodiment from about 0.01 to about 100 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron. An advantage of the inventive process is that at least in one embodiment the gas bubbles or liquid droplets may be characterized by having a relatively narrow distribution of average diameters.

"Relative span" is often referred to as "span." It is a dimensionless parameter calculated from volume distribution. Volume median diameter (VMD), D[v,0.1] and D[v,0.9] are diameters representing the points at which 10% and 90%, respectively, of the volume of bubbles or droplets dispersed is in bubbles or droplets of smaller diameter. The span may be defined as D[v,0.9] minus D[v,0.1] which is then divided by the VMD (D[v,0.5]). In one embodiment, the span for the bubbles or droplets of reactant in the reaction mixture may be in the range from about 1.3 to about 5, and in one embodiment about 1.8 to about 2.5. In one embodiment, the process may be conducted in a single process microchannel and the span may be in the range of from about 1.3 to about 2.5. In one embodiment, the process may be conducted in a scaled-up process employing multiple process microchannels and the span may be in the range from about 1.3 to about 5.

The volume-based mean diameter for the bubbles or droplets of reactant in the reactant mixture may be in the range from about 0.1 to about 25 microns, and the span may be in the range from about 1 to about 5. In one embodiment, the volume-based mean diameter may be in the range from about 1 to about 10 microns, and the span may be in the range from about 1.8 to about 2.5. In one embodiment, the bubbles may have a volume-based mean diameter in the range from about 1 to about 25 microns, and a span in the range from about 1.9 to about 2.5.

The process microchannels 310 are microchannels. The second reactant stream channels 374 may be microchannels although they may have larger dimensions that would not characterize them as microchannels. The process microchannels 310, and second reactant stream channels 374, may have at least one internal dimension of height or width of up to about 10 mm, and in one embodiment up to about 5 mm, and in one embodiment up to about 2 mm, over all or only part of the length of the channels, for example, over about 1% to about 100% of the length of the channels, and in one embodiment over about 5% to about 100% of the length, and in one embodiment over about 20% to about 80% of the length. In one embodiment the height or width may be in the range from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.5 mm. The height or width may be in the range from about 0.15 to about 10 mm, and in one embodiment from about 0.2 to about 10 mm, and in one embodiment from about 0.3 to about 10 mm. The height or width may be in the range from about 0.2 to about 5 mm, and in one embodiment from about 0.2 to about 3 mm, and in one embodiment from about 0.3 to about 2 mm. The other internal dimension of height or width may be of any value, for example, it may range up to about 100 cm, and in one embodiment from about 0.01 to about 100 cm, and in one embodiment from about 0.1 cm to about 100 cm, and in one embodiment from about 0.1 to about 75 cm, and in one embodiment from about 0.1 to about 50 cm, and in one embodiment about 0.2 cm to about 25 cm. The length of the process microchannels and second reactant stream channels may be of any value, although, as suggested by the drawings, the length of the second reactant stream channels may be less than the length of the next adjacent process microchannels. The lengths of each of these channels may be in the range up to about 10 meters, and in one embodiment in the range from about 0.01 to about 10 meters, and in one embodiment from about 0.01 to about 5 meters, and in one embodiment from about 0.01 to about 2.5 meters, and in one embodiment from about 0.01 to about 1 meter, and in one embodiment from about 0.02 to about 0.5 meters, and in one embodiment from about 0.02 to about 0.25 meter.

The porous support 400 and/or the porous catalyst or porous sorption medium 400 may have a thickness in the range from about 0.25 to about 10 mm, and in one embodiment in the range from about 0.25 to about 5 mm, and in one embodiment in the range from about 0.25 to about 1 mm. The thickness may be defined as the distance from the microchannel wall to which the porous catalyst or porous sorption medium is attached to the surface of the porous catalyst or porous sorption medium adjacent the gap or bulk flow region in the process microchannel. Referring to FIGS. 5 and 6, the thickness of the porous catalyst or porous sorption medium 400 may be the distance from the surface of the process microchannel wall 330 to the top 317 of the porous catalyst or porous sorption medium 400 positioned on the wall 330. The gap 315 adjacent to the porous catalyst or porous sorption medium 400 may have a height in the range from about 0.02 to about 5 mm, and in one embodiment in the range from about 0.1 to about 2 mm. The height of the gap 315 may be the distance perpendicular to the direction of bulk flow in the microchannel from the top 317 of the porous catalyst or porous sorption medium 400 to the opposite interior wall within the microchannel or to the top 317 of a porous catalyst or porous sorption medium 400 on the opposite interior wall. For example, referring to FIGS. 5, 5a, 5c, 5d and 6, the height of the gap 315 in each of the process microchannels 310 illustrated in these figures is the distance from the top 317 of the porous catalyst or porous sorption medium 400 on the wall 330 to the top 317 of the porous catalyst or porous sorption medium 400 on the wall 332. The height of the gap 315 in FIG. 5b is the distance from the top 317 of the porous catalyst or porous sorption medium 400 on wall 330 to the surface of the opposite interior wall 332. The ratio of the thickness of the porous catalyst or porous sorption medium 400 to the height of the gap 315 may be in the range from about 0.1 to about 20, and in one embodiment in the range from about 1 to about 10.

In one embodiment, a continuous metal path may extend through the porous support 400 from the surface of the microchannel wall 330 to the top 317 of the porous support, and the height of the gap 315 may be equal to or less than about three times the thickness of the porous support 400, and in one embodiment less than about two times the thickness of the porous support, and in one embodiment less than the thickness of the porous support.

In one embodiment, the porous support 400 may not have a pillar structure and the distribution of line densities (as measured through the thickness of the porous support at locations spanning the face of the porous support) may be non-Gaussian. The term "pillar structure" may refer to any porous support which has substantially the same pattern of fully solid material and fully open area extending through the thickness (smallest dimension) of the porous support. There may be no interconnecting metal between the distinct pillars. The term "line density" may refer to the average density of the porous support averaged through the thickness along a line orthogonal to the interface between the porous support 400 and the gap 315.

The ratio of the cross-sectional area of bulk flow region 315 to the cross-sectional area of the process microchannel 310 may be in the range from about 0.01 to about 10, and in one embodiment in the range from about 0.05 to about 5.

The porous support 400 may have a tortuosity in the range from about 1 to about 10, and in one embodiment in the range from about 1 to about 7, and in one embodiment in the range from about 1 to about 5, and in one embodiment in the range from about 1 to about 3, and in one embodiment in the range from about 1 to about 2. The porous catalyst may have a tortuosity in the range from about 1 to about 20, and in one embodiment in the range from about 2 to about 5. The porous sorption medium may have a tortuosity in the range from about 1 to about 5, and in one embodiment in the range from about 1 to about 3.

The effective thermal conductivity of the combined porous support and heat transfer wall may be in the range from about 0.5 to about 500 W/m-K, and in one embodiment in the range from about 1 to about 500 W/m-K, and in one embodiment in the range from about 3 to about 500 W/m-K, and in one embodiment in the range from about 5 to about 500 W/m-K, and in one embodiment in the range from about 10 to about 500 W/m-K. The thermal conductivity of the porous catalyst may be in the range from about 1 to about 500 W/m-K, and in one embodiment in the range from about 1 to about 150 W/m-K. The thermal conductivity of the porous sorption medium may be in the range from about 0.2 to about 500 W/m-K, and in one embodiment in the range from about 0.5 to about 50 W/m-K. The porous support may have a shortest path of continuous solid from the open channel to the adjacent solid wall which may be no more than about three times, and in one embodiment no more than about two times, and in one embodiment about the same thickness of the porous support.

The porosity of the porous support 400 may be in the range from about 1% to about 99%, and in one embodiment in the range from about 10% to about 75%. The porosity of the porous catalyst may be in the range from about 10% to about 90%, and in one embodiment in the range from about 20% to about 80%. The porosity of the porous sorption medium may be in the range from about 1% to about 90%, and in one embodiment in the range from about 10% to about 50%.

The average pore size of the porous support 400 may be in the range up to about 700 microns, and in one embodiment in the range from about 0.1 micron to about 700 microns. In one embodiment, at least about 20% of the pore volume, and in one embodiment at least about 50% of the pore volume may have an average pore size in the range from about 0.1 to about 700 microns, and in one embodiment in the range from about 0.3 to about 500 microns, and in one embodiment in the range from about 1 to about 200 microns. In one embodiment, the porous support may comprise coating layer having an average pore size in the range up to about 10 microns, and in one embodiment in the range from about 0.1 nm to about 1 micron, and in one embodiment in the range from about 0.1 to about 2 nm, and in one embodiment in the range from about 2 to about 50 nm, and in one embodiment in the range from about 50 nm to about 1 micron.

The heat exchange channels 360 may be microchannels or they may have larger dimensions. Each of the heat exchange channels 360, may have a cross section having any shape, for example, a square, rectangle, circle, semi-circle, etc. Each of the heat exchange channels 360 may have an internal height or gap of up to about 10 mm, and in one embodiment in the range from about 0.05 to about 10 mm, and in one embodiment from about 0.05 to about 5 mm, and in one embodiment from about 0.05 to about 2 mm. The width of each of these channels may be of any dimension, for example, up to about 3 meters, and in one embodiment from about 0.01 to about 3 meters, and in one embodiment from about 0.1 to about 3 meters. The length of each of the heat exchange channels 152 and 220 may be of any dimension, for example, up to about 10 meters, and in one embodiment from about 0.01 to about 10 meters, and in one embodiment from about 0.01 to about 5 meters, and in one embodiment from 0.01 to about 2.5 meters, and in one embodiment from about 0.01 to about 1 meter, and in one embodiment from about 0.02 to about 0.5 meter, and in one embodiment from about 0.02 to about 0.25 meter.

The process microchannel 310, second reactant stream channel 374, and/or heat exchange channels 360 may have cross sections that are rectangular, or alternatively they may have cross sections having any shape, for example, a square, circle, semi-circle, trapezoid, etc. The shape and/or size of the cross section of the process microchannel 310, second reactant stream channel 374, and/or heat exchange channel 360 may vary over its length. For example, the height or width may taper from a relatively large dimension to a relatively small dimension, or vice versa, over the length of the microchannel.

The separation between adjacent process microchannels, second reactant stream channels and/or heat exchange channels may be in the range from about 0.05 mm to about 50 mm, and in one embodiment about 0.1 to about 10 mm, and in one embodiment about 0.2 mm to about 2 mm.

The process microchannels 310, second reactant stream channels 374 and/or heat exchange channels 360 may have their interior walls coated with a lipophobic coating (the same coating may also provide hydrophobic properties) to reduce surface energy. Teflon may be an example of a coating material that may exhibit both lipophobic and hydrophobic tendencies. The surface of the apertured section 380 that faces the interior of the process microchannel 310 may be coated with a lipophobic coating to reduce droplet drag and promote the formation of smaller droplets. The coating on the apertured section may reduce the energy required to detach a droplet from the surface of the apertured section. In addition, the drag exerted on the second reactant stream may be lower during droplet detachment and while flowing beyond the apertured section downstream in the process microchannel. In one embodiment, a hydrophobic coating may be applied to the apertured section to assist with the detachment of droplets. In one embodiment, fluids may not wet surfaces coated with the lipophobic coating. As such, the fluids may slip past the surface and thus negate or reduce the usual no-slip boundary condition of fluids against a wall. As the fluids slip, the local friction factor may decrease as a result of reduced drag and the corresponding pressure drop may be reduced per unit length of the channels. The local heat transfer rate may increase as a result of forced convection over a coated surface as opposed to conductive heat transfer through a stagnant film. The effect of the coating may have a different impact on different types of non-Newtonian fluids. For the case of pseudoplastic (power law) fluid without yield may appear Newtonian above shear rates that are fluid dependent. The viscosity of the fluid may be higher when the shear rate is below a certain value. If the shear rate is locally larger because of the coated wall, then the fluid may be able to shear droplets more easily, move with less energy (lower pumping requirements), and have better heat transfer properties than if the coating were not used. For the case of pseudoplastic (power law) fluid with yield may still have a yield stress, at the wall the yield stress may be greatly reduced with the use of the lipophobic coating. Heat transfer and frictional properties may be enhanced if the apparent yield is low when the coating is used as compared to when the coating is not used. The shear-related effects may be more pronounced for non-Newtonian fluids than for Newtonian fluids.

The microchannel reactor 100 and microchannel separator 200 may be constructed of any material that provides sufficient strength, dimensional stability and heat transfer characteristics for carrying out the inventive process. Examples of suitable materials may include steel (e.g., stainless steel, carbon steel, and the like), aluminum, titanium, nickel, and alloys of any of the foregoing metals, plastics (e.g., epoxy resins, UV cured resins, thermosetting resins, and the like), monel, inconel, ceramics, glass, composites, quartz, silicon, or a combination of two or more thereof. The microchannel reactor may be fabricated using known techniques including wire machining, conventional machining, laser cutting, photochemical machining, electrochemical machining, molding, water jet, stamping, etching (for example, chemical, photochemical or plasma etching) and combinations thereof. The microchannel reactor may be constructed by forming layers or sheets with portions removed that allow flow passage. A stack of sheets may be assembled via diffusion bonding, laser welding, diffusion brazing, and similar methods to form an integrated device. In one embodiment, the method used to bond or braze or join a stack of sheets together may provide good thermal contact at the interface between stacked layers of structured or porous support material within the same process microchannel and at the interface between the porous support material and the heat transfer wall. In this way the effective thermal conductivity of the combination of porous support and heat transfer wall in series may not be significantly decreased by a contact resistance. The effective thermal conductivity of the combined heat transfer wall and porous support may not be less than about 30% of the effective thermal conductivity of the porous support. In one embodiment, the effective thermal conductivity of the combined wall and porous catalyst may not be less than about 50%, and in one embodiment not less than about 80% of the effective thermal conductivity of the porous support.

The microchannel reactor may have appropriate manifolds, valves, conduit lines, etc. to control flow of the reactants and product, and the flow of heat exchange fluid. These are not shown in the drawings, but can be readily provided by those skilled in the art.

The microchannel reactor core 110 and microchannel separator core 210 may be made by a process which comprises laminating or diffusion bonding thin sheets of any of the above-indicated materials (e.g., metal, plastic or ceramic) so that each layer has a defined geometry of channels and openings through which to convey fluids. After the individual layers have been created, the porous supports may be inserted and the desired catalyst or sorption medium may be applied to the porous supports. The catalyst or sorption medium may be applied to the porous supports prior to inserting the porous supports into the desired process microchannels. The layers may then be stacked in a prescribed order to build up the lamination. The layers may be stacked side-by-side or one above the other. The completed stack may then be diffusion bonded to prevent fluids from leaking into or out of the microchannel reactor or between streams. After bonding, the device may be trimmed to its final size and prepared for attachment of pipes and manifolds. An additional step for the process microchannels that contain the catalyst or sorption medium may be to integrate the catalyst into the device prior to final assembly.

Feature creation methods may include photochemical etching, milling, drilling, electrical discharge machining, laser cutting, and stamping. A useful method for mass manufacturing is stamping. In stamping, care should be taken to minimize distortion of the material and maintain tight tolerances of channel geometries, for example, less than about ±0.5 mm displacement of feature location. Preventing distortion, maintaining shim alignment and ensuring that layers are stacked in the proper order are factors that should be controlled during the stacking process.

The stack may be bonded through a diffusion or brazing, or glueing or reactive joining process among others. In these process, the stack may be subjected to elevated temperatures and or pressures to achieve the desired thermal contact of layers. Selection of these parameters may require modeling and experimental validation to find bonding conditions that enable sufficient thermal contact between metal layers.

The next step, after joining, may be to machine the device. A number of processes may be used, including conventional milling with high-speed cutters, as well as highly modified electrical discharge machining techniques. A full-sized bonded microchannel reactor unit or sub-unit that has undergone post-bonding machining operations may comprise, for example, tens, hundreds or thousands of shims.

The process microchannels 310, second reactant stream channels 374, and heat exchange channels 360 that may be used in the microchannel reactor core 110 or microchannel separator core 210 may have rectangular cross sections and be aligned in side-by-side vertically oriented planes or horizontally oriented stacked planes. These planes may be tilted at an inclined angle from the horizontal. These configurations may be referred to as parallel plate configurations. Various combinations of process microchannels, second reactant stream channels and heat exchange channels may be employed. Combinations of these rectangular channels may be arranged in modularized compact repeating units for scale-up.

The cross-sectioned shape and size of the process microchannels 310, may vary along their axial length to accommodate changing hydrodynamics within the channel. For example, if a reaction is conducted and one of the reactants is in excess, the fluidic properties of the reaction mixture may change over the course of the reaction. Surface features may be used to provide a different geometry, pattern, angle, depth, or ratio of size relative to the cross-section of the process microchannel along its axial length to accommodate these hydrodynamic changes.

The process microchannels 310 and the second reactant stream channels 374 may be formed from parallel spaced sheets and/or plates, the second reactant stream channels being adjacent to the process microchannels. The heat exchange channels 360 may be formed from parallel spaced sheets and/or plates. The heat exchange channels may be adjacent to the process microchannels, the second reactant stream channels, or both the process microchannels and the second reactant stream channels. The process microchannels and second reactant stream channels may be aligned in interleaved side-by-side planes or interleaved planes stacked one above another.

The process microchannel 310 and the second reactant stream channel 374 may comprise circular tubes aligned concentrically. The process microchannel may be in an annular space and the second reactant stream channel may be in the center space or an adjacent annular space. The process microchannel may be in the center space and the second reactant stream channel may be in an adjacent annular space.

The microchannel reactor 100 and microchannel separator 200 may have appropriate manifolds, valves, conduit lines, etc. to control flow of the process fluid, and the flow of the heat exchange fluid. These are not shown in the drawings, but can be readily provided by those skilled in the art.

In one embodiment, relatively short contact times, high selectivity to the desired product and relatively low rates of deactivation of the catalyst may be achieved by limiting the diffusion path required for the porous catalyst. For example, this may be achieved when the catalyst is in the form of a thin layer on the porous support. This may allow for increased space velocities. In one embodiment, the thin layer of catalyst can be produced using chemical vapor deposition. This thin layer may have a thickness in the range up to about 1 micron, and in one embodiment from about 0.1 to about 1 micron, and in one embodiment about 0.25 micron. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film is in intimate contact with the porous support. This may leverage high heat transfer rates attainable in the microchannel reactor and allows for close control of temperature. The result is the ability to operate at increased temperature (faster kinetics) without promoting the formation of undesired by-products, thus producing higher productivity and yield and prolonging catalyst life.

The heat source and/or heat sink may be used for cooling, heating or both cooling and heating. The heat source and/or heat sink may comprise one or more heat exchange channels. The heat source may comprise one or more non-fluid heating elements such as one or more electric heating elements or resistance heaters. The heat sink may comprise one or more non-fluid cooling elements. These may be adjacent to the process microchannels and/or second reactant stream channels. In one embodiment, the heat source and/or heat sink may not be in contact with or adjacent to the process microchannels and/or second reactant stream channels, but rather may be remote from either or both the process microchannels and/or second reactant stream channels, but in thermal contact with the process microchannels and/or second reactant stream channels. The non-fluid heating and/or non-fluid cooling elements can be used to form one or more walls of the process microchannels 310 and/or second reactant stream channels 374. The non-fluid heating and/or cooling elements may be built into one or more walls of the process microchannels and/or second reactant stream channels. The non-fluid heating and/or cooling elements may be thin sheets, rods, wires, discs or structures of other shapes embedded in the walls of the process microchannels and/or second reactant stream channels. The non-fluid heating and/or cooling elements may be in the form of foil or wire adhered to the process microchannel walls and/or second reactant stream channel walls. Heating and/or cooling may be effected using Peltier-type thermoelectric cooling and/or heating elements. Multiple heating and/or cooling zones may be employed along the length of the process microchannels and/or second reactant stream channels. Similarly, heat transfer fluids at different temperatures in one or more heat exchange channels may be employed along the length of the process microchannels and/or second reactant stream channels. The heat source and/or heat sink can be used to provide precise temperature control within the process microchannels and/or second reactant stream channels.

The management of heat exchange in the microchannel reactor 100 may provide advantageous control of the conversion of the reactants and the selectivity to the desired products. The heat exchange channels 360 may be adapted for heat exchange fluid to flow in the heat exchange channels in a direction that is co-current with the flow of fluid in process microchannels and/or staged addition channels that are adjacent to or in thermal contact with the heat exchange channels. Alternatively, the heat exchange fluid may flow through the heat exchange channels in a direction that is countercurrent to the flow of fluid through the process microchannels and/or staged addition channels. Alternatively, the heat exchange channels may be oriented relative to the process microchannels and/or staged addition channels to provide for the flow of heat exchange fluid in a direction that is cross-current relative to the flow of fluid through the process microchannels and/or staged addition channels. The heat exchange channels may have a serpentine configuration to provide a combination of cross-flow and co-current or counter-current flow.

The heat exchange fluid used in the heat exchange channels to heat and/or cool the microchannel reactor core 110 or microchannel separator core 210 may be any fluid. The heat exchange fluid may comprise one or more of air, steam, liquid water, gaseous nitrogen, liquid nitrogen, oils such as mineral oil, and heat exchange fluids such as Dowtherm A and Therminol which are available from Dow-Union Carbide. The heat exchange fluid may comprise one or more organic compounds containing 1 to about 5 carbon atoms per molecule such as methylenechloride, fluorochloromethanes (e.g., dichlordifluoromethane), hydrocarbons containing 1 to about 5 carbon atoms per molecule (e.g., methane, ethane, ethylene, propanes, butanes, pentanes, etc.), or a mixture of two or more thereof.

The heat exchange fluid may comprise the feed composition, staged addition feed stream and/or product. This can provide process pre-heat, cool-down and/or an increase in overall thermal efficiency of the process.

In one embodiment, the heat exchange channels may comprise process microchannels wherein an endothermic or exothermic process is conducted. Examples of endothermic processes that may be conducted in the heat exchange channels include steam reforming and dehydrogenation reactions. In one embodiment, the incorporation of a simultaneous endothermic reaction to provide an improved cooling may enable a typical heat flux of roughly an order of magnitude or more above the convective cooling heat flux. Examples of exothermic processes that may be conducted in the heat exchange channels include water-gas shift reactions, methanol synthesis reactions and ammonia synthesis reactions.

In one embodiment, the heat exchange fluid may undergo a phase change as it flows through the heat exchange channels. This phase change may provide additional heat addition or removal from the process microchannels beyond that provided by convective heating or cooling. For a liquid heat exchange fluid being vaporized, the additional heat being transferred may result from the latent heat of vaporization required by the heat exchange fluid. An example of such a phase change may be a heat exchange fluid that undergoes boiling or partial boiling. In one embodiment, the amount of heat exchange fluid boiling in the heat exchange channels may be in the range from about 0.1 to about 99% by volume of the total amount of heat exchange fluid in the heat exchange channel, and in one embodiment about 5 to about 30% by volume.

In one embodiment, the temperature of the reactant streams entering the microchannel reactor may be within about 200° C., and in one embodiment within about 100° C., and in one embodiment within about 50° C., and in one embodiment within about 20° C., of the temperature of the product exiting the microchannel reactor.

The use of controlled heat exchange between heat exchange channels in thermal contact with or adjacent to the process microchannels and/or staged addition channels may allow for uniform temperature profiles for the process microchannels and/or staged addition channels. This provides for the possibility of a more uniform heat exchange at more rapid rates than can be obtained with conventional processing equipment such as mixing tanks. For a microchannel reactor employing multiple process microchannels and staged addition channels, the temperature difference between the process microchannels and/or staged addition channels at least one common position along the lengths of the process microchannels may be less than about 5° C., and in one embodiment less than about 2° C., and in one embodiment less than about 1° C.

The heat exchange channels in thermal contact with or adjacent to either the process microchannels and/or staged addition channels may employ separate temperature zones along the length of such channels. For example, in one embodiment, the temperature in a first zone near the entrance to the process microchannel may be maintained at a temperature above or below a second temperature in a second zone near the end of the process microchannel. A cool down or quench zone may be incorporated into the process microchannels to cool the product. Numerous combinations of thermal profiles are possible, allowing for a tailored thermal profile along the length of the process microchannels and/or staged addition channels, including the possibility of heating or cooling zones before and/or after the reaction zone in the process microchannels to heat or cool the reactants and/or product.

The heat exchange fluid entering the heat exchange channels may be at a temperature in the range from about −40° C. to about 650° C., and in one embodiment in the range from about 0° C. to about 600° C., and in one embodiment in the range from about 20° C. to about 500° C. The heat exchange fluid exiting the heat exchange channels may be at a temperature in the range from about −40° C. to about 650° C., and in one embodiment in the range from about 0° C. to about 600° C., and in one embodiment in the range from about 20° C. to about 500° C. The residence time of the heat exchange fluid in the heat exchange channels may be in the range from about 5 ms to about 1 minute, and in one embodiment from about 20 ms to about 1 minute, and in one embodiment from about 50 ms to about 1 minute, and in one embodiment about 100 ms to about 1 minute. The pressure drop for the heat exchange fluid as it flows through the heat exchange channels may be in the range up to about 1 atm/m, and in one embodiment up to about 0.5 atm/m, and in one embodiment up to about 0.1 atm/m, and in one embodiment from about 0.01 to about 1 atm/m. The heat exchange fluid may be in the form of a vapor, a liquid, or a mixture of vapor and liquid. The Reynolds Number for the flow of vapor through the heat exchange channels may be in the range from about 10 to about 5000, and in one embodiment about 100 to about 3000. The Reynolds Number for the flow of liquid through heat exchange channels may be in the range from about 10 to about 10000, and in one embodiment about 100 to about 5000.

The heat flux for heat exchange in the microchannel reactor core 110 or the microchannel separator core 210 may be in the range from about 0.01 to about 500 W/cm$^2$. The heat flux for convective heat exchange or convective heating in the microchannel reactor core 110 or microchannel separator core 210 may be in the range from about 0.01 to about 250 watts per square centimeter (W/cm$^2$) of surface area of the process microchannels in the microchannel separation core, and in one embodiment from about 0.1 to about 50 W/cm$^2$, and in one embodiment from about 1 to about 25 W/cm$^2$, and in one embodiment from about 1 to about 10 W/cm$^2$. The heat flux for phase change heat exchange may range from about 1 to about 500 W/cm$^2$, and in one embodiment, from about 1 to about 100 W/cm$^2$, and in one embodiment from about 1 to about 50 W/cm$^2$, and in one embodiment from about 1 to about 25 W/cm$^2$, and in one embodiment from about 1 to about 10 W/cm$^2$.

The pressure within each individual heat exchange channel 360 may be controlled using passive structures (e.g., obstructions), orifices and/or mechanisms upstream of the heat exchange microchannels 360 or in the microchannels. By controlling the pressure within each heat exchange microchannel, the temperature within each heat exchange microchannel can be controlled. A higher inlet pressure for each heat exchange fluid may be used where the passive structures, orifices and/or mechanisms let down the pressure to the desired heat exchange microchannel pressure. By controlling the temperature within each heat exchange microchannel, the temperature in the process microchannels in thermal contact with the heat exchange microchannel can be controlled. Thus, for example, each process microchannel may be operated at a desired temperature by employing a specific pressure in the heat exchange microchannel in thermal contact with the process microchannel. This provides the advantage of precisely controlled temperatures for each process microchannel. The use of precisely controlled temperatures for each process microchannel 310 may provide the advantage of a tailored temperature profile and an overall reduction in the energy requirements for the reaction or separation process.

In one embodiment, the catalyst may be regenerated. This may be done by flowing a regenerating fluid through the process microchannels in contact with the catalyst. The regenerating fluid may comprise hydrogen or a diluted hydrogen stream. The diluent may comprise nitrogen, argon, steam, methane, carbon dioxide, or a mixture of two or more thereof. The concentration of $H_2$ in the regenerating fluid may range up to about 100% by volume, and in one embodiment from about 1 to about 100% by volume, and in one embodiment about 1 to about 50% volume. The temperature of the regenerating fluid may be from about 20 to about 600° C., and in one embodiment about 20 to about 400° C., and in one embodiment about 80 to about 200° C. The pressure within the process microchannels during this regeneration step may range from about 1 to about 100 atmospheres absolute pressure, and in one embodiment about 1 to about 10 atmospheres. The residence time for the regenerating fluid in the process microchannels may range from about 0.001 to about 10 seconds, and in one embodiment about 0.01 second to about 1 second.

The contact time of the reactants and product with the catalyst within the process microchannels may be in the range up to about 100 seconds, and in one embodiment in the range from about 1 microsecond (μs) to about 100 seconds, and in one embodiment from about 1 millisecond (ms) to about 100 seconds, and in one embodiment in the range from about 1 ms to about 50 seconds, and in one embodiment in the range from about 1 ms to about 25 seconds, and in one embodiment in the range from about 1 ms to about 10 seconds, and in one embodiment from about 1 ms to about 1 second, and in one embodiment from about 1 ms to about 500 ms, and in one embodiment about 1 ms to about 200 ms, and in one embodiment about 1 ms to about 100 ms, and in one embodiment about 1 ms to about 50 ms, and in one embodiment about 1 ms to about 20 ms, and in one embodiment about 1 ms to about 10 ms. The contact time may be in the range from about 1 to about 1000 μs, and in one embodiment in the range from about 1 to about 500 μs. In one embodiment the contact time may be in the range from about 50 to about 150 μs. In one embodiment, the contact time may be in the range from about 800 to about 950 μs, and in one embodiment from about 850 to about 925 μs. In one embodiment, the reactants may be combined with up to about 50% by volume diluent (e.g., nitrogen gas) and the contact time may be up to about 25 seconds, and in one embodiment up to about 10 seconds, and in one embodiment up to about 1 second. In one embodiment, the reactants may be combined with up to about 25% by volume diluent and the contact time may be up to about 50 seconds, and in one embodiment up to about 25 seconds, and in one embodiment up to about 5 seconds. In one embodiment, the reactants may be combined with up to about 10% by volume diluent and the contact time may be up to about 100 seconds, and in one embodiment up to about 50 seconds, and in one embodiment up to about 10 seconds.

The flow rate of fluid flowing in the process microchannels may be in the range from about 0.001 to about 500 lpm (liters per minute), and in one embodiment about 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of fluid flowing in the process microchannels may be in the range from about 0.01 to about 200 m/s, and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the fluid flowing in the process microchannels may be in the range from about 0.0001 to about 100000, and in one embodiment about 0.001 to about 10000.

The weight hourly space velocity (WHSV) for the flow of the reactants and product in the microchannel reactor core 310 may be at least about 0.1 (ml feed)/(g catalyst)(hr). The WHSV may range from about 0.1 to about 5000, and in one embodiment, the WHSV may range from about 1 to about 500 (ml feed)/(g catalyst)(hr), and in one embodiment the WHSV may be in the range from about 10 to about 500 (ml feed)/(g catalyst)(hr).

The space velocity (or gas hourly space velocity (GHSV)) for the flow of the process fluids in the process microchannels may be at least about 1000 $hr^{-1}$ (normal liters of feed per hour per liter of volume within the process microchannels), and in one embodiment at least about 2000 $hr^{-1}$, and in one embodiment at least about 4000 $hr^{-1}$, and in one embodiment at least about 7000 $hr^{-1}$, and in one embodiment at least about 10000 $hr^{-1}$. The space velocity may be in the range from about 1000 to about 100000 $hr^{-1}$, and in one embodiment in the range from about 4000 to about 40000 $hr^{-1}$. The volume within the process microchannels may include all volume in the process microchannels in which a process fluid may flow in a flow-through manner or a flow-by manner. The volume may include the volume within any microgrooved supports positioned in the microchannels as well as the volume within any surface features that may be present in the process microchannels.

The temperature of the reactants entering the microchannel reactor core 110 may be in the range from about −40° C. to about 950° C., and in one embodiment about 0° C. to about 600° C., and in one embodiment from about 20° C. to about 500° C., and in one embodiment from about 20° C. to about 250° C., and in one embodiment from about 20° C. to about 200° C.

The temperature within the process microchannels 310 may be in the range from about −40° C. to about 1050° C., and in one embodiment from about 0° C. to about 600° C., and in one embodiment from about 20° C. to about 500° C., and in one embodiment from about 20° C. to about 250° C., and in one embodiment from about 20° C. to about 200° C.

The temperature of the product exiting the microchannel reactor core 110 may be in the range from about −40° C. to about 650° C., and in one embodiment about 0° C. to about 600° C., and in one embodiment from about 20° C. to about 500° C., and in one embodiment from about 20° C. to about 250° C., and in one embodiment from about 20° C. to about 200° C.

The pressure within the process microchannels may be in the range up to about 250 atmospheres absolute pressure, and in one embodiment up to about 100 atmospheres, and in one embodiment up to about 50 atmospheres. In one embodiment the pressure may be in the range from about 1 to about 50 atmospheres absolute pressure, and in one embodiment from about 10 to about 40 atmospheres, and in one embodiment from about 20 to about 30 atmospheres.

The pressure drop of the reactants and/or products as they flow in the process microchannels may be in the range up to about 20 atmospheres per meter of length of the process microchannel (atm/m), and in one embodiment up to about 15 atm/m, and in one embodiment up to about 5 atm/m, and in one embodiment up to about 2 atm/m, and in one embodiment up to about 1 atm/m.

The pressure drop for the second reactant feed stream flowing through the apertured section 374 may be in the range up to about 0.1 atm, and in one embodiment from about 0.001 to about 0.1 atm, and in one embodiment from about 0.001 to about 0.05 atm, and in one embodiment about 0.001 to about 0.005 atm.

The reactants and products flowing in the process microchannels may be in the form of a vapor, a liquid, or a mixture of vapor and liquid. The Reynolds Number for the flow of vapor in the process microchannels may be in the range from about 10 to about 10000, and in one embodiment about 100 to about 3000. The Reynolds Number for the flow of liquid in the process microchannels may be about 10 to about 10000, and in one embodiment about 100 to about 3000.

The structured wall reactors disclosed herein may be referred to as intense reactors. The use of these reactors may provide a method of intensifying the productivity per unit volume of a chemical reactor. The use of thick porous catalysts in thermal contact with the heat transfer wall of a process microchannel may provide the combination of unexpectedly high thermal conductivities and rates of reaction. A "thick" porous catalyst or structured wall may have a thickness of at least about 0.25 mm. The porous catalyst may serve to both hold the active catalyst supported thereon and transfer heat to or from the heat transfer wall. Reactants and products may move convectively and/or diffusively within the porous catalyst. The porous catalyst may comprise a first catalyst structure and at least one second catalyst structure. The first catalyst structure may comprise the porous support and the second catalyst structure may comprise an active catalyst (e.g., metal, metal oxide, acid, etc.) coated or applied to the first catalyst structure. Diffusion within the first catalyst structure may be molecular in nature and not Knudsen to maintain minimal resistance to mass transfer within the first catalyst structure. The second catalyst structure may be positioned on the first catalyst structure. The second catalyst structure may comprise the direct application of an active catalyst layer or a series of sublayers. The catalyst sublayers may include a buffer layer, a surface area layer or layers, and an active catalyst layer. The surface area layer may comprise an active catalyst for the desired reaction.

The porous catalyst may comprise primary pores and secondary pores. The primary pores may be larger than the secondary pores. The fluid flowing through the porous catalyst may flow primarily through the primary pores. The secondary pores may retain the catalyst. The pressure drop for the flow of fluid through the porous catalyst may be less than about 20%, and in one embodiment less than about 15%, and in one embodiment less than about 10%, and in one embodiment less than about 5%, and in one embodiment less than about 2%, and in one embodiment less than about 1%. The pressure drop increase for the flow of fluid through the porous catalyst after the active catalyst is added to the porous support may be less than about 20% as compared to before the active catalyst is added, and in one embodiment less than about 15%, and in one embodiment less than about 10%, and in one embodiment less than about 5%, and in one embodiment less than about 2%, and in one embodiment less than about 1%.

The structured wall reactor may be useful for endothermic reactions or exothermic reactions. For endothermic reactions, heat may be added at a sufficient rate to drive very fast reactions without creating cold spots in the reactor that reduce the reaction rate. For exothermic reactions, heat may be removed at a sufficient rate to avoid hot spots that may reduce the selectivity to the desired product, such as the case with styrene produced from ethylbenzene and oxygen, or reduce the thermodynamic driving force for the conversion of a reactant, such as the case with methanol synthesis.

The thickness of the porous support or the first catalyst structure may be thicker than a direct wall coated catalyst, whose typical thickness may range from 1 to 100 microns. The direct wall coated catalyst may also have average or mean pore sizes that are in the Knudsen diffusion range, or on the order of about 2 microns or less.

The use of thick porous catalysts in the disclosed structured wall reactors increases the capacity or productivity of any individual microchannel in a multichannel reactor. By increasing the productivity of an individual channel, the overall number of channels required to achieve a desired capacity may be decreased. Further, the higher capacity process channels in turn may require fewer heat transfer channels within a multichannel reactor system. For example, a thin wall coated microchannel reactor with a channel gap of 250 microns may be positioned next to a heat transfer channel of 250 microns and a heat transfer wall of 250 microns. The resulting multichannel reactor system may have only 25% of the total volume disposed as volume for the process reaction. By contrast, a structured wall reactor may have porous catalysts with a first catalyst structure thickness of 0.04 inch (1 mm) positioned on opposite interior walls of a process microchannel and a channel gap of 0.02 inch (0.51 mm) between the porous catalysts. A heat exchange channel may be positioned on either side of the process microchannel. The heat exchange channel may be an internal height or gap of 0.01 inch (0.25 mm) and an intervening wall of 0.01 inch (0.25 mm). The net result is the total process channel of 0.1 inch (2.54 mm) in a repeating unit of 0.13 inch (3.3 mm) for a surprisingly large percentage of greater than 76% process total volume within the core of the microchannel reactor. In one embodiment more than about 50% of the volume of the device may be found within the process microchannels inclusive of reaction zone, heat transfer zone and flow distribution zones if required. In one embodiment, more than about 75% or more than about 85% of the volume of the reactor may be found within the process microchannels. For these examples, the volume of the heat exchange channels may be less than about 50%, and in one embodiment less than about 40%, and in one embodiment less than about 25% of the volume of the reactor device. While these numbers may be illustrative, they represent an improvement in the utilization of microchannel heat exchange channels. That is, the heat exchange channels may be able to support a very high rate of heat transfer, but may not be fully utilized in the case of a thin wall coated catalyst. This structured wall reactor design decouples the required surface area for heat transfer and the required surface area for chemical reaction within an intimate multichannel microchannel reactor where the heat is added or removed as the reaction proceeds. The area for heat transfer may be planar as in the case of a flat wall or enhanced as in the case of a structured wall. The area on the reaction wall may be extended by the structured or porous wall. Each of the process microchannels and heat exchange channels may be independently optimized while sharing a common heat transfer wall. If the process reaction is slower, the structured wall may be built up to a thickness such that the corresponding heat release or demand may be more closely matched with the capability of the heat exchange channel.

An advantage of using the structured wall reactor is that a reduced pressure drop may be achieved for a given channel productivity (especially at high channel productivities) when a channel gap is provided adjacent to the structured wall. The size of the channel gap may be tailored to keep pressure drop in a desired range at high productivity. Temperature gradients within the structured wall reactors may be controlled with a high level of precision. In contrast, prior art examples of flow-through supported catalysts and flow-through packed beds of catalyst particulates may not offer as much control over the pressure drop vs. temperature gradient relationship as provided herein. In some embodiments the structured wall reactors may include surface features on or in the walls of the channel which may enhance mixing and/or heat transfer. These embodiments may provide more ability to reduce mass transport resistance to the surface of the catalyst structure than prior art flow-through and packed bed catalyst structures, especially when operated at high channel productivities.

A disadvantage of some prior art embodiments is the contact resistance at the interface between the catalyst structure or packed bed and the heat transfer wall. In contrast, in one embodiment of the structured wall reactor the porous support or first catalyst structure may be bonded directly to the heat transfer wall. This may minimize or eliminate such contact resistance, and thus enhance heat transfer and control over the catalyst temperature.

The effective thermal conductivity through the porous support or first catalyst structure to the heat transfer wall may be greater than about 0.5 W/m-K, and in one embodiment greater than about 1 W/m-K, and in one embodiment greater than about 2 W/m-K.

The effective mass diffusivity through the porous support or first catalyst structure may be at least about 20% of the mass diffusivity of the reactants and/or products through a corresponding straight path through the structure or orthogonal to the direction of flow. The tortuosity of the mass diffusion path of the porous support or the first catalyst may be less than about 5, and in one embodiment less than about 4, and in one embodiment less than about 3, and in one embodiment less than about 2. The first catalyst structure average pore diameter after deposition of the second catalyst structure on the first catalyst structure may be greater than about 10 microns, and in one embodiment greater than about 20 microns, and in one embodiment greater than about 30 microns. The second catalyst structure may be a thin coating on the first catalyst structure. The second catalyst structure may have a thickness that is less than about 100 microns, and in one embodiment in the range from about 1 to about 100 microns, and in one embodiment in the range from about 1 to about 25 microns. The mean pore size for the second catalyst structure may be any size, and one embodiment may be in the Knudsen regime.

The majority of the fluid flowing in the process microchannels of the structured wall reactor may not flow convectively through the pore structure of the first catalyst structure, but rather may flow convectively through the gap or open channel adjacent to the porous catalyst.

Multiphase reactions, including the reaction of a gas and a liquid or a gas and a liquid on a solid heterogeneous may be a particularly challenging reaction system. All three phases should be in contact for a reaction to proceed. In many conventional reactors and microreactors, the liquid layer is in the form of a film. The film thickness may range from about 50 microns in a falling film microreactor to about 2 or 3 mm in a conventional trickle bed reactor. Diffusion drives the gases through the liquid film and the liquid products away from the surface for renewal of reactants on the solid catalyst. For this range of thicknesses and a typical diffusivity of about 0.00001 $cm^2$/sec, the time for diffusion may be on the order of about 2.5 seconds to 1000 seconds for a 1 mm thick film. Considering the need for multiple iterations of diffusion through the liquid film, the characteristic time for reaction in a multiphase system may be on the order of minutes to hours with conventional reactors or microreactors.

For the structured wall reactor described herein, the desired liquid phase may have a characteristic dimension that is less than about 10 microns, and in one embodiment less than about 1 micron, and in one embodiment less than about 0.5 micron such that the droplet movement may be dominated by Brownian motion. Small liquid droplets may be formed in a continuum of gas (for systems where the majority of the volume is gas rather than liquid). The process using the structured wall reactor may involve first forming a fine aerosol as the gas and liquid are mixed or in the ensuing section of the reactor where passive mixing and shearing structures reduce the droplet size.

It may be expected that liquid phase reactions may be advantaged by the use of the structured wall reactors. However, unlike gas phase reactions that may or may not require mixing of the fluid in the main process microchannel, a liquid phase reaction may be expected to require mixing in the main process microchannel. The flow-by gap that may be adjacent to the porous catalyst would be the main passage for convective flow in the structured wall reactor. Molecules may enter the structured wall primarily by diffusion but also by a small convective current. To enable mixing in the main channel, surface features may be used at the interface between the main flow process microchannel and the structured wall. The surface features may underlie the porous support or may be used on an interior microchannel wall opposite or adjacent the porous catalyst. The surface features may be used to induce both lateral and transverse velocity vectors in an otherwise laminar flow stream. In one embodiment it may be possible for flow in the process microchannel to be transitional or turbulent.

For liquid phase reactions, slow diffusivity may make it difficult to traverse the open gap in the main flow process microchannel. For example, for a channel gap of 0.025 cm and a typical liquid phase diffusivity of 0.00001 $cm^2$/sec, the corresponding time for diffusion may be 62.5 seconds. For a desired reaction time in a liquid phase reaction on the order of seconds to minutes, this time for diffusion may be too slow. For some reactions, diffusion alone across the gap of the main flow process microchannel may be acceptable.

A structured wall reactor with a porous catalyst placed under a surface feature layer and adjacent to a heat transfer wall may provide for desired enhanced reaction times. Flow within the structured wall may be diffusive although there may be a small contribution from convection (on the order of about 10% or less of the main process microchannel flow velocity). One advantage provided by the structured wall reactor may be the additional time that the reactants may spend in contact with the catalyst without facing the convective currents in the main flow process microchannel that move the reactants down stream. The net result may be more time that the reactant molecules may spend in a reactor system near the catalyst.

For some slow reactions with minimal series reactions, the additional time reactants spend diffusing within thick structured wall sections may be particularly advantageous. If the series reactions have a higher activation energy than the desired reactions, then the thermal control achieved with the structured wall may also minimize the overreaction of the product. For fast reactions, the thickness of the structured wall and hence the corresponding amount of catalyst required may be reduced. For liquid phase reactions with strong series reactions and whose activation energy is near that of the desired reaction or reactions, the added time spent within a thick structured wall may not be advantageous. For this embodiment, a relatively thin structured wall may be used.

A thick structured wall may be defined as having a thickness equal to or greater than about 0.25 mm. A thin structured wall may be defined as less than about 0.25 mm. A thick structured wall may have a thickness in the range from about 0.25 to about 5 mm or more, and in one embodiment in the range from about 0.25 to about 3 mm, and in one embodiment in the range from about 0.25 to about 1 mm. The thick structured wall may be particularly useful when the effective thermal conductivity of the structured wall is sufficiently high, the pore size is sufficiently large, and the pore tortuosity is sufficiently low.

The use of the structured wall reactor for integrating fast reaction kinetics with improved heat and mass transport characteristics may be beneficial for exothermic reactions as well as endothermic reactions. Exothermic reactions, such as partial oxidation reactions, may be faced with two competing reaction pathways—the desired reaction with a first heat of reaction and at least one undesired reaction with at least one second heat of reaction. For many exothermic reactions, the second heat of reaction may be higher than the first heat of reaction. For both cases, the heat of reaction may be negative, thereby indicating a net generation of heat as the reaction proceeds. In addition, the activation energy for the first desired reaction may be less than the activation energy for the second undesired reaction. If heat is not adequately removed from the catalyst as it forms, it may increase the local temperature on the catalyst surface. As the temperature increases, the effect may be more pronounced on the second reaction with the higher activation energy. This undesired reaction may become relatively more favored than at the lower temperature. As the second reaction becomes more favored it may proceed at an increased speed and in turn it may release more heat per unit volume because the second heat of reaction is higher than the first heat of reaction. The cascading effect may lead to: pronounced temperature rises on the catalyst; potential catalyst sintering and deactivation; thermal hotspots; lower selectivity to the desired reaction; and/or potential thermal runaway for the reactor leading to unsafe operation.

Conventional exothermic reactors, such as fixed bed reactors, typically mitigate the effect of relatively poor heat removal from a catalyst particle by diluting the feed and thus limiting the total amount of reaction and corresponding heat release per unit volume that may be generated. One method of diluting the feed is to run with an excess of one of the reactants or add a non reactive diluent to the reactant stream. Operating with an excess of one reactant or an additional diluent may act to increase the reactor volume, require a downstream separation, and add reactant or diluent recycle equipment that may include a compressor. An improved system may be achieved with the use of the disclosed structured wall reactors where the exothermic reactions may be safely operated near their stoichiometric feed ratio and recycle equipment may be eliminated.

Another common practice to mitigate local hot spot and thermal run-away may be to dilute the catalyst with a catalytically inert but thermally conductive material, so as to improve heat dissipation. However, this may result in an increase in reactor size for the same throughput. A higher pressure drop is often another penalty to this practice. These problems may be overcome by using the disclosed structured wall reactors.

Exothermic reactions have been successfully operated in microchannel reactors and improved heat removal characteristics have been demonstrated. Structures of catalysts used for exothermic reactions may include wall coated catalysts, catalysts coated on dense engineered structures such as fins, packed catalyst powders or pellets within a microchannel, flow-through foam structures, and porous flow-by structures either inserted adjacent to a microchannel wall or integral with a microchannel wall. The disclosed structured wall reactors, in at least one embodiment, may provide an improvement over these structures. The disclosed structured wall reactor, in at least one embodiment, may employ a flow-by porous catalyst that is in intimate thermal contact with the heat transfer wall of the microchannel. As such the porous catalyst may be either bonded to or formed integrally with the microchannel wall. Any heat transfer contact resistance between the catalyst in the structured wall and the heat transfer wall may be regarded as negligible. The rate of heat generated from this catalyst may be relatively high and the heat removal rate on the other side of the heat transfer wall should be sufficient to keep up with and remove the heat that is generated. For example, the heat generated by the catalyst may be in the range from about 1 to about 200 $W/cm^2$. This heat may be removed using one or more of the following features:

A heat exchange fluid that boils either fully or partially, to remove the high rate of heat generation in an adjacent heat exchange channel.

An endothermic reaction that employs a porous catalyst structure integrated with the heat transfer wall in an adjacent channel.

Heat transfer enhancement features embedded within the heat transfer wall, such that the rate of heat transfer may be substantially above that obtained with a flat microchannel wall. A substantial rate of enhanced heat transfer may be at least about 25% higher, and in one embodiment at least about 50% higher, and in one embodiment at least about 100% higher than a corresponding flat microchannel wall operated under the same conditions.

Turbulent flow of a heat transfer fluid in an adjacent channel.

Laminar flow of a gas or liquid in an adjacent channel.

The heat and mass transfer in a smooth microchannel may be limited by the flow boundary layer thickness. The flow regime in microchannels may be laminar due to small hydraulic diameters. The laminar flow regime may be marked by a thick boundary layer which offers resistance to heat and mass transfer from the channel wall to the bulk of the fluid, or vice-versa. One way to enhance the heat and mass transfer between the channel wall and the bulk flow is by employing surface features on or in the channel wall that enhance mixing. Examples of surface features that may be provided on or in the wall to enhance heat and mass transfer may include those illustrated in FIGS. 20-28 and 41-43. These may include spherical depressions (FIGS. 20 and 23) and frustrum depressions (FIGS. 21 and 24). Angled rectangular depressions (FIGS. 22 and 25) may create flow mixing in the width dimension. Another way to enhance heat and mass transfer may be to place the features in the bulk flow region which helps divert the flow from the bulk flow region to the channel walls. Examples of features that may be employed in the bulk flow region may include vanes (FIG. 26) and air foils (FIG. 27).

A consideration in designing heat and mass transfer enhancement features is the pressure drop penalty. It may be desirable that the heat and mass enhancement be greater than the pressure drop increase.

Alternate embodiments with hybrid combinations of these features may be employed to remove the high rate of heat generation from an exothermic reaction in a process microchannel comprising the porous catalyst structure.

The disclosed structured wall reactors may be characterized by high heat fluxes with modest or manageable temperature gradients. Managing temperature gradients may be important for minimizing the mechanical thermal strain of the device or catalyst coating for good adhesion. It may also enhance control of hot spots and provide for high selectivity to desired reactions. The structured wall reactor may be characterized by a heat flux intensity that is greater than about 100 $W/m^2$-K, and in one embodiment greater than about 1000 $W/m^2$-K, and in one embodiment greater than about 5000 $W/m^2$-K. The heat flux intensity may be in the range from about 1000 to about 800,000 $W/m^2$-K, and in one embodiment in the range from about 2000 to about 800,000 $W/m^2$-K, and in one embodiment in the range from about 5000 to about 800,000 $W/m^2$-K. Heat flux intensity may be achieved through the use of the disclosed porous catalyst structures, which in at least one embodiment are thermally conductive and whose thickness may be matched with heat flux and effective thermal conductivity. For the example, as indicated in Table 2 of Example 1, the SMR reaction may exhibit a heat flux intensity value in the range from about 2000 to about 39000 W/m$^2$-K.

As the reaction time or contact time decreases the mass flux intensity for the structured wall reactor may increase provided the porous catalyst structure can provide more catalyst sites and manage the thermal gradients. The mass flux intensity for the reactor may be at least about 1 mole converted per square meter per second (moles/m$^2$/sec), and in one embodiment at least about 2 moles/m$^2$/sec, and in one embodiment up to about 20 moles/m$^2$/sec. The mass flux intensity may be in the range from about 1 to about 20 moles/m$^2$/sec, and in one embodiment in the range from about 2 to about 20 moles/m$^2$/sec. The standard flowrate per microchannel may be at least about 0.1 liter/min, and in one embodiment at least about 0.5 liter/min, and in one embodiment at least about 1 liter/min. For example, for a flowrate of 1 liter/min of reactant converted per microchannel wherein the microchannel has a length of 10 cm, a gap of 0.1 mm and a channel width of 4.1 mm, the mass flux intensity may exceed 1.8 moles/m$^2$-sec.

Ultrafast reactions in the structured wall reactors may require a balancing of kinetics, heat transport, mass transport, and pressure drop. The flow channel for bulk flow may be substantially open such that at least about 95% of the bulk flow travels through an open channel free of obstructions. The bulk flow regime may be either laminar, transitional, or turbulent. The bulk flow may be laminar as defined by a Reynolds number less than about 2200, but behave turbulently or demonstrate turbulent characteristics locally as incited by surface features that may create movement in the flow not aligned parallel with the direction of bulk flow.

The disclosed structured wall reactor may be used for an upgrading chemical reaction that converts a feedstock to a valuable product under ultrafast processing conditions (<4 ms, >10 W/cm$^2$, >75% approach to theoretical maximum conversion, dP/L<15 atmosphere per meter). Nonvaluable products for this purpose may be water, nitrogen, hydrogen cyanide, and carbon dioxide. One or more of the non-valuable products may be co-produced with valuable products.

If the catalyst is relatively active, it may be positioned directly as a thin layer on a single layered microgrooved support or thin layered, porous, thermally conductive treatment or coating layer such as annodized Al$_2$O$_3$ or TiO$_2$ nanotubes, carbon nanotubes, and the like. The fast catalyst may be positioned within a porous support that is connected to a non-porous wall to further increase the available number of active sites for reaction. The porous support may be thicker, thinner, or the same thickness as the non-porous wall. The reactants may diffuse into the porous support and the resulting products may diffuse out of the porous support. The pores may be at least about 5 times the size of the molecular mean free path of the reactants within the pore. The pores may be interconnected to facilitate interior diffusion. A catalyst may be positioned on the surface of the porous support. The porous support may comprise a thin high surface area support. An active catalyst, in the form of a metal, metal oxide, acid, and the like, may be deposited directly on the interior and exterior surfaces of the porous support.

A heat exchange channel may be positioned adjacent to the process microchannel containing the porous catalyst. The heat exchange channel may be a microchannel. An endothermic or exothermic process may be conducted in the heat exchange channel. For example, an endothermic reaction, such as the SMR reaction, may be conducted in the process microchannel, and a combustion reaction may be conducted in the heat exchange channel. The combustion reaction may be a catalytic reaction and the catalyst may be positioned in thermal contact with a non-porous wall on the side opposite an integral, porous endothermic reaction catalyst. The non-porous wall may be referred to as a heat transfer wall. If the rate of reaction is sufficiently high, the combustion catalyst may be positioned directly on the wall. If the reaction rate is fast but not sufficient to drive an ultrafast endothermic reaction, the combustion catalyst may be positioned in a second porous wall intimately connected to the non-porous wall. The thickness and thermal characteristics of the first and second porous wall may not necessarily need to be the same as the rates of reaction may be different for the two reactions.

In one embodiment, it may be advantageous for the heat exchange channel or heat transfer side to have the ability to generate a non-uniform rate of heat to match the thermal load required by the process microchannel or process side. For example, more heat may be consumed near the inlet of the process microchannel where concentrations may be highest. One method of tailoring the rate of heat generation by the heat exchange channel when a combustion reaction is conducted in the heat exchange channel may be to use a distributed addition of air or oxidant into the heat exchange channel, such that more thermal energy may be generated as more oxidant is added. In one embodiment, the heat transfer channel may use an axially-graded catalyst structure or composition such that more heat may be generated near the inlet of the heat transfer channel. The porous wall may have a first porosity, thickness, thermal conductivity and/or intrinsic catalyst activity near the entrance to the heat exchange channel that is different than a second porosity, thickness, thermal conductivity and/or intrinsic catalyst activity near the exit of the heat transfer channel.

For the case of the SMR reaction in the process microchannel, natural gas may be combusted in the heat exchange channel to tailor the temperature profile in the reactor. If the fuel contains hydrogen or carbon monoxide, the fuels may be oxidized within the heat exchange channel either partially or fully prior to entering a combustion zone to assist with the preheat of fuel and air. In this manner, the length of the preheat channel section for fuel and air may be reduced as compared to the chase where they are only preheated with recuperative heat from the exhaust stream.

For an average heat flux exceeding about 100 W/cm$^2$, the SMR reaction process may include the following features. The open flow channel gap may be less than the porous catalyst thickness. The non-porous wall, whose thermal conductivity may be on the order of about 25 W/m-K, may be less than about 2 mm thick, for an average thermal gradient of about 80° C. or less. The wall may have a thickness that is less than about 1 mm for an average thermal gradient of about 40° C. or less.

The effective thermal conductivity of the porous catalyst may be greater than about 0.7 W/m-K, and in one embodiment greater than about 3 W/m-K, and in one embodiment greater than about 5 W/m-K. The tortuosity of the porous catalyst may be less than about 5, and in one embodiment less than about 3.

An advantage of the disclosed structured wall reactor, at least in one embodiment, is that the gap distances between the process microchannels, second reactant stream channels, and heat exchange channels may be the same whether the process is intended for laboratory or pilot plant scale or for full production scale. As a result, the bubble or droplet size distribution of the second reactant in the reactant mixture used in the reaction process may be substantially the same whether the microchannel reactor is built on a laboratory or pilot plant scale or as a full scale plant unit.

Example 1

Chemical reactions and heat/mass transfers in microchannel reactors containing porous catalysts are modeled using Fluent—a Computational Fluid Dynamics (CFD) software package. The reaction is a steam methane steam reforming (SMR) reaction. SMR is an endothermic reaction. The SMR reaction is integrated with a combustion reaction involving the combustion of natural gas. The combustion reaction is an exothermic reaction. The SMR reaction and combustion reaction are conducted in adjacent microchannels. The SMR reaction channel contains a large pore porous catalyst. The combustion reaction is not modeled. Thermal boundary conditions are imposed on the heat transfer surface separating the adjacent SMR reaction and natural gas combustion microchannels. CFD cases are modeled covering a wide range of parameters, and their impact on the reactor performance is used to evaluate reactor designs.

The (SMR) reaction may be represented by the following equation:

$$CH_4 + H_2O \Leftrightarrow CO + 3H_2$$

Also, the water gas shift (WGS) reaction, which is exothermic, is also considered because of the importance of $CO_2$ formation on the SMR catalyst. The WGS reaction may be represented by the following equation:

$$CO + H_2O \Leftrightarrow H_2 + CO_2$$

The following kinetics are assumed. The subscript "1" refers to the SMR reaction and the subscript "2" refers to the WGS reaction. The following rate expressions for the reaction kinetics are used:

$$r_1 = k_1(P_{CH4}P_{H2O} - P_{CO}P_{H2}^3/K_1)$$

$$r_2 = k_2(P_{CO}P_{H2O} - P_{H2}P_{CO2}/K_2)$$

The reaction rates are in kmol/m³·cat·sec. The pressures (P) in the above equations are in atmospheres. The reaction rate constants follow the Arrhenius form as follows:

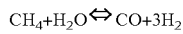

$$k_1 = A_1 \exp(-E_1/RT)$$

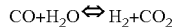

$$k_2 = A_2 \exp(-E_2/RT)$$

The activation energy for the SMR reaction is assumed to be $E_1 = 1.695E8$ J/Kmol. The activation energy for the WGS reaction is assumed to be $E_2 = 6.713E+7$ J/Kmol. The pre-exponential factors are assumed to be $A_1 = 1.275E+08$ and $A_2 = 1.466$ E+03.

In these reaction rate expressions, the reverse reactions are taken into account through the respective chemical equilibrium constants $$K_1 = \exp(-26830/T + 30.114)$$

$$K_2 = \exp(440/T - 4.036)$$

The parameters in the kinetics are the result of best fitting of the model predictions using experimental data for an SMR catalyst based on a 5 wt % Rh dispersed on a MgO stabilized alumina. This set of kinetics may not necessarily be typical for all SMR catalysts, but may be illustrative of the comparative impact of reactor geometry and design on performance.

The reactor geometry used in the CFD simulations is illustrated in FIG. 54. The cross section of the reactor channel has a rectangular shape. The aspect ratio of the cross section is large enough to justify two dimensional models. The catalyst is integrated with the perimeter walls of the channel with a thickness (h). The flow-by gap size is (w). The reactor length (L) is assumed to be 7 inches (177.8 mm). Various combinations of h and w are tested. The symmetric feature of this geometry is utilized by only modeling half of the geometry as illustrated in FIG. 55.

The following conditions are imposed on the boundaries:
Inlet: total mass flow rate, mass fraction of each species and temperature (a 3 to 1 molar ratio of steam to methane is used in the inlet feed stream).
Outlet: pressure. 345 psia (2.38 MPa or 23.5 atmospheres) is assumed for all cases unless specified otherwise.
Wall: no slip velocity and one of the following thermal conditions:
temperature imposed, either constant or a certain profile
heat flux, either constant or a certain profile
The catalyst is a porous catalyst, within which, fluid flow, heat/mass transfer and chemical reactions are modeled.

A microchannel inlet is placed a certain length upstream of the catalyst. No reaction is modeled in this entrance section. The actual length of this entrance is a matter of numerical experiment to provide for laminar flow that is fully developed when reaching the catalyst. In general, an entrance length equal to twenty times that of the flow gap may be sufficient for fully developed laminar flow.

A section of a typical mesh is shown in FIG. 56. The distribution of the grid lines is set such that the absolute dimension of the catalyst grid lines is smaller than the dimension of the flow-by gap. The grid spacing for the mesh is chosen to provide adequate resolution of gradients in both the catalyst layer and in the bulk flow region. The CFD model results are reproduced for at least one case using a grid with double the number of nodes, and on a grid with quadruple the number of nodes, showing the results to be grid independent.

A gaseous mixture containing the following species is used: Methane ($CH_4$), steam ($H_2O$), hydrogen ($H_2$), carbon monoxide (CO) and carbon dioxide ($CO_2$). Ideal gas is assumed to calculate the density of the mixture. The heat capacity, thermal conductivity and viscosity of the mixture are each estimated to be the mass-fraction weighted-average of the corresponding properties for the constituents. The material properties of each individual species are, in general, functions of the temperature. An exception to this is the mass diffusivity of each individual species. For part of the modeling cases, when the reactor wall temperature and the feed inlet temperature are specified at a constant temperature (i.e. 850° C.), the mass diffusivity of each species is independent of the temperature. The error introduced by this simplification is small since the temperature variation within the reactor for these simulations is usually less than 20° C. The actual values are obtained from Chemcad (a process simulation package) at 850° C. The values of mass diffusivity for each species is as follows:

|  | $CH_4$ | $H_2O$ | $H_2$ | CO | $CO_2$ |
|---|---|---|---|---|---|
| Mass diffusivity, D, m²/s | 1.03E-5 | 1.7E-5 | 3.44E-5 | 1.01E-5 | 7.67E-6 |

When solving the species mass transport equations, the binary mass diffusion coefficients are used directly. A dilute system is assumed with extra steam present.

For flow simulation in the catalyst structure, Darcy's law is used. The following parameters are provided to the Fluent code, α: permeability
C, inertial resistance factor These parameters may be defined differently for different coordinate directions. In this example, only isotropic catalyst structures are considered. Under this condition, α and C are constant.

$$\nabla p = -\frac{\mu}{\alpha} v - C\left(\frac{1}{2}\rho v^2\right)$$

The effective thermal conductivity of the catalyst structure is calculated by the following equation, $$k_{eff} = \gamma k_f + (1-\gamma)k_s$$

γ=porosity of the porous medium
$k_f$=fluid phase thermal conductivity
$k_s$=solid medium thermal conductivity γ and $k_s$ are defined while Fluent is used to calculate the $k_f$ of the mixture based on the thermal conductivity of all species and the mixing law selected.

In general, both bulk and Knudsen diffusion contribute to the mass transport rate within the pore volume, although a much greater fraction of diffusion is from bulk or molecular diffusion within the first pore size and a much greater fraction of diffusion is from Knudsen from the second pore size that is found in the thin catalyst coating that covers the interior volume of the first and larger set of pores. For some embodiments, a metal active catalyst is directly coated on the first set of pores without the use of a second and higher surface area coating in the form of a ceramic. For equimolar binary counter-diffusion, the effective diffusivity may be calculated by $$D_{eff} = \frac{1}{1/D_e + 1/D_k}$$

$D_{eff}$=effective diffusivity within the porous medium
$D_e$=bulk diffusivity in the pore
$D_k$=Knudsen diffusivity The bulk diffusivity of species i in the pores of the porous medium is affected by the connection of the pores of different sizes. A simple parallel pore model yields the following equation for the effective bulk diffusivity, whereby the molecules experience an effective diffusivity resulting from a non-straight or tortuos diffusion path. The effect of tortuosity is to increase the resistance to diffusion by increasing the diffusion length.

$$D_e = \frac{D}{\delta}$$

D=molecular mass diffusivity of species i
δ=tortuosity factor of the porous medium For a large pore medium, it is assumed that the contribution from the Knudsen diffusion is relatively small.

The Reynolds number for the process stream is determined by the equation:

$$Re = \frac{Hu\rho}{\mu}$$

where H is the hydraulic diameter, and u is the average stream velocity. Re is in the range of 200-2000. It is assumed that the flow is laminar. In alternate embodiments, transition and even turbulent flow regimes may be used. Flow may be in the laminar flow regime and induced into a transition or local turbulent flow regime by the use of surface features. The increase of local eddies or apparent turbulence may be expected to reduce the effect of external mass transport resistance. As such, larger fluid gaps adjacent to the porous catalyst may be possible because convective forces may bring the reactants to the edge of the catalyst in addition to diffusive forces. A large gap may be used to reduce the pressure drop per length. The use of non-laminar flow may be advantageous in increasing local heat transfer.

For some simulations, the catalyst activity distribution in the porous catalyst is along the axial direction.

For each type of distribution only a linear function is assumed.

To determine optimal regions of performance within design constraints a series of statistically designed experiments are used in conjunction with CFD simulations. Each designed experiment is intended to cover one range of interest for three to four variables of interest, chosen from the following: external flow-by gap adjacent to the catalyst; flow rate of fluid per bulk flow region volume; catalyst thickness; catalyst tortuosity; catalyst effective thermal conductivity; catalyst activity gradient in flow direction; temperature boundary condition gradient; and heat flux boundary condition. Other important variables not changed during these simulations include channel length, catalyst activity gradient in catalyst thickness direction, catalyst internal pore size, Reynolds number, reaction system, and exothermic vs. endothermic reactions.

Each designed experiment is set up and analyzed using a design-of-experiment methodology, such as Design Expert® (by Stat-Ease®), to predict the effect of varying four independent variables at once, each over a limited range. In this way, the experimental space is adequately covered with a minimal number of CFD runs with a hybrid response surface design (16 runs), plus two additional runs to better estimate the lack of fit. By limiting the range of each variable, a quadratic (second order) fit is used to model the effect of each of the four variables on the methane conversion to carbon oxides and heat flux over the range covered by the designed experiment. Three designed experiments of 18 simulations each are performed (plus 3 additional runs in Set #1 with a flow-by gap of 0.05 mm), as summarized in Tables 1-4. In Table 1, the ranges given are the ranges over which the model is fit, although the actual experimental conditions sometimes exceed these bounds for better interpolation in the given ranges. For each of the sets of simulations, a linear (axial direction) wall temperature boundary condition is assumed, with the minimum and maximum value shown in Table 1 as inlet end and outlet end wall temperatures. Each simulation assumes that the catalyst covers the two major walls in the reaction channel, and the flow-by gap is the non-catalyst containing region between the two catalysts. The other dimensions of the reaction channel are held constant at 4.06 mm (width) and 177.8 mm (axial length). The simulated reaction chamber has a rectangular cross section.

The simulations show the interaction between the various resistances to methane conversion, namely internal mass transport (tortuosity and catalyst thickness), external mass transport (gap size and flow rate), heat transport (catalyst thermal conductivity and catalyst thickness), and reactivity (catalyst thickness and catalyst kinetic factor slope). In this example, conversion of the limiting reactant (methane) to desired products (CO and $CO_2$) is called "conversion".

TABLE 1

Conditions modeled for each of the three sets of simulations.

| | Set 1 | Set 2 | Set 3 |
|---|---|---|---|
| Space velocity (1/ms) | 0.24-2.0 | 0.24-2.0 | 0.24-2.0 |
| Flow-by gap (mm) | 0.178-0.762 | 0.356-1.27 | 0.178-0.762 |
| Average catalyst thickness (mm) | 0.0762-0.33 | 0.127 | 0.127 |
| Catalyst activity slope (axial direction) | 0 | −1 to 1 | −1 to 1 |
| Catalyst thickness slope (lateral direction) | 0 | 0 | 0 |
| Catalyst thermal conductivity (W/m-K) | 0.7-3.0 | 1.5 | 1.5 |
| Catalyst pore tortuosity | 2 | 2-10 | 2 |
| Inlet end wall temperature (° C.) | 840 | 850 | 650-809 |
| Outlet end wall temperature (° C.) | 840 | 850 | 850 |

Results from each of the three sets of modeling are shown in Tables 2-4 and in FIGS. 61-66 and 68-76. Expected equilibrium $CH_4$ conversion and selectivity to CO at 840° C. and 2.38 MPa (23.5 atmospheres) are 78.9% and 59.9%, respectively, assuming an inlet molar ratio for steam to methane of 3:1. Expected equilibrium $CH_4$ conversion and selectivity to CO at 850° C. and 2.38 MPa are 81.1% and 61.4%, respectively. In Tables 2-4, the average heat flux is estimated as the reaction heat for isothermal reaction at 850° C. to the predicted conversion and selectivity values given in the same tables. The catalyst activity slope is normalized such that a slope of 1 represents a linear increase of 100% of the average catalyst activity from the inlet of the reactor to the outlet of the reactor (i.e. from 50% of the average activity at the inlet to 150% of the average activity at the outlet).

TABLE 2

Results of CFD simulations for Set #1 in Table 1.

| Conditions | | | | Results | | | | |
|---|---|---|---|---|---|---|---|---|
| flow-by gap mm | catalyst thickness mm | catalyst thermal conductivity W/m-K | space velocity $ms^{-1}$ | CH4 conversion % | selectivity to CO % | pressure drop per unit length psi/inch | productivity SLPM CH4 converted | average heat flux $W/cm^2$ |
| 0.470 | 0.203 | 1.85 | 0.883 | 52.9% | 59.1% | 0.01 | 2.38 | 26.1 |
| 0.470 | 0.203 | 1.85 | 2.644 | 27.1% | 60.0% | 0.04 | 3.65 | 40.0 |
| 0.762 | 0.076 | 3.00 | 1.652 | 18.2% | 68.6% | 0.01 | 2.49 | 27.7 |
| 0.178 | 0.330 | 0.70 | 1.652 | 67.9% | 58.8% | 0.23 | 2.16 | 23.7 |
| 0.178 | 0.330 | 3.00 | 1.652 | 71.0% | 60.5% | 0.23 | 2.26 | 24.8 |
| 0.470 | 0.025 | 1.85 | 0.196 | 60.2% | 68.8% | 0.01 | 0.60 | 6.7 |
| 0.178 | 0.076 | 0.70 | 1.652 | 56.3% | 68.5% | 0.11 | 1.79 | 20.0 |
| 0.762 | 0.330 | 3.00 | 1.652 | 25.4% | 55.0% | 0.01 | 3.46 | 37.7 |
| 0.913 | 0.203 | 1.85 | 0.196 | 65.8% | 58.3% | 0.01 | 1.28 | 14.0 |
| 0.027 | 0.203 | 1.85 | 0.196 | 78.7% | 60.5% | 0.33 | 0.04 | 0.5 |
| 0.178 | 0.076 | 3.00 | 1.652 | 57.2% | 68.4% | 0.11 | 1.82 | 20.3 |
| 0.762 | 0.330 | 0.70 | 1.652 | 22.8% | 53.4% | 0.01 | 3.11 | 33.7 |
| 0.470 | 0.396 | 1.85 | 0.196 | 78.9% | 60.3% | 0.01 | 0.79 | 8.7 |
| 0.762 | 0.076 | 0.70 | 1.652 | 17.7% | 68.7% | 0.01 | 2.42 | 26.9 |
| 0.470 | 0.203 | 0.10 | 0.196 | 76.6% | 59.3% | 0.01 | 0.77 | 8.4 |
| 0.470 | 0.203 | 3.60 | 0.196 | 78.3% | 60.5% | 0.01 | 0.78 | 8.6 |
| 0.050 | 0.232 | 1.85 | 0.250 | 78.6% | 63.8% | 0.27 | 0.11 | 1.2 |
| 0.050 | 0.338 | 1.85 | 1.000 | 77.5% | 60.0% | 0.78 | 0.42 | 4.6 |
| 0.050 | 0.374 | 1.85 | 2.000 | 75.2% | 59.7% | 1.57 | 0.82 | 8.9 |
| 0.178 | 0.076 | 0.70 | 1.120 | 65.3% | 65.5% | 0.64 | 1.41 | 15.6 |
| 0.470 | 0.203 | 0.70 | 2.000 | 31.3% | 59.0% | 0.39 | 3.19 | 35.0 |

TABLE 3

Results of CFD simulations for Set #2 in Table 1.

| Conditions | | | | Results | | | | |
|---|---|---|---|---|---|---|---|---|
| flow-by gap mm | space velocity $ms^{-1}$ | catalyst activity slope (normalized) | tortuosity | CH4 conversion % | selectivity to CO % | pressure drop per unit length psi/inch | productivity SLPM CH4 converted | average heat flux $W/cm^2$ |
| 1.270 | 1.652 | −1.0 | 10.0 | 9.0% | 53.8% | 0.07 | 2.04 | 22.2 |
| 0.813 | 0.196 | 0.0 | 12.1 | 57.0% | 56.9% | 0.01 | 0.99 | 10.8 |
| 0.813 | 0.196 | −1.5 | 6.0 | 62.4% | 57.3% | 0.01 | 1.08 | 11.8 |
| 1.270 | 1.652 | −1.0 | 2.0 | 14.3% | 55.0% | 0.01 | 3.25 | 35.4 |
| 0.356 | 1.652 | 1.0 | 10.0 | 33.6% | 58.1% | 0.39 | 2.14 | 23.4 |
| 0.356 | 1.652 | −1.0 | 10.0 | 34.9% | 58.4% | 0.39 | 2.22 | 24.3 |
| 0.813 | 0.883 | 0.0 | 6.0 | 27.3% | 54.4% | 0.06 | 2.13 | 23.1 |

TABLE 3-continued

Results of CFD simulations for Set #2 in Table 1.

| Conditions | | | | Results | | | | |
|---|---|---|---|---|---|---|---|---|
| flow-by gap mm | space velocity ms$^{-1}$ | catalyst activity slope (normalized) | tortuosity | CH4 conversion % | selectivity to CO % | pressure drop per unit length psi/inch | productivity SLPM CH4 converted | average heat flux W/cm$^2$ |
| 0.119 | 0.196 | 0.0 | 6.0 | 79.9% | 60.3% | 0.17 | 0.20 | 2.2 |
| 0.356 | 1.652 | 1.0 | 2.0 | 47.6% | 59.5% | 0.43 | 3.03 | 33.2 |
| 0.356 | 1.652 | −1.0 | 2.0 | 47.5% | 59.0% | 0.43 | 3.02 | 33.1 |
| 0.813 | 0.196 | 0.0 | 1.0 | 72.0% | 59.0% | 0.01 | 1.24 | 13.6 |
| 0.813 | 0.196 | 1.5 | 6.0 | 62.2% | 58.1% | 0.01 | 1.07 | 11.8 |
| 1.270 | 1.652 | 1.0 | 2.0 | 13.9% | 54.9% | 0.10 | 3.16 | 34.4 |
| 1.507 | 0.196 | 0.0 | 6.0 | 39.6% | 53.3% | 0.01 | 1.27 | 13.8 |
| 1.270 | 1.652 | 1.0 | 10.0 | 8.5% | 53.1% | 0.10 | 1.93 | 21.0 |
| 0.813 | 2.644 | 0.0 | 6.0 | 11.7% | 56.0% | 0.36 | 2.72 | 29.6 |
| 0.356 | 1.120 | 1.0 | 4.0 | 51.8% | 58.9% | 0.24 | 2.24 | 24.5 |
| 0.813 | 0.240 | −0.7 | 2.0 | 65.8% | 57.9% | 0.01 | 1.39 | 15.2 |

TABLE 4

Results of CFD simulations for Set #3 in Table 1.

| Conditions | | | | Results | | | | |
|---|---|---|---|---|---|---|---|---|
| flow-by gap mm | space velocity ms$^{-1}$ | catalyst activity slope (normalized) | Inlet end temperature °C. | CH4 conversion % | selectivity to CO % | pressure drop per unit length psi/inch | productivity SLPM CH4 converted | average heat flux W/cm$^2$ |
| 0.762 | 1.652 | 1.0 | 809.0 | 22.5% | 55.6% | 0.19 | 3.07 | 33.5 |
| 0.470 | 0.196 | 1.5 | 729.5 | 71.8% | 56.4% | 0.19 | 0.72 | 7.8 |
| 0.470 | 0.196 | 0.0 | 850.2 | 80.4% | 61.9% | 0.02 | 0.80 | 8.8 |
| 0.470 | 2.644 | 0.0 | 729.5 | 21.0% | 57.4% | 0.57 | 2.83 | 31.0 |
| 0.025 | 0.196 | 0.0 | 729.5 | 80.9% | 54.5% | 0.29 | 0.04 | 0.5 |
| 0.178 | 1.652 | 1.0 | 809.0 | 67.6% | 60.6% | 0.93 | 2.15 | 23.7 |
| 0.470 | 0.196 | 0.0 | 608.8 | 65.9% | 59.9% | 0.02 | 0.66 | 7.2 |
| 0.178 | 1.652 | −1.0 | 809.0 | 67.0% | 61.9% | 0.93 | 2.13 | 23.5 |
| 0.470 | 0.196 | −1.5 | 729.5 | 71.8% | 56.4% | 0.02 | 0.72 | 7.8 |
| 0.178 | 1.652 | −1.0 | 650.0 | 44.9% | 59.3% | 0.79 | 1.43 | 15.7 |
| 0.470 | 0.883 | 0.0 | 729.5 | 44.0% | 55.9% | 1.14 | 1.98 | 21.6 |
| 0.762 | 1.652 | −1.0 | 809.0 | 22.7% | 55.6% | 0.19 | 3.10 | 33.8 |
| 0.914 | 0.196 | 0.0 | 729.5 | 58.4% | 54.3% | 0.69 | 1.13 | 12.3 |
| 0.762 | 1.652 | −1.0 | 650.0 | 13.1% | 56.9% | 0.16 | 1.79 | 19.5 |
| 0.762 | 1.652 | 1.0 | 650.0 | 14.3% | 54.0% | 0.16 | 1.96 | 21.3 |
| 0.178 | 1.652 | 1.0 | 650.0 | 50.2% | 58.1% | 0.79 | 1.60 | 17.5 |
| 0.178 | 1.120 | 1.0 | 650.0 | 59.6% | 57.2% | 0.50 | 1.29 | 14.1 |
| 0.470 | 2.000 | −0.7 | 750.0 | 27.2% | 56.8% | 0.39 | 2.77 | 30.2 |

The second order curve fits obtained via Design Expert® from the CFD simulation predictions for methane conversion in Tables 2-4 are given below and are valid for the conditions given in Table 1. Any predictions above the equilibrium conversion are an artifact of the second order curve fit and may be interpreted as equilibrium performance.

Set #1 CH$_4$ conversion=0.78761−0.088396*flow-by gap+0.38702*cat thickness−0.073673*thermal cond.−0.097051*space velocity+0.021792*thermal cond.$^2$+0.032052*space velocity$^2$−0.38582*flow-by gap*space velocity Set #2 CH$_4$ conversion=1.28115−0.62771*flow-by gap+4.56159E-004*cat act. slope−0.075597*tortuosity−0.49660*space velocity+0.14936*flow-by gap$^2$+0.042053*cat act. slope$^2$+3.97359E-003*tortuosity$^2$+0.10697*space velocity$^2$+0.011668*flow-by gap*tortuosity+3.95832E-003*tourosity*space velocity Set #3 CH$_4$ conversion=3.30112−7.69760E-003*min. wall T+0.11116*cat thick grad+0.31130*flow-by gap−0.38360*space velocity+5.98185E-006*min. wall T$^2$+0.032067*cat thick grad$^2$+0.26405*flow-by gap$^2$+0.066265*space velocity$^2$−1.32052E-004*min. wall T*cat thick grad−1.04666E-003*min. wall T*flow-by gap+2.06407E-004*min. wall T*space velocity−0.030540*cat thick grad*flow-by gap+6.24499E-003*cat thick grad*space space velocity−0.28702*flow-by gap*space velocity The axial gradient in the catalyst thickness has little effect on the predicted methane conversion in the range covered by the simulations.

FIG. 59 shows a typical parity plot for Design Expert quadratic curve-fit model predictions versus CFD predictions for methane conversion. The second order curve fits are obtained by backward elimination assuming an alpha-out value of 0.05 to eliminate statistically insignificant parameters (except for Set #3, where backward elimination is not used). The quadratic fit predictions are within ±4% of the CFD predictions.

In FIGS. 60-66, graphs made using the model based on the CFD predictions of Set #1 (see Tables 1 and 2) are shown. These graphs show the effect of changing gap size, space velocity, catalyst thickness, and catalyst thermal conductivity on predicted methane conversion, all else being constant. FIG. 60 shows that with a sufficiently thick catalyst (about 0.4-0.45 mm for the conditions of these simulations), a region of high space velocity (approaching 1 ms$^{-1}$) exists in which equilibrium conversion can be achieved. Faster intrinsic kinetics (not included in this example) would make possible equilibrium conversion at even higher space velocities and or thinner catalyst structures. FIG. 61 shows the model predictions of methane conversion for a higher catalyst effective thermal conductivity (3 W/m-K). FIG. 62 depicts the predicted methane fractional conversion as a function of thermal conductivity and space velocity for a fixed gap (0.2 mm) and catalyst thickness (0.374 mm), showing little dependence on thermal conductivity at low space velocities and/or low thermal conductivity. This suggests that heat transfer limitations may not be controlling over the range shown. It may be expected that the effective thermal conductivity will be more important as the average heat flux increases for the reaction.

FIG. 63 shows the effect of flow-by gap size and space velocity on the predicted conversion for a fixed effective catalyst thermal conductivity (1.85 W/m-K) and catalyst thickness (0.374 mm). Both kinetic limitations and external mass transport limitations on the conversion both limit the conversion as conditions tend toward the upper right quadrant in FIG. 63. FIGS. 64-66 show the predicted heat flux, flow per channel, and productivity for the same conditions as in FIG. 63.

The smaller the flow-by gap, the higher the space velocity which can be used while still maintaining high reactant conversion. If high space velocity is the desired outcome, then the constraint on pressure drop (which increases with decreasing flow-by gap for a given space velocity) may limit the maximum achievable space velocity.

Although the ability to reach ultra-high space velocities while still maintaining high reactant conversion by the use of a very small flow-by gap may be significant, the ability to reach high productivity (reactant converted or product made per unit time) per channel while maintaining high reactant conversion and/or selectivity to desired product(s) may be more important for some applications. Maximum productivity may not necessarily increase as flow-by gap decreases, but rather, there may be an optimal range of flow-by gap sizes which maximize productivity while maintaining conversion at an acceptable level. These optimal values may change as the reaction kinetics change and if the flow regime in the bulk flow channel is moved from laminar to transition or turbulent, even only if locally so.

A region of high productivity and conversion may be found for a given degree of catalyst intrinsic kinetic activity given the right combination of gap size and space velocity. This region may be seen in FIG. 67 for the conditions used in Set #1 of Table 1, where the productivity (2.2 SLPM CH$_4$ converted at 85% approach to equilibrium conversion) is more than 2.5 times higher than the next highest productivity at higher conversions (0.8 SLPM CH$_4$ converted at 95% approach to equilibrium). For the predictions in FIG. 67, the high productivity points occur for a space velocity of 1.65 ms$^{-1}$ and a gap size of 0.178 mm (catalyst thermal conductivity ranges from 0.7-3 W/m-K). In the case where a slightly lower conversion per pass (i.e. 75-95% approach to equilibrium) may be tolerated, the much higher productivity may be very attractive. These data are only intended to span the experimental space, thus the combination of 1.65 ms$^{-1}$ space velocity and 0.178 mm flow-by gap may not necessarily be optimal, but show the existence of a region approaching equilibrium conversion where a high productivity may be predicted. A similar region may be found for the predictions in set #3 at the same combination of gap size and space velocity.

The high productivity region may include those conditions at which heat and mass transport limitations are relatively unimportant and the approach to equilibrium conversion of limiting reactant to desired product is in the range from about 60 to about 98%, and in one embodiment in the range from about 75 to about 95%, and in one embodiment in the range from about 85 to about 95%. The conditions for which heat and mass transport limitations may be relatively unimportant (have a limited effect on the overall rate of reaction) may be defined as those conditions for which a 20% decrease in total flow rate results in a 15% or greater decrease in moles of desired product formed. When the decrease in productivity is more than 15%.

$$\text{productivity decrease} = \frac{\chi_1 F_1 - \chi_2 F_2}{\chi_1 F_1} \cdot 100\% \geq 15\%$$

where $\chi_1$ and $\chi_2$ are the fractional molar conversions of limiting reactant to the desired product before (subscript 1) and after (subscript 2) the 20% decrease in flow and $F_1$ and $F_2$ are the inlet molar flow rates of the limiting reactant before and after the decrease in flow.

Although gap size and space velocity ranges corresponding to the high productivity region may vary with intrinsic kinetic catalyst activity (that is reaction temperature and catalyst kinetics) and heat and mass transport considerations, the approach used herein may be used to identify design options within the enhanced productivity region. Because the design approach used herein enables taking even ultra-fast reactions to a regime in which heat and mass transport limitations do not strongly influence the overall rate of reaction, a high productivity region may be created where a reaction is not taken completely to equilibrium, since as a reaction approaches equilibrium, the intrinsic reaction kinetics may slow down as the concentration of limiting reactant(s) becomes small.

Since high conversions to desired product may be desirable, a window may exist in which a reasonably high approach to equilibrium may be maintained and a much higher productivity (or molar flow of desired product per channel) may be achieved using the disclosed design approach. This window may exist independent of the catalyst kinetic activity unless the catalytic reaction rate is so slow that the desired approach to equilibrium cannot be reached. The productivity decrease of at least 15% for a decrease of 20% in the flow rate may ensure that heat and mass transport limitations are not the dominant limitation on the rate of reaction.

For example, in a traditional process, one might try to achieve a higher productivity by increasing the conversion via an increase in the temperature of a reversible reaction. With the structured wall reactors disclosed herein, when transport limitations are not dominant, it may be more productive to increase the flow rate and the temperature. This may leave the conversion unchanged.

In one embodiment, using the second order model for methane conversion based on the data from set #1, the reactor may have a flow-by gap of 0.25 mm, a catalyst thickness of 0.33 mm, and a catalyst thermal conductivity of 1.85 W/m-K. If the reactor is operated at a space velocity of 0.25 ms$^{-1}$, a predicted productivity of 0.53 SLPM CH$_4$ converted per channel may be expected. However, using the space velocity range suggested herein, the predicted productivity may be nearly doubled to 1.03 SLPM CH$_4$ at 0.5 ms$^{-1}$ space velocity by operating at a 94% approach to equilibrium conversion.

FIGS. 68-73 show methane conversion predictions from the quadratic model curve fits of set #2 in Tables 1 and 3. FIG. 68 shows the effects of tortuosity and space velocity. FIGS. 70 and 74 show that the slope of the intrinsic catalyst kinetic activity may not have a major effect on predicted methane conversion for tortuosities of 2 and 10, respectively. FIGS. 72 and 73 compare predicted methane conversion as a function of flow-by gap and space velocity for tortuosities of 1 and 5, respectively.

FIGS. 74-76 show methane conversion predictions from the quadratic model curve fits of set #3 in Tables 1 and 4. Comparison of FIGS. 74 and 75 show the effect on predicted methane conversion of reducing the inlet wall temperature from 850° C. to 650° C., respectively. FIG. 76 also shows the effect of changing the inlet wall temperature with a linear temperature gradient between the inlet end and the outlet end (850° C.), holding the flow-by gap constant at 0.18 mm.

As the reaction is operated with shorter reaction times (that is, less than about 10 ms, and in one embodiment less than about 5 ms, and in one embodiment less than about 2 ms) the importance of transport resistance considerations may increase. As the flowrate increases corresponding to a reduction in contact time, the effect of external mass transport resistance may increase. The approach to theoretical conversion may be more challenging to achieve for laminar flow in a microchannel as the allowable time for diffusion decreases. Smaller diffusion gaps may be required to minimize the effect of external mass transport resistance at shorter contact times. The time for convection, or the true residence time versus contact time, or the average residence time, may decrease linearly with increasing flowrate. The corresponding diffusion effect from the bulk flow to the porous catalyst may be a squared effect with distance. A factor of 4× increase in bulk flowrate may only require a 2× reduction in the gap size to maintain the same resistance to external mass transfer.

As the contact time decreases, the heat or thermal demand may increase. For endothermic reactions, the porous catalyst should be able to transport sufficient heat into the structure. For exothermic reactions, the porous catalyst should be able to remove sufficient heat.

Heat may be added or removed through the porous catalyst as opposed to having to transfer completely through the structure. Heat may move in the direction from the wall to the gap for endothermic reactions and from the gap to the wall for exothermic reactions. The concentration of reactants may decrease from the gap to the wall and may work counter to the direction of heat transport for endothermic reactions. As such, a thick porous catalyst may be colder where the concentration of reactants is highest. The impact of effective diffusion within the porous catalyst may help move mass (diffuse molecularly) to warmer interior catalyst sites within the porous catalyst near the heat transfer wall. As the reaction rate is reduced locally in the porous catalyst near the gap as the endothermic reaction consumes the local heat, the resulting thermal gradient may also assist with reactant diffusion to the hot interior. The diffusivity may increase with temperature and the chemical potential driving force for reactions driven near extinction or toward equilibrium at interior walls may also serve to increase the utilization of interior catalyst sites.

For exothermic reactions, the reaction rate may be highest near the gap, where the concentration of reactant is also highest. The heat evolved from the exothermic reaction may conduct through the porous catalyst structure and to a lesser degree, moves with the diffusing reactant molecules. Mitigation of hot spots may be a concern for many exothermic reactions. The impact of effective thermal conductivity of the porous catalyst may be expected to be more important for exothermic reactions than endothermic reactions—especially if unwanted and non-selective side reactions are possible. For the case of exothermic reactions, the porous catalyst may be thermally conductive, i.e., greater than about 1 W/m/K, and in one embodiment greater than about 3 W/m/K, and in one embodiment greater than about 5 W/m/K. The first set of pores that permit molecular diffusion may also have a lateral gradient within the structure. It may be advantageous to have a first sub porosity that is greater than a second sub porosity that comprises the first pore size. The first sub porosity that is larger may reduce the local reaction rate nearest the gap and in turn reduce the rate of local heat generation that may in turn conduct throughout the entire porous catalyst structure. The second sub porosity may be closer to the heat transfer wall and creates more active sites for the catalytic reaction than the first sub porosity. As such, the distance for conduction to the heat transfer wall may be reduced. By this manner, thermal gradients within the porous catalyst may be reduced and the formation of unwanted side reactions may be reduced.

The same porous structure that comprises a first subporosity and a second sub porosity in the lateral direction may also be advantageous for endothermic reactions, especially as the heat flux requirement increases above about 25 W/cm$^2$, and in one embodiment above about 50 W/cm$^2$.

The thermal resistance of the heat transfer wall may become important if the wall is very thick or non conducting. The heat transfer wall may be made of materials with a thermal conductivity at the reaction conditions of at least about 1 W/m-K, and in one embodiment at least about 10 W/m-K. The thickness may be less than about 2 mm, and in one embodiment less than about 1 mm.

As the intrinsic reaction rate increases either with the aid of a promoter or new composition or other change, the total amount of active material may decrease to create the same production volume. The porous catalyst may either be made smaller (shorter or thinner) or more flow may be transferred through the microchannel to increase the overall reactor productivity.

For slower reactions, the total amount of catalyst in the reactor may be increased. The thickness of the porous catalyst may be increased until the net increase in thickness is offset by a corresponding reduction in either internal mass transfer or heat transfer. Model results suggest that thick layers of a porous catalyst may be used. In one embodiment, the thickness of the catalyst (a catalyst comprising large pores for molecular diffusion, either as a catalyst such as a catalyst metal with large pores, or a large pore support, typically having an active catalyst deposited on the exterior of the large pore support either with or without intervening support layer(s)) may be in the range from about 0.04 mm to about 2 mm, and in one embodiment from about 0.05 mm to about 1 mm.

An advantage of the disclosed structured wall reactor may be derived from increasing the effective residence time or holding up the reactants in the reaction zone. The thickness of the catalyst structure may be thicker than the gap or open channel for the fluid flow. The catalyst may have a void fraction based on the volume partially filled with a metallic or conducting porous matrix. Fluid reactants and products may fill the void volume contained within the catalyst structure. A larger volume for fluid molecules within the catalyst structure may allow the reactants additional time for reaction without convective forces forcing the reactants out of the reactor and away from the catalyst though the gap.

For example, if a void fraction of 0.5 and gaseous molecules that follow an ideal gas law are assumed, the pressure within a slice or section of the porous catalyst may be identical to the pressure within the adjacent gap at an equal axial location. The ratio of moles in the catalyst to the moles in the half channel (defined by the plane of symmetry between an open channel with the catalyst on both side walls) may be equal to the volume ratio accessible by gases. For the case of a 50 micron adjacent gap and a 1000 micron catalyst (and the 0.5 void volume), the number of molecules in the porous catalyst may be 10 times the number of molecules in the adjacent gap. The reactants may spend on the order of about 10 times longer within the porous catalyst than within the gap.

The effect of additional reaction time may be advantageous for some reaction chemistries and may be disadvantageous for others. For the case of hydrocarbon reforming or other reactions which do not have undesired side reactions, the additional time may be beneficial for achieving higher overall conversions. For the case of oxidation reactions or other reactions which have undesired side reactions, the additional time that the products spend in contact with the catalyst may give rise to a reduction in product selectivity. For the case of parallel reactions and little change in local temperature, the additional time spent within the porous catalyst may increase the conversion and keep the selectivity the same. If there is a significant change in local temperature, parallel reactions may experience a change in selectivity depending upon the activation energy ratio between the desired and undesired reactions.

For reactions without undesired side reactions, a catalyst which is thicker than the adjacent gap may be useful for increasing the effective reaction time. For sufficiently fast chemical reactions, the additional volume and associated catalyst contained within the porous catalyst may not be required to approach equilibrium performance at reaction times less than about 100 ms.

Effective use of the internal porosity of the porous catalyst may require that it be open for facile molecular diffusion and not be based on small pores that promote Knudsen diffusion. The criteria to distinguish between the two mechanisms may be based on calculating the molecule mean free path and comparing that to the pore diameter. The mean free path ($\lambda$) may be defined by the following equation:

$$\lambda = \frac{k_B T}{\sqrt{2}\,\pi\sigma_{ii}^2 P}$$

If $\lambda$ is significantly greater than the pore diameter, Knudsen diffusion may dominate. For the SMR reaction at 850° C. and 25 atm, a pore size of about 20 nm may be roughly equal to the mean free path. Under the same conditions and a pore size of 200 nm, the ratio of mean free path to pore diameter may be less than about 1 and molecular diffusion may dominate over Knudsen diffusion. For the case of methanol oxidation to formaldehyde at 600° C. and 1 atm, a pore size of about 200 nm may lead to Knudsen diffusion, while a pore diameter of about 2 microns or greater may lead to molecular diffusion.

The performance results show little impact in the axial grading of catalyst activity. The wall temperature is maintained at a sufficient temperature (840 or 850° C.) such that unlimited heat flux is allowed wherever needed. For real reactors, the available heat flux may be limited by the method of heat addition (e.g., endothermic process reaction) or heat removal (e.g., exothermic process reaction) or allowable thermal gradients in the intervening wall between the process microchannel and heat transfer channel for mechanical design or materials consideration.

The impact of lateral catalyst gradients may be an important optimizing parameter to further reduce the reaction contact time in a manner that controls the thermal gradients within the catalyst structure. In addition to concerns about unwanted selectivity to side products if a hot spot forms in the porous structure, there may be an advantage for mechanical integrity of the porous catalyst and associated catalyst coatings by reducing the thermal gradients. Improved adhesion and a reduction in coating spalling may be anticipated by reducing the thermal gradients. Thermal gradients may create thermal strain in a catalyst coating that sits upon the porous support. If the coating has a thermal expansion coefficient that is sufficiently different from the base material of the porous support, spalling induced from thermal strain may be increasingly important and should be minimized.

For a catalyst which has a coefficient of thermal expansion greater or lesser than the surface to which it is attached, a change in temperature may cause high strains in the catalyst causing cracking or other damage to the catalyst. To reduce this effect, a material (or materials) with an intermediate coefficient of thermal expansion value (for example, within about 25% to about 75% of the difference in thermal expansion, in the temperature range of room temperature to typical operating temperature, between layers on either side of the intermediate layer) may be layered between the catalyst and the surface, reducing the strain on the catalyst. A layer which has low mechanical stiffness, such as a porous foam structure, may be applied between the catalyst and the surface. The intermediate layer should be resilient enough to deform due to the thermal expansion difference without exceeding its allowable stress. For example, 316 stainless steel has a coefficient of thermal expansion of $9.7\times10^{-6}$ in/in/° F. and alumina ceramic is $8.2\times10^{-6}$ in/in/° F. If these materials are attached to each other and heated to 1000° F., the compressive stress produced in the stainless steel would be $(9.7\times10^{-6}-8.2\times10^{-6})(1000)(28\times10^{-6})$=42,000 PSI and tensile stress would be $(9.7\times10^{-6}-8.2\times10^{-6})(1000)(60\times10^{-6})$=90,000 PSI. The tensile strength for alumina of 38,700 PSI would be exceeded and the material would fail. FIG. 77 shows the high compressive stress in the higher coefficient of thermal expansion material and high tensile stress in the lower coefficient of thermal expansion material. With an intermediate material modeled as having a modulus of elasticity 0.01 times that of stainless steel, the stress is reduced by 57%, as shown in FIG. 78.

The SMR reaction may be carried out at a contact time that is less than about 1 ms using a porous catalyst. Further reductions in contact time may be achieved by increasing the catalyst thickness and in doing so minimizing heat and mass transport limitations. SMR process contact times in the range from about 90 to about 900 microseconds (μs) may be achieved. At a 900 μs contact time, the approach to equilibrium conversion may be greater than about 99%. At a 90 μs contact time the approach to equilibrium may be about 21%.

The use of simulations indicate that the variables for pushing the performance of the SMR reaction in a microchannel reactor may be catalyst thickness, porosity, tortuosity, effective thermal conductivity, and open flow gap adjacent the catalyst. These may be used to provide a method to achieve near equilibrium conversion at contact times of about 500 μs.

The impact of a gap adjacent to the catalyst for reactant flow may be a significant factor in the performance of the microchannel reactor. Small gaps may reduce diffusional resistance, while large gaps may exacerbate diffusional resistance. For laminar flow process microchannels, a flow-by gap may be an important variable in reactor performance when the microchannel is run with short contact times.

FIG. 79 shows the effect of space velocity (or flow rate) and flow-by gap (or diffusional distance) on the predicted approach to equilibrium methane conversion for a fixed catalyst thickness (0.28 mm) and catalyst thermal conductivity (0.9 W/m-K). The experimental results collected at 900 µs are shown by the dot in FIG. 79 where the approach to equilibrium conversion is 99%.

The simulations show the importance of both the flow-by gap and space velocity on the approach to equilibrium. As the space velocity increases at equal gap, the approach to equilibrium drops. This may be a result of an increased demand on the available number of catalyst sites. As the flow-by gap increases at equal space velocity, the drop in approach to equilibrium is more pronounced. This may be a result of an increase in the external mass transfer resistance and an increased demand on the fixed number of catalyst sites. The diffusional distance of reactants to the catalyst wall may increase with the flow-by gap and the effective or apparent activity of the catalyst may be reduced.

The challenge for realizing high apparent catalyst activity may become greater as the microchannel gap is increased. As the space velocity increases, the contribution from external mass transfer resistance may become more pronounced as indicated by a closer spacing of the iso-approach lines on the right hand side of FIG. 79.

The impact of catalyst thickness is shown in FIG. 80. The overall approach to equilibrium may be increased with thicker catalysts, as long as the catalyst effective thermal conductivity is held high (minimize internal heat transfer resistance) and the tortuosity is relatively low (minimize internal mass transfer resistance). In this simulation, the open channel is held constant at 0.05 mm, the thermal conductivity is held at 1.85 W/m-K and the tortuosity is held at 2.

For these simulations, the activity per unit thickness is held constant. Thicker catalysts may add additional active sites to convert the reactants. The additional sites may be accessible and contribute to the reaction provided that internal heat and mass transfer limitations do not dominate. For tortuosity values greater than about 5, an increase in the catalyst thickness over about 0.2 mm may have little impact on increasing the approach to equilibrium.

The predicted performance suggests that at a space velocity of 2 ms$^{-1}$ or a contact time of 500 µs near equilibrium performance may be achieved with a catalyst thickness approaching about 0.45 mm. This performance prediction may be predicated on a very low tortuosity catalyst support (tortuosity=2) and a fairly high effective thermal conductivity (1.85 W/m-K) for the support.

Example 2

A single channel microreactor with adjacent cross flow combustion channels is built from Inconel 625. The test device (see FIG. 81) includes a single 11.4 mm long open reactor channel with a 0.356 mm open gap that is reduced to a 0.076 mm open gap for reactant flow. Three heat exchange channels are adjacent to the reactor channel. A heat transfer wall separates the reactor channel and the heat exchange channels. A 0.28 mm thick SMR catalyst is held against the heat transfer wall. The channel has a width of 10.7 mm. A catalyst slurry is washcoated on a FeCrAlY substrate, resulting in a total catalyst loading of 0.0125 grams, as measured after calcination at 350° C., to form the SMR catalyst. The washcoat slurry contains 10 wt % Rh/4.5 wt % MgO/85.5 wt % Al$_2$O$_3$. The SMR catalyst is held against the heat transfer wall by two Inconel strips of metal along the sides of the catalyst insert. The catalyst insert extends across the 0.076 mm gap to maintain good thermal contact between the catalyst and the heat transfer wall. An SMR process gas flows in the reactor channel.

The heat exchange channels consist of three parallel cross-flow oriented cylindrical (2.54 mm diameter) channels in which a catalytic hydrogen combustion reaction is conducted. The combustion reaction provides exothermic heat to the SMR reaction. A wall thickness of 1.52 mm separates the SMR process channel and the tangent plane intersecting the edge of the combustion channels. A combustion gas mixture of hydrogen and air is used. The hydrogen is fed into the air stream in each combustion channel through a small jet (circular cross section with a 0.254 mm diameter) immediately upstream (0.76 mm) of the overlap with the SMR process microchannel. To overcome potentially poor mixing of the hydrogen and air in the 2.54 mm cylindrical channels, a static mixer is inserted into each channel prior to heat treatment. Each static mixer has two offset spiral twisted strips of Inconel 625 with a 2.54 mm diameter. This provides a flow pattern that is tortuous to enhance mixing. Before SMR catalyst insertion and application of the combustion catalyst to the combustion channel, the device is heat treated in air at 950° C. for two hours. The combustion catalyst is applied to the heat treated combustion channel interior walls and static mixer surfaces by soaking for two minutes at room temperature in a 10 wt % palladium nitrate solution. The device is then dried at 100° C. for 30 minutes followed by calcination at 850° C. for 1 hour. After the combustion catalyst is applied to the combustion channels, the SMR catalyst is inserted into the SMR reactor channel and header and footer connections are welded to the device.

The SMR feed stream contains steam and methane at a steam to methane molar ratio of 3:1. The flow in the SMR reactor channel is at flow rates of 0.61 SLPM and 6.2 SLPM (standard liters per minute at 0° C. and 1 bar (0.987 atmosphere)) which equate to contact times of about 90 and 900 microseconds. Heat transfer wall temperatures are measured by thermocouples in the metal wall between the SMR reactor channel and the combustion channels in 3 locations along the SMR reactor channel flow length. Outlet pressure and average heat transfer wall temperature for the 900 microsecond condition are 12.9 bar (12.7 atmospheres) and 840° C., and for the 90 microsecond condition they are 11.4 bar (11.25 atmospheres) and 810-745° C. The reactor is less isothermal at 90 microseconds corresponding to the heat transfer challenge of further intensification of the microchannel reactor. Inlet gases are preheated to 835° C. for the 900 microsecond case and 765° C. for the 90 microsecond case. The contact time is calculated as follows:

$$\text{contact time} = \frac{\text{open channel volume}}{\text{flow rate at } STP}$$

where channel volume is the volume through which gas flows adjacent to the catalyst and the flow rate at STP is the total inlet flow of reactants calculated at 0° C. and 1 bar (0.987 atmosphere).

Inlet gas flows are metered via a Brooks mass flow meter and steam is produced by continuous vaporization of a water stream metered by a high pressure liquid chromatography (HPLC) pump. Dry outlet gas concentrations are measured by gas chromatograph which is calibrated daily. Dry outlet flow rate is measured by dry test meter. The approach to equilibrium methane conversion (which may be expressed as a fraction or a percent) is calculated as $$\chi_{CH4} = \left(\frac{y_{CO} + y_{CO2}}{y_{CO} + y_{CO2} + y_{CH4}}\right)_{dry\,outlet\,gas} \quad (2)$$

$$approach = \frac{(\chi_{CH4})_{measured\,or\,predicted}}{(\chi_{CH4})_{equilibrium\,at\,T,P}} \quad (3)$$

where $y_i$ is the mole fraction of species i in the dry outlet gas stream. Equilibrium values for the dry outlet mole fractions are calculated using the NASA-Lewis equilibrium code for the inlet composition (3:1 steam to methane) at the process channel outlet pressure and the average temperature in the heat transfer wall.

The results of the single channel microreactor CFD simulations are shown in Table 5, while the experimental results are presented in Table 6.

At 837° C. average reactor temperature and 12.9 bar (12.7 atmospheres) outlet pressure with 3:1 steam to carbon ratio and 900 microsecond contact time (0.62 SLPM) a methane conversion of 88% is observed, and the approach to equilibrium is more than 98%. The corresponding CFD run predicts 80% approach to equilibrium. The mass flux intensity for this condition is 0.82 mole methane converted/m²/sec.

At 811° C. average reactor temperature and 12.1 bar (11.9 atmospheres) outlet pressure with a 3:1 steam to carbon ratio and a microsecond contact time (6.2 SLPM), a methane conversion of 17% is observed, and the approach to equilibrium is 19.7%. This experimental condition yields a surprisingly high mass flux intensity of 1.6 moles methane converted/m²/sec. The heat flux intensity for case 2 is 16,500 W/m²-K. The corresponding CFD run predicts 15% approach to equilibrium. FIG. 82 shows the time on stream plot for this case, where the catalyst performance is fairly stable over 200 hours.

TABLE 5

|  | Case 1 | Case 2 |
|---|---|---|
| CH$_4$ flow rate (SLPM) | 0.153 | 1.55 |
| Steam flow rate (SLPM) | 0.461 | 4.74 |
| Total flow (SLPM) | 0.614 | 6.29 |
| Outlet pressure (bar) | 12.63 | 11.14 |
| Temperature (° C.) | 835 | 806 |
| Predicted Conversion | 71.5% | 13.3% |
| Contact time (microseconds) | 900 | 90 |
| Equilibrium conversion at Temp | 89.1% | 86.4% |
| Predicted Approach to Equilibrium | 80% | 15% |

The CFD simulations of experimental conditions assume an effective thermal conductivity of 1.8 W/m-K and a tortuosity factor of 2. Also assumed is that the catalyst is equally disposed within the wall structure laterally. An entrance length of 20 equivalent diameters is included in the simulation while the experiments introduce the reactant directly into the microchannel.

The experimental results exceed the model simulations and suggest that the selected reaction kinetics may be somewhat conservative. The CFD simulations are considered valid for predicting trends and highlighting the importance or lack of importance of several key variables.

TABLE 6

|  | 1 | 2 |
|---|---|---|
| SMR contact time (microseconds) | 900 | 90 |
| Time on Stream for sample (hr) | 73 | 10 |
| Molar Steam to Carbon Ratio | 3.0 | 3.0 |
| Percent excess combustion air | 450% | 260% |
| Inlet flows and compositions | | |
| SMR CH$_4$ flow rate (SLPM) | 0.153 | 1.55 |
| SMR steam flow rate (SLPM) | 0.461 | 4.64 |
| Air flow rate (SLPM) | 5.4 | 5.0 |
| Fuel H$_2$ flow rate (SLPM) | 0.508 | 0.81 |
| Gas stream temperatures | | |
| SMR inlet gas temperature (° C.) | 837 | 788 |
| SMR outlet gas temperature (° C.) | 802 | 754 |
| Air inlet gas temperature (° C.) | 806 | 732 |
| Exhaust gas temperature (° C.) | 912 | 862 |
| Gas stream pressures and pressure drops | | |
| SMR inlet pressure (bar) | 13.0 | 13.0 |
| SMR outlet pressure (bar) | 12.9 | 12.1 |
| SMR pressure drop (bar) | 0.1 | 0.9 |
| Air inlet pressure (bar) | 1.47 | 1.43 |
| Air pressure drop (bar) | 0.13 | 0.1 |
| SMR performance | | |
| SMR CH4 conversion (GC, percent) | 88.2 | 17 |
| Selectivity: CO (percent) | 38.3 | 43 |
| Average reactor web temp. (° C.) | 837 | 811 |
| Equilibrium conversion at temp. (° C.) | 89.1 | 86.4 |
| Approach to equilibrium (percent) | 99 | 19.7 |
| Average heat flux (W/cm²) | 18.9 | 21.3 |
| Combustion performance | | |
| Combustion H$_2$ conversion (percent) | 100 | 100 |

Example 3

0.7% K$_2$O-15% MoO$_3$/SiO$_2$—TiO$_2$ catalyst is prepared by the sol-gel method. 20.0 g tetraethylorthosilicate and 27.29 g titanium isopropoxide are dissolved in 200 ml isopropyl alcohol solution with stirring. In another beaker, 2.93 g ammonium paramolybdate are dissolved in 13.65 g H$_2$O and then 0.30 g 45% KOH solution are added. The aqueous solution is dropped slowly into the alcohol solution (1 ml/min). After all of the aqueous solution is added, the resulting gel is stirred for additional 15 min. The gel is dried at 110° C. overnight and calcined at 550° C. for 5 hours. The catalyst is crushed and sieved to 60-100 mesh.

The catalyst (5 g) is mixed with 45 g H$_2$O and 95 g 6-mm ZrO$_2$ beads in a jar. The mixture is ball-milled for three days. The resulting slurry (10 wt %) is then diluted to 2.5 wt % by H$_2$O. The average particle size in the slurry is about 1 micron. The slurry is dropped onto the microgrooved support strip illustrated in FIG. 38 by pipette and then dried at 120° C. for 1 hour. The microgrooved support strip is made of stainless steel 304. The microgrooved support strip has a length of 2.500 inches (6.35 cm), a width of 0.500 inch (1.27 cm), and a thickness of 0.002 inch (50.8 microns). The microgrooves in the microgrooved support have a width of 0.007 inch (178 microns). The spacing between the microgrooves is 0.007 inch (178 microns). This washcoating procedure is repeated twelve times. The catalyst-coated microgrooved support strip is then calcined at 500° C. for 1 hour. The catalyst loading is 28.8 mg. A microphotograph (50×) of the catalyst coated microgrooved support strip is shown in FIG. 39.

The catalyst coated microgrooved support strip is welded in the microchannel device shown in FIG. 40. The microchannel device, which is fabricated from FeCrAlY, has an internal volume of 0.039 ml (volume for gas flow above the microgrooved strips).

A feed gas composition, which contains 18.8% ethylbenzene and 81.2% air, flows into the microchannel device. The feed gas flow rate is 2.93 ml/min. The ethylbenzene to oxygen molar ratio is 1.1. The contact time based on reactor volume is 0.8 second. The process is operated for 96 hour with no evidence of catalyst deactivation. The test set up and methodology are described in Example 7. The process is conducted at atmospheric pressure. The WHSV (weight hourly space velocity) is 5.5 g ethylbenzene/g catalyst/hour. The GHSV based on reactor volume is 4508 $hr^{-1}$. The GHSV based on the catalyst is 6104 ml/g-cat/hour. The GHSV for the ethylbenzene is 1148 ml/g-cat/hour. The contact time is 784 ms. The products are analyzed by GC. At an average temperature of 412° C., 86% ethylbenzene conversion and 94% styrene selectivity are achieved. The styrene yield is 81%. The styrene yield is 930 ml/g-cat/hour. $O_2$ conversion is 98%.

Example 4

3.00 g ammonium paramolybdate $((NH_4)_6Mo_7O_{24}.4H_2O)$ are dissolved in 150 ml $H_2O$ with constant stirring. The pH of the solution is adjusted from 5.3 to 1.2 by concentrated nitric acid. A second solution is prepared by dissolving 3.12 g $Fe(NO_3)_3.6H_2O$ in 25 ml $H_2O$. The iron solution is dropped quickly into the Mo solution with stirring. The mixture is then heated to its boiling point (around 97° C.). A yellow precipitate is formed. The slurry is kept at this temperature for another 2 h. In this period, $H_2O$ is added to keep the slurry volume stable. The slurry is filtered with a Buchner funnel. The obtained solid is then mixed with 200 ml boiling water and stirred for 5 min. After filtration, the solid is dried at 120° C. overnight and then calcined at 400° C. for 4 h in air at 3.5° C./min heating rate. The catalyst is crushed and sieved to 60-100 mesh for testing. The resulting Fe—Mo based catalyst may be represented by the formula $Mo_{2.2}FeO_x$.

Reactor with Flat Walls:

A 0.2 g portion of the powder (60-100 mesh) is packed into a microchannel reactor with an internal channel cross section of 0.060×0.25×1.15 inches, fitted with a jacket to permit heat transfer oil to flow around the device. The reactor is installed into a test facility and operated for methanol oxidation. A feed stream containing 6.9% methanol, 0.7% water, 5.8% oxygen and the balance nitrogen is admitted to the heated reactor. The flow rate is adjusted to give a GHSV of 35,868 volumes of feed gas per volume of catalyst per hour. The reactor effluent is passed through a water scrubbing solution for fixed periods of time. The water solution and the scrubbed off-gas are analyzed by GC to determine the product distribution.

At 300° C. the conversion of methanol is measured at 99.5% and the selectivity to the following products is: formaldehyde 90.4%, hydrogen 0.3%, carbon monoxide 2.1%, carbon dioxide 3.3%, dimethyl ether 4.1% and methyl formate 0.03%.

Reactor with Structured Wall:

A 3 g aliquot of the $Mo_{2.2}FeO_x$ catalyst is mixed with 27 g $H_2O$ and 60 g 6-mm $ZrO_2$ beads in a jar. The mixture is ball-milled for three days. The obtained slurry (10 wt %) is then diluted to 5 wt % by $H_2O$. The particle size in the slurry is about 2 microns. The slurry is pumped into a reactor with structured walls using a syringe and then drained out to washcoat the interior walls of the reactor. The reactor is described in Example 5. The catalyst coated reactor is dried at 120° C. for 1 hour. The washcoating process is repeated four times. The catalyst coated support structure is calcined at 350° C. for 1 hour. The catalyst loading is 80 mg.

The reactor is installed into a test facility and operated for methanol oxidation. A feed stream comprising of 6.9% methanol, 0.7% water, 5.9% oxygen and the balance nitrogen is admitted to the reactor situated in a furnace. A thermocouple attached to the reactor wall near the center is used to control the temperature. The flow rate is adjusted to give a GHSV of 23,997 volumes of feed gas per volume of catalyst per hour. The effluent gas is scrubbed and the products analyzed as above.

At a temperature of 300° C. the methanol conversion is 79.6%, and the selectivity to the following products is: formaldehyde 95.5%, hydrogen 0.1%, carbon monoxide 0.6%, carbon dioxide 0.35%, dimethyl ether 3.3% and methyl formate 0.24%.

At a temperature of 330° C. the methanol conversion is measured to be 100%, and the selectivity to the following products is: formaldehyde 94.9%, hydrogen 0.4%, carbon monoxide 1.4%, carbon dioxide 0.95%, dimethyl ether 2.4% and methyl formate 0.32%.

Data from several experiments with the Fe—Mo based catalyst in the flat wall and structured wall reactors are shown in FIG. 83.

Example 5

A catalyst of nominal composition 20%$V_2O_5$-10% $MoO_3$/$TiO_2$ is prepared by mixing 1.23 g of ammonium heptamolybdate (1.0 g MoO3) with 2.57 g of ammonium metavanadate (2 g V2O5), 5.54 g of oxalic acid and 40 ml of water. A 7 g portion of $TiO_2$ (Degussa P-25, about 45 $m^2$/g) is added and the mixture is stirred for one hour at ambient temperature. The resulting slurry is dried in vacuo at 120° C. overnight. The solids are crushed to give a powder and calcined at 450° C. for four hours in air.

Reactor with a Flat Wall:

The catalyst is crushed and sieved to a 60 to 100 mesh powder. A 0.2 g portion of the powder is packed into a specially designed microchannel reactor with an internal channel cross section of 0.060×0.25×1.15 inches (1.52×6.35×29.21 mm), fitted with a jacket to permit heat transfer oil flow around the device. The reactor is installed into a test facility and operated for methanol oxidation.

A feed stream containing 9.3% methanol, 0.9% water, 7.8% oxygen and the balance nitrogen is admitted to the heated reactor. The flow rate is adjusted to give a GHSV of 35,901 volumes of feed gas per volume of catalyst per hour. The reactor effluent is passed through a water scrubbing solution for fixed periods of time. The water solution and the scrubbed off-gas are analyzed by GC to determine the product distribution.

At 260° C. the conversion of methanol is measured as 88.5% and the selectivity to the following products is: formaldehyde 85.9%, hydrogen 0.02%, carbon monoxide 5.5%, carbon dioxide 0.26%, dimethyl ether 4.6% and methyl formate 3.7%.

Reactor with Structured Wall:

A lab-scale reactor is constructed for the evaluation of formaldehyde synthesis catalysts using a structured wall. The reactor is constructed from stainless steel and has a single process channel that is approximately 3.4 inches (8.64 cm) in length and 0.338 inch (8.59 mm) in width. The reactor is constructed using a body plate, two successive layers of microgrooved support strips, spacer strips to create a microchannel gap, two additional successive layers of microgrooved supports, and a second body plate. After the entire assembly is stacked the perimeter of the stack is seam welded to seal the reactor.

The body plate and the microgrooved support strips have outer dimensions of 0.57 inch (14.48 mm) (width) and 3.5 inches (8.89 cm) (length). The body plate is 0.115 inch (2.92 mm) thick and each microgrooved support strip is 0.010 inch (0.254 mm) thick. The body and microgrooved support strips have 0.116 inch (2.95 mm) of perimeter metal along the length, yielding a process channel that is 0.338 inch (8.59 mm) in width. The microchannel is created by two spacers 3.5 inches (8.89 cm) in length by 0.116 inch (2.95 mm) in width that lay along the length of the reactor on top of the perimeter material of the microgrooved support strips. The thickness of the spacer sets the microchannel gap. 0.010 inch (0.254 mm) thick microchannel spacers are used in the formaldehyde synthesis reactors. Each layer in the stack has circular features which align with like features in layers above and below. Alignment pins may be placed through these features to ensure proper stacking and to hold the layers in place during welding.

After the perimeter (side) of the reactor is welded to seal the layers, manifolds and 0.25 inch (6.35 mm) tubing are attached. Catalyst is applied to the reactor after fabrication is completed by in-situ washcoat of a powdered slurry. In this washcoat process the slurried catalyst is pumped into the reactor, filled to the height of the reactor, and drained. Successive coatings and drying between each catalyst application may be necessary to achieve the desired catalyst loading and uniformity. Finally the catalyst is calcined and the reactor is ready for testing.

Four types of surface feature patterns are used with the microgrooved support strips: circles (FIG. 88), horizontal bars (FIG. 89), chevrons (FIG. 90), and zig-zag (FIG. 91). In all cases the patterns are through etched by photochemical machining. The through etched circles are 0.012 inch (0.305 mm) in diameter with approximately 0.008 inch (0.203 mm) of material edge-to-edge between the etched circles. The through-etched horizontal bars are 0.012 inch (0.305 mm) in length and 0.338 inch (8.59 mm) in width. Horizontal refers to the microgrooves oriented orthogonal to the gas flow, and flow is normally in the vertical direction during operation. There is 0.009 inch (0.229 mm) of material between the etched horizontal bars. The chevrons are two through-etched linear grooves of equal length (approximately 0.24 inch (6.1 mm)) intersecting at an apex with a 45° angle. The through-etched legs of the chevrons are 0.012 inch (0.305 mm) in width and are separated from the next chevron by 0.009 inch (0.229 mm) of material. The zig-zag pattern comprises one leg sloping downward at a 45° angle for approximately 0.16 inch (4.06 mm), then upward at a 45° angle for approximately 0.16 inch (4.06 mm), then downward again at a 45° angle for about 0.16 inch (4.06 mm) (with upward and downward referring to the direction of the groove relative to the normal direction of reactant feed flow during operation.) The etched microgrooves of the zig-zag feature are 0.015 inch (0.381 mm) in width and the spacing between the grooves is 0.015 inch (0.381 mm).

For formaldehyde synthesis testing two versions of the reactor are constructed, each with a different pair of microgrooved support strips. In one version of the reactor circle microgrooved support strips are adjacent to both body plates and zig-zag microgrooved support plates were placed on the interior, adjacent to each side of the microchannel gap. In a second version of the reactor horizontal bar microgroove support strips are adjacent to both body plates and chevron microgrooved support strips are placed on the interior, adjacent to each side of the microchannel gap (FIG. 92). In all cases the catalyst is washcoated with the apex pointing up relative to gravity.

A 3 g sample of the 20% $V_2O_5$-10% $MoO_3/TiO_2$ catalyst is mixed with 57 g $H_2O$ and 240 g 6-mm $ZrO_2$ beads in a jar. The mixture is ball-milled for four days. The particle size in the slurry is about 1 micron. In a washcoating process, the slurry (5 wt %) is pumped into the reactor with structured walls and an internal channel geometry of 0.338 inches (8.59 mm) wide×(0.01 inch (0.254 mm) of open flow by gap+2 sides×2 strips×0.01 inch (0.254 mm) high)×3.4 inches (8.64 cm) in length. After draining out, the catalyst coated reactor is dried at 120° C. for 1 hour. The washcoating process is repeated ten times. The catalyst coated support structure is then calcined at 350° C. for 1 hour. The catalyst loading is 100 mg. The reactor is fitted with a jacket to permit a forced flow of air around the microchannel for good temperature control.

A feed stream containing 19.6% methanol, 2.0% water, 16.5% oxygen and the balance nitrogen is admitted to the heated reactor. The flow rate is adjusted to give a GHSV of 121,359 volumes of feed gas per volume of catalyst per hour. The reactor effluent is passed through a water scrubbing solution for fixed periods of time. The water solution and the scrubbed off-gas are analyzed by GC to determine the product distribution.

At a temperature of 360° C. the conversion of methanol is measured as 97.0% and the selectivity to the following products is: formaldehyde 89.6%, hydrogen 0.03%, carbon monoxide 9.3%, carbon dioxide 0.27%, dimethyl ether 0.7% and methyl formate 0.16%. The productivity of formaldehyde is 27.12 g/g-cat/hr.

Data from several experiments with the flat wall and structured wall reactors are summarized in FIG. 84.

Example 6

A simulation is conducted to determine the ability of a composite support structure formed from five microgrooved support strips (see, FIGS. 34-36) to remove heat generated by a highly active catalyst supported by the composite support structure. The simulation is conducted by first determining the approximate heat released by the oxidative dehydrogenation of ethylbenzene to styrene if it is conducted, using air as the source of oxygen, in a microchannel with a gap of 0.0508 cm, a width of 0.859 cm and length of 8.33 cm using a contact time (CT) of 100 milliseconds (ms) resulting in an inlet flow of 34.7 sccm ethylbenzene. The microgrooved support strips are assumed to be present on the opposing walls whose planar dimensions are 0.859 cm and 8.33 cm (heat transfer walls). It is assumed that the catalyst would achieve a conversion of ethylbenzene of 70% and a molar selectivity to styrene of 88%. The molar selectivity to CO is assumed to be 3% and the molar selectivity to $CO_2$ is assumed to be 9%. The ethylbenzene:oxygen ratio is 0.9:1. The heat released from the reaction is approximately 10.2 W.

A model domain representing a section of the microgrooved support strips 0.254 cm by 254 micron deep by 68.6 micron wide is constructed in MECHANICA simulating a section of a microgrooved assembly located the inlet end of the microchannel. The composite support structure is assumed to contain 5 layers of microgrooved support strips, each strip being 50.8 micron thick (in the stack height dimension) and each containing microgrooves of 45 micron depth and 61 micron width (leaving metal ribs with cross sections of 50.8 micron by 45.7 micron). The microgrooves in the top layer are at an angle of 0° to the center axis and at 90° to the center axis in the second layer. In the third layer the microgrooves once again are at an angle of 0° to the center axis and at 90° to the center axis in the fourth layer. In the fifth layer the microgrooves once again are at an angle of 0° to the center axis thus the microgrooves in each layer of the assembly form a right angle with those in adjacent layers. The top layer is assumed to be in contact with the reactant fluid and the fifth layer is assumed to be in intimate contact with a heat transfer wall held isothermal at 500° C.

The average heat flux out of the heat transfer walls is calculated to be 0.688 W/cm² and it is further assumed that the peak heat flux would be 1.65 times the average thus for a section of reactor close to the inlet the heat flux through the wall was taken to be 1.138 W/cm². Based on this the total heat generated by the action of the catalyst in the model domain is calculated to be 0.0154 W and this reaction heat is then applied as a boundary condition across the surfaces in the domain presumed to have catalyst adhering to them. The surface of the microgrooved support strip adjacent to the heat transfer wall is set isothermal at 500° C. When the model is run this condition is found to cause a minimal rise on the catalyst covered surfaces. The total heat load in the model domain is then increased by a factor of 10 and the model is re-run. This is equivalent to a heat flux of 11.38 W/cm² from the model domain at the isothermal boundary. This results in a maximum temperature rise of 3.5° C. From the thickness of the model domain 0.0254 cm, the temperature rise, 3.5° C., and the heat flux at the boundary, 11.38 W/cm² the effective thermal conductivity of the microgrooved assembly can be estimated as approximately 8.26 W/m-K. This is about 52% of that used for the parent material (stainless steel 316).

Example 7

Structured Wall Test Reactors #1 and #2 are fabricated. The reactors contain inlet and outlet tubing, headers and footers, a body cover plate, a body backing plate and a microgrooved assembly. The inlet and outlet tubing is welded to the header and footer of each device. Each is a 3 inch (7.62 cm) length of ⅛ inch (0.318 cm) OD SS316 tube with a tubular wall thickness of 0.035 inch (0.089 cm). The headers and footers are fabricated from SS316 bar stock via conventional machining and have outer dimensions of 0.820 inch×0.375 inch×0.375 inch (2.08×0.953×0.953 cm). One of the 0.375 inch×0.820 inch (0.953×2.08 cm) faces is given a 45° 0.020 inch (0.0508 cm) chamfer on each of the 0.375 inch (0.953 cm) long edges. This face is the "top" of the piece. A 0.180 inch (0.457 cm) deep by 0.520 inch (1.32 cm) long by 0.069 inch (0.175 cm) wide slot is cut in one of the 0.820 inch×0.375 inch (2.08× 0.953 cm) faces (orthogonal to the top face) such that the long axis of the slot is located 0.227 inch (0.577 cm) from the bottom face of the piece and the short axis of the slot is located 0.410 inch (1.04 cm) from the 0.375 inch (0.953 cm) long edge of the face. The slot is flat bottomed and terminated in a full round. On the face opposite the slot is drilled a 0.069 inch (0.175 cm) through hole with a 0.125 inch (0.318 cm) counter bore to a depth of 0.125 inch (0.318 cm). The through hole is centered on the location of the slot.

The process microchannel is in the form depicted in FIG. 40 and is assembled using a body cover plate (right side of FIG. 40), a body backing plate and a microgrooved composite support structure. The microgrooved composite support structure contains two microgrooved support strips such as those depicted in FIGS. 37-40. The microgrooved support strips are stacked one on top of the other. The microgrooved composite support structure is attached to the body backing plate. The body cover plate and body backing plate are fabricated from FeCrAlY plate. The body backing plate has overall dimensions of 3.900 inches (9.91 cm) by 0.750 inch (1.91 cm) and is 0.190 inch (0.483 cm) thick. In cross section the part has a raised central tenon 0.502 inch (1.275 cm) wide that runs the length of the device.

The tenon is formed by removing material 0.124 inch (0.315 cm) from either side of the tenon to a depth of 0.074 inch (0.188 cm). The lip of the step so formed is given a 0.030 inch (0.076 cm) 45° chamfer on either side as shown in the lower left of FIG. 85. The body cover plate has overall dimensions of 3.900 inches (9.91 cm) by 0.750 inch (1.91 cm) and is 0.190 inch (0.483 cm) thick. A deep slot is cut down the center of the part 0.505 inch (1.283 cm) wide and 0.080 inch (0.203 cm) deep extending the entire length of the part as shown in FIG. 86. A 0.030 inch (0.076 cm) wide 0.002 inch (50.8 microns) rib of material is left running down the center of the deep slot as shown in FIG. 40. The outside edges of the part adjacent to the slot is given a 0.030 inch (0.076 cm) 45° chamfer. The chamfers on the body cover plate and body backing plate mate after assembling to provide a groove suitable for seal welding. The body backing plate and body cover plate are toleranced and fabricated to provide a friction fit to minimize my pass.

The microgrooved support strips are fabricated via photochemical machining from 0.002 inch (50.8 microns) thick stainless steel 304. Each strip is 2.500 inches (6.35 cm) long and 0.500 inch (1.27 cm) wide. The microgrooves are parallel to each other, 0.007 inch (178 microns) wide and separated from adjacent grooves by 0.007 inch (178 microns) of the base material. The microgrooves form a 20° angle from the center line (long axis of the microgrooved support strip). The microgrooves start approximately 0.030 inch (0.076 cm) from the edge of the strip measuring 0.500 inch (1.27 cm) and each individual microgroove stops approximately 0.007 inch (178 microns) from the long (2.5 inches, 6.35 cm) edge of the strip (see FIGS. 37 and 38). A large central rib (0.064 inch, 1.63 cm wide) is located half way down the length of the microgrooved support strip. The microgrooved assembly is made by stacking two microgrooved support strips, one on top of the other. The angled direction of the microgrooves is alternated to produce a lattice like structure as shown in FIGS. 34 and 35. The microgrooved composite support structure is then saturated with isopropyl alcohol (to aid in positioning and to maintain flatness) and tack welded to the body backing plate tack welds being placed at the front and back edges and on the middle of the large central rib to produce an assembly as depicted on the left hand side in FIG. 40. The microgrooved composite support structure is centered on the body backing plate in both the axial and side to side dimensions. Any overhang of the microgrooved support strips is removed with a fine diamond hone. Once completely assembled, the device is in the form of a microchannel with an inlet and outlet gap of 0.006 inch (152 microns) that is approximately 0.503 inch (1.28 cm) wide and 3.900 inches (9.91 cm) long. In the portion of the channel containing the microgrooved composite support structure the gap is reduced to 0.002 inch (50.8 microns) the balance of the channel being occupied by the microgrooved composite support structure. The main flow path is through the 0.002 inch (50.8 microns) channel that sits above the 0.004 inch (102 microns) microgrooved composite support structure.

The microgrooved composite support structure and the body cover plates are cleaned first in an ultrasonic bath containing isopropanol, then a 20% nitric acid solution, and then deionized water. Each cleaning step has a duration of 30 minutes at 90% power output. The bath temperature is 25° C. The cleaned parts are then heated in stagnant air while increasing the temperature at a rate of 3.5° C. per minute to 650° C. and held at that temperature for 10 hours.

The catalyst described in Example 3 is prepared and washcoated on the microgrooved composite support structure using the procedure described in Example 3. The resulting microchannel reactor is designated as Structured Wall Test Reactor #2.

The body cover plate is placed on the body backing plate and a seam weld is applied to close the device forming the microchannel reactor body assembly. The header and footer, after having their respective inlet and outlet tubing welded to them are also welded to the body assembly such that the slot on the header or footer is aligned with the channel formed by the body assembly which is shown in FIG. 87. A test set-up for the microchannel reactor is shown in FIG. 97.

Referring to FIG. 97, ethylbenzene (EB) is pumped into a microchannel vaporizer at a rate of 0.10 ml/min via a HPLC piston pump outfitted with pulse dampeners. The ethylbenzene is heated, vaporized, and superheated to 200° C. before mixing with an air stream. The air is fed into the system with a mass flow controller. The air is preheated before mixing with the ethylbenzene stream by an electrical heating tape that is wrapped around the outside of the feed tube. The surface of the tube is held at held at 200° C. The total feed rate of the air stream ranges from 42-87 SCCM giving an ethylbenzene:oxygen mole ratio ranging from 2.1 to 1.0.

The mixed feed stream of ethylbenzene and oxygen flows through a 200 mesh screen before reaching the orifice and split section. All of the lines and the orifice are heated with and electrical heating tape holding the outside surface of the tubing at 200° C. An orifice with a diameter of 0.0007 inch (17.8 microns) is placed immediately upstream of the reactor. The orifice has a pressure drop that is significantly larger than the pressure drop across the reactor. The feed rate to the reactor is controlled by varying the back pressure of the split stream. The pressures upstream and downstream of the orifice are controlled in order to maintain the total flow to the reactor from 2 to 6 SCCM. The split stream is condensed via a microchannel heat exchanger and collected in two chilled product collection drums. The gasses exit through the back pressure regulator, septa sampling point, and bubble flow meter, before going to a vent. Samples of this exit gas stream are collected by a gas tight syringe and the liquid is collected and analyzed.

The microchannel reactor is installed inside an electrically powered ceramic heating element. This heater provides a temperature ranging from 350° C. to 500° C.

The product of the reactor is mixed with room temperature nitrogen flow of 15 SCCM from a second mass flow controller to help increase the total flow rate through the downstream components. The diluted product is condensed in a chilled, 2 mm glass bead packed sample collection drum. The product is collected in a chilled, open volume knock-out drum before the gas stream is sent through a bubble flow meter and to the on-line GC system. The flow rates of both the split and product gas streams are recorded.

There are two GCs that provide the analysis for the system. The product gas stream is analyzed by an Agilent 5890 GC equipped with two TCD detectors, three sample valves, and a sample pump. $H_2$, $O_2$, $N_2$, $CH_4$, CO, $CO_2$, ethane and ethylene are quantified in the 5890GC with an analysis time of approximately 20 min. The liquid feed, liquid collected from the split stream knockout drum, split stream gas, liquid product and product stream gas are analyzed by an Agilent 6890GC with a FID detector. Benzene, toluene, ethylbenzene and styrene are quantified in approximately 20 min.

The start-up procedure for the system is as follows. $N_2$ flow at 200 SCCM purges the system as the devices begin to heat. The back pressure is increased on the split stream in order to push flow through the reactor. The reactor flow is established at 5 SCCM. The vaporizer is heated to 200° C. while the heat tracing is heated to 200° C. The reactor is heated to an average temperature of 380° C. at a rate of 3° C./min in the ceramic heater (clam shell furnace). Once the temperatures are steady ethylbenzene and air flows are stepped in, while the $N_2$ flow is stepped out until an ethylbenzene:oxygen mole ratio of 2:1 and reactor inlet flow 4 SCCM is reached. The system is left until steady state and a full sample is recorded. The temperature is then increased at a rate of 2° C./min in 10° C. increments while taking product GC samples. The temperature ramp stops once full oxygen conversion has been reached. The temperature is held constant and a sample is taken at 412° C. average temperature. Next the ethylbenzene:oxygen mole ratio is decreased to 1.8:1, 1.5:1, and 1.1:1 consecutively. This increases conversion of the ethylbenzene and selectivity to styrene.

Conversion of the ethylbenzene and selectivity to styrene is determined using a methodology based on oxygen balance. This method involves determining the conversion of ethylbenzene based on performing an oxygen balance and assumes the following stoichiometry to dominate.

$$C_8H_{10} + 0.5O_2 \rightarrow C_8H_8 + H_2O \qquad \text{Equation 1}$$

$$C_8H_{10} + 6.5O_2 \rightarrow 8CO + 5H_2O \qquad \text{Equation 2}$$

$$C_8H_{10} + 10.5O_2 \rightarrow 8CO_2 + 5H_2O \qquad \text{Equation 3}$$

The conversion of ethylbenzene is approximated as shown in the equations below:

$$x_{EB} = 1 - \frac{n_{ST,out} + \frac{1}{8}(n_{CO,out} + n_{CO_2,out})}{n_{EB,in}} \qquad \text{Equation 4}$$

where $n_{CO,out}$, $n_{CO_2,out}$, and $n_{ST,out}$ are calculated as follows:

$$n_{CO,out} = n_{dry\,gas,out} \cdot f_{CO,out,dry} \qquad \text{Equation 5}$$

$$n_{CO_2,out} = n_{dry\,gas,out} \cdot f_{CO_2,out,dry} \qquad \text{Equation 6}$$

$$n_{ST,out} = n_{O,in} - n_{O,out} - \frac{5}{8} \cdot (n_{CO,out} + n_{CO_2,out}) \qquad \text{Equation 7}$$

In the above equations, $n_{dry\,gas,out}$ is the measured molar outlet dry flow rate, $f_{i,out,dry}$ is the mole fraction of component i (CO, $CO_2$, or $O_2$) in the dry outlet flow as measured by gas chromatograph, 5/8 is the assumed stoichiometric ratio of $H_2O$ to CO or $CO_2$ formed during combustion, and $$n_{O,in} = 2 \cdot n_{O_2,in} + 2 \cdot 0.21 \cdot n_{air,in} \qquad \text{Equation 8}$$

$$n_{O,out} = n_{dry\,gas,out}(f_{CO,out,dry} + 2 \cdot f_{CO_2,out,dry} + 2 \cdot f_{O_2,out,dry}) \qquad \text{Equation 9}$$

where $n_{i,in}$ is the inlet molar flow rate of component i ($O_2$ or air). The above calculations assume a perfect oxygen balance wherein the molar flow rate of water out of the system is equal to the molar flow rate of missing oxygen atoms. It is further assumed that one mole of water is formed for every mole of styrene produced, and five moles of water are formed for every eight moles of CO or $CO_2$ produced.

The weight selectivity to styrene is calculated as follows:

$$Sel_{ST} = \frac{n_{ST,out} \cdot MW_{ST}}{n_{EB,in} \cdot x_{EB} \cdot MW_{EB}} \quad \text{Equation 10}$$

Furthermore, the carbon selectivity to CO, and $CO_2$ is calculated as shown below.

$$Sel_{CO} = \frac{n_{CO,out}}{(n_{CO,out} + n_{CO_2,out} + 8 \cdot n_{ST,out})} \quad \text{Equation 11}$$

$$Sel_{CO_2} = \frac{n_{CO_2,out}}{(n_{CO,out} + n_{CO_2,out} + 8 \cdot n_{ST,out})} \quad \text{Equation 12}$$

The selectivity to non-COx (taken to approximate the carbon selectivity to styrene) is calculated by subtracting the sum of the selectivity to CO and the selectivity to $CO_2$ from 100%.

The results of testing the device are summarized in Table 7 where comparison is given between similar catalysts tested in a powdered state using a quartz tube reactor (inner diameter 4 mm). The catalyst is online under reactive conditions for 96.5 hours in the Structured Wall Test Reactor #2 (see, Table 8).

TABLE 7

Test conditions and reactor performance for Structured Wall Test Reactor #2. Contact time is based on reactor volume including volume within microgrooved support strips.
Catalyst 0.7% $K_2O$—15% $MoO_3/SiO_2$—$TiO_2$
Oxygen Source Air

| Device | (Type) | Quartz Tube | | SW Test Reactor #2 | | | | | | | |
|---|---|---|---|---|---|---|---|---|---|---|---|
| Condition | (#) | 1 | 2 | 3 | 4 | 5 | 6 | 7 | 8 | 9 | 10 |
| $M_{cat}$ | (mg) | 400 | 400 | 28.8 | 28.8 | 28.8 | 28.8 | 28.8 | 28.8 | 28.8 | 28.8 |
| WHSV | ($hr^{-1}$) | 13 | 13 | 8.8 | 7.8 | 9 | 7.4 | 5.5 | 6.4 | 6.2 | 6.3 |
| CT | (ms) | 100 | 100 | 2228 | 2514 | 1902 | 2071 | 2439 | 2096 | 2163 | 2433 |
| GHSV | ($l_{feed}/(hr\, l_{channel})$) | 36000 | 36000 | 1616 | 1432 | 1892 | 1738 | 1476 | 1718 | 1664 | 1480 |
| T | (° C.) | 450 | 495 | 401 | 415 | 417 | 416 | 418 | 420 | 410 | 416 |
| EB:$O_2$ | (mol/mol) | 2 | 2 | 1.8 | 1.8 | 1.5 | 1.3 | 1.1 | 1.1 | 1.1 | 1.3 |
| Dilution | ($N_2$:Reactants) | 2 | 2 | 0 | 0 | 0 | 0 | 0 | 0 | 0 | 0 |
| Conversion | | | | | | | | | | | |
| EB | (%) | 37.6 | 43.1 | 42.1 | 40.9 | 59.0 | 74.8 | 86.7 | 77.7 | 74.0 | 76.2 |
| $O_2$ | (%) | 91.3 | 98.8 | 83.6 | 97 | 95.4 | 97.8 | 99.1 | 96.9 | 90.2 | 99.7 |
| Selectivity | | | | | | | | | | | |
| Styrene | (mol %) | 91.8 | 92.5 | 93.3 | 90.6 | 93.7 | 94.4 | 94 | 92.9 | 93.3 | 94.4 |
| CO | (mol %) | 2.7 | 2.5 | 1.7 | 2.3 | 1.4 | 1.5 | 1.5 | 1.9 | 1.5 | 1.2 |
| CO2 | (mol %) | 5.5 | 4.9 | 5.1 | 7.1 | 4.9 | 4.2 | 4.5 | 5.2 | 5.2 | 4.4 |
| Yield | | | | | | | | | | | |
| Styrene Yield | mol(%) | 34.5 | 39.9 | 39.3 | 37.1 | 55.3 | 70.6 | 81.5 | 72.2 | 69.0 | 71.9 |

TABLE 8

Time on stream under reactive conditions for Structured Wall Test Reactor #2

| | Condition (#) | | | | |
|---|---|---|---|---|---|
| | 3 Reactor #2 | 5 Reactor #2 | 8 Reactor #2 | 9 Reactor #2 | 10 Reactor #2 |
| Time on stream (h:m) | 1:45 | 6:15 | 13:20 | 15:00 | 22:30 |

TABLE 9

Temperature profiles for Structured Wall Test Reactor #2

| | | Data Point | | | | |
|---|---|---|---|---|---|---|
| | | 1 | 2 | 4 | 6 | 7 |
| | | Reactor Type | | | | |
| | | Quartz Tube | Quart Tube | Reactor #2 | Reactor #2 | Reactor #2 |
| WHSV | ($hr^{-1}$) | 13 | 13 | 7.8 | 7.4 | 5.5 |
| T | (° C.) | 450 | 495 | 415 | 416 | 418 |
| EB:O2 | (mol/mol) | 2 | 2 | 1.8 | 1.3 | 1.1 |

TABLE 9-continued

Temperature profiles for Structured Wall Test Reactor #2

| | | Data Point | | | | |
|---|---|---|---|---|---|---|
| | | 1 | 2 | 4 | 6 | 7 |
| | | Reactor Type | | | | |
| | | Quartz Tube | Quart Tube | Reactor #2 | Reactor #2 | Reactor #2 |
| Time on stream | (h:m) | 1:40 | 3:40 | 3:49 | 26:09 | 47:49 |
| pressure drop | (psid) | 3.95 | 6.71 | 0.03 | 0.1* | 0.06 |
| Top of catalyst bed | (° C.) | 450 | 495 | N/A | N/A | N/A |
| ¾" from top of cat bed | (° C.) | 385 | 399 | N/A | N/A | N/A |
| 0.3 inches from start of coupon | (° C.) | N/A | N/A | 415 | 416 | 418 |
| 0.8 inches from start of coupon | (° C.) | N/A | N/A | 418 | 418 | 419 |
| 1.3 inches from start of coupon | (° C.) | N/A | N/A | 414 | 415 | 413 |
| 1.8 inches from start of coupon | (° C.) | N/A | N/A | 408 | 408 | 403 |
| 2.3 inches from start of coupon | (° C.) | N/A | N/A | 397 | 398 | 388 |

The yield increases are achieved at lower WHSV in the Structured Wall Test Reactor #2 but also at significantly reduced temperatures thus productivity may be increased markedly by increasing temperature. As the selectivity is not dramatically reduced by operation at 495° C. (condition 2 in Table 7) it is anticipated that the WHSV may be increased in the microchannel reactor employing the microgrooved catalyst support.

Example 8

Structured Wall Test Reactor #1 is prepared in a manner similar to that described in Example 7 using the catalyst described in Examples 3 and 7. Testing is conducted in a manner analogous to that described in Example 7 with several exceptions. One of these is that the flow of nitrogen used to aid in the down stream purge is 25 SCCM for conditions 3 through 7 and 0 SCCM for conditions 8 through 13. In addition the microgrooved test device described in Example 7 is placed in a clam shell furnace such that the bottom (outlet of the microchannel) of the body assembly even with the bottom of the 3 inches long heating zone of the clam shell furnace thus approximately 0.9 inch (2.29 cm) sticks out above the heated zone. In this example the device is placed in the clam shell furnace such that the top (inlet of the microchannel) is even with the top of the heating zone thus approximately 0.9 inch (2.29 cm) sticks out below the heated zone. This leads to a more pronounced temperature profile (15° C. from inlet to outlet for Example 7 vs. 50° C. for Example 8) as can be seen by comparing Tables 11 and 9.

TABLE 10

Test conditions and reactor performance for Structured Wall Test Reactor #1. Contact time is based on reactor volume including volume within microgrooved support strips.
Catalyst 0.7% $K_2O$—15% $MoO_3/SiO_2$—$TiO_2$
Oxygen Source Air

| Device Condition | (Type) | Quartz Tube | | SW Test Reactor #1 | | | | | | | | | |
|---|---|---|---|---|---|---|---|---|---|---|---|---|---|
| | (#) | 1 | 2 | 3 | 4 | 5 | 6 | 7 | 8 | 9 | 10 | 11 | 12 | 13 |
| $M_{cat}$ | (mg) | 400 | 400 | 24.3 | 24.3 | 24.3 | 24.3 | 24.3 | 24.3 | 24.3 | 24.3 | 24.3 | 24.3 | 24.3 |
| WHSV | (hr⁻¹) | 13 | 13 | 16 | 14 | 18 | 13 | 13 | 14 | 11 | 11 | 11 | 10 | 6 |
| CT | (ms) | 100 | 100 | 1620 | 1852 | 1440 | 1994 | 1787 | 1660 | 2112 | 2112 | 2112 | 2324 | 2450 |
| GHSV | ($I_{feed}$/(hr $I_{channel}$)) | 36000 | 36000 | 2222 | 1944 | 2500 | 1805 | 2014 | 2169 | 1704 | 1704 | 1704 | 1549 | 1469 |
| T | (° C.) | 450 | 495 | 395 | 454 | 415 | 423 | 423 | 416 | 415 | 425 | 426 | 426 | 426 |
| EB:$O_2$ | (mol/mol) | 2 | 2 | 2.1 | 2.1 | 2.1 | 2.1 | 1.8 | 1.8 | 1.8 | 1.8 | 1.8 | 1.8 | 1 |
| Dilution | ($N_2$:Reactants) | 2 | 2 | 0 | 0 | 0 | 0 | 0 | 0 | 0 | 0 | 0 | 0 | 0 |
| | | | | | | | Conversion | | | | | | | |
| EB | (%) | 37.6 | 43.1 | 30.9 | 32.1 | 39.1 | 52.7 | 73.2 | 43.1 | 42.9 | 40.4 | 37.0 | 37.6 | 53.7 |
| $O_2$ | (%) | 91.3 | 98.8 | 59.2 | 95.7 | 82.8 | 95.1 | 97.4 | 79.9 | 84.9 | 88.1 | 92.1 | 91.4 | 89 |
| | | | | | | | Selectivity | | | | | | | |
| Styrene | (mol %) | 91.8 | 92.5 | 95.7 | 89.2 | 94.2 | 96.0 | 97.4 | 93.9 | 93.2 | 91.7 | 87.4 | 90.3 | 85.1 |
| CO | (mol %) | 2.7 | 2.5 | 0.0 | 2.8 | 1.0 | 0.6 | 0.4 | 1.8 | 2.1 | 2.5 | 3.4 | 2.7 | 4.1 |
| CO2 | (mol %) | 5.5 | 4.9 | 4.3 | 7.9 | 4.7 | 3.4 | 2.1 | 4.3 | 4.8 | 5.7 | 9.2 | 7.0 | 10.9 |
| | | | | | | | Yield | | | | | | | |
| Styrene Yield | mol(%) | 34.5 | 39.9 | 29.6 | 28.6 | 36.8 | 50.6 | 71.3 | 40.5 | 40.0 | 37.0 | 32.3 | 34.0 | 45.7 |

TABLE 11

Temperature profiles for Structured Wall Test Reactor #1

| | | Condition # | | | | |
|---|---|---|---|---|---|---|
| | | 1 | 2 | 4 | 6 | 7 |
| | | Reactor Type | | | | |
| | | Quartz Tube | Quart Tube | Reactor #1 | Reactor #1 | Reactor #1 |
| WHSV | (hr$^{-1}$) | 13 | 13 | 14 | 13 | 13 |
| T | (° C.) | 450 | 495 | 454 | 423 | 423 |
| EB:O2 | (mol/mol) | 2 | 2 | 2.1 | 2.1 | 1.8 |
| Time on stream | (h:m) | 1:40 | 3:40 | 3:30 | 25:10 | 26:30 |
| pressure drop | (psid) | 3.95 | 6.71 | 2.06 | 1.25 | 0.99 |
| Top of catalyst bed | (° C.) | 450 | 495 | N/A | N/A | N/A |
| ¾" from top of cat bed | (° C.) | 385 | 399 | N/A | N/A | N/A |
| 0.3 inchs from start of coupon | (° C.) | N/A | N/A | 454 | 423 | 423 |
| 0.8 inches from start of coupon | (° C.) | N/A | N/A | N/A | N/A | N/A |
| 1.3 inches from start of coupon | (° C.) | N/A | N/A | 437 | 405 | 406 |
| 1.8 inches from start of coupon | (° C.) | N/A | N/A | N/A | N/A | N/A |
| 2.3 inches from start of coupon | (° C.) | N/A | N/A | 404 | 374 | 375 |

TABLE 12

Time on stream under reactive conditions for Structured Wall Test Reactor #1

| | Conditon (#) | | | | | | |
|---|---|---|---|---|---|---|---|
| | 3 | 5 | 8 | 9 | 10 | 11 | 12 | 13 |
| | Reacor #1 | Reacor #1 | Reacor #1 | Reacor #1 | Reacor #1 | Reacor #1 | Reacor #1 | Reacor #1 |
| Time on stream (h:m) | 1:30 | 6:20 | 18:20 | 20:35 | 22:15 | 41:20 | 65:35 | 73:00 |

In Example 8 the advantages of the microgrooved support structure are apparent when the same catalyst is run in both a packed bed in a quartz tube (4 mm inner diameter) and the microgrooved reactor. In this case when condition 2 and condition 7 in Table 10 are compared the microgrooved reactor allows for improve conversion and selectivity at a similar weight hourly space velocity (WHSV) and lower temperature. The term WHSV is used herein to refer to the mass of reactant (for example, ethylbenzene) per unit of time contacting a given mass of catalyst. The enhanced productivity of Microgroove Test Reactor #1 vs. Microgroove Test Reactor #2, where Microgroove Test Reactor #1 has a higher conversion at greater WHSV, may be due to the larger pressure drop experienced by Microgroove Test Reactor #1, a on possible outcome of which may be that part of the bulk flow is diverted from the flow by channel into the microgrooved structure.

The results for two structured wall test reactors (Examples 7 and 8) show that the enhanced ability of the structured wall reactor to remove heat allows for conversion to be increased beyond 40% while at the same time maintaining high selectivity.

Example 9

When a 0.7% $K_2O$-15% $MoO_3/SiO_2$—$TiO_2$ catalyst, similar to that described in Example 3 without the further processing required for wash coating, is tested in an oxidative dehydrogenation of ethylene to form styrene in a quartz tube reactor (O.D.=0.25" I.D.=0.157") a pronounced inlet to outlet temperature gradient on the tube wall is noted. The effective thermal conductivity (approximately 0.12 W/m/K) of the catalyst as a packed bed at room temperature is relatively low. Therefore a large exotherm in the center of the bed is expected. The CFD program Fluent combined with a kinetic model for the oxidative dehydrogenation reaction of ethylbenzene in which the mechanism is as assumed is used to determine to what level temperature a hot spot might reach. The kinetic parameters are adjusted to give approximate fit of the model output to a sub-set of the experimental data. Neither reaction network nor parameters are fully optimized but the general scheme, the formation of styrene from ethylbenzene followed by the subsequent oxidation of styrene to CO or $CO_2$, appear justified for the data set as the temperature rises in the direction of the outlet. The adjusted kinetic parameters are then used to model a packed bed microchannel reactor operating at 100 ms and a 500° C. wall temperature. The simulation of the 0.06 inch (1.52 mm) gap packed bed microchannel demonstrates that, in this instance for the set of selected kinetics and effective thermal conductivity, the packed bed microchannel has similar selectivity versus conversion behavior as that of the tube and further demonstrates that removal of diluent (reducing the diluent nitrogen from two times reactant flow) (air and ethyl benzene feed to reactor) to one time flows) results in a temperature run away. When this result is compared to that obtained for the structured wall test reactors it can be seen that the increased effective thermal conductivity provided by the microgroove structure (as shown in Example 6) may be useful for obtaining high conversion while at the same time maintaining desirable selectivity. When data collected in a quartz tube is compared to that collected in a microchannel test device containing structured wall features (the structured wall test device) it is evident that high conversion may be achieved while maintaining desirable selectivity to styrene.

Two geometries are considered: A quartz tube, 0.250 inches (6.35 mm) outside diameter tube (0.157 inches (3.99 mm) diameter), and the 0.060 inches (1.52 mm) gap packed bed microchannel reactor (FIG. 93). The microchannel packed bed reactor full dimensions of the channel are:

0.152 cm (0.060 inches) in height 0.635 cm (0.250 inches) in width 2.921 cm (1.150 inches) in length The dimensions are shown in FIG. 93. The mesh used to model this reactor has 37,500 volume elements.

A method is used for measuring the thermal conductivity of both structured adsorbents and small volume powder beds. The test method is based on an ASTM standard, "Standard Test Method for Steady-State Thermal Transmission Properties by Means of the Heat Flow Meter Apparatus," C 518-04.

The test apparatus is amenable to the measurement of materials with volumes in the range of 2 to 5 cc. The test device consists of wide diameter stacked, cylindrical material volumes positioned between a heat source and a heat sink, per the ASTM recommendations. The assembly is maintained at constant and controlled temperatures. A variac-controlled heater serves as the heat source; a circulating water bath maintains the lower temperature of the system—such that a known heat flux is pushed through the sample to be evaluated. Based on a simple one-dimensional heat transfer model, the effective thermal conductivity is calculated as the heat flux (W/cm$^2$) multiplied by the thickness of the sample (in cm) and divided by the measured temperature differential across the sample (in °C.). The resulting numerical value is modified to fit the conventional SI thermal conductivity units of W/m-K.

The proper axial alignment of all components and parallel positioning of all material layers is desired for achieving uni-axial heat transfer for accurate measurements. Proper selection of reference material thickness and thermal conductivity allows minimal heat loss from the equipment and easy control of temperature gradients across the assembly. All components are relatively easily stacked and positioned on one another through the use of centering/alignment rings.

For powder testing, an even distribution and a flat contact surface are enabled by repeated shaking of the sample chamber. If necessary, sample powder beds can be compressed prior to testing using a one-inch die press. Fabric samples are tested both perpendicularly to the weave and in the fiber direction. The effective thermal conductivity in the fiber direction is measured by rolling the fabric into short tubes, placing them in a circular plastic retainer, and carefully cutting these into planar disks. Under these circumstances, the plastic retainer serves as the sample chamber and is constrained between two reference disks.

The device is designed based on available industry test standards for thermal conductivity measurement. The following two references are specifically consulted for the design:

ASTM, "Standard Test Method for Steady-State Thermal Transmission Properties by Means of the Heat Flow Meter Apparatus," C 518-04.

Salmon, D., "Thermal conductivity of insulations using guarded hot plates, including recent developments and sources of reference materials," Meas. Sci. Technol. 12, R89-R98, 2001.

The device is used to measure the thermal conductivities of several catalyst samples and the follow results are obtained.

TABLE 13

Thermal conductivity of several substrates and catalysts

| sample | Calculated Density (g/ml) | Thermal Conductivity Measured (W/m-K) | Thermal Conductivity Expected k sample expected (W/m-K) |
|---|---|---|---|
| PTFE Disk, solid | | 0.209 | 0.23 |
| Pyrex Disk, solid | | 0.996 | 1.12 |
| Meso V—Mg—Ox | 0.56 | 0.087 | N/A |
| 0.7% K$_2$O-15% MoO3/SiO$_2$—TiO$_2$ | 1.09 | 0.126 | N/A |
| Meso V—Mg—Ox | 0.57 | 0.082 | N/A |
| 0.7% K$_2$O-15% MoO3/SiO$_2$—TiO$_2$ | 1.04 | 0.122 | N/A |

The thermal conductivity for K—MoO$_3$/SiO$_2$—TiO$_2$ is found to be 0.122 to 0.126 W/m/K for temperatures less than 75° C. It is assumed that the gas phase thermal conductivity is the limiting phase and its thermal conductivity increases as the half order in absolute temperature thus an increase in temperature from 50° C. (323° K) to 500° C. (773° K) may provide an improvement of 1.5×, so the effective thermal conductivity may increase to 0.12 W/m/K to 0.23 W/m/K.

The next feature of reactor operation is the inlet flow composition. Table 14 shows the mole fractions to be used for the quartz tube case. Table 15 shows the settings for the microchannel packed bed reactor case.

TABLE 14

Settings for the quartz tube cases including experimental results.
Quartz Tube

| | | | | | |
|---|---|---|---|---|---|
| I.D. | | 0.157 (in) | | | |
| Bed Depth | | 1.0 (in) | | | |

| | | Tube Case 1 | Tube Case 2 | Tube Case 3 | Tube Case 4 |
|---|---|---|---|---|---|
| EB | (sccm) | 18.31 | 18.31 | 18.31 | 18.31 |
| Air | (sccm) | 42.4 | 42.4 | 62.5 | 82.5 |
| N$_2$ | (sccm) | 120.5 | 120.5 | 100.5 | 80.5 |
| P$_{in}$ | (psig) | 6.88 | 7.7 | 7.08 | 7.03 |
| T$_{top}$ | (° C.) | 443 | 497 | 470 | 526 |
| T$_{bot}$ | (° C.) | 452 | 501 | 528 | 590 |
| Conversion | | | | | |
| EB | (%) | 5.8 | 31 | 44.2 | 51.8 |
| O$_2$ | (%) | 33.1 | 100 | 100 | 98.4 |
| Selectivity | | | | | |
| ST | (mol %) | 74.4 | 88.2 | 87.9 | 85.9 |
| CO | (mol %) | 7.4 | 2.7 | 2.2 | 3.1 |
| CO2 | (mol %) | 18.1 | 9.1 | 9.9 | 11.3 |

TABLE 15

Settings for the packed bed microchannel reactor case

Microchannel Packed Bed (MCPB)

| | | | | |
|---|---|---|---|---|
| Gap | | 0.06 (in) | | |
| Width | | 0.25 (in) | | |
| Bed Depth | | 1.15 (in) | | |
| CT | | 100 (ms) | | |
| Vo | | 169.6 (sccm) | | |

| | | MCPB Case 1 | MCPB Case 2 | MCPB Case 3 | MCPB Case 4 |
|---|---|---|---|---|---|
| EB:O$_2$ | (mol/mol) | 2 | 2 | 2 | 1 |
| Dilution | (mol/mol) | 2 | 1 | 0 | 0 |

TABLE 15-continued

Settings for the packed bed microchannel reactor case

| EB | (sccm) | 16.7 | 25.1 | 50.2 | 29.4 |
|---|---|---|---|---|---|
| Air | (sccm) | 39.8 | 59.7 | 119.4 | 140.2 |
| $N_2$ | (sccm) | 113.1 | 84.8 | 0.0 | 0.0 |
| Total | (sccm) | 169.6 | 169.6 | 169.6 | 169.6 |
| $P_{out}$ | (psig) | 2 | 2 | 2 | 2 |
| $T_{g,in}$ | (° C.) | 500 | 500 | 500 | 500 |
| $T_{wall}$ | (° C.) | 500 | 500 | 500 | 500 |

The first reaction is the oxidative dehydrogenation of ethylbenzene to styrene ($\Delta H_f^\circ = -70.080$ kJ/gm-mole), $$C_6H_5C_2H_5 + \frac{1}{2}O_2 \rightarrow C_6H_5C_2H_3 + H_2O,$$

the second is the undesired series reaction partial oxidation of styrene to carbon monoxide and water ($\Delta H_f^\circ = -1,998.912$ kJ/gm-mole), $$C_6H_5C_2H_3 + 6O_2 \rightarrow 8CO + 4H_2O,$$

and the third reaction, the complete styrene combustion ($\Delta H_f^\circ = -4,262.872$ kJ/gm-mole), is $$C_6H_5C_2H_3 + 10O_2 \rightarrow 8CO_2 + 4H_2O.$$

The reaction mechanism used in the model is shown below. It shows the assumed reaction network for the mechanisms. This network is assumed and may not be generally applicable. The choice of the oxidation reaction order reflects an understanding of the experimental information available at the time and may not be generally applicable. Specifically in Table 14 the downstream, end of bed external tube wall temperature is quite often higher than the upstream value. This would indicate that the reactor bed favors the production of styrene first followed by oxidation, partial or complete, as parallel secondary reactions. That would mean the first reaction would increase the bed temperature down the length until the other two reactions "kick off" styrene partial and complete oxidation.

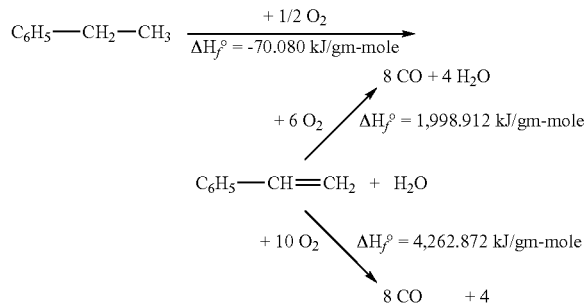

Reaction Mechanism Used in the Model

All of the reactions rates are calculated on a per volume basis, assuming a similar particle density to that of experiments. After some iterations of the quartz tube model in Fluent, the following pre-exponential factors give approximation of the conversions and selectivities reported in Table 14. The volumetric rate for the first reaction, oxidative dehydrogenation of ethylbenzene, is:

$$r_1 = 2.40 \times 10^7 \frac{m^{3/2}}{kgmole^{1/2} \cdot s} \exp\left[-\frac{70,000,000 \frac{J}{kgmole}}{8314 \frac{J}{kgmole \cdot K}}\left(\frac{1}{T}\right)\right] C_{EB} C_{O_2}^{0.5}$$

where
$r_1$ [kgmole/m³/s]=Rate of oxidative dehydrogenation of ethylbenzene reaction
$C_{EB}$ [kgmole/m³]=Ethylbenzene molar concentration
$C_{O_2}$ [bar]=Oxygen molar concentration
T [K]=absolute temperature The second volumetric rate of reaction, partial oxidation of styrene to carbon monoxide, is;

$$r_2 = 6.00 \times 10^8 \frac{m^3}{kgmole \cdot s} \exp\left[-\frac{83,000,000 \frac{J}{kgmole}}{8314 \frac{J}{kgmole \cdot K}}\left(\frac{1}{T}\right)\right] C_{ST} C_{O_2}$$

$r_2$ [kgmole/m³/s]=Rate of styrene partial oxidation reaction
$C_{ST}$ [kgmole/m³]=Styrene partial pressure The third volumetric rate, complete oxidation of styrene to carbon dioxide, is given by $$r_3 = 1.05 \times 10^6 \frac{m^3}{kgmole \cdot s} \exp\left[-\frac{30,000,000 \frac{J}{kgmole}}{8314 \frac{J}{kgmole \cdot K}}\left(\frac{1}{T}\right)\right] C_{ST} C_{O_2}$$

$r_3$ [kgmole/m³/s]=Rate of styrene partial oxidation reaction

As applied the kinetic model approximates the conversion versus selectivity results obtained in the quartz tube test. The model tends to under predict deep oxidation and thus over predict selectivity thus providing a conservative case for comparing the effects of thermal conductivity (i.e. less heat released per mole oxygen consumed if selectivity to styrene is high that if low). In addition the model does not have a rigorous treatment of effective conductivity accounting for convection and thermal radiation heat transfer. The kinetic rate equations were assumed to hold over a wide range of temperatures the range of said temperatures probably being too large for the cases evaluated (for example, see FIG. 94). These shortcomings do not undermine the general trends seen in the model. In the model of the tube the wall boundary condition is set to be isothermal at the temperature measured at the top of the bed. The model predict s 1.1 W/cm², 2.7 W/cm², 3.8 W/cm² and 13.7 W/cm² of heat flux (leaving) across the wall boundary for cases 1 to 4 in Table 14.

No improvement in predicted performance is obtained by applying the kinetics developed for the tube to the packed bed microchannel reactor (see FIG. 95) as both appear to have the same conversion versus selectivity behavior. Thus it may have been expected that running the reaction in a microchannel packed bed would not in this instance provide an advantage in hot spot reduction. This is likely due as when maximum temperature rise versus ethyl benzene conversion is plotted for cases 1 & 2 along side that predicted by the quartz tube model (see FIG. 96) both results appear to follow the same curve. Cases 3 & 4 (without dilution, see Table 15) are run in the microchannel packed bed model convergence as an issue due the large temperature rise predicted. In the model of the microchannel packed bed the wall boundary condition is set to be isothermal at 500° C. ($T_{wall}$ in Table 15). The model predicts 4.1 W/cm² for case 1 in table 3 and 6.4 W/cm² of heat flux (leaving) across the wall boundary for case 2 in Table 15.

The selectivity to styrene may fall as the conversion of ethylbenzene approaches approximately 45% (repeated run of a fresh sample of catalyst described in Example 3) and the simulations indicate that at this range of conversion, even when the model has better selectivity to styrene (i.e. less heat release), that a significant hot spot may arise in both the quartz tube and microchannel packed bed. Thus when conversion predicted in the quartz tube is 39.4% the boundary wall flux is estimated to be heat 3.8 W/cm² and when the conversion of ethylbenzene in the microchannel packed bed model is 37.7% the boundary wall flux is estimated to be heat 4.1 W/cm² both values expected to produce large maximum temperature rises (see FIG. 96). If a microgrooved support structure is employed a much lower temperature rise would be expected at similar heat flux. For a boundary heat flux of 11.38 W/cm² a microgrooved support structure is predicted to only experience a 3.5° C. temperature rise (see Example 6). Further support for this is provided by the results for the structured wall reactors as given where it can be seen that conversion may continue to be increased without undue penalty to styrene selectivity. When conditions 1 and 2 in Table 10 are compared to condition 7 it can be seen that for similar WHSV based on ethylbenzene that the structured wall reactor is capable of increasing conversion of ethylbenzene, improving selectivity and thus improving yield.

Example 10

This example discloses a simulation for the use of a long flow length structured wall for the oxidative dehydrogenation of ethylbenzene (EB) to styrene. Data is gathered over a 0.7% $K_2O$-15% $MoO_3/SiO_2$—$TiO_2$ catalyst (prepared as described in Example 3 and tested as described in Example 7) deployed in a structured wall microchannel test reactor and the results are used to estimate the parameters in a kinetic model of the oxidative dehydrogenation reaction of EB to styrene. The primary reactions considered in the model are:

$$C_8H_{10}+0.5O_2 \rightarrow C_8H_8+H_2O \quad \text{Equation 1}$$

$$C_8H_8+6O_2 \rightarrow 8CO+4H_2O \quad \text{Equation 2}$$

$$C_8H_8+10O_2 \rightarrow 8CO_2+4H_2O \quad \text{Equation 3}$$

The rates of reaction are represented as:

$$r_{EB} = k_{o1}\exp\left[\frac{-E_{a1}}{RT}\right]C_{EB}C_{O_2}^{0.5} \quad \text{Equation 4}$$

$$r_{ST} = k_{o2}\exp\left[\frac{-E_{a2}}{RT}\right]C_{ST}C_{O_2} \quad \text{Equation 5}$$

$$r_{st} = k_{o3}\exp\left[\frac{-E_{a3}}{RT}\right]C_{ST}C_{O_2} \quad \text{Equation 6}$$

The reaction scheme above is not considered to be definitive but is satisfactory for representing the results of the experiments. The values of the parameters in Equations 4, 5 and 6 are reported in Table 16.

TABLE 16

Kinetic Parameters used in equations 4, 5 & 6
0.7% $K_2O$-15% $MoO_3/SiO_2$—$TiO_2$

| Reaction | Parameter | Value | Units |
|---|---|---|---|
| EB to ST | $k_{o1}$ | 8.66E−02 | ($m^{9/2}$ s−1 $kmol^{-1/2}$ $mg^{-1}$) |
|  | $E_{a1}$ | 71063 | (J/mol) |
| ST to CO | $k_{o2}$ | 2.38E+05 | ($m^6 kgmol^{-1} s^{-1} mg^{-1}$) |
|  | $E_{a2}$ | 165542 | (J/mol) |
| ST to $CO_2$ | $k_{o3}$ | 2.48E+03 | ($m^6 kgmol^{-1} s^{-1} mg^{-1}$) |
|  | $E_{a3}$ | 130195 | (J/mol) |

The above information is used to simulate a long flow length structured wall reactor employing a catalyst using the CFD program Fluent. The catalyst is positioned in the structured wall and may be referred to as a porous catalyst. The flow length is 56 inches (142.24 cm) and the channel has a width of 0.25 inch (6.35 mm). The reactor comprises a channel which may be referred to as a process microchannel. The process microchannel has a structured wall with a 0.060 inch (1.52 mm) depth on either side of a 0.030 inch (0.76 mm) flow-by gap. The CFD model domain consists of a two-dimensional representation of the geometry using a symmetry boundary condition at the center of the flow-by channel. Thus the model has a 0.015 inch (0.381 mm) flow-by zone and one 0.060 inch (1.52 mm) deep structured wall. The full 56 inches (142.24 cm) flow length is represented. The boundary of the structured wall opposite that bounding the flow-by zone is modeled as being isothermal at three temperature levels, namely, 390° C., 400° C. and 410° C. Several exit pressures are modeled: 2 psig (1.14 atmospheres absolute pressure), 3 psig (1.20 atmospheres), 5 psig (1.34 atmospheres) and 7 psig (1.48 atmospheres).

The porous support in the structured wall for the catalyst is assumed to be made of stainless steel, having the properties given in the Fluent database. The effective material properties assumed for the porous support are given in Table 17.

TABLE 17

Properties of the structured wall

| Density $Kg/m^3$ | Heat capacity J/kg-K | Thermal Conductivity of Structured Wall W/m-K | Void Porosity | Coefficient in Darcy's law $1/m^2$ |
|---|---|---|---|---|
| 8030 | 502.5 | 8.13 | 0.5 | 6.77E9 |

The properties in the above Table 17 are for the porous support only. In the simulation, the catalyst and the process fluid in the catalyst are considered as one pseudo-homogeneous medium, and the properties of this medium are assumed to be a weighted average of the catalyst and the fluid. For example, the thermal conductivity of the porous catalyst is calculated by $$k_{eff}=\epsilon k_f+(1-\epsilon)k_s$$

Where e is the porosity, $k_f$ is the thermal conductivity of the fluid, and $k_s$ is the thermal conductivity of the catalyst. Other properties are calculated in the same way.

Two feed compositions (EB:$O_2$=1.3 and EB:$O_2$=2) are considered and two flow rates are simulated for EB:$O_2$=1.3 (see Tables 18 and 19, where mass-f represents mass fraction).

TABLE 18

Feed Composition and flow for EB:O$_2$ = 1.3

|  | EB:O$_2$ = 1.3 | | | EB:O$_2$ = 1.3 | | |
| --- | --- | --- | --- | --- | --- | --- |
|  | kmol/hr | kg/hr | mass-f | kmol/hr | kg/hr | mass-f |
| EB | 1.390E−03 | 1.476E−01 | 0.501 | 1.570E−03 | 1.667E−01 | 0.501 |
| O$_2$ | 1.069E−03 | 3.422E−02 | 0.116 | 1.208E−03 | 3.865E−02 | 0.116 |
| N$_2$ | 4.022E−03 | 1.126E−01 | 0.382 | 4.543E−03 | 1.272E−01 | 0.382 |
| total | 6.482E−03 | 2.945E−01 |  | 7.321E−03 | 3.326E−01 |  |

TABLE 19

Feed composition and flow for EB:O$_2$ = 2

|  | EB:O$_2$ = 2 | | |
| --- | --- | --- | --- |
|  | kmol/hr | kg/hr | mass-f |
| EB | 1.57E−03 | 1.667E−01 | 0.607 |
| O$_2$ | 7.90E−04 | 2.512E−02 | 0.092 |
| N$_2$ | 2.95E−03 | 8.269E−02 | 0.301 |
| total | 5.31E−03 | 2.745E−01 |  |

The results of the simulation for the EB:O$_2$ ratio of 2 for each of the temperatures are summarized in Table 20. The amount of catalyst assumed per unit volume of the porous support in the structured wall is also included in the table (6.78E8 mg of catalyst per m$^3$ of porous support). The conversion of EB is relatively insensitive to temperature for these cases over the range of simulated temperatures. The same trend is also observed for the selectivity to styrene. By analyzing the detailed concentration profiles over the length of the reactor, it is clear that the limited availability of O$_2$ is the main reason why EB conversion is not higher. The EB/O$_2$ ratio of 2 is the stoichiometric ratio of the main reaction and thus as the side reactions consume oxygen the main reaction becomes oxygen limited.

TABLE 20

Structured wall reactor performance
Catalyst loading: 6.78E8 mg-cat/m$^3$

|  |  | EB:O$_2$ = 2 | | |
| --- | --- | --- | --- | --- |
| Temperature | ° C. | 410° C. | 400° C. | 390° C. |
| Pressure out | psig | 2 | 2 | 2 |
| flow rate | kmol/hr | 0.00157 | 0.00157 | 0.00157 |
| Conversion | EB | 62.3% | 62.8% | 61.7% |
| Conversion | O$_2$ | 97.8% | 93.5% | 87.1% |
| Selectivity | Styrene | 96.9% | 97.4% | 97.8% |
|  | CO | 0.6% | 0.4% | 0.3% |
|  | CO$_2$ | 2.5% | 2.2% | 1.9% |
| Maximum Temp | ° C. | 473 | 447 | 425 |
| Pressure in | psig | 3.2 | 3.2 | 3.1 |

The impact of the catalyst activity on the reactor performance (assessed by varying the assumed catalyst loading on the structured wall) is also examined and the results are summarized in Table 21. Two levels of the catalyst loading are examined. At a given pressure the effect of increasing the loading is small as the cases are already oxygen limited. Increasing the pressure has a detrimental effect as the side reactions are assumed to be first order in oxygen and the main reaction only half order.

TABLE 21

Structured wall reactor performance
Impact of catalyst activity on the performance

| EB:O$_2$ = 2 |  | Catalyst loading: 1.02E9 mg/m$^3$ | | Catalyst loading: 6.78E8 mg/m$^3$ | |
| --- | --- | --- | --- | --- | --- |
| Temperature | ° C. | 390 | 390 | 390 | 390 |
| Pressure out | psig | 2 | 5 | 2 | 5 |
| flow rate | kmol/hr | 0.00139 | 0.00139 | 0.00139 | 0.00139 |
| Conversion | EB | 66.8% | 64.0% | 63.9% | 65.7% |
| Conversion | O$_2$ | 98.4% | 100.0% | 90.0% | 96.2% |
| Selectivity | Styrene | 97.7% | 96.9% | 97.8% | 97.5% |
|  | CO | 0.4% | 0.6% | 0.3% | 0.4% |
|  | CO$_2$ | 2.1% | 2.5% | 1.9% | 2.1% |
| Maximum Temp | ° C. | 456 | 515 | 425 | 438 |
| pressure in | psig | 3 | 5.9 | 3 | 5.9 |

The temperature profiles along the length of the reactor at two locations are plotted in FIG. 98. The lower curve is along the centerline of the flow-by regime. The upper curve represents a depth of 0.01 inch (0.25 mm) inside the structured wall. A large temperature spike is observed inside the structured wall where the reactions take place. The location of the maximum temperature is near the inlet of the reactor where the reaction rate is fastest. Most of the reaction heat is conducted out through the perimeter wall of the structure, and only a small percentage of heat flows into the flow-by regime. As a result of this, only a modest temperature rise in the gas stream is observed. The temperature of the gas stream is effectively constant over the length of the reactor. A more significant temperature rise is seen when the reactor is operated at higher temperature. This is due to higher reaction rates at higher temperature.

Compared to the conventional packed reactor (for which temperature gradients are expected to be hundreds of degrees), the temperature rise observed in the structured wall reactor for this highly exothermic reaction system is small due to the effective heat removal mechanism of the structured walls. But still the absolute temperature rise in the reactor may be of concern. One solution to moderate the temperature rise in the reactor may be to distribute the catalyst activity non-uniformly along the length of the reactor.

For a strong exothermic reaction system such as this the maximum temperature may be observed near the inlet of the reactor. This may be because at the beginning of the reactor the reactant concentrations may be highest, leading to the highest reaction rates. In order to moderate the reaction rates, one solution may be to distribute the catalyst activity (catalyst loading) non-uniformly along the length of reactor. The CFD simulation demonstrates the efficiency of non-uniform catalyst distribution along the reactor length as a design option coupled with the porous support in the structured walls as the support for the catalyst. A similar effect may be obtained by varying the thickness of the structured wall or the pore size or length of the structured wall along the length of the process microchannel.

Three different levels of the catalyst activity are present along the length of the reactor. For the first 10 inches (25.4 cm), the baseline activity is applied. Over the next 25.4 cm of reactor, the catalyst activity is doubled. From the 51 cm mark to the end of the reactor (56 in or 142 cm), the catalyst activity is tripled. The rest of the flow conditions can be found in Table 22 below. For comparison, the uniform catalyst activity distribution case is included, with an activity level of twice the baseline activity.

TABLE 22

| $EB/O_2 = 1.3$ | case # | 1 | 2 |
|---|---|---|---|
| Kinetics | 0-10" | 2X | 1X |
|  | 10-20" | 2X | 2X |
|  | 20-56" | 2x | 3X |
| Temperature | °C. | 390 | 390 |
| Pressure out | psig | 7 | 7 |
| Flow rate, EB | kmol/hr | 0.00139 | 0.00139 |
| Conversion | EB | 71.4% | 74.9% |
| Conversion | $O_2$ | 80.6% | 85.4% |
| Selectivity | Styrene | 96.1% | 96.0% |
|  | CO | 0.6% | 0.6% |
|  | $CO_2$ | 3.3% | 3.4% |
| Maximum T | °C. | 428 | 416 |
| pressure in | psig | 8.2 | 8.2 |

The temperature profiles along the length of the reactor are plotted at two locations as shown in FIG. 99. In FIG. 99, the lower curve is along the centerline of the flow-by regime, and the upper curve is inside the porous catalyst. The segmented temperature distribution inside the structured wall or porous catalyst is the result of using different catalyst activity levels along the reactor length. Steep temperature gradients are observed at those axial locations where a step change in catalyst activity is imposed. In this case, the temperature at the perimeter wall of the structured wall is set to remain constant at the same value as that of the inlet stream temperature which is 390° C. This rigid constant temperature may be hard to maintain considering that the metal frame beyond the structured wall may facilitate the heat conduction in all possible directions. Since such a metal frame is not included in the current CFD model, as a simplification, a constant wall temperature is imposed. If the heat conduction in the solid heat transfer channel wall is factored into the temperature distribution picture, the steep temperature variations may be relieved to a certain degree. If the large temperature variation is a real concern, one solution may be to gradually vary the catalyst active ingredient loading over a certain length of the reactor.

FIG. 100 shows the temperature profiles along the length of the reactor for the case with uniform catalyst activity distribution. The temperature rise inside the structured wall is about 38° C. By distributing the catalyst activity favorably, this temperature rise is cut to 26° C. while the overall ethylbenzene conversion is increased from 71.4% to 74.9%. The selectivity to styrene is virtually the same for both cases.

Example 11

This example discloses a simulation for the use of a long flow length structured wall reactor for the oxidative dehydrogenation of methanol to formaldehyde. A catalyst is positioned in the structured wall. This catalyst may be referred to as a porous catalyst. The production of formaldehyde ($CH_2O$) via the partial oxidation of methanol ($CH_3OH$) over a mixed oxide catalyst is exothermic and in conventional technology may be conducted over a packed bed catalyst. Although conversion may be increased with increasing temperature the reaction may be limited by the ability to effectively removed heat from the catalyst bed. In this example it is shown that the use of a microchannel reactor containing a structured wall catalyst may allow for high heat removal rates and the elimination of hot spots (temperature rise less than 3° C.) combined with pressure drop much lower than that expected for a packed bed of similar length (less than 2 psi (0.14 atmosphere) versus 50 psi (3.40 atmospheres)).

A series of simulations is conducted using kinetic data collected over two catalysts in a packed bed microchannel. The first catalyst is a 20% $V_2O_5$-10% $MoO_3/TiO_2$ (Catalyst A). The second catalyst is a 20% $V_2O_5$-10% $MoO_3/CeO_2$ (Catalyst B). The following materials are used in the preparation of the catalyst: ammonium metavanadate ($NH_4VO_3$, available from Aldrich), ammonium heptamolybdate (($NH_4$)$_6Mo_7O_{24}$·4$H_2O$, available from Aldrich), and cerium (VI) oxide, ($CeO_2$, available from Alfa Aesar). The catalyst is prepared as follows:

1. Dissolve 3.677 g of $NH_4VO_3$ in a 7.92 g of oxalic acid and 50 g DI water solution.
2. Dissolve 1.755 g of ($NH_4$)$_6Mo_7O_{24}$·4$H_2O$ in about 5 g DI water and add into the above solution.
3. Add 10 g of $CeO_2$ powder into the resulting solution from the previous steps under vigorously agitating.
4. Slowly vaporize water using a rotary evaporator under vacuum and heating.
5. Dry the resulting paste from step #4 in air overnight then in a vacuum oven @110° C.
   Calcine the powder @400° C. for 1 hr at 3° C./min heating up and down.

The packed bed microchannel has a gap of 0.060 inch (1.52 mm) and a width of 0.25 inch (6.35 mm). The bed is packed to a depth of 0.78 inch (1.98 cm). For both catalysts the results are used to estimate the parameters in a kinetic model of the oxidative dehydrogenation of methanol to formaldehyde. The primary reactions considered in the model are:

$$CH_3OH + 0.5O_2 \rightarrow CH_2O + H_2O \qquad \text{Equation 1}$$

$$CH_2O + 0.5O_2 \rightarrow CO + H_2O \qquad \text{Equation 2}$$

$$CH_3OH \rightarrow 0.5H_3COCH_3 + 0.5H_2O \text{ (dimethyl ether formation)} \qquad \text{Equation 3}$$

Other by products are observed over each of the catalysts, for example, methyl formate, $CO_2$ and hydrogen, but at low levels and the CO and dimethyl ether serve to approximate all other by-products. The rates of each reaction are represented as using the following:

$$r_{CH_2O} = k_{o1} \exp\left[\frac{-E_{a1}}{RT}\right] C_{CH_3OH}^{0.5} \qquad \text{Equation 4}$$

$$r_{CO} = k_{o2} \exp\left[\frac{-E_{a2}}{RT}\right] \frac{C_{CH_2O} C_{O_2}}{\left(1 + K_{ads,o} \exp\left[\frac{-E_{ads}}{RT}\right] C_{O_2}\right)^2} \qquad \text{Equation 5}$$

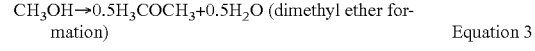
$$r_{DME} = k_{o3} \exp\left[\frac{-E_{a3}}{RT}\right] C_{CH_3OH} \qquad \text{Equation 6}$$

The reaction scheme above is not considered to be definitive but is satisfactory for representing the results of the experiments. The values of the parameters in Equations 4, 5 and 6 for each of the catalysts are reported in Tables 23 and 24 respectively.

TABLE 23

Kinetic Parameters for 20% $V_2O_5$-10% $MoO_3/TiO_2$ (Catalyst A)
Data gathered in Structured Wall Microchannel Reactor

| Reaction | Parameter | Value | Units |
|---|---|---|---|
| $CH_3OH \rightarrow CH_2O$ | $k_{o1}$ | 2.69E−02 | ($m^{3/2}$ $kmol^{1/2}$ $mg^{-1}$ $s^{-1}$) |
| | $E_{a1}$ | 78,272 | (J/mol) |
| $CH_2O + 1/2O_2 \rightarrow CO + H_2O$ | $k_{o2}$ | 2.57E−05 | ($m^6$ $kmol^{-1}$ $mg^{-1}$ $s^{-1}$) |
| | $E_{a2}$ | 7,248 | (J/mol) |
| | $K_{o2}$ | 2.07E−02 | (m3/kmol) |
| | $E_{ads.2}$ | 5,920 | (J/mol) |
| $2CH_3OH \rightarrow DME + H_2O$ | $k_{o3}$ | 3.14E−02 | ($m^3$ $mg^{-1}$ $s^{-1}$) |
| | $E_{a3}$ | 85,841 | (J/mol) |

TABLE 24

Kinetic Parameters for 20% $V_2O_5$-10% $MoO_3/CeO_2$ (Catalyst B)
Data gathered in packed bed microchannel Reactor

| Reaction | Parameter | Value | Units |
|---|---|---|---|
| $CH_3OH \rightarrow CH_2O$ | $k_{o1}$ | 6.00E−07 | ($m^{3/2}$ $kmol^{1/2}$ $mg^{-1}$ $s^{-1}$) |
| | $E_{a1}$ | 35,906 | (J/mol) |
| $CH_2O + 1/2O_2 \rightarrow CO + H_2O$ | $k_{o2}$ | 2.80E+05 | ($m^6$ $kmol^{-1}$ $mg^{-1}$ $s^{-1}$) |
| | $E_{a2}$ | 133,990 | (J/mol) |
| | $K_{o2}$ | 2.07E−02 | (m3/kmol) |
| | $E_{ads.2}$ | 5,920 | (J/mol) |
| $2CH_3OH \rightarrow DME + H_2O$ | $k_{o3}$ | 1.30E−06 | ($m^3$ $mg^{-1}$ $s^{-1}$) |
| | $E_{a3}$ | 41,109 | (J/mol) |

The reaction rates have the unit of kmol/mg-cat/s. The catalyst loading level in term of mg-cat per unit catalyst packing is needed in order to convert the rates to volume packing based. The baseline catalyst loading capacity is 2.74E8 $mg_{cat}/m^3_{SW}$.

The above information is used to simulate a long flow length structured wall reactor using the CFD program Fluent. A catalyst is positioned in the structured wall and may be referred to as a porous catalyst. The reactor, which is in the form of a microchannel, has a flow length is 56 inches (142.24 cm) and the channel has a width of 0.25 inch (6.35 mm). The channel has an overall gap of 0.150 inch (3.81 mm) as is envisioned as having 0.060 inch (1.52 mm) depth of structured wall on either side of a 0.030 inch (0.762 mm) flow by gap. The CFD model domain consists of a two-dimensional representation of the geometry using a symmetry boundary condition at the centre of the flow by channel (thus the model consists of a 0.015 inch (0.381 mm) flow by zone and 0.060 inch (1.52 mm) structured wall). The full 56 inch (142.24 cm) flow length is represented. The boundary of the structured wall opposite that bounding the flow by zone is modeled as being isothermal at three temperature levels, namely, 300° C., 330° C. and 360° C. In all cases the outlet pressure is set as 2 psig (1.14 atmospheres absolute pressure). The flow rates are given in the following Table 25.

| | | FLW1 |
|---|---|---|
| Total Inlet Flow | (SLPM) | 4 |
| Reactor Length | (in) | 56 |
| Width | (in) | 0.25 |
| Gap (inclusive of SW) | (in) | 0.15 |
| Flow-by | (in) | 0.03 |
| Structured Wall | (in) | 0.06 |
| CT | (ms) | 516 |
| Total Molar Flow | (kmol/s) | 2.973E−06 |
| Air:MeOH | (mol/mol) | 4 |
| MeOH:$H_2O$ | (mol/mol) | 9.79 |
| Molar Flows | | |
| MeOH | (kmol/s) | 5.828E−07 |
| $H_2O$ | (kmol/s) | 5.953E−08 |
| $O_2$ | (kmol/s) | 4.895E−07 |
| $N_2$ | (kmol/s) | 1.842E−06 |
| Mass Flows | | |
| MeOH | (kg/s) | 1.865E−05 |
| $H_2O$ | (kg/s) | 1.072E−06 |
| $O_2$ | (kg/s) | 1.567E−05 |
| $N_2$ | (kg/s) | 5.156E−05 |
| Total Mass Flow | (kg/s) | 8.695E−05 |
| Mass Fractions | | |
| MeOH | (—) | 0.214 |
| $H_2O$ | (—) | 0.012 |
| $O_2$ | (—) | 0.180 |
| $N_2$ | (—) | 0.593 |
| | | 1.000 |

The porous support for the catalyst in the structured wall is assumed to be made of stainless steel. The material properties of the structured wall are based on those from the Fluent data base and are given in Table 26.

TABLE 26

Properties of the structured wall

| Density $Kg/m^3$ | Heat capacity J/kg-K | Thermal Conductivity of Structured Wall W/m-K | Void Porosity | Coefficient in Darcy's law $1/m^2$ |
|---|---|---|---|---|
| 8030 | 502.5 | 8.13 | 0.5 | 6.77E9 |

The properties in the above Table 26 are for the porous support only. In the simulation, the catalyst and the processed fluid in the catalyst is considered as one pseudo-homogeneous medium, and the properties of this medium are calculated by weighted averaging of the catalyst material and the fluid. For example, the thermal conductivity of the catalyst is calculated by $$k_{eff} = \epsilon k_f + (1-\epsilon)k_s$$

Where e is the porosity and the $k_f$ is the thermal conductivity of the fluid and $k_s$ is the thermal conductivity of the porous catalyst. Other properties are calculated in the same way.

The CFD simulations of the structured wall reactor at the three temperatures are summarized in Table 27. The Catalyst A kinetics are used with the baseline catalyst loading capacity of 2.74E8 $mg_{cat}/m^3_{SW}$.

TABLE 27

Results of modeling for Catalyst A

| | T = 300° C. | T = 330° C. | T = 360° C. |
|---|---|---|---|
| $X_{MeOH}$ | 66.5% | 96.0% | 99.9% |
| $X_{O2}$ | In Excess | In Excess | In Excess |
| SEL $CH_2O$ | 76.7% | 80.8% | 84.1% |
| SEL CO | 22.1% | 18.1% | 14.8% |
| SEL DME | 1.2% | 1.0% | 1.0% |

The methanol conversion achieved in the structured wall reactor increases when the operating temperature increases. The same trend is observed for the selectivity to CH$_2$O. The selectivity to by-product CO decreases as temperature increases, while the selectivity to DME (dimethyl ether) shows little change over the range of temperature studied. These observations are the result of the relative rates of each reaction and their respective activation energies and rate forms. The rate of formaldehyde production has an apparent activation energy at 7.83E7 J/kmol, and the formation of CO from formaldehyde has an apparent activation energy at 7.25E6 J/kmol. The adsorption term in the CO formation rate has little effect on the overall rate. As DME is formed directly from methanol in this case any increase in temperature is offset by reduction in the methanol partial pressure due to changes in the rate of the main reaction. The mass fraction of methanol along the reactor length is plotted in FIG. 101. The upper curve is along the center of the flow-by channel, and the lower curve is at the middle of the structured wall. At any axial location, the methanol concentration in the flow-by channel is higher than that in the structured wall because the methanol is converted to the products in the structured wall. The CH$_2$O mass fraction is shown in FIG. 102.

For this exothermic reaction system better thermal management mechanism may be related to effective heat removal scheme.

In the conventional packed bed reactor, the catalyst particles may be immersed in the process stream. The heat generated in the catalyst particles has to be conducted out of the catalyst particles. See, FIG. 103. The energy may directly heat up the process stream and the high temperature may build up over the length of the reactor. This may lead to poor selectivity for most of the exothermic reaction system.

In the case of a structured wall reactor, the heat generated by the reactions may be removed predominantly from the opposite side of the walls to the process stream and it may be removed from the reaction zone. See, FIG. 103. The direct effect of this heat removal scheme may be the lower temperature rise in the reactor, or in tighter temperature control.

The temperature profiles along the reactor length are plotted in FIG. 104 at two locations. The upper curve (after 5 inches) is along the center of the flow-by channel and the lower curve (after 5 inches) is at the middle of the structured wall. The overall temperature variation is small. This reflects the good heat transfer capabilities of the structured wall.

The temperature profile in the transverse direction at a point 6 inches (15.24 cm) from the beginning of the structured wall (SW) is provided in FIG. 105. FIG. 106 is a plot of temperature distribution in the reactor, the baseline temperature being 360° C. FIG. 107 is a plot of the heat flux profile along the reactor wall.

The low pressure drop results from the use of a flow-by regime. The fluid does not have to flow through the porous catalyst which may be a much larger source of momentum loss. As shown in the FIG. 108, total pressure drop over a 56 inch (142.24 cm) long reactor is 1.6 psi (0.11 atmosphere).

A CFD simulation is conducted for the structured wall geometry described above using the kinetics from catalyst B and a catalyst loading of 1.42E9 mg$_{cat}$/m$^3$$_{SW}$. The heat transfer wall is set to be isothermal at the desired temperature (300, 320 and 345° C.). The feed inlet temperature is set to the wall temperature. The exit pressure is set at 2 psig (1.36 atmospheres absolute pressure). The void fraction of the structured wall is set at 0.5. Feed flowrates are given in Table 25. The results are summarized in Table 28:

TABLE 28

Results of modeling for Catalyst B

|  | T = 300° C. | T = 320° C. | T = 345° C. |
| --- | --- | --- | --- |
| X$_{MeOH}$ | 60.1% | 70.5% | 82.3% |
| X$_{O2}$ | In Excess | In Excess | In Excess |
| SEL CH$_2$O | 91.5% | 86.5% | 75.5% |
| SEL CO | 4.6% | 9.8% | 21.0% |
| SEL DME | 3.8% | 3.7% | 3.5% |

For the purposes of comparison a case is run using the kinetics for catalyst B in a domain similar to that used for the structured wall (gap=0.150 inch (3.81 mm), width=0.25 inch (6.35 mm) and length=56 inches (142.24 cm) with the structured wall replaced by a packed bed with a void fraction of 0.5, heat capacity of 1000/kg-K, density of 2000 kg/m$^3$. The effective thermal conductivity of the packed bed is assumed to be 0.25 W/m-k. Cold flow pressure drops are assessed for each case, structured wall and packed bed, using the inlet flow (see Table 25) and an isothermal (300° C.) domain temperature under non-reacting conditions.

The methanol conversion achieved in the structured wall reactor increases as the operating temperature increases, while under the same conditions the selectivity to CH$_2$O falls. The CH$_2$O oxidation reaction to CO gains relative importance at high temperature, while the selectivity to DME is not strongly dependent to the temperature. These behaviors are the expected outcome based on the relative apparent activation energies of each of the reactions modeled. Based on the kinetics used the temperature has the opposite impact on the selectivity to the product for catalyst A and catalyst B.

A conclusion that may be made by comparing the temperature profiles in FIGS. 109 and 110 is that the structured wall may reduce hot spot formation by orders of magnitude when compared to a packed bed reactor. The structured wall reactor (FIG. 109) shows a temperature rise of only 2° C. even at the highest temperature (thus conversion and selectivity to CO i.e. maximum heat load). In FIG. 109, the upper curve (after 5 inches) is for the temperature measured along the center line of the flow-by regime, and the lower curve (after 5 inches) is for the temperature measured along the middle of the structured wall. In the packed bed reactor channel shown in FIG. 110 the temperature rise is in excess of 210° C.

In addition to the reduction of the hot spot magnitude, the predicted cold flow pressure drop is also greatly reduced. The cold flow pressure drop for the structured wall case is estimated to be 1.4 psi (0.095 atmosphere) and the cold flow pressure drop for the packed bed case is estimated to be 50 psi (3.40 atmospheres).

Example 12

A simulation of a packed bed catalyst in a microchannel is conducted using the CFD package Fluent and the kinetics published by Diakov et al (Chem. Eng. Sci, v. 57, p. 1563-1569) to simulate the partial oxidation of methanol to formaldehyde over a mixed oxide catalyst. The domain simulated represents a microchannel with a gap of 0.060 inch (1.52 mm) a width of 0.25 inch (6.35 mm) and a packed bed depth of 1.15 inches (2.92 cm). The bed is assumed to have an effective thermal conductivity of 0.12 W/m-K, density of 1000 kg/m$^3$ and constant pressure heat capacity of 25,000 J/gmol-K for the catalyst particles. The void fraction of the bed is assumed to be 0.35. The feed rate is 12.95 g/hr. The mass fraction of methanol in the feed is 0.112, the mass fraction of oxygen is 0.112 and the mass fraction of water is 0.019. The balance of the feed is nitrogen. The contact time for this condition is 100 ms. Simulations are conducted for using isothermal heat transfer boundary conditions (feed set to wall temperature) for four temperature levels 300° C., 312.5° C., 325° C. and 350° C. Outflow pressure for each simulation is set to 0 psig (1.0 atmosphere absolute pressure). The results for these cases are found in Table 29.

TABLE 29

| Boundary Temp | 300° C. | 312.5° C. | 325° C. | 350° C. |
|---|---|---|---|---|
| Maximum Temperature | 307° C. | 331° C. | 478° C. | 500° C. |
| Pressure Drop | 1.7 psi | 1.9 psi | 2.4 psi | 2.6 psi |
| Conversion of Methanol | 64.1% | 96.7% | 100% | 100% |
| Selectivity to Formaldehyde | 99.6% | 99.5% | 99.2% | 99.2% |

Based on these simulation results it can be seen that, although the above indicated kinetics do not predict a significant penalty for generation of a hot spot, it is clear that a significant hot spot is generated under these conditions. At a low conversion of 64.1% (and temperature of 300° C.) the hot spot formation is relatively small at 7° C., but this increases with conversion to approximately 18° C. at 96.7% conversion and 312.5° C. The temperature rise reaches a maximum of 153° C. at a reaction temperature of 325° C. and a conversion of 100%. This behavior, a large increase in temperature rise for a small increase in conversion, may not be due to the increase in conversion but due to the large increase in reaction rate with increasing temperature, which decreases the volume of catalyst in which the reaction takes place, thus intensifying the hot spot. If the apparent activation energy for the formation of any of the by-products (CO via cracking of formaldehyde or partial oxidation of reactant or product, $CO_2$, methyl formate, dimethyl ether or DMM) is greater than the main reaction, then the hot spot may have significant negative impact on the selectivity to formaldehyde. In addition, this may make the packed bed prone to thermal run-away.

Example 13

A simulation using the reactor depicted in FIG. 111 is conducted. The simulation is conducted to study the effect of a structured wall (SW) and surface features (SF) in a microchannel. The reactor has three distinct regimes: flow-by; surface feature; and structured wall. The dimensions for each regime are as follows:

The dimensions of the flow-by channel are:
Gap: 0.04 inch (1.02 mm)
Width: 0.16 inch (4.06 mm)
Length: 1.8 inches (4.57 cm)

The surface feature regime has the same width and length as those of the flow-by regime. It is 0.02 inch (0.508 mm) thick. There are 10 surface features over a 1.8 inch (4.57 cm) long section. The surface feature has a 60° angle pointing to the flow direction. The width of each surface feature is 0.015 inch (0.381 mm).

The thickness of the structured wall regime is 0.03 inch (0.762 mm). Structured walls and surface features are on both sides of the flow-by regime.

An SMR reaction in the microchannel reactor is the focus of the example. The WGS reaction is also considered because of its importance on the SMR catalyst.

Two distinct reaction zones are present in this reactor configuration. On the walls of all the recessed surface features a thin catalyst layer is applied. The catalyst is also loaded inside of the wall structures which are behind the surface feature shims. In order to verify the performance enhancement by integrating the surface features and structured walls a baseline reactor is constructed by keeping surface features only (omitting the structured wall features). In the latter case, the catalyst is applied on the walls of the recessed surface features.

The reactions on the surface feature walls are modeled as surface reactions while the reactions inside the structured walls are modeled as volumetric reactions. For the volumetric reactions the following kinetics are used throughout this work $$r_1 = k_1(P_{CH4}P_{H2O} - P_{CO}P_{H2}^3/K_1)$$

$$r_2 = k_2(P_{CO}P_{H2O} - P_{H2}P_{CO2}/K_2)$$

The reaction rates are in $kmol/m^3$-cat·sec, and the pressures $P_i$ in the above equations are in atmosphere. The reaction rate constants are given as following, $$k_1 = A_1 \exp(-E_1/RT)$$

$$k_2 = A_2 \exp(-E_2/RT)$$

The activation energy for SMR reaction, $E_1 = 1.695E8$ J/Kmol; and for WGS reaction, $E_2 = 6.713E+7$ J/Kmol. The pre-exponential factors are $A_1 = 1.275E+08$ and $A_2 = 1.466E+03$.

In these reaction rate expressions, the reverse reactions have been taken into accounts whose rates are calculated based on the chemical equilibrium constants given as following, $$K_1 = \exp(-26830/T + 30.114)$$

$$K_2 = \exp(4400/T - 4.036)$$

The rate expressions for the surface reaction are of the same form as those of the volumetric reactions. The activation energies are also the same as those of the volumetric reactions. The only difference is in the pre-exponential factors. Specifically, the pre-exponential factor for SMR reaction is 2.3E4, for WGS reaction it is 0.1223.

The parameters in the kinetics are the result of best fitting the model predictions with reaction rate experimental data. This set of kinetics is not necessary valid for all the SMR catalysts.

The structured walls (porous catalyst supports) are made of the stainless steel. Material properties are from the Fluent database for steel and they are listed in the following Table 30.

TABLE 30

| Density $Kg/m^3$ | Heat capacity J/kg-K | Effective Thermal Conductivity W/m-K | Void Porosity | tortuosity | Coefficient in Darcy's law $1/m^2$ |
|---|---|---|---|---|---|
| 8030 | 502.5 | 8.13 | 0.5 | 2 | 6.77E9 |

The properties in the above Table 30 are for the catalyst support structure only. In the simulation, the catalyst bed and the processed fluid in the bed is considered as one pseudo-homogeneous medium, and the properties of this medium are calculated by weighted averaging of the catalyst material and the fluid. For example, the thermal conductivity of the bed is calculated by $$k_{eff} = \epsilon k_f + (1-\epsilon)k_s$$

Where e is the porosity, $k_f$ is the thermal conductivity of the fluid and $k_s$ is the thermal conductivity of the structured wall. Other properties are calculated in the same way.

For flow simulation in the catalyst structure, the following formula is used:

$$\nabla p = -\mu A u$$

in which A is the viscous resistance coefficient whose value is listed in Table 30.

In general, both the bulk and Knudsen diffusion contribute to the mass transport rate within the pore volume. For equimolal binary counter-diffusion, the effective diffusivity can be calculated by $$D_{eff} = \frac{1}{1/D_e + 1/D_k}$$

$D_{eff}$=effective diffusivity within the porous medium
$D_e$=bulk diffusivity in the pore
$D_k$=Knudsen diffusivity The bulk diffusivity of species i in the pores of the porous medium is affected by the connection of the pores of different sizes. A simple parallel pore model yield the following equation for the effective bulk diffusivity, $$D_e = \frac{D}{\delta}$$

D=molecular mass diffusivity of species i
δ=tortuosity factor of the porous medium For the type of structured walls used in this study, the tortuosity factor is smaller than typical values of catalyst substrate. In this study it is assumed to be 2.

The mass diffusivity of each species is summarized in the following Table 31. The temperature dependence of these diffusivities are not considered since the temperature variation within the reactor is less than 20 degree.

TABLE 31

| | $CH_4$ | $H_2O$ | $H_2$ | CO | $CO_2$ |
|---|---|---|---|---|---|
| Mass diffusivity, D, m²/s | 1.03E−5 | 1.7E−5 | 3.44E−5 | 1.01E−5 | 7.67E−6 |

The Flow Conditions are:
The contact time based on flow-by channel volume is 3.7 ms.
Flow rate: 4.0E-5 kg/s
Steam/methane ratio=3
Temperature: 840° C.
Temperature on the wall: 840° C.
Pressure at the outlet of the reactor: 345 psi (23.48 atmospheres).

The predicted methane conversion under the flow conditions used is 53.9%. For comparison, the methane conversion of surface feature only case is also reported. It shows that with the surface features (SF) and structured wall (SW) combination, the methane conversion is increased by 28%. The pressure drop over the length of the reactor is approximately 0.1 psi for both cases.

| | SF + SW | SF only |
|---|---|---|
| Methane conversion | 53.9% | 42.2% |

The addition of 0.060 inch (1.52 mm) thickness of structured wall per reactant channel is not necessarily the optimal thickness, but in some designs the addition of this thickness of structured wall may represent about a 20% increase in the total repeating unit thickness (taking into account all adjacent heat exchange channels and walls needed to supply heat to the reaction). Thus, even for this unoptimized case, the increase in methane conversion (28%) is significantly higher than the increase in total repeating unit thickness (which scales with reactor cost).

Also, with such a short reactor simulation length (only 10 surface features) and such a large gap (0.040 inch (1.016 mm)) the results are likely strongly influenced by bulk channel mass transport resistance in the flow development region near the inlet where the surface features set up the desired flow pattern. In regions where the reaction is subject to significant bulk channel mass transport control, the surface-feature-only and the surface-feature+structured wall cases may give equivalent performance (i.e. methane conversion). If the reactor length is longer (more surface features) and/or if the gap is smaller, the impact of the structured wall on performance may be even greater.

Example 14

A device for evaluating multiple catalysts on a porous wall within a microchannel reactor is illustrated in FIG. 112. In this device six parallel process channels are aligned on a sheet as shown in the FIG. 112. The channels are adjacent to at least one or more structured wall shims that are used to hold the catalyst. Different or similar or identical catalyst compositions are applied to each channel independently through the individual outlet ports of the channel. A single process flow stream enters the device and is nearly equally divided into the six process channels using flow distribution features (see as the serpentine path in the figure). The flow distribution channels provide a pressure drop that is at least 2×, and in one embodiment 5× above the pressure drop in the connecting or process channels. By this manner, flow is passively distributed to channels in a way that may be perturbed much if the conversion in any one channel is high or low. By this manner, the evaluation of different catalyst formulations may not affect the measurement of other channels within the unit. Each channel has a separate outlet port connected such that the flowrate and molar composition could be measured to quantify the performance of the individual catalyst in the channel. A wall shim separates the porous catalyst layer and the heat transfer channel. Alternatively, the heat transfer layer may be a partial etch shim such that a wall is created between the two fluid passageways. The stack of the shims is shown in FIG. 113.

Flow is cross flow between the process channels where six catalysts may be evaluated at one time and the heat transfer channels. The design could be modified to enable counter or co-flow between the process channels and the heat transfer channels.

Also not shown, thermocouple wells may be created within the wall that separates the heat exchange channels and the porous catalyst or structured wall layer or layers to get a good measurement of the catalyst temperature. Fluid flow on the heat exchanger side is also passively distributed with the use of distribution features to create sufficiently uniform flow between the heat transfer channels. Sufficiently uniform is defined as a quality factor (or degree of flow maldistribution) less than 20%.

FIG. 114 shows the stacked layers that create a multiple catalyst testing test device based on the use of structured wall catalyst. Outlet tubes (six holes shown) can be welded or joined to the face of the sealed device and inlet tubes. Inlet tubes for each of the heat transfer fluid and process feed can also be attached to the larger holes. One outlet of the heat transfer fluid is also created and a tube may be connected.

The device may be operated with one, two, or all of the channels at one time. The concept may also be applied for testing any number of parallel microchannels with porous walls at one time. It may be advantageous to test 12, 24, 48 or more or any number of channels. It may also be advantageous to connect the individual outlet ports to an automated means for measuring flowrate and composition, including gas or liquid chromatography, NMR, UV vis, species sensors, or others.

While the disclosed technology has been explained in relation to various detailed embodiments, it is to be understood that various modifications thereof may become apparent to those skilled in the art upon reading the specification. Therefore, it is to be understood that the invention disclosed herein is intended to include such modifications as may fall within the scope of the appended claims.

The invention claimed is:

1. A process for conducting a chemical reaction in a microchannel reactor, the microchannel reactor comprising:
   at least one microchannel, the microchannel comprising at least one heat transfer wall;
   a porous catalyst in the microchannel on the heat transfer wall, the porous catalyst comprising a porous support and an active catalyst, the porous support comprising primary pores and secondary pores, the primary pores being larger than the secondary pores;
   the active catalyst being in the secondary pores;
   a bulk flow region adjacent to the porous catalyst;
   a heat source and/or heat sink in thermal contact with the heat transfer wall;
   the process comprising flowing a first reactant and a second reactant in the microchannel through the bulk flow region in contact with the catalyst to form a product, and exchanging heat between the heat source and/or heat sink and the heat transfer wall.

2. The process of claim 1 wherein:
   the porous support comprises grooves that are stamped, etched, cut or machined in one or more thermally conductive support strips positioned in the microchannel adjacent to and in contact with the heat transfer wall.

3. The process of claim 1 wherein:
   the process is conducted with a contact time in the range from about 0.4 to about 4 ms, a heat flux in the range from about 10 to about 100 $W/cm^2$, and a pressure drop in the microchannel less than about 15 atmospheres per meter.

4. The process of claim 1 wherein the process comprises conducting an equilibrium limited chemical reaction:
   the process being conducted with a contact time in the range from about 0.4 to about 4 ms, a heat flux in the range from about 10 to about 100 $W/cm^2$, a pressure drop in the microchannel less than about 15 atmospheres per meter, and an approach to equilibrium conversion of at least about 75%.

5. The process of claim 1 wherein:
   the porous support comprises: a composite structure containing multiple layers of one or more thermally conductive metals, silicon carbide, graphite, alumina, or a combination thereof; a macroporous layer comprising SiCN, SiC, $TiO_2$, $SiO_2$, $ZrO_2$, or $Al_2O_3$; sol gel deposited $SiO_2$, $Al_2O_3$ or $TiO_2$; surfactant templated $SiO_2$; anodized $Al_2O_3$ or $TiO_2$; $Al_2O_3$, $TiO_2$ or carbon nanotubes; multiwall or single wall nanotubes; or one or more zeolites.

6. The process of claim 1 wherein:
   the porous support and the heat transfer wall comprise: a sintered metal powder on a sheet of solid metal; or a porous layer of pure metal on a solid sheet of metal alloy.

7. The process of claim 1 wherein the porous catalyst comprises: Pt/$Al_2O_3$ nanofibers; a carbon nanotube-Co/$SiO_2$ composite; gold nanoparticles supported on carbon nanotubes; or metal nanowires in $Al_2O_3$ or $TiO_2$ nanotubes.

8. The process of claim 1 wherein the process is conducted in a microchannel reactor, the microchannel reactor comprising a plurality of the microchannels adapted to be operated in parallel, the microchannels being process microchannels, a header for providing for the flow of fluid into the process microchannels, a footer for providing for the flow of fluid out of the process microchannels.

9. The process of claim 8 wherein a second reactant stream channel is adjacent each process microchannel and an apertured section for permitting the flow of one or more reactants into the process microchannel is positioned between the second reactant stream channel and the process microchannel.

10. The process of claim 1 wherein the heat source and/or heat sink is adjacent to the microchannel.

11. The apparatus of claim 1 wherein the heat source and/or heat sink is remote from the microchannel.

12. The process of claim 1 wherein the heat source and/or heat sink comprises at least one heat exchange channel.

13. The process of claim 12 wherein the heat exchange channel comprises a microchannel.

14. The process of claim 1 wherein the heat source and/or heat sink comprises at least one electric heating element, resistance heater and/or non-fluid cooling element.

15. The process of claim 14 wherein the electric heating element, resistance heater and/or non-fluid cooling element is adjacent to the microchannel.

16. The process of claim 14 wherein the microchannel comprises one or more walls and the electric heating element, resistance heater and/or non-fluid cooling element is part of at least one of the walls of the microchannel.

17. The process of claim 14 wherein the microchannel comprises one or more walls and at least one of the walls of the microchannel is formed from the electric heating element, resistance heater and/or non-fluid cooling element.

18. The process of claim 12 wherein a heat exchange fluid is in the heat exchange channel.

19. The process of claim 1 wherein the microchannel is formed from parallel spaced sheets and/or plates.

20. The process of claim 1 wherein a second reactant stream channel is adjacent to the microchannel, the microchannel and the second reactant stream channel being formed from parallel spaced sheets and/or plates.

21. The process of claim 1 wherein the heat source and/or heat sink comprises a heat exchange channel, the heat exchange channel and the microchannel being formed from parallel spaced sheets and/or plates.

22. The process of claim 1 wherein the first reactant and the second reactant are mixed upstream of the microchannel.

23. The process of claim 1 wherein the first reactant and the second reactant are mixed in the microchannel.

24. The process of claim 8 wherein the first reactant and the second reactant are mixed in the header.

25. The process of claim 9 wherein the second reactant flows from the second reactant stream channel into the process microchannel.

26. The process of claim 1 wherein a reaction zone is in the microchannel, the second reactant contacting the first reactant in the reaction zone.

27. The process of claim 1 wherein a mixing zone and a reaction zone are in the microchannel, the mixing zone being upstream of the reaction zone, the second reactant contacting the first reactant in the mixing zone.

28. The process of claim 1 wherein a mixing zone and a reaction zone are in the process microchannel, the mixing zone being upstream of the reaction zone, part of the second reactant contacting the first reactant in the mixing zone, and part of the second reactant contacting the first reactant in the reaction zone.

29. The process of claim 18 wherein the heat exchange fluid undergoes a phase change in the heat exchange channel.

30. The process of claim 12 wherein an endothermic process is conducted in the heat exchange channel.

31. The process of claim 12 wherein an exothermic process is conducted in the heat exchange channel.

32. The process of claim 18 wherein the reactants flow in the microchannel in a first direction, and the heat exchange fluid flows in the heat exchange channel in a second direction, the second direction being cross current relative to the first direction.

33. The process of claim 18 wherein the reactants flow in the microchannel in a first direction, and the heat exchange fluid flows in the heat exchange channel in a second direction, the second direction being cocurrent or counter current relative to the first direction.

34. The process of claim 18 wherein the heat exchange fluid comprises the first reactant, the second reactant, the product, or a mixture of two or more thereof.

35. The process of claim 18 wherein the heat exchange fluid comprises one or more of air, steam, liquid water, carbon monoxide, carbon dioxide, gaseous nitrogen, liquid nitrogen, inert gas, gaseous hydrocarbon, oil, and liquid hydrocarbon.

36. The process of claim 1 wherein the reaction comprises one or more of the following reactions: acetylation addition, acylation, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, water-gas shift, dehalogenation, dimerization, epoxidation, esterification, Fischer-Tropsch reaction, halogenation, hydrohalogenation, homologation, hydration, dehydration, hydrogenation, dehydrogenation, oxidative dehydrogenation, hydrocarboxylation, hydroformylation, hydrogenolysis, hydrometallation, hydrosilation, hydrolysis, hydrotreating, isomerization, methylation, demethylation, metathesis, methanol synthesis, nitration, oxidation, partial oxidation, polymerization, reduction, reformation, steam methane reforming reaction, reverse water gas shift, sulfonation, telomerization, transesterification, dimerization, trimerization, oligmerization, Sabatier reaction, carbon dioxide reforming, preferential oxidation, preferential methanation, or a combination of two or more of the foregoing reactions.

37. The process of claim 12 wherein an endothermic reaction is conducted in the microchannel and an exothermic reaction is conducted in the heat exchange channel.

38. The process of claim 37 wherein the endothermic reaction is a steam reforming reaction and the exothermic reaction is a combustion reaction.

39. The process of claim 1 wherein the reaction comprises a Fischer-Tropsch reaction.

40. The process of claim 1 wherein the pressure within the microchannel is in the range up to about 250 atmospheres absolute pressure.

41. The process of claim 1 wherein the contact time for the reaction is in the range from about 1 microsecond to about 100 seconds.

42. The process of claim 1 wherein the product is removed from the microchannel, the process further comprising flowing a regenerating fluid through the microchannel in contact with the catalyst.

43. The process of claim 1 wherein the reaction is an ultrafast reaction.

44. The process of claim 1 wherein the process is conducted with a heat flux intensity, the heat flux intensity being in the range from about 1000 to about 800,000 $W/m^2$-K.

45. The process of claim 1 wherein the process is conducted with a mass flux intensity, the mass flux intensity being in the range from about 1 to about 20 moles/$m^2$/sec.

* * * * *